(12) United States Patent
Tischfield et al.

(10) Patent No.: US 9,994,893 B2
(45) Date of Patent: Jun. 12, 2018

(54) COMPOSITIONS AND METHODS FOR FUNCTIONAL QUALITY CONTROL FOR HUMAN BLOOD-BASED GENE EXPRESSION PRODUCTS

(71) Applicant: Rutgers, The State University of New Jersey, New Brunswick, NJ (US)

(72) Inventors: Jay Tischfield, Martinsville, NJ (US); Andrew Brooks, New York, NY (US); Stephanie Frahm, Flemington, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 851 days.

(21) Appl. No.: 14/365,060

(22) PCT Filed: Dec. 13, 2012

(86) PCT No.: PCT/US2012/069561
§ 371 (c)(1),
(2) Date: Jun. 12, 2014

(87) PCT Pub. No.: WO2013/090613
PCT Pub. Date: Jun. 20, 2013

(65) Prior Publication Data
US 2014/0342938 A1    Nov. 20, 2014

Related U.S. Application Data

(60) Provisional application No. 61/570,257, filed on Dec. 13, 2011.

(51) Int. Cl.
| | | |
|---|---|---|
| *C12Q 1/68* | (2018.01) | |
| *C40B 30/04* | (2006.01) | |
| *C40B 60/12* | (2006.01) | |
| *G06F 19/24* | (2011.01) | |
| *G06F 19/20* | (2011.01) | |

(52) U.S. Cl.
CPC ......... *C12Q 1/6851* (2013.01); *C12Q 1/6876* (2013.01); *G06F 19/20* (2013.01); *G06F 19/24* (2013.01); *C12Q 2600/166* (2013.01)

(58) Field of Classification Search
CPC ...................................................... C12Q 1/68
USPC ........................................................... 506/9
See application file for complete search history.

(56) References Cited

U.S. PATENT DOCUMENTS

| | | | |
|---|---|---|---|
| 2005/0095634 A1 | 5/2005 | Baker et al. | |
| 2006/0063170 A1 | 3/2006 | Erlander et al. | |
| 2006/0204989 A1 | 9/2006 | Kopreski et al. | |
| 2006/0246577 A1 | 11/2006 | Schroeder et al. | |
| 2006/0281108 A1* | 12/2006 | Monforte ............. | C12Q 1/6848 435/6.16 |
| 2010/0057371 A1* | 3/2010 | Denisov ............... | C12Q 1/6806 702/19 |
| 2011/0027862 A1 | 2/2011 | Bates et al. | |

OTHER PUBLICATIONS

Opitz et al., Imparct of RNA Degradation on Gene Expression Profiling, BMC Medical Genomics, 2010, 3(36), 1-14.*
Shmueli et al., GeneNote: Whole Genome Expression Profiles in Normal Human Tissues, Molecular Biology and Genetics, 2003, 326, 1067-1072. (Year: 2003).*
International Search Report PCT/US2012/069561, dated Apr. 5, 2013. 16 Pages.
Auer et al., "Chipping away at the chip bias: RNA degradation in microarray analysis." Nat Genet. Dec. 2003;35(4):292-3.
Baechler et al., "Expression levels for many genes in human peripheral blood cells are highly sensitive to ex vivo incubation." Genes Immun. Aug. 2004;5(5):347-53.
Becker et al., "mRNA and microRNA quality control for RT-qPCR analysis." Methods. Apr. 2010;50(4):237-43.
Beelman et al., "Degradation of mRNA in eukaryotes" Cell. Apr. 21, 1995;81(2):179-83.
Bijlani et al., "Prediction of biologically significant components from microarray data: Independently Consistent Expression Discriminator (ICED)." Bioinformatics. Jan. 2003;19(1):62-70.
Biosystems, A., Essentials of Real Time PCR. 2006.
Bustin et al., "Pitfalls of quantitative real-time reverse-transcription polymerase chain reaction." J Biomol Tech. Sep. 2004;15(3):155-66.
Copois et al., "Impact of RNA degradation on gene expression profiles: assessment of different methods to reliably determine RNA quality." J Biotechnol. Jan. 20, 2007;127(4):549-59.
Fleige et al., "Comparison of relative mRNA quantification models and the impact of RNA integrity in quantitative real-time RT-PCR." Biotechnol Lett. Oct. 2006;28(19):1601-13.
Fleige et al., "RNA integrity and the effect on the real-time qRT-PCR performance." Mol Aspects Med. Apr.-Jun. 2006;27(2-3):126-39.
Gingrich, J., T. Rubio, and C. Karlak, Effect of RNA Degradation on Data Quality in Quantitative PCR and Microarray Experiments. Bio-Rad Bulletin #5452, 2006.
Houseley et al. "The many pathways of RNA degradation." Cell. Feb. 20, 2009;136(4):763-76.
Ibberson et al., "RNA degradation compromises the reliability of microRNA expression profiling." BMC Biotechnol. Dec. 21, 2009;9:102.
Kuschel et al. "Characterization of RNA quality using the Agilent 2100 Bioanalyzer" Agilent Technologies Note, 2000.
Li et al., "RNase L mediates the antiviral effect of interferon through a selective reduction in viral RNA during encephalomyocarditis virus infection." J Virol. Apr. 1998;72(4):2752-9.
Min et al., "Variability of gene expression profiles in human blood and lymphoblastoid cell lines." BMC Genomics. Feb. 8, 2010;11:96.
Morey et al., "Microarray validation: factors influencing correlation between oligonucleotide microarrays and real-time PCR." Biol Proced Online. 2006;8:175-93.

(Continued)

*Primary Examiner* — Amy M Bunker
(74) *Attorney, Agent, or Firm* — Klarquist Sparkman, LLP

(57) ABSTRACT

Methods for assessing the integrity of an RNA sample from a given tissue or blood type are disclosed.

13 Claims, 78 Drawing Sheets

(56) References Cited

OTHER PUBLICATIONS

Mueller et al., "A microfluidic system for high-speed reproducible DNA sizing and quantitation." Electrophoresis. Jan. 2000;21(1):128-34.
Mueller et al., "RNA Integrity Number (RIN)—Standardization of RNA Quality Control." Agilent Technologies Application Note, 2004.
Newbury et al. "Turnover in the Alps: an mRNA perspective. Workshops on mechanisms and regulation of mRNA turnover." EMBO Rep. Feb. 2006;7(2):143-8.
Nolan et al., "Quantification of mRNA using real-time RT-PCR." Nat Protoc. 2006;1(3):1559-82.
Opitz et al. "Impact of RNA degradation on gene expression profiling." BMC Med Genomics. Aug. 9, 2010;3:36. p. 1-14.
Palmer, M. and E. Prediger, Assessing RNA Quality. Ambion TechNotes, 2004. 11(1).
Pant et al., "Analysis of allelic differential expression in human white blood cells." Genome Res. Mar. 2006;16(3):331-9.
Pfaffl et al., "Validation of lab-on-chip capillary electrophoresis systems for total RNA quality and quantity control." Biotechnology & Biotechnological Equipment, 2008. 22(3): p. 829-834.
Port et al., "Correcting false gene expression measurements from degraded RNA using RTQ-PCR." Diagn Mol Pathol. Mar. 2007;16(1):38-49.
Probst et al., "Characterization of the ribonuclease activity on the skin surface." Genet Vaccines Ther. May 2006 29;4:4.
Qiagen/PreAnalytiX, PAXgene Blood RNA Kit Handbook. 2009.
Quellhorst et al.,"Validating Microarray Data Using RT2 Real-Time PCR" SABiosciences Corpoaration., 2005.
Raines et al., "Ribonuclease A." Chem Rev. May 7, 1998;98(3):1045-1066.
Riedmaier et al., "Comparison of two available platforms for determination of RNA quality." Biotechnology & Biotechnological Equipment, 2010. 24(4): p. 2154-2159.
Roche, RealTime Ready Universal ProbeLibrary: Redefining and revolutionizing real-time qPCR assays. 2009.
Safran et al., "Human Gene-Centric Databases at the Weizmann Institute of Science: GeneCards, UDB, CroW 21 and HORDE." Nucleic Acids Res. Jan. 1, 2003;31(1):142-6.
Samuel et al. "PKR and RNase L contribute to protection against lethal West Nile Virus infection by controlling early viral spread in the periphery and replication in neurons." J Virol. Jul. 2006;80(14):7009-19.
Schoor et al., "Moderate degradation does not preclude microarray analysis of small amounts of RNA" Biotechniques. Dec. 2003;35(6):1192-6, 1198-201.
Schroeder et al., "The RIN: an RNA integrity number for assigning integrity values to RNA measurements." BMC Mol Biol. Jan. 31, 2006;7:3.
Shmueli et al., "GeneNote: whole genome expression profiles in normal human tissues." C R Biol. Oct.-Nov. 2003;326(10-11):1067-72.
Strand et al., "RNA quality in frozen breast cancer samples and the influence on gene expression analysis—a comparison of three evaluation methods using microcapillary" BMC Mol Biol. May 22, 2007;8:38.
Su et al., "A gene atlas of the mouse and human protein-encoding transcriptomes." Proc Natl Acad Sci U S A. Apr. 20, 2004;101(16):6062-7.
Takano et al., "A multiplex endpoint RT-PCR assay for quality assessment of RNA extracted from formalin-fixed paraffin-embedded tissues." BMC Biotechnol. Dec. 17, 2010;10:89.
Thompson et al., "Characterization of the effect of sample quality on high density oligonucleotide microarray data using progressively degraded rat liver RNA." BMC Biotechnol. Sep. 13, 2007;7:57.
Troyanskaya et al. "Nonparametric methods for identifying differentially expressed genes in microarray data." Bioinformatics. Nov. 2002;18(11):1454-61.
Vermeulen et al., "Measurable impact of RNA quality on gene expression results from quantitative PCR." Nucleic Acids Res. May 2011;39(9):e63.
Watson, J.D., Molecular biology of the gene, 6th edition. 2008, Cold Spring Harbor, N.Y.: Cold Spring Harbor Laboratory Press.
Wilkes et al., "Evaluation of a novel approach for the measurement of RNA quality." BMC Res Notes. Apr. 1, 2010;3:89.
Wu et al., "BioGPS: an extensible and customizable portal for querying and organizing gene annotation resources." Genome Biol. 2009;10(11):R130., 8 Pages.
Yanai et al., "Genome-wide midrange transcription profiles reveal expression level relationships in human tissue specification." Bioinformatics. Mar. 1, 2005;21(5):650-9.

* cited by examiner

Figure 5

Assay details:

Use Universal ProbeLibrary probe: #72, cat.no. 0468895300.1

| Primer | Length | Position | Tm | %GC | Sequence |
|---|---|---|---|---|---|
| Left Primer | 20 | 302-321 | 60 | 55 | cactactgggctcagggaaa |
| Right Primer | 20 | 353-372 | 59 | 50 | tcacagtccttcacgaggaa |
| Amplicon (71 nt) | | | | | |
| cactactgggctcagggaaagctgtgctgccagtgtgtgagccaggaacattcctgtg aaggactgtga | | | | | |

[ Download pack insert ] [ PDF report ] [ Text report ] [ Order probes or set ]

Transcript overview:

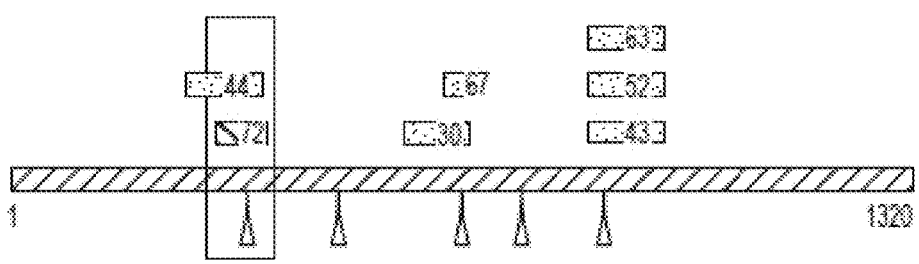

Detailed view:

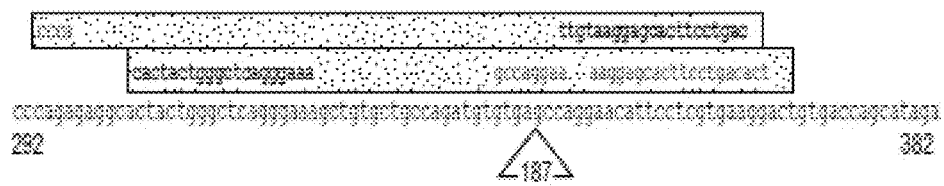

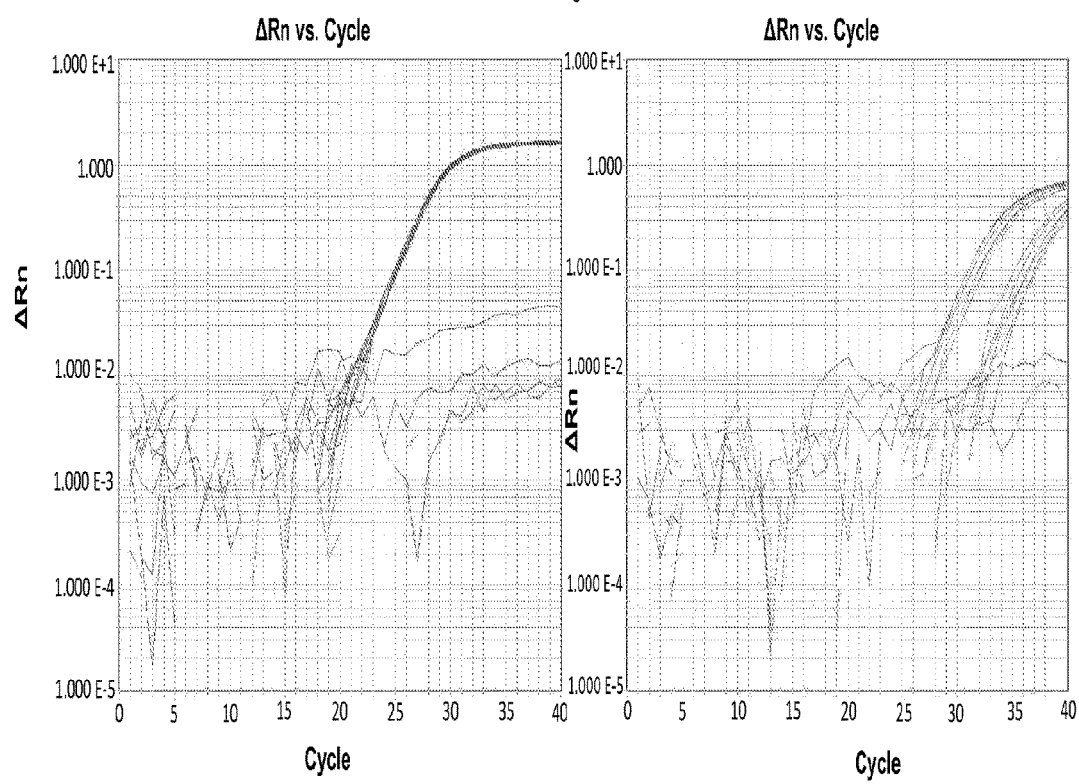

Nanodrop ND-8000 RNA Yield Data

| Sample ID | ng/μl | A260 | A280 | 260/280 | 260/230 | Constant | Yield (μg) |
|---|---|---|---|---|---|---|---|
| A | 30.48 | 0.762 | 0.315 | 2.42 | 0.18 | 40 | 3.66 |
| B | 6.99 | 0.175 | 0.038 | 4.59 | 0.05 | 40 | 0.84 |
| C | 28.46 | 0.712 | 0.303 | 2.35 | 0.12 | 40 | 3.42 |
| D | 28.08 | 0.702 | 0.29 | 2.42 | 0.19 | 40 | 3.37 |
| E | 65.4 | 1.635 | 0.711 | 2.3 | 0.32 | 40 | 7.85 |

Figure 7A

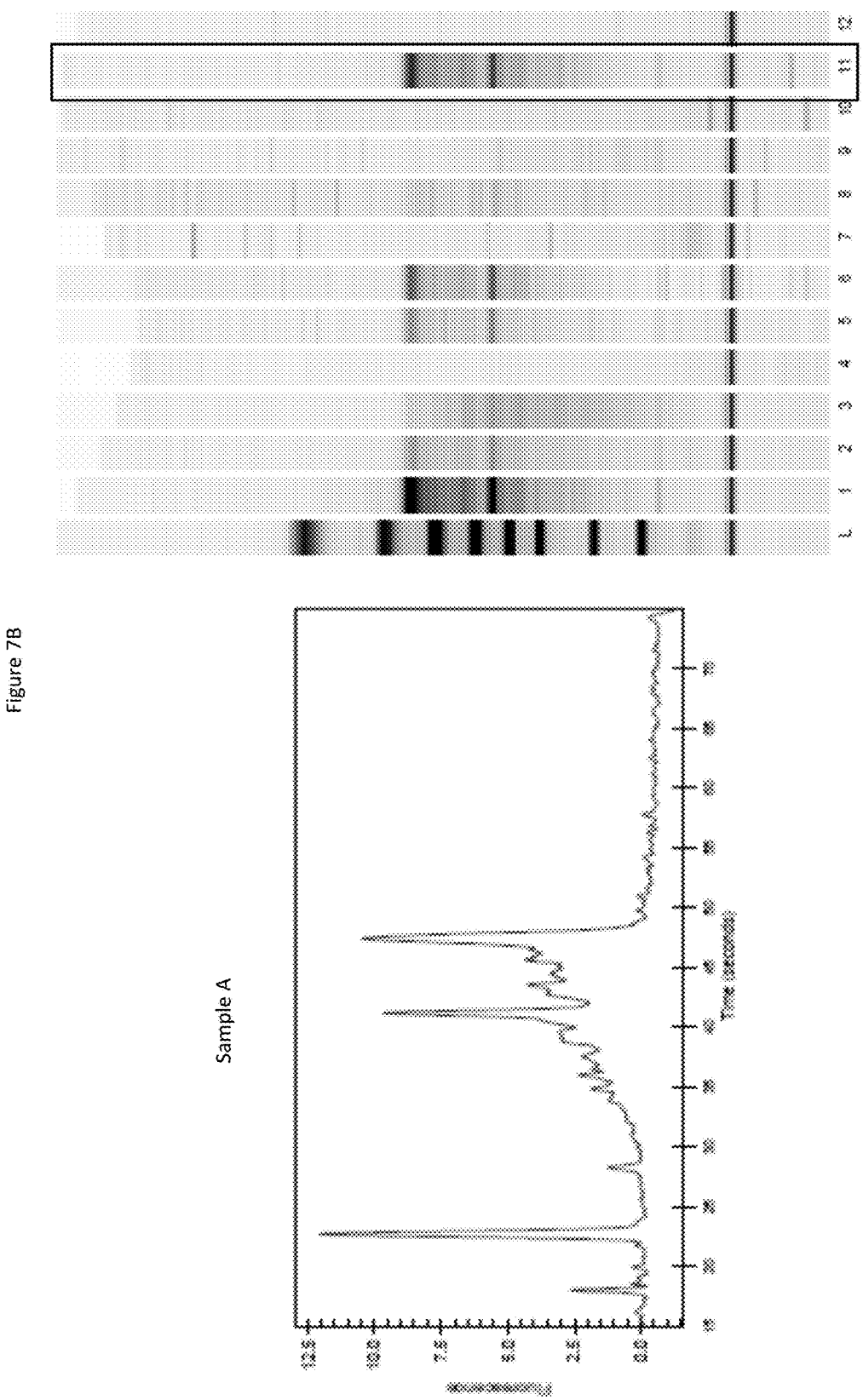

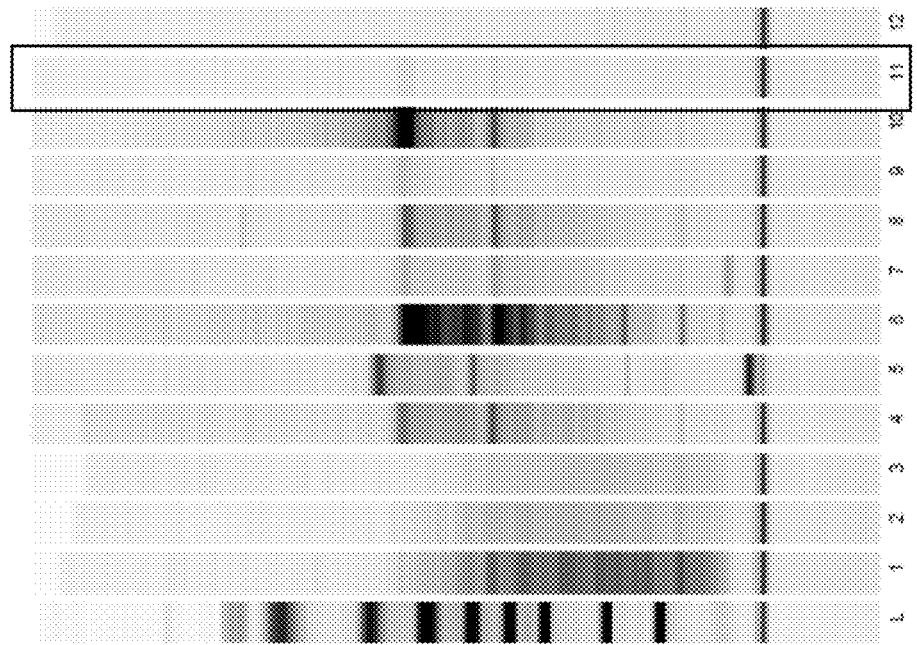
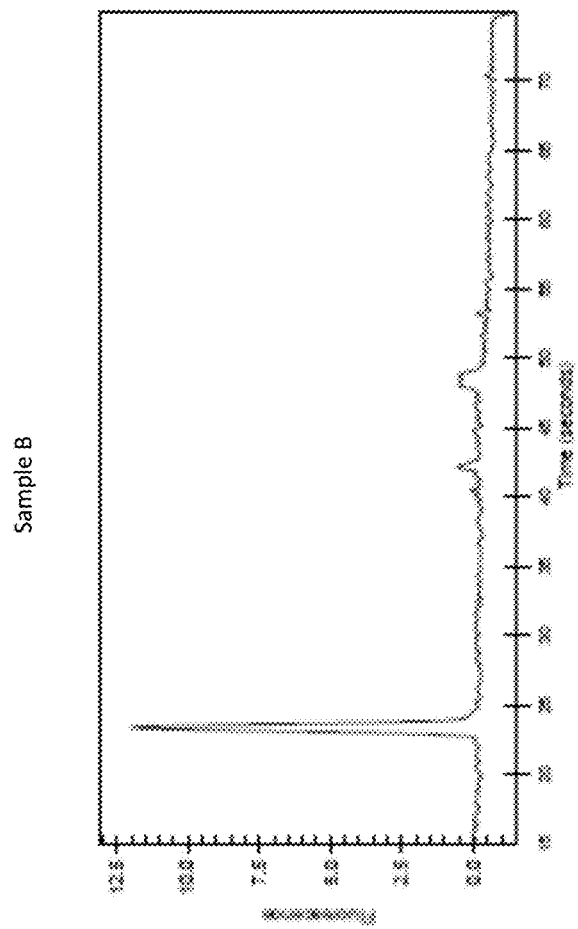
Figure 7C

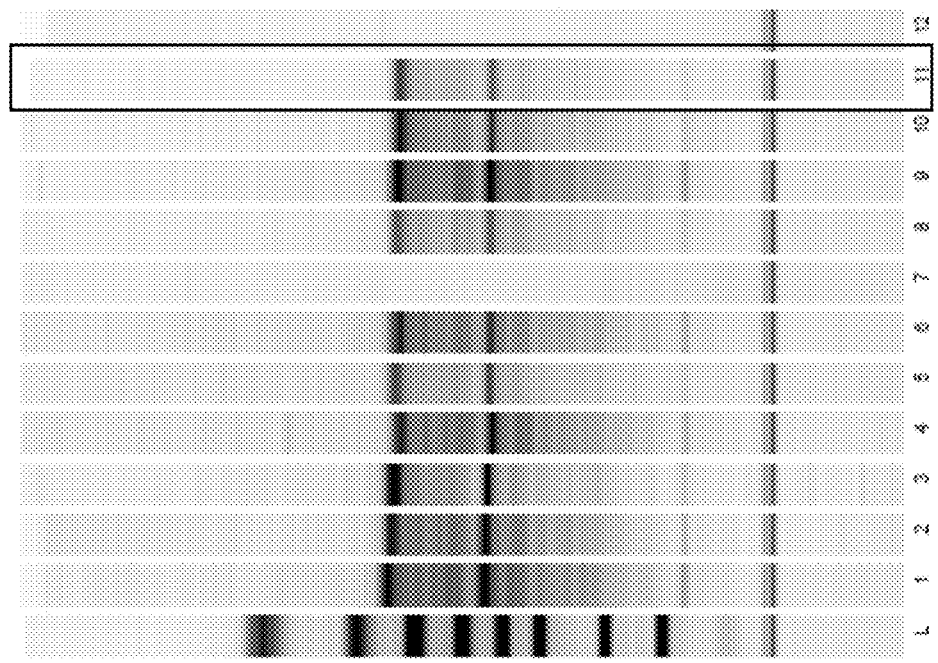
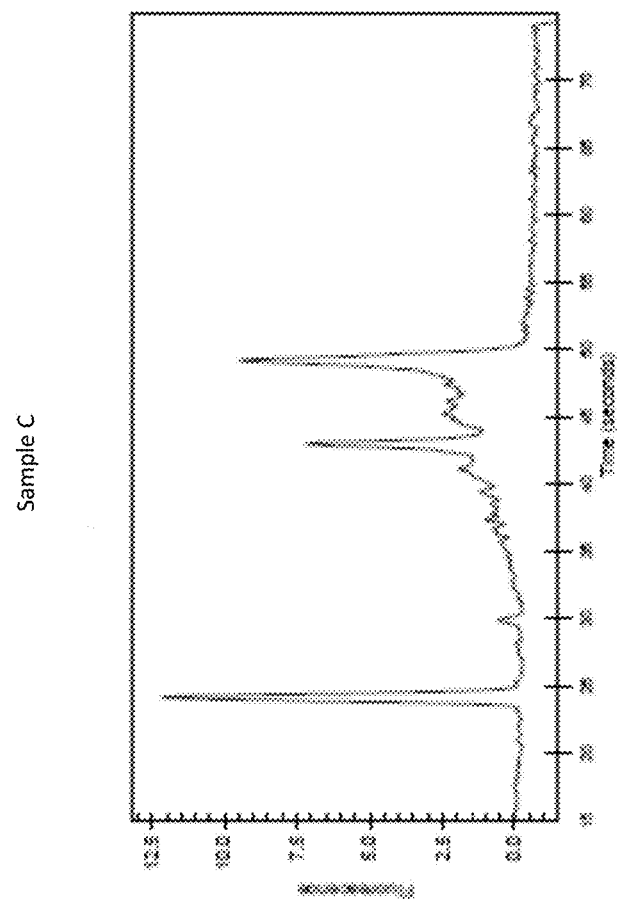
Figure 7D

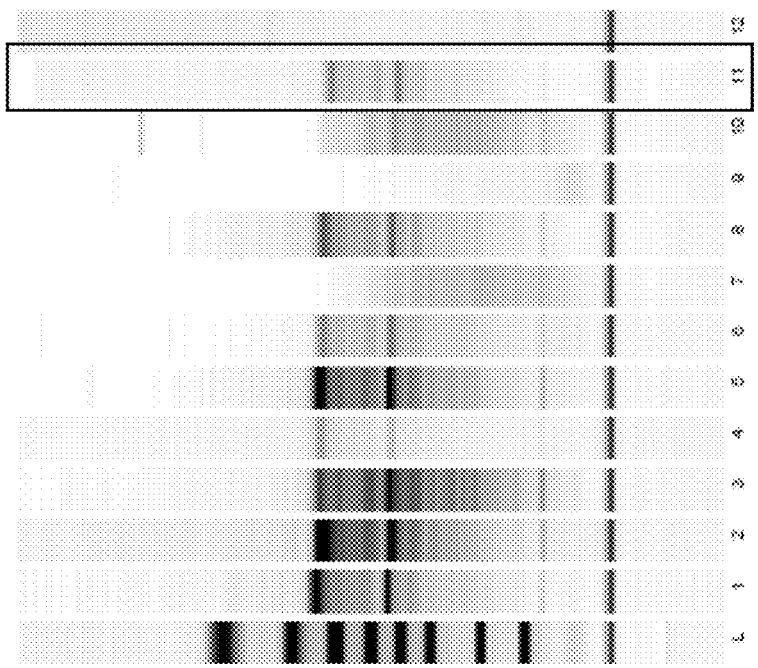
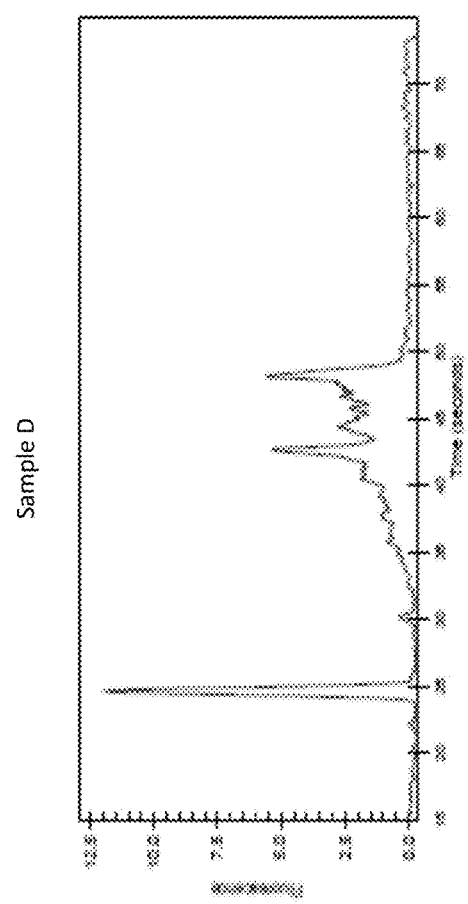
Figure 7E

Figure 8A

Nanodrop ND-8000 cDNA Yield Data

| Sample ID | ng/μl | A260 | A280 | 260/280 | 260/230 | Constant | Yield (μg) |
|---|---|---|---|---|---|---|---|
| A | 199.21 | 6.037 | 3.115 | 1.94 | 1.94 | 33 | 5.98 |
| B | 161.39 | 4.891 | 2.516 | 1.94 | 1.88 | 33 | 4.84 |
| C | 214.14 | 6.489 | 3.368 | 1.93 | 1.91 | 33 | 6.42 |
| D | 225.02 | 6.819 | 3.535 | 1.93 | 1.91 | 33 | 6.75 |
| E | 210.83 | 6.389 | 3.303 | 1.93 | 1.91 | 33 | 6.32 |

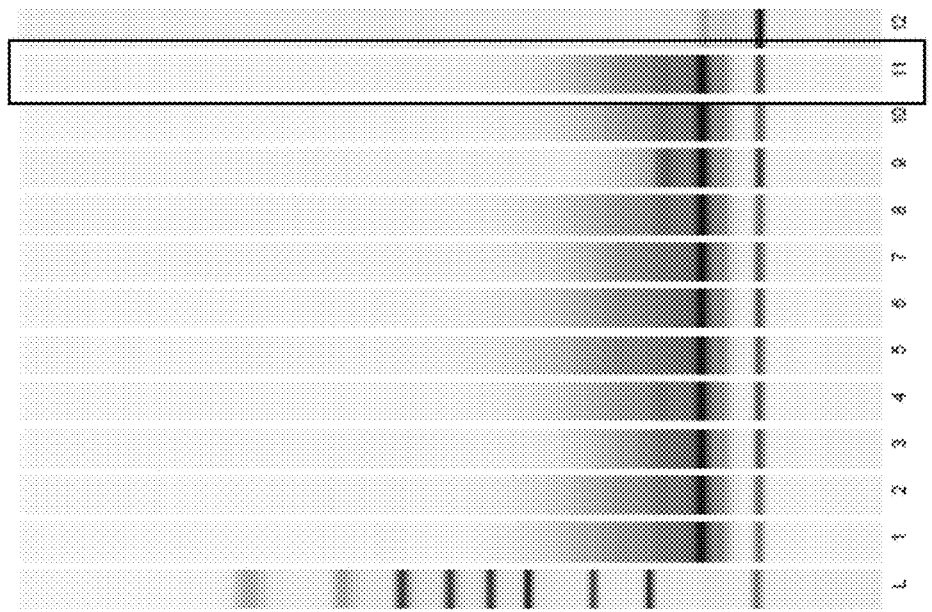
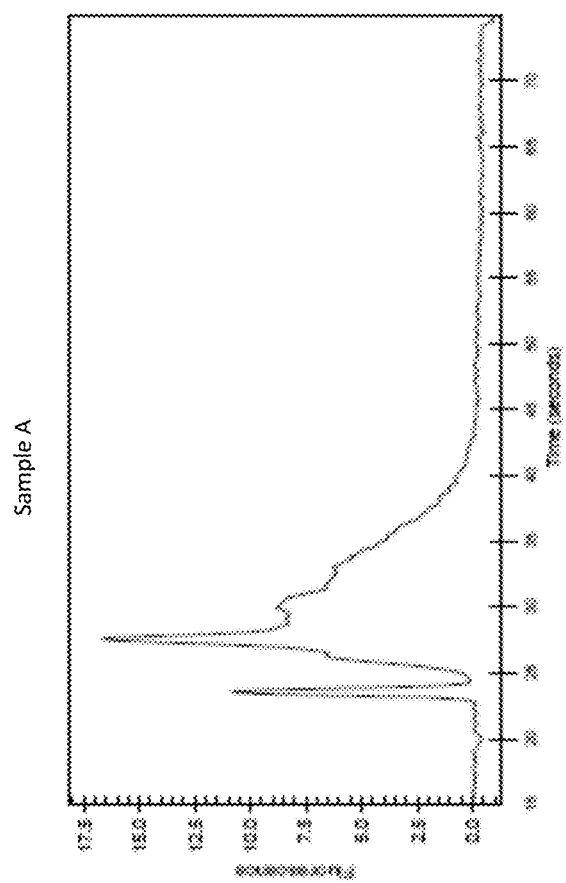
Figure 8B

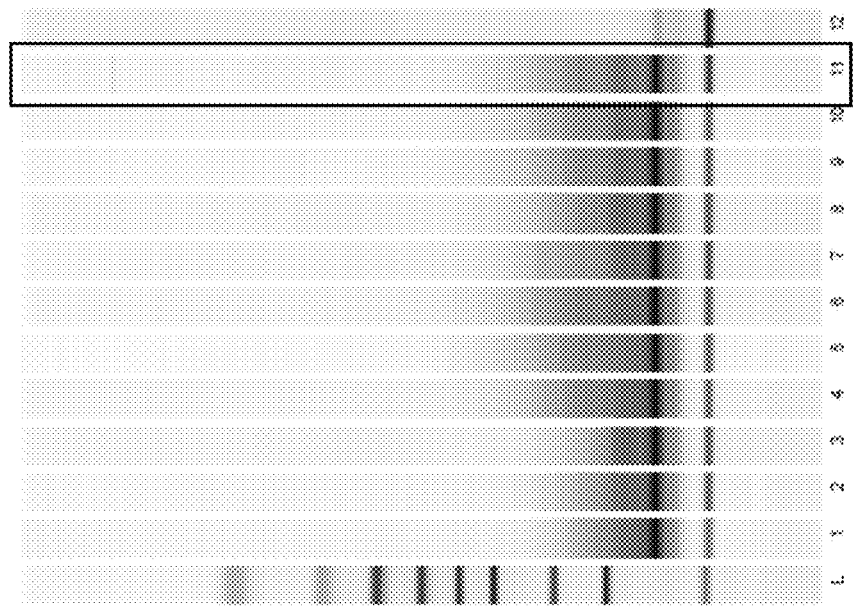
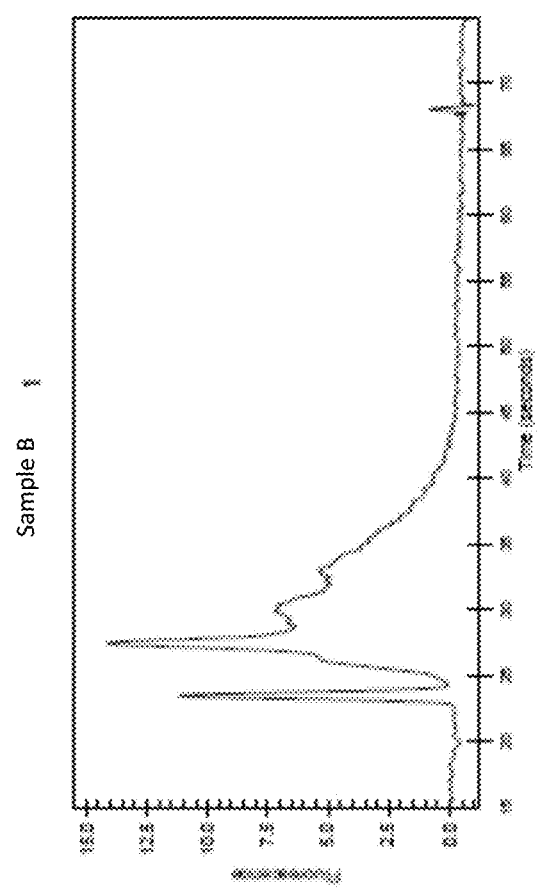
Figure 8C

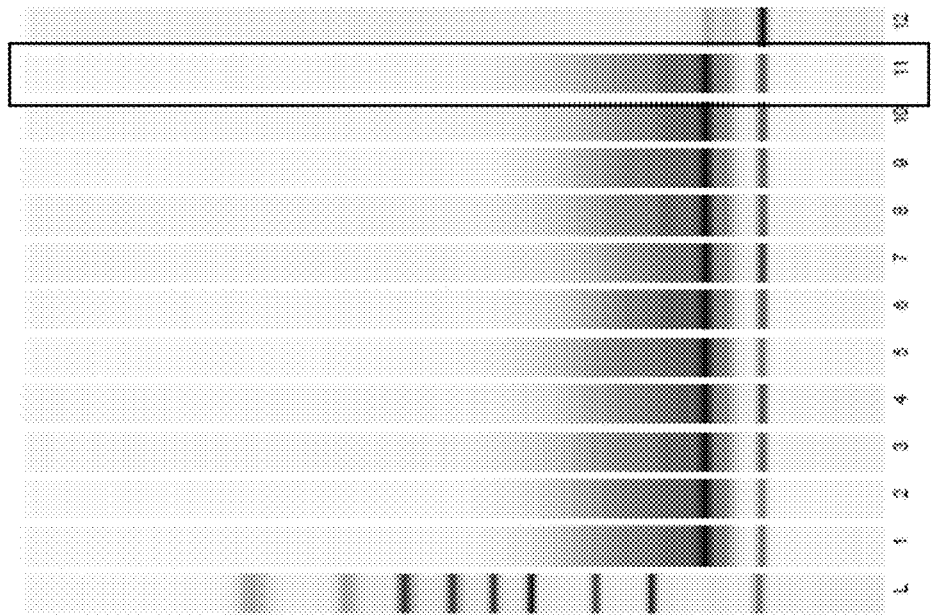
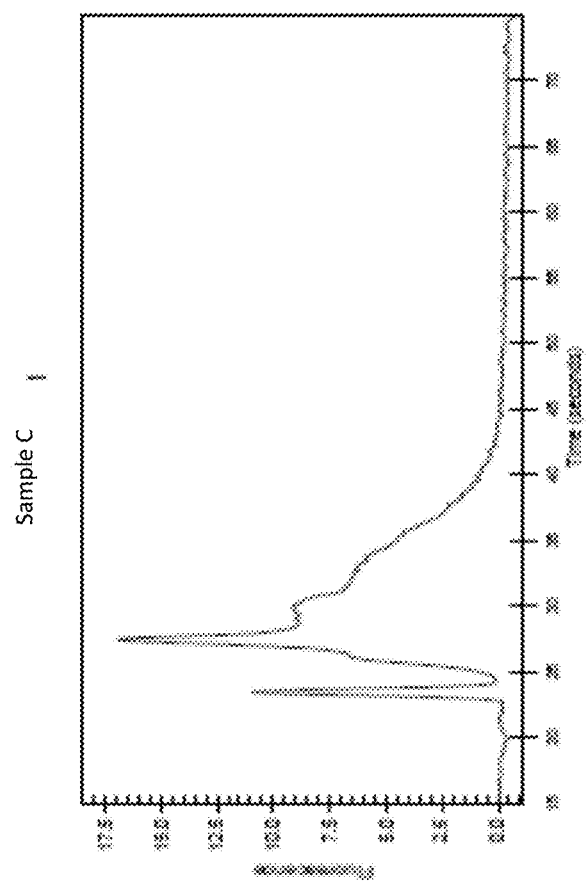
Figure 8D

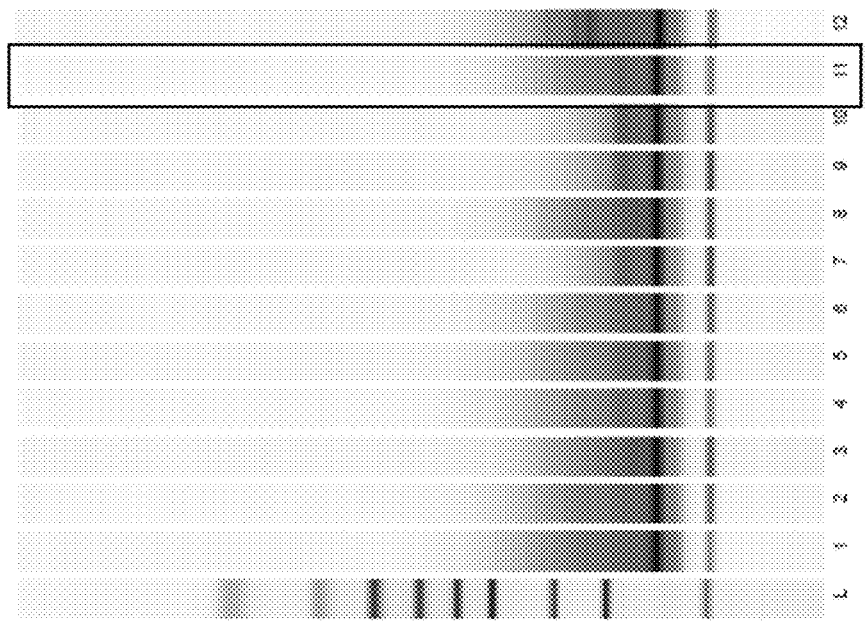
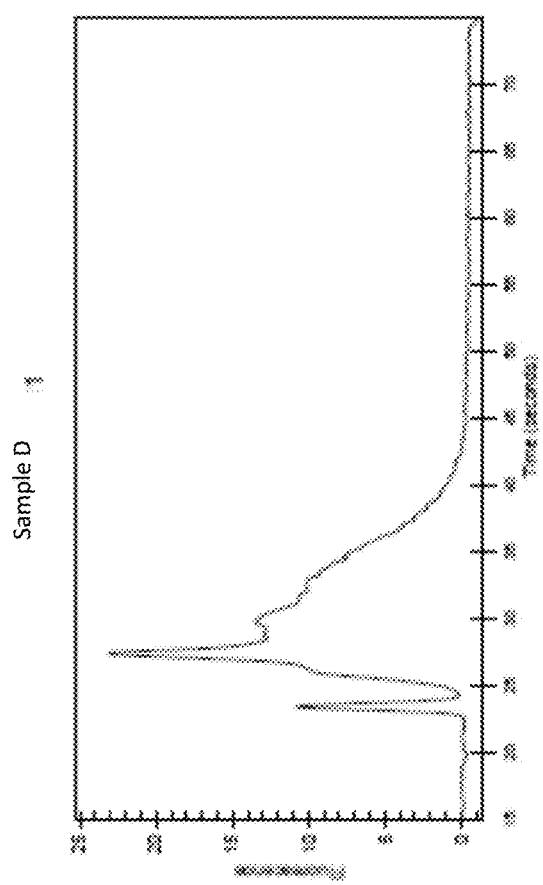
Figure 8E

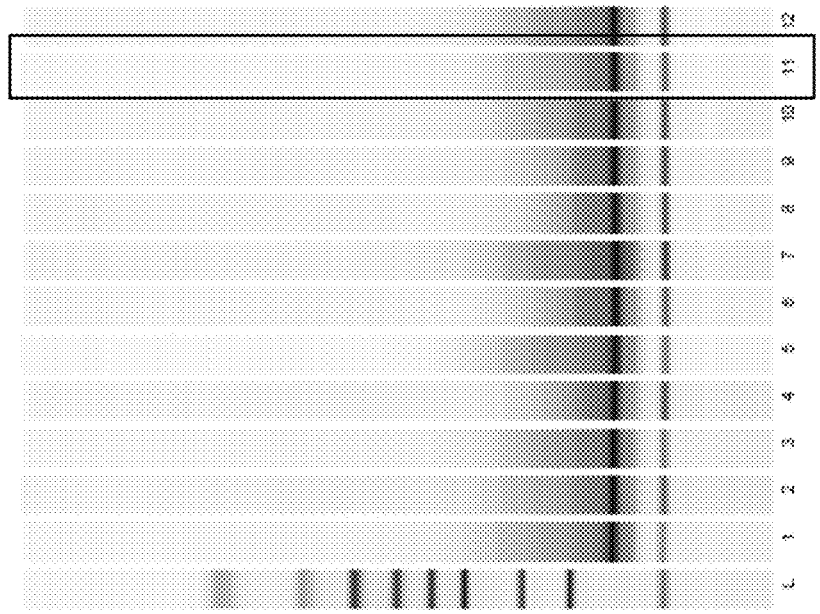
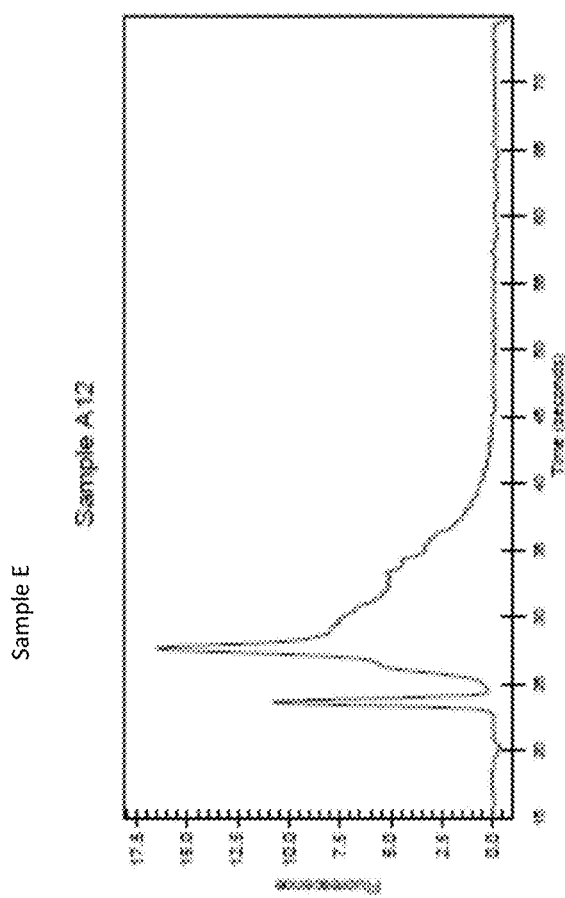
Figure 8F

Figure 9P
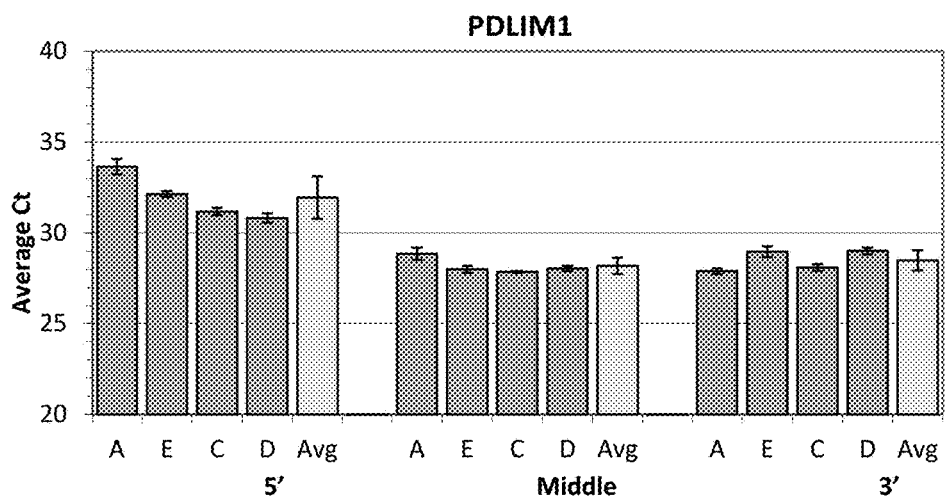
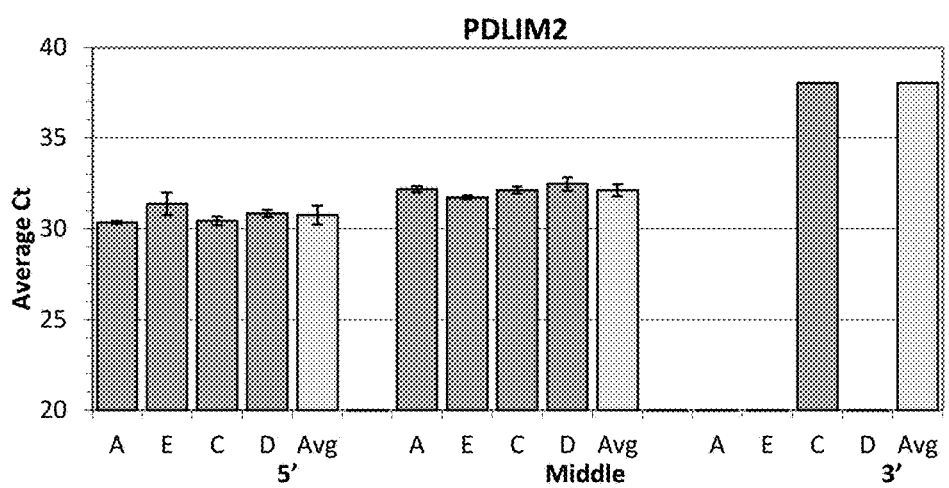
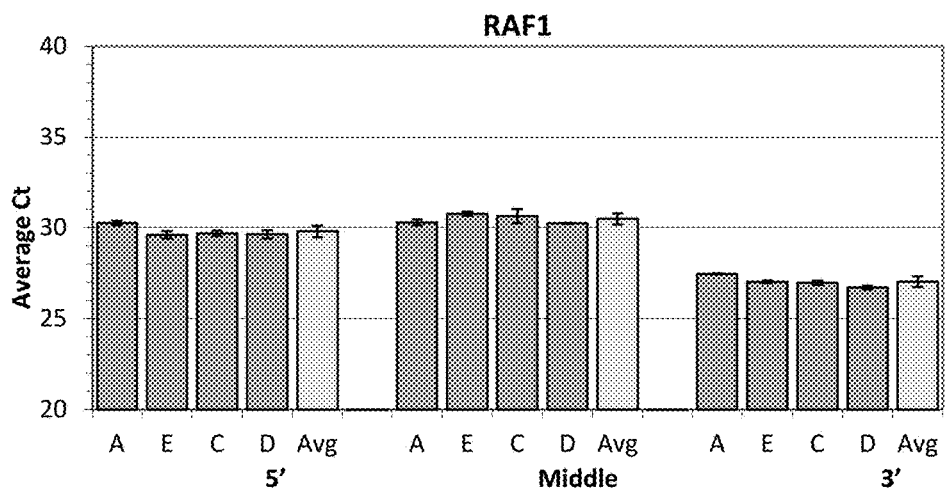

Figure 9Q
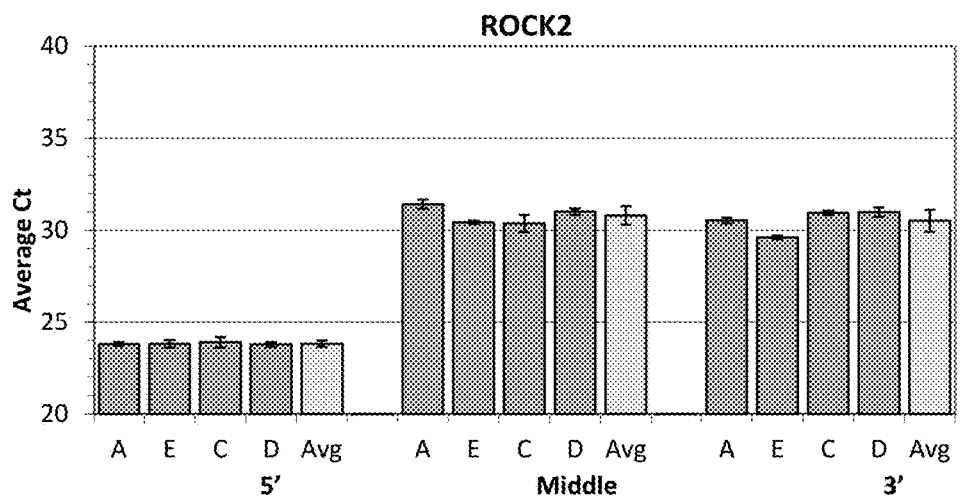
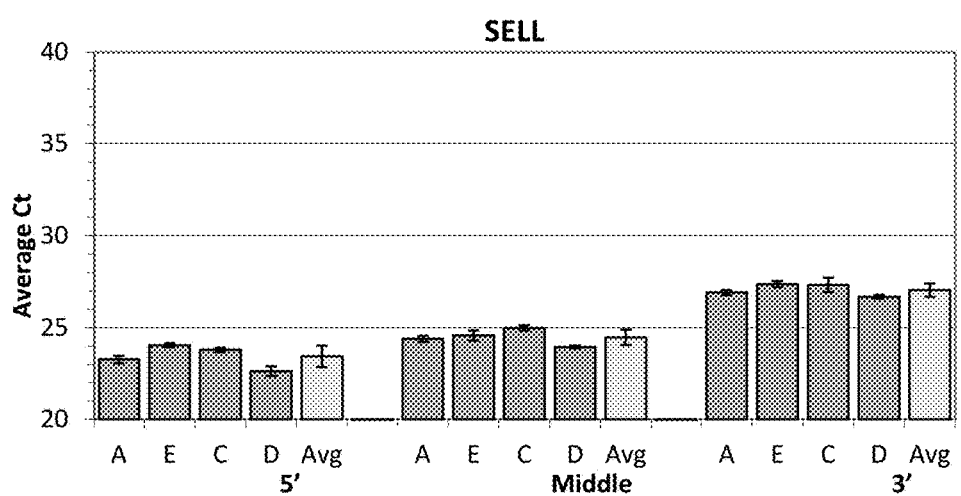
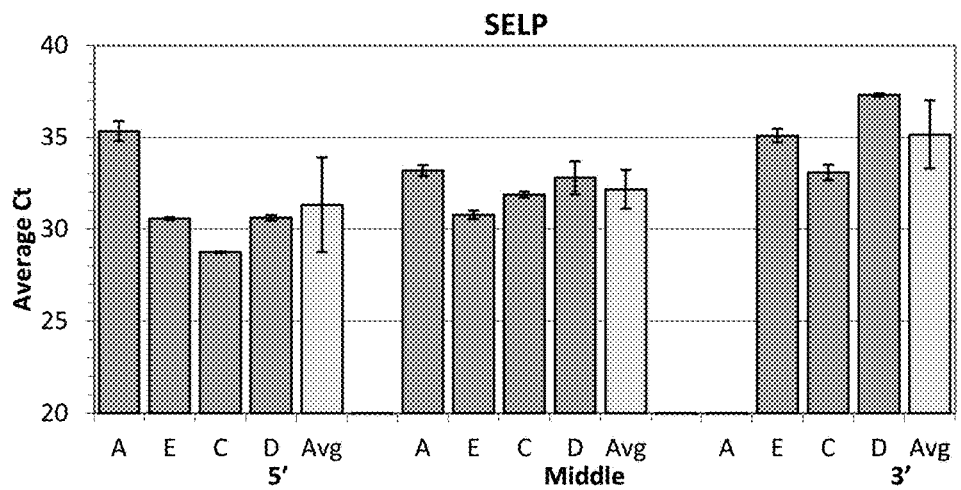

Figure 10A
RNA quality data for freeze/thaw cycle treatment (lanes 1-5) and heat treatment (lanes 6-10)
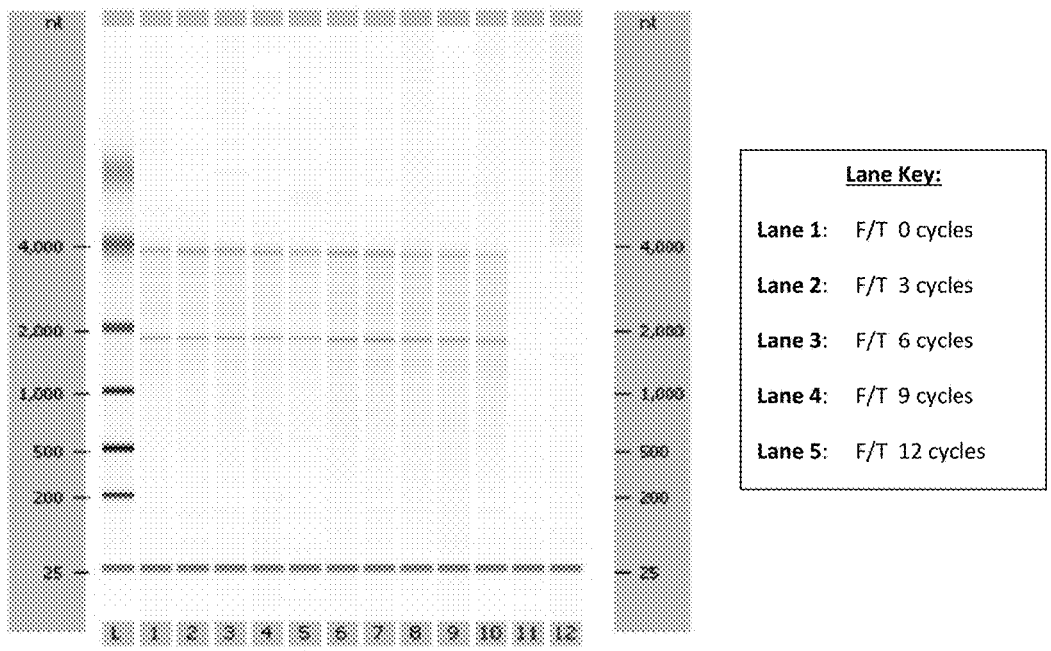
Lane Key:
Lane 1:   F/T  0 cycles
Lane 2:   F/T  3 cycles
Lane 3:   F/T  6 cycles
Lane 4:   F/T  9 cycles
Lane 5:   F/T  12 cycles
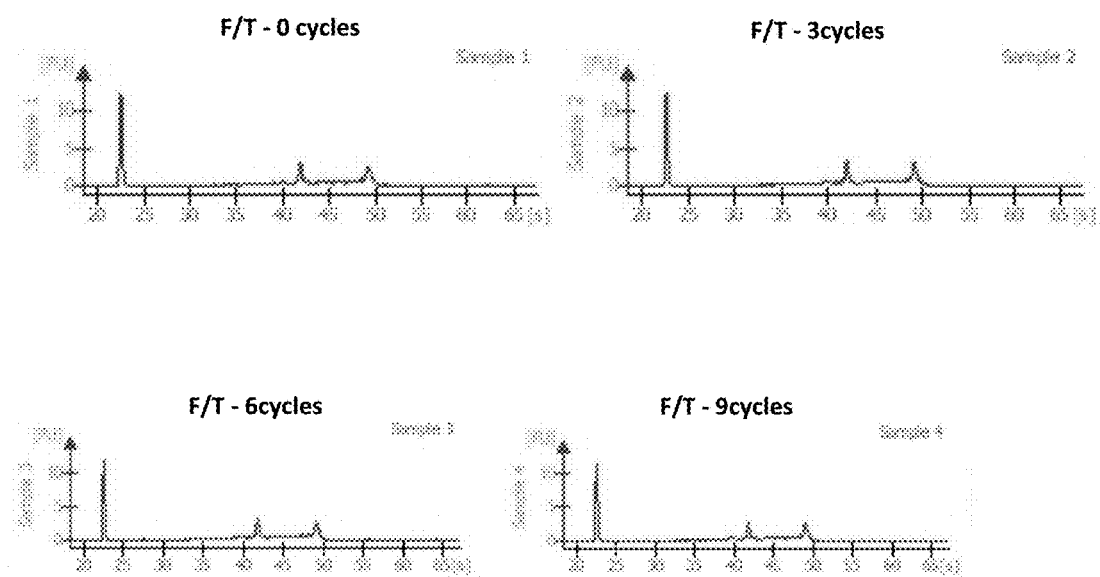

Figure 10C
RNA quality data for RNase A degradation treatment (lanes 1-7)
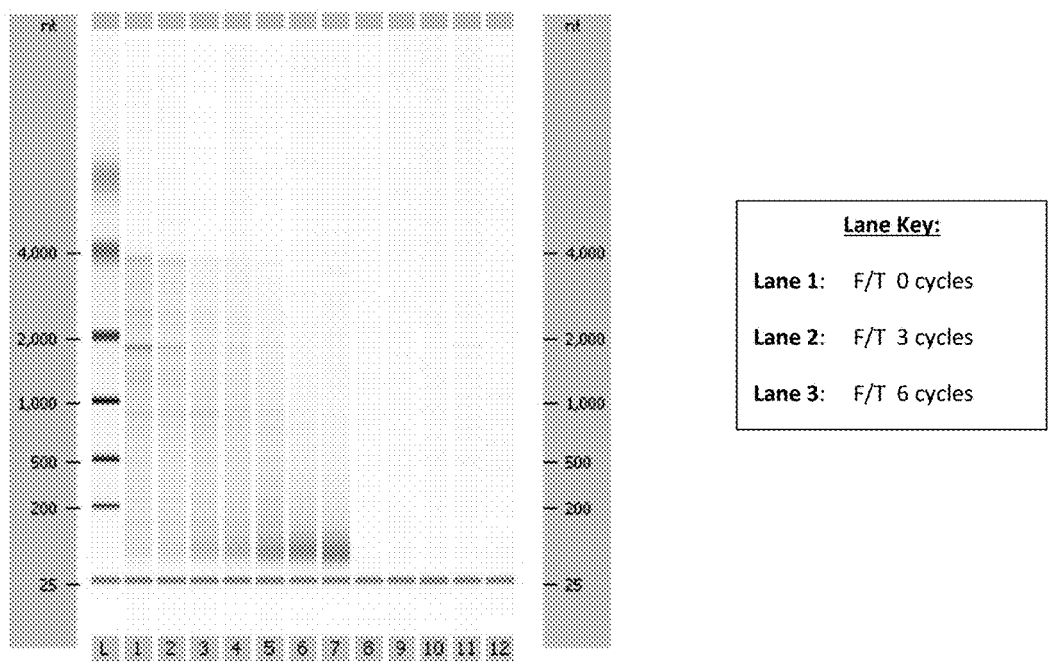
Lane Key:
Lane 1:  F/T  0 cycles
Lane 2:  F/T  3 cycles
Lane 3:  F/T  6 cycles
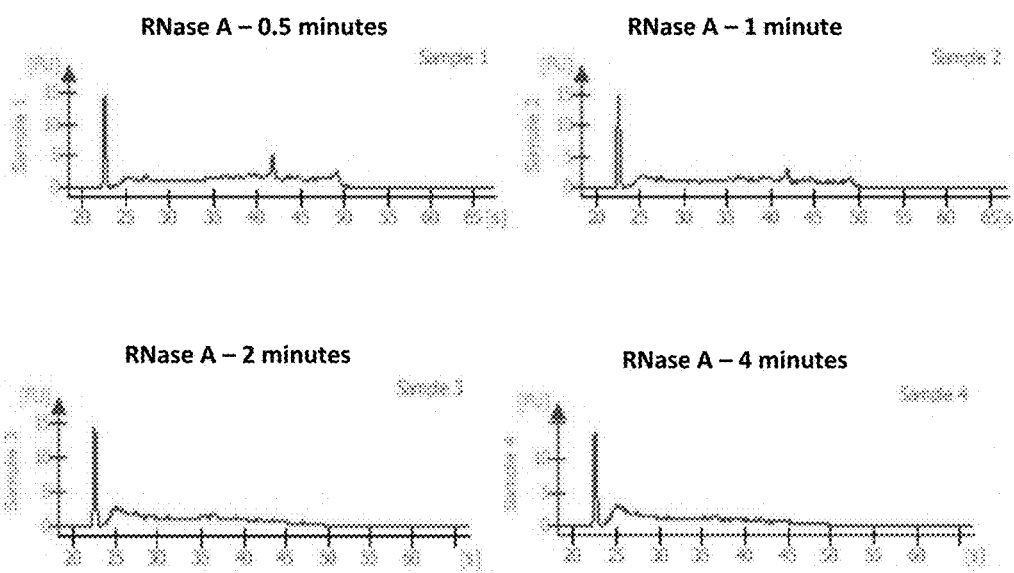

Nanodrop ND-8000 Native RNA Yield Data

| Sample ID | ng/μl | A260 | A280 | 260/280 | 260/230 | Constant | Yield (μg) |
|---|---|---|---|---|---|---|---|
| Pre-Cleanup | 47.86 | 1.196 | 0.529 | 2.26 | 0.37 | 40.00 | 3.35 |
| Post-Cleanup | 48.38 | 1.209 | 0.591 | 2.04 | 1.77 | 40.00 | 3.38 |

Pre-Cleanup Bioanalyzer 2100 Data

Post-Cleanup Bioanalyzer 2100 Data

Figure 12A

Nanodrop ND-8000 Manually Extracted RNA Yield Data

| Sample ID | ng/µl | A260 | A280 | 260/280 | 260/230 | Constant | Yield (µg) |
|---|---|---|---|---|---|---|---|
| A | 51.01 | 1.275 | 0.539 | 2.37 | 0.37 | 40 | 4.08 |
| B | 54.81 | 1.37 | 0.582 | 2.35 | 0.43 | 40 | 4.38 |
| C | 47.86 | 1.196 | 0.529 | 2.26 | 0.37 | 40 | 3.83 |
| D | 50.08 | 1.252 | 0.535 | 2.34 | 0.39 | 40 | 4.01 |
| E | 82.94 | 2.074 | 0.952 | 2.18 | 0.58 | 40 | 6.64 |

Figure 12B
Manually Extracted RNA Bioanalyzer 2100 Data
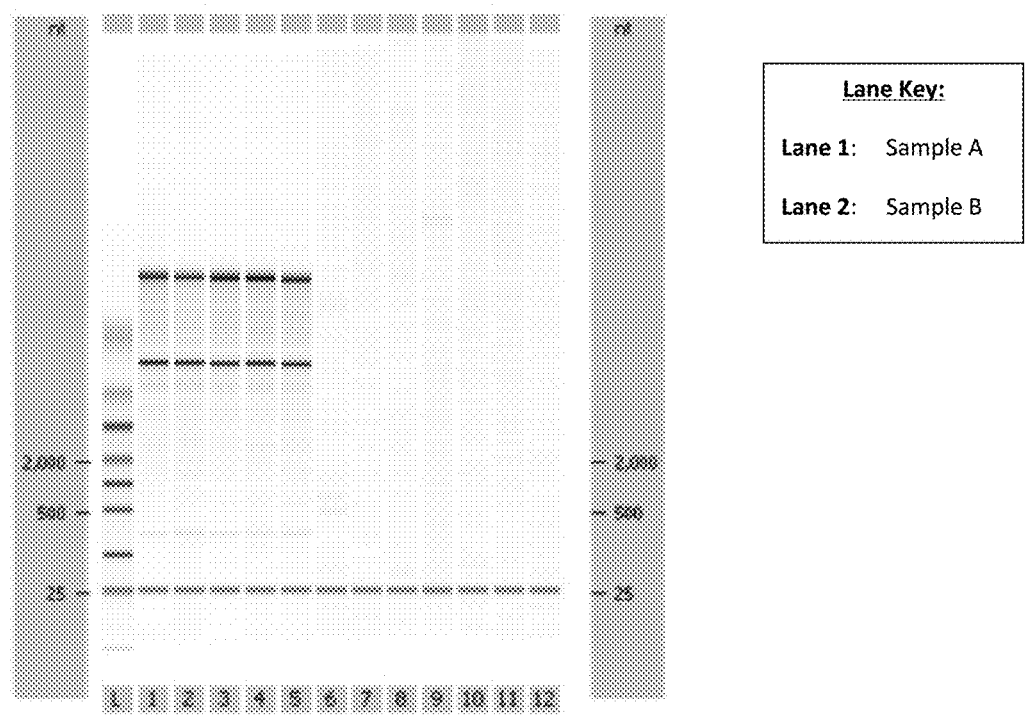
Lane Key:
Lane 1: Sample A
Lane 2: Sample B
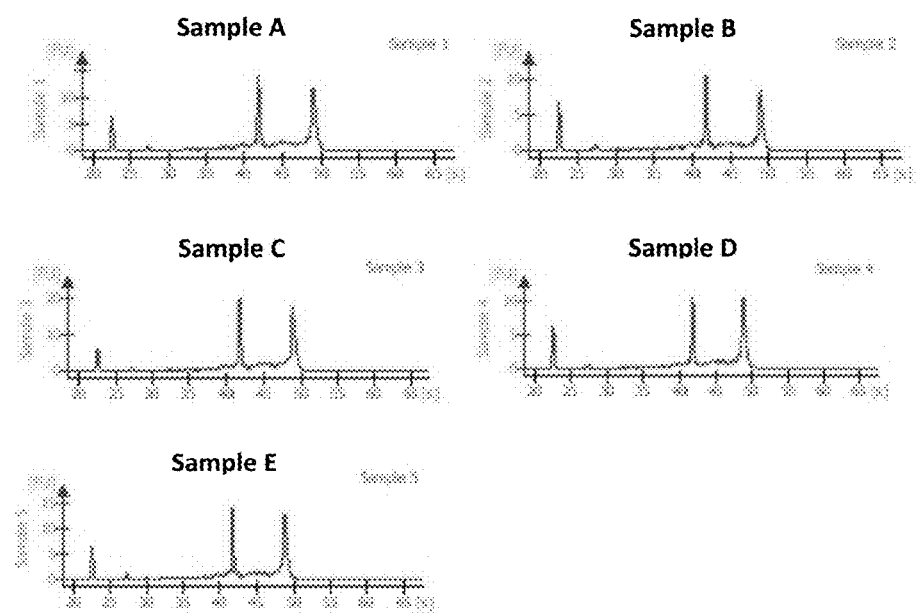

Figure 13A

Nanodrop ND-8000 RNase A Degradation and Column-Purified RNA Yield Data

| Sample ID | ng/µl | A260 | A280 | 260/280 | 260/230 | Constant |
|---|---|---|---|---|---|---|
| RNase A - 0.5 minute | 21.55 | 0.539 | 0.298 | 1.81 | 0.39 | 40.00 |
| RNase A - 1 minute | 21.95 | 0.549 | 0.321 | 1.71 | 0.63 | 40.00 |
| RNase A - 2 minutes | 19.18 | 0.480 | 0.272 | 1.76 | 0.62 | 40.00 |
| RNase A - 4 minutes | 23.66 | 0.591 | 0.364 | 1.63 | 0.24 | 40.00 |
| RNase A - 8 minutes | 19.43 | 0.486 | 0.289 | 1.68 | 0.25 | 40.00 |
| RNase A - 16 minutes | 11.43 | 0.286 | 0.186 | 1.53 | 0.74 | 40.00 |

Figure 13B
RNase A Degradation and Column-Purified RNA Bioanalyzer 2100 Data
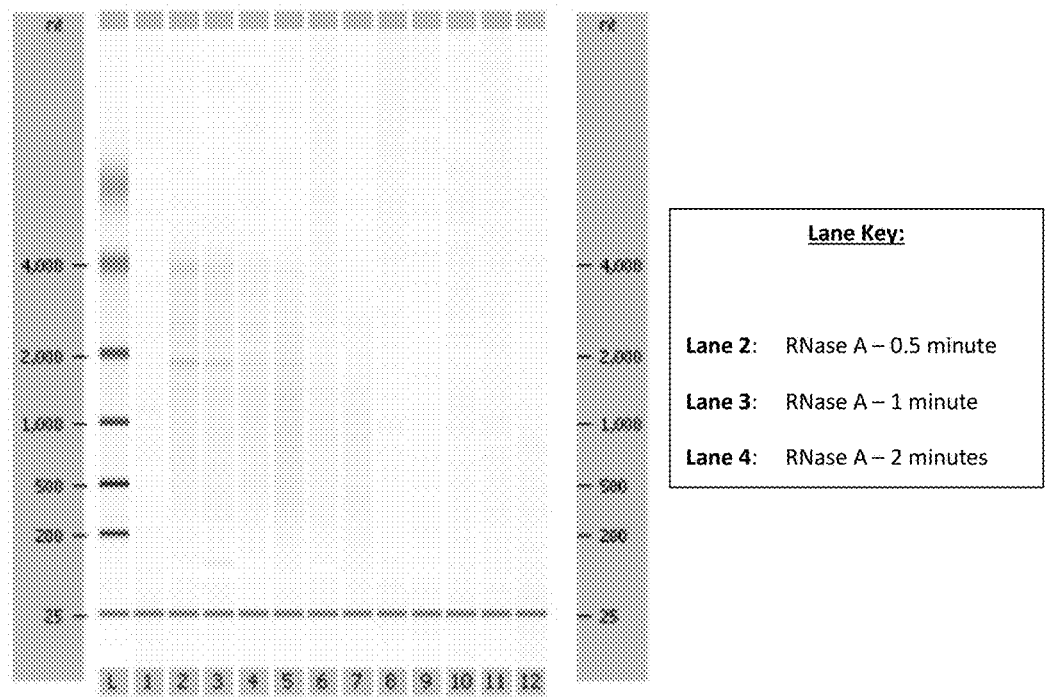
Lane Key:
Lane 2: RNase A – 0.5 minute
Lane 3: RNase A – 1 minute
Lane 4: RNase A – 2 minutes
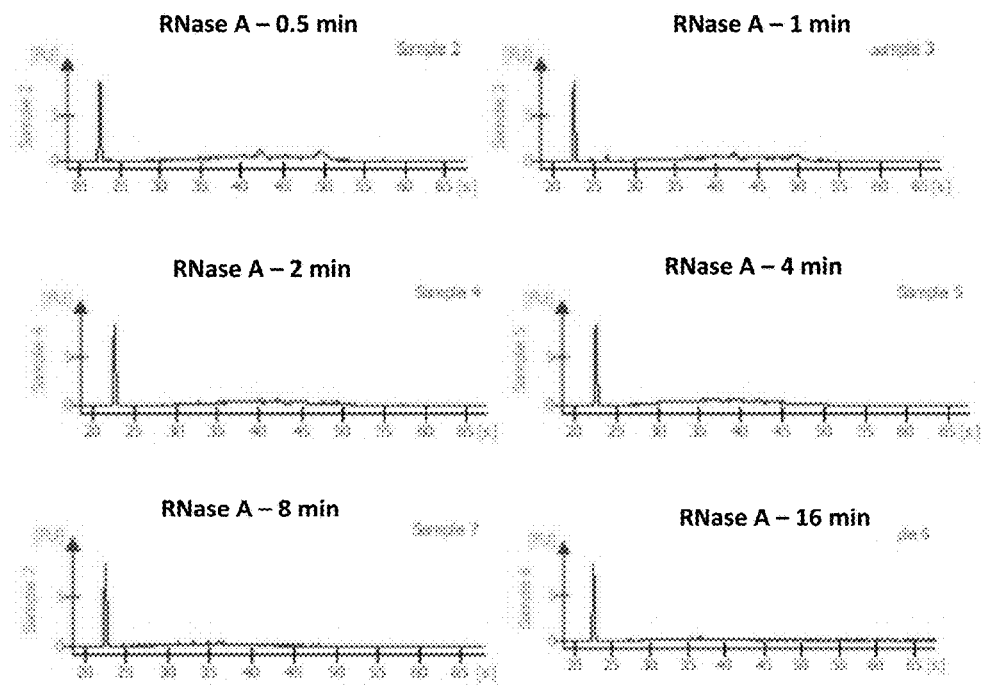

Figure 14A

Nanodrop ND-8000 cDNA Yield Data

| Sample ID | ng/μl | A260 | A280 | 260/280 | 260/230 | Constant | Yield (μg) |
|---|---|---|---|---|---|---|---|
| RNase A - 0 minute | 302.51 | 9.167 | 4.673 | 1.96 | 2.19 | 33 | 9.08 |
| RNase A - 0.5 minute | 233.56 | 7.077 | 3.624 | 1.95 | 2.17 | 33 | 7.01 |
| RNase A - 1 minute | 214.29 | 6.494 | 3.321 | 1.96 | 2.19 | 33 | 6.43 |
| RNase A - 2 minutes | 205.72 | 6.234 | 3.162 | 1.97 | 2.2 | 33 | 6.17 |
| RNase A - 4 minutes | 200.53 | 6.077 | 3.119 | 1.95 | 2.17 | 33 | 6.02 |
| RNase A - 8 minutes | 178.55 | 5.411 | 2.781 | 1.95 | 2.14 | 33 | 5.36 |
| RNase A - 16 minutes | 160 | 4.848 | 2.486 | 1.95 | 2.15 | 33 | 4.80 |

LabChip 90 HT Microcapillary Electrophoresis cDNAQuality Data:

LabChip 90 HT Microcapillary Electrophoresis cDNAQuality Data (continued):

Figure 14D
LabChip 90 HT Microcapillary Electrophoresis cDNAQuality Data (continued):
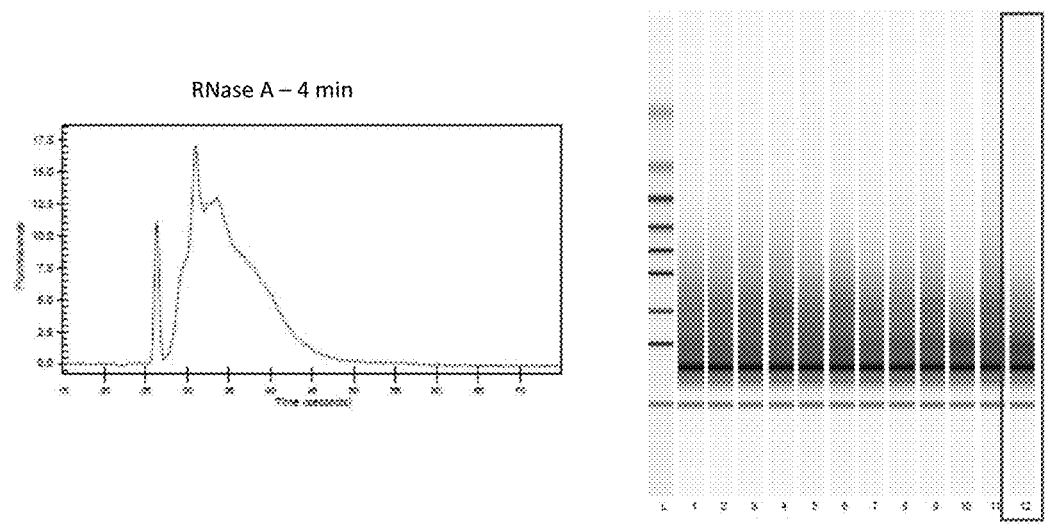
RNase A – 4 min
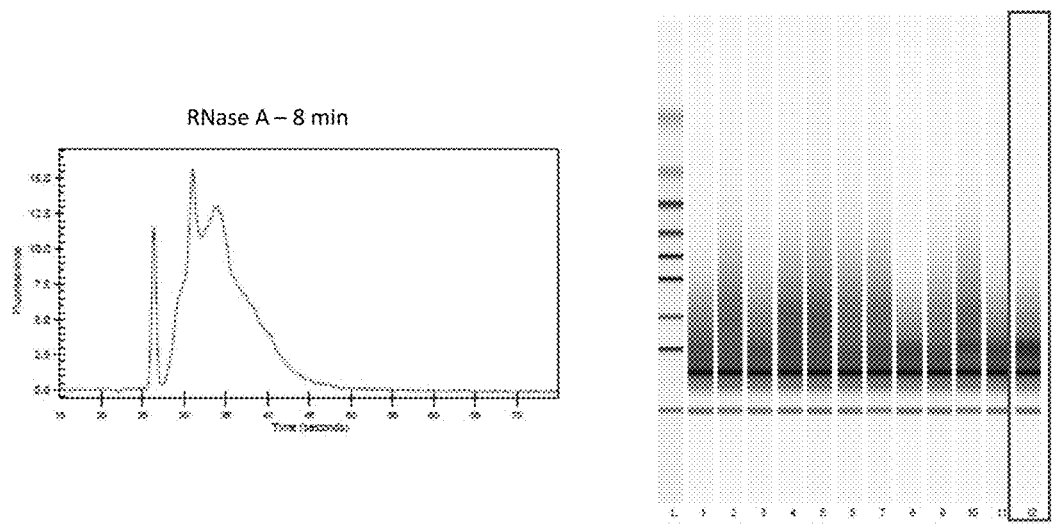
RNase A – 8 min LabChip 90 HT Microcapillary Electrophoresis cDNAQuality Data (continued):

Figure 15A
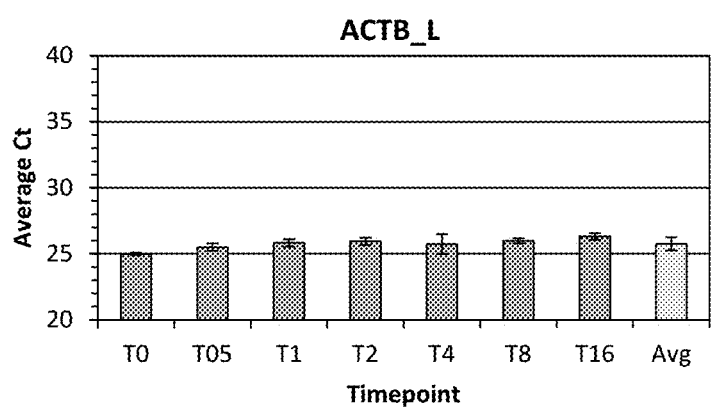
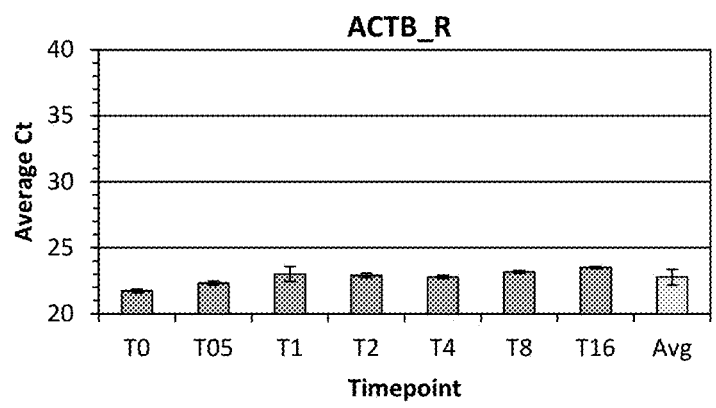

Figure 15C
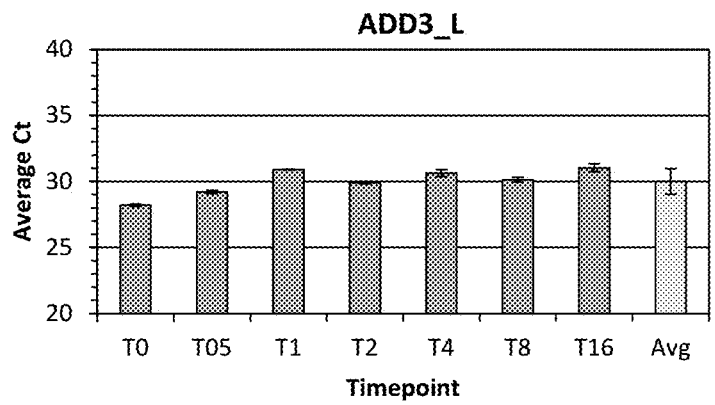
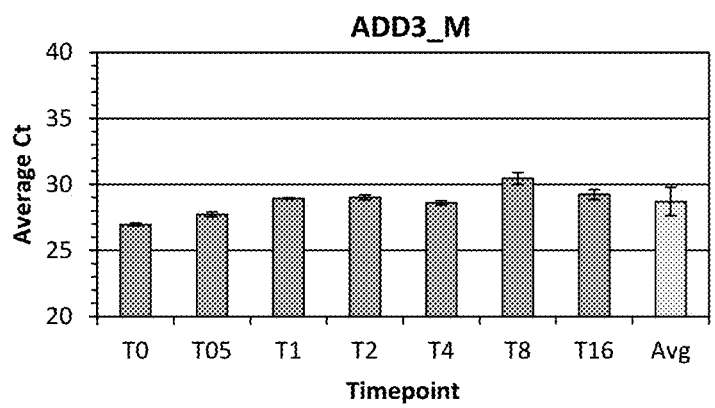
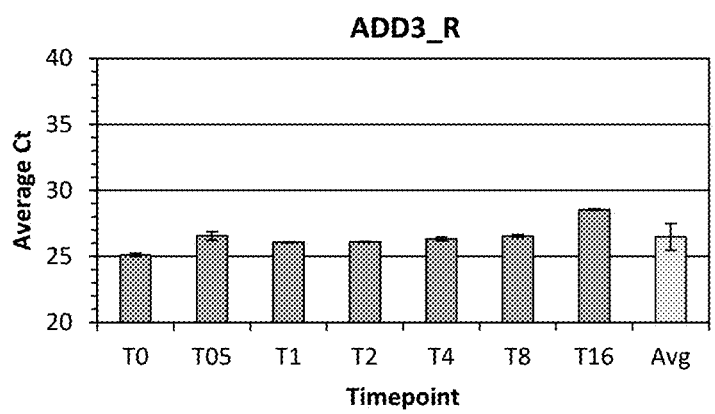

Figure 15E
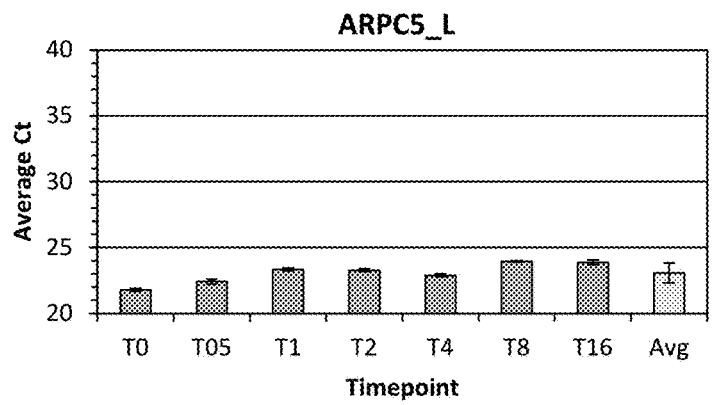
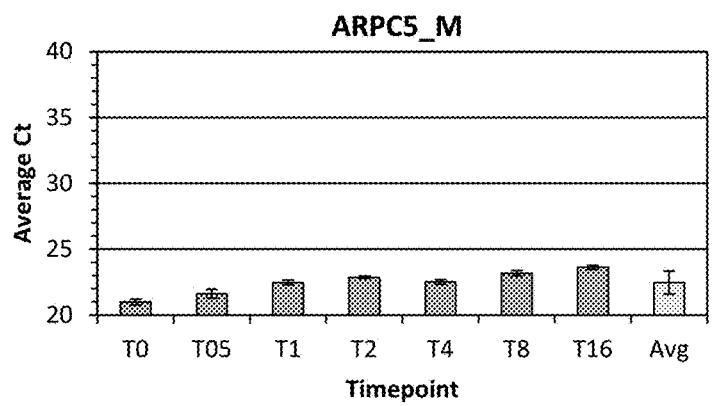
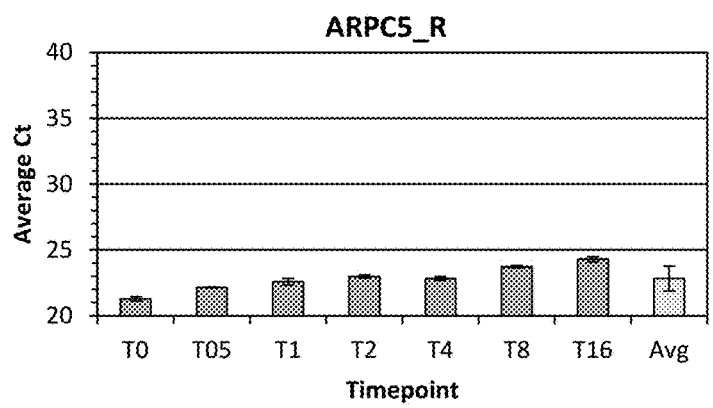

Figure 15H
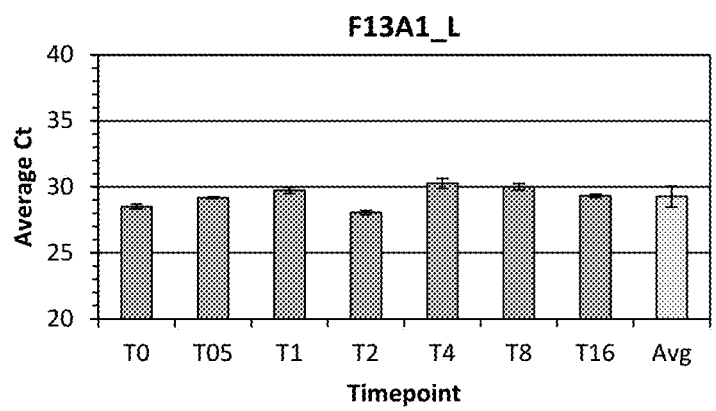
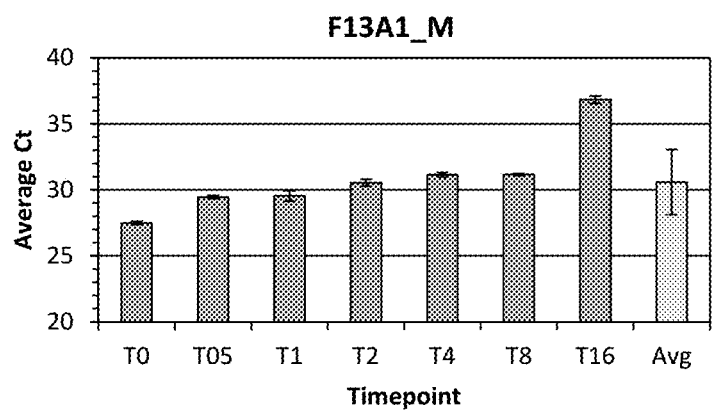
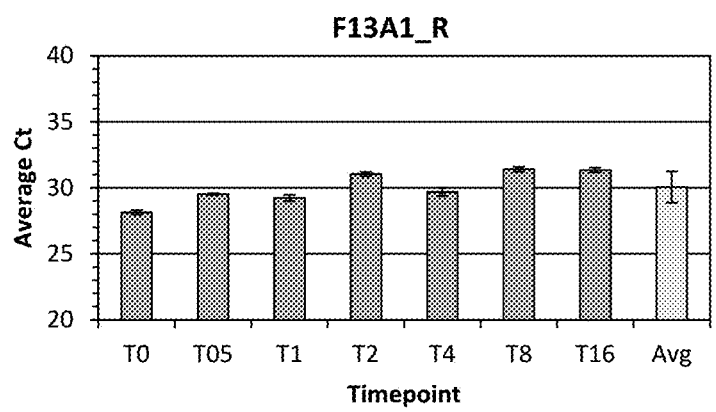

Figure 15J
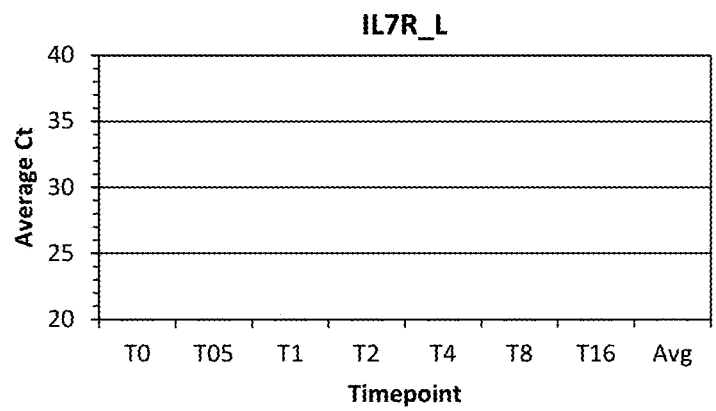
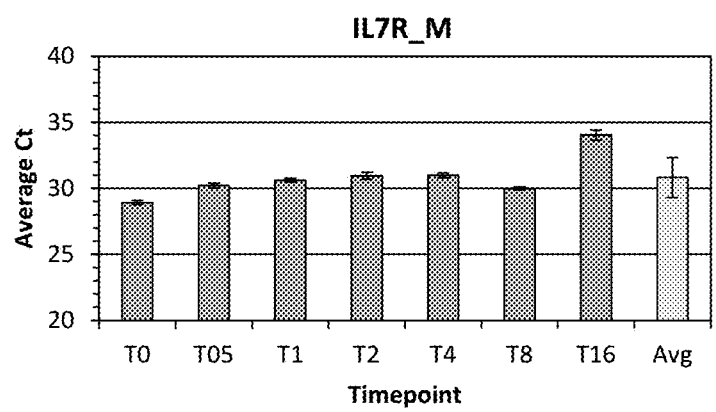
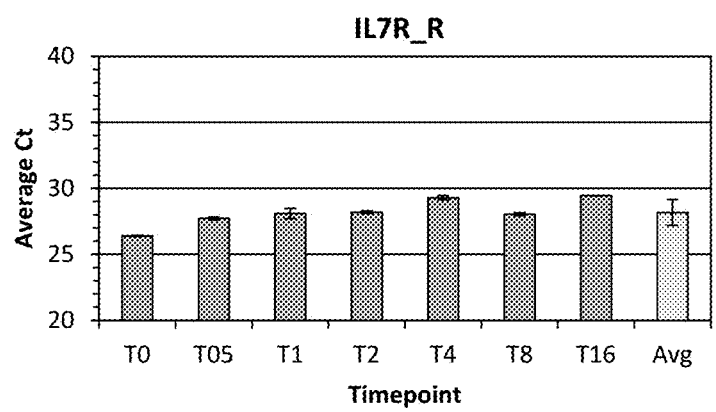

Figure 15P
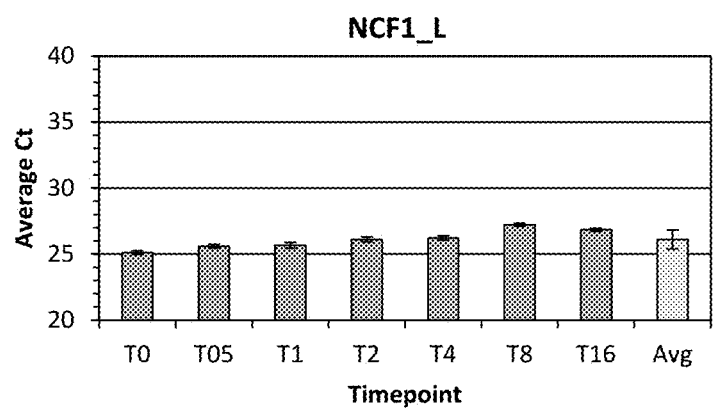
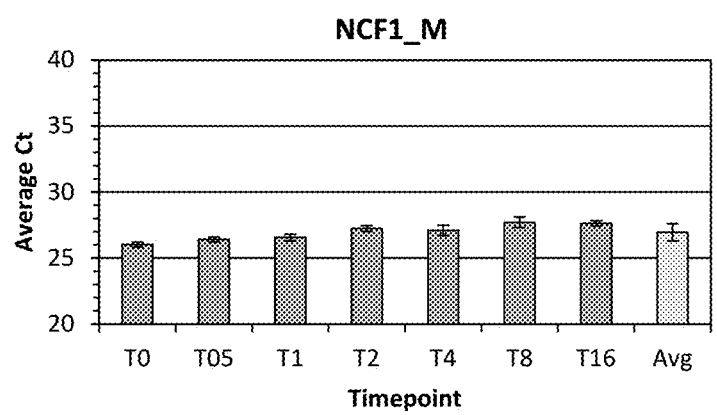
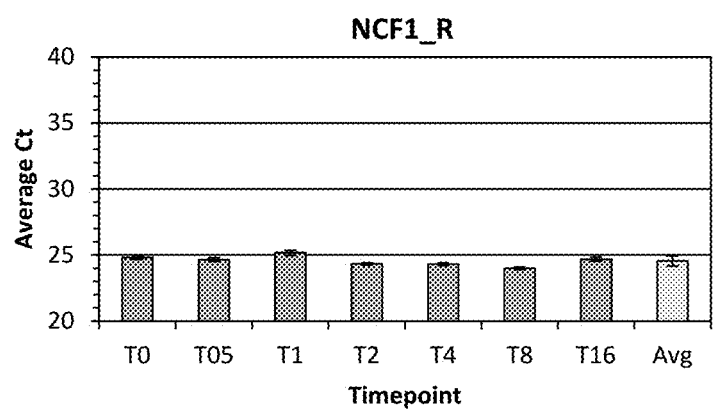

Figure 15R
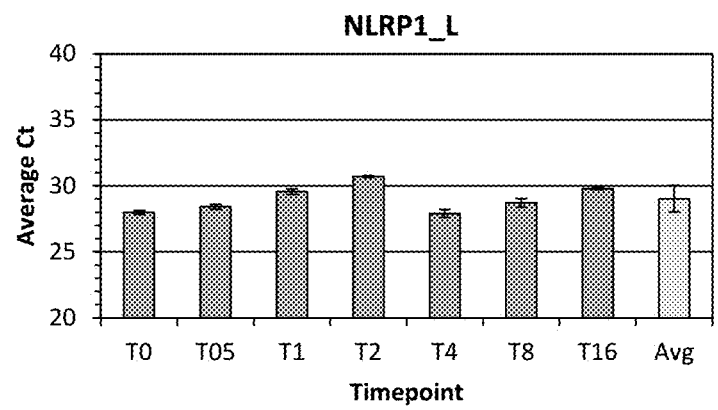
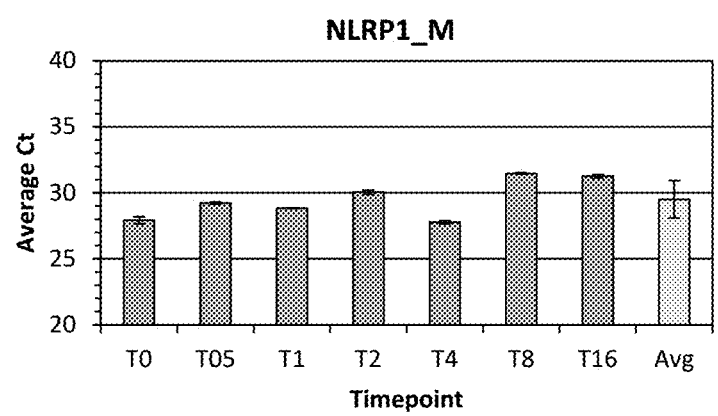
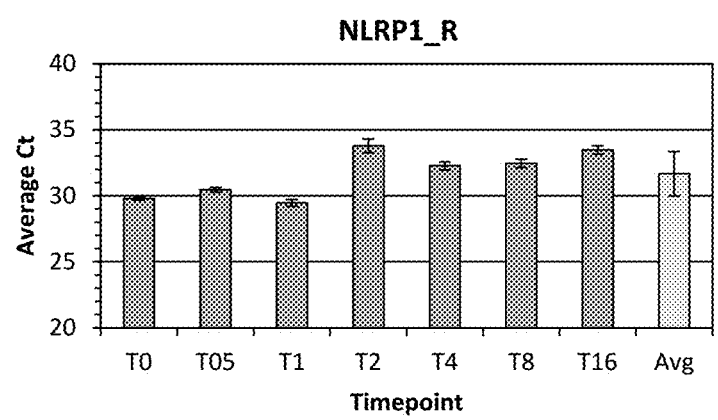

SEQUENCE LISTING

<160> NUMBER OF SEQ ID NOS: 556

<210> SEQ ID NO 1
<211> LENGTH: 8
<212> TYPE: DNA
<213> ORGANISM: Artificial Sequence
<220> FEATURE:
<223> OTHER INFORMATION: Synthetic

<400> SEQUENCE: 1 cagcctgg                                                                 8

-continued

```
<210> SEQ ID NO 2
<211> LENGTH: 18
<212> TYPE: DNA
<213> ORGANISM: Artificial Sequence
<220> FEATURE:
<223> OTHER INFORMATION: Synthetic

<400> SEQUENCE: 2
ccaaccgcga gaagatga                                                     18

<210> SEQ ID NO 3
<211> LENGTH: 20
<212> TYPE: DNA
<213> ORGANISM: Artificial Sequence
<220> FEATURE:
<223> OTHER INFORMATION: Synthetic

<400> SEQUENCE: 3
ccagaggcgt acagggatag                                                   20

<210> SEQ ID NO 4
<211> LENGTH: 8
<212> TYPE: DNA
<213> ORGANISM: Artificial Sequence
<220> FEATURE:
<223> OTHER INFORMATION: Synthetic

<400> SEQUENCE: 4 ccagggca                                                                 8

<210> SEQ ID NO 5
<211> LENGTH: 18
<212> TYPE: DNA
<213> ORGANISM: Artificial Sequence
<220> FEATURE:
<223> OTHER INFORMATION: Synthetic

<400> SEQUENCE: 5
gcggtggctg taggttgt                                                     18

<210> SEQ ID NO 6
<211> LENGTH: 21
<212> TYPE: DNA
<213> ORGANISM: Artificial Sequence
<220> FEATURE:
<223> OTHER INFORMATION: Synthetic

<400> SEQUENCE: 6
gcctgcatat ccacacttca c                                                 21

<210> SEQ ID NO 7
<211> LENGTH: 8
<212> TYPE: DNA
<213> ORGANISM: Artificial Sequence
<220> FEATURE:
<223> OTHER INFORMATION: Synthetic

<400> SEQUENCE: 7 cttcagcc                                                                 8

<210> SEQ ID NO 8
<211> LENGTH: 22
<212> TYPE: DNA
<213> ORGANISM: Artificial Sequence
<220> FEATURE:
<223> OTHER INFORMATION: Synthetic
```

<400> SEQUENCE: 8
tcatcccact attccacaga ga          22

<210> SEQ ID NO 9
<211> LENGTH: 21
<212> TYPE: DNA
<213> ORGANISM: Artificial Sequence
<220> FEATURE:
<223> OTHER INFORMATION: Synthetic

<400> SEQUENCE: 9
gctcttccca gaaagaagg a          21

<210> SEQ ID NO 10
<211> LENGTH: 8
<212> TYPE: DNA
<213> ORGANISM: Artificial Sequence
<220> FEATURE:
<223> OTHER INFORMATION: Synthetic

<400> SEQUENCE: 10 tcctgctc          8

<210> SEQ ID NO 11
<211> LENGTH: 27
<212> TYPE: DNA
<213> ORGANISM: Artificial Sequence
<220> FEATURE:
<223> OTHER INFORMATION: Synthetic

<400> SEQUENCE: 11
tggtctcagc ttatctacaa tcatatc          27

<210> SEQ ID NO 12
<211> LENGTH: 20
<212> TYPE: DNA
<213> ORGANISM: Artificial Sequence
<220> FEATURE:
<223> OTHER INFORMATION: Synthetic

<400> SEQUENCE: 12
ccaaaaggga caatgaggaa          20

<210> SEQ ID NO 13
<211> LENGTH: 8
<212> TYPE: DNA
<213> ORGANISM: Artificial Sequence
<220> FEATURE:
<223> OTHER INFORMATION: Synthetic

<400> SEQUENCE: 13 cagcctcc          8

<210> SEQ ID NO 14
<211> LENGTH: 21
<212> TYPE: DNA
<213> ORGANISM: Artificial Sequence
<220> FEATURE:
<223> OTHER INFORMATION: Synthetic

<400> SEQUENCE: 14
tcccagaggc ctatcttttt c          21

<210> SEQ ID NO 15
<211> LENGTH: 22

```
<212> TYPE: DNA
<213> ORGANISM: Artificial Sequence
<220> FEATURE:
<223> OTHER INFORMATION: Synthetic

<400> SEQUENCE: 15
ttcaaattgg tacttccctg gt                                              22

<210> SEQ ID NO 16
<211> LENGTH: 8
<212> TYPE: DNA
<213> ORGANISM: Artificial Sequence
<220> FEATURE:
<223> OTHER INFORMATION: Synthetic

<400> SEQUENCE: 16 tccaggtc                                                               8

<210> SEQ ID NO 17
<211> LENGTH: 24
<212> TYPE: DNA
<213> ORGANISM: Artificial Sequence
<220> FEATURE:
<223> OTHER INFORMATION: Synthetic

<400> SEQUENCE: 17
ctggaatgtc attatcagac acaa                                            24

<210> SEQ ID NO 18
<211> LENGTH: 20
<212> TYPE: DNA
<213> ORGANISM: Artificial Sequence
<220> FEATURE:
<223> OTHER INFORMATION: Synthetic

<400> SEQUENCE: 18
tcagagacgt cgggttcact                                                 20

<210> SEQ ID NO 19
<211> LENGTH: 8
<212> TYPE: DNA
<213> ORGANISM: Artificial Sequence
<220> FEATURE:
<223> OTHER INFORMATION: Synthetic

<400> SEQUENCE: 19 ctcctgcc                                                               8

<210> SEQ ID NO 20
<211> LENGTH: 21
<212> TYPE: DNA
<213> ORGANISM: Artificial Sequence
<220> FEATURE:
<223> OTHER INFORMATION: Synthetic

<400> SEQUENCE: 20
caagttcgtg gacgaagaag a                                               21

<210> SEQ ID NO 21
<211> LENGTH: 20
<212> TYPE: DNA
<213> ORGANISM: Artificial Sequence
<220> FEATURE:
<223> OTHER INFORMATION: Synthetic

<400> SEQUENCE: 21
```
gcagctgtca tgtttccttg                                          20

<210> SEQ ID NO 22
<211> LENGTH: 8
<212> TYPE: DNA
<213> ORGANISM: Artificial Sequence
<220> FEATURE:
<223> OTHER INFORMATION: Synthetic

<400> SEQUENCE: 22 cctggagc                                                        8

<210> SEQ ID NO 23
<211> LENGTH: 23
<212> TYPE: DNA
<213> ORGANISM: Artificial Sequence
<220> FEATURE:
<223> OTHER INFORMATION: Synthetic

<400> SEQUENCE: 23
aatgataaag ccagaagaaa gca                                      23

<210> SEQ ID NO 24
<211> LENGTH: 20
<212> TYPE: DNA
<213> ORGANISM: Artificial Sequence
<220> FEATURE:
<223> OTHER INFORMATION: Synthetic

<400> SEQUENCE: 24
cagtgcgagg aagttcttga                                          20

<210> SEQ ID NO 25
<211> LENGTH: 8
<212> TYPE: DNA
<213> ORGANISM: Artificial Sequence
<220> FEATURE:
<223> OTHER INFORMATION: Synthetic

<400> SEQUENCE: 25 ctgcctct                                                        8

<210> SEQ ID NO 26
<211> LENGTH: 19
<212> TYPE: DNA
<213> ORGANISM: Artificial Sequence
<220> FEATURE:
<223> OTHER INFORMATION: Synthetic

<400> SEQUENCE: 26 ctcggggtc tacttcgag                                            19

<210> SEQ ID NO 27
<211> LENGTH: 19
<212> TYPE: DNA
<213> ORGANISM: Artificial Sequence
<220> FEATURE:
<223> OTHER INFORMATION: Synthetic

<400> SEQUENCE: 27
ggacctgggt gaccttgat                                           19

<210> SEQ ID NO 28
<211> LENGTH: 8
<212> TYPE: DNA
<213> ORGANISM: Artificial Sequence

```
<220> FEATURE:
<223> OTHER INFORMATION: Synthetic

<400> SEQUENCE: 28 tctggagc                                                                  8

<210> SEQ ID NO 29
<211> LENGTH: 20
<212> TYPE: DNA
<213> ORGANISM: Artificial Sequence
<220> FEATURE:
<223> OTHER INFORMATION: Synthetic

<400> SEQUENCE: 29
ctgctctttg tgcattcagc                                                    20

<210> SEQ ID NO 30
<211> LENGTH: 22
<212> TYPE: DNA
<213> ORGANISM: Artificial Sequence
<220> FEATURE:
<223> OTHER INFORMATION: Synthetic

<400> SEQUENCE: 30
gcttcatagc atccgttgat ct                                                 22

<210> SEQ ID NO 31
<211> LENGTH: 8
<212> TYPE: DNA
<213> ORGANISM: Artificial Sequence
<220> FEATURE:
<223> OTHER INFORMATION: Synthetic

<400> SEQUENCE: 31 aggagctg                                                                  8

<210> SEQ ID NO 32
<211> LENGTH: 20
<212> TYPE: DNA
<213> ORGANISM: Artificial Sequence
<220> FEATURE:
<223> OTHER INFORMATION: Synthetic

<400> SEQUENCE: 32
tcagtgcctg ttttgtcacc                                                    20

<210> SEQ ID NO 33
<211> LENGTH: 20
<212> TYPE: DNA
<213> ORGANISM: Artificial Sequence
<220> FEATURE:
<223> OTHER INFORMATION: Synthetic

<400> SEQUENCE: 33
tccactctcc cgctacactt                                                    20

<210> SEQ ID NO 34
<211> LENGTH: 8
<212> TYPE: DNA
<213> ORGANISM: Artificial Sequence
<220> FEATURE:
<223> OTHER INFORMATION: Synthetic

<400> SEQUENCE: 34 ttcctggc                                                                  8
```

```
<210> SEQ ID NO 35
<211> LENGTH: 20
<212> TYPE: DNA
<213> ORGANISM: Artificial Sequence
<220> FEATURE:
<223> OTHER INFORMATION: Synthetic

<400> SEQUENCE: 35
cactactggg ctcagggaaa                                              20

<210> SEQ ID NO 36
<211> LENGTH: 20
<212> TYPE: DNA
<213> ORGANISM: Artificial Sequence
<220> FEATURE:
<223> OTHER INFORMATION: Synthetic

<400> SEQUENCE: 36
tcacagtcct tcacgaggaa                                              20

<210> SEQ ID NO 37
<211> LENGTH: 8
<212> TYPE: DNA
<213> ORGANISM: Artificial Sequence
<220> FEATURE:
<223> OTHER INFORMATION: Synthetic

<400> SEQUENCE: 37 ttcctctg                                                            8

<210> SEQ ID NO 38
<211> LENGTH: 20
<212> TYPE: DNA
<213> ORGANISM: Artificial Sequence
<220> FEATURE:
<223> OTHER INFORMATION: Synthetic

<400> SEQUENCE: 38
ctctgctcct cctgcttgtc                                              20

<210> SEQ ID NO 39
<211> LENGTH: 21
<212> TYPE: DNA
<213> ORGANISM: Artificial Sequence
<220> FEATURE:
<223> OTHER INFORMATION: Synthetic

<400> SEQUENCE: 39
tcatagcgac actgcacact c                                            21

<210> SEQ ID NO 40
<211> LENGTH: 8
<212> TYPE: DNA
<213> ORGANISM: Artificial Sequence
<220> FEATURE:
<223> OTHER INFORMATION: Synthetic

<400> SEQUENCE: 40 tgtggctg                                                            8

<210> SEQ ID NO 41
<211> LENGTH: 23
<212> TYPE: DNA
<213> ORGANISM: Artificial Sequence
<220> FEATURE:
<223> OTHER INFORMATION: Synthetic
```

<400> SEQUENCE: 41
tcctgttttt cttcaacttg ctc                                                    23

<210> SEQ ID NO 42
<211> LENGTH: 20
<212> TYPE: DNA
<213> ORGANISM: Artificial Sequence
<220> FEATURE:
<223> OTHER INFORMATION: Synthetic

<400> SEQUENCE: 42
gtagatccca aagcccaaaa                                                        20

<210> SEQ ID NO 43
<211> LENGTH: 8
<212> TYPE: DNA
<213> ORGANISM: Artificial Sequence
<220> FEATURE:
<223> OTHER INFORMATION: Synthetic

<400> SEQUENCE: 43 cccagcag                                                                      8

<210> SEQ ID NO 44
<211> LENGTH: 18
<212> TYPE: DNA
<213> ORGANISM: Artificial Sequence
<220> FEATURE:
<223> OTHER INFORMATION: Synthetic

<400> SEQUENCE: 44
ggctggctgt gcttttct                                                          18

<210> SEQ ID NO 45
<211> LENGTH: 22
<212> TYPE: DNA
<213> ORGANISM: Artificial Sequence
<220> FEATURE:
<223> OTHER INFORMATION: Synthetic

<400> SEQUENCE: 45
tttttgtgag gacagtcatt cc                                                     22

<210> SEQ ID NO 46
<211> LENGTH: 8
<212> TYPE: DNA
<213> ORGANISM: Artificial Sequence
<220> FEATURE:
<223> OTHER INFORMATION: Synthetic

<400> SEQUENCE: 46 ctggctcc                                                                      8

<210> SEQ ID NO 47
<211> LENGTH: 19
<212> TYPE: DNA
<213> ORGANISM: Artificial Sequence
<220> FEATURE:
<223> OTHER INFORMATION: Synthetic

<400> SEQUENCE: 47
ctccagcttc tgctcctga                                                         19

<210> SEQ ID NO 48

```
<211> LENGTH: 18
<212> TYPE: DNA
<213> ORGANISM: Artificial Sequence
<220> FEATURE:
<223> OTHER INFORMATION: Synthetic

<400> SEQUENCE: 48
ggagcaagcc accttcac                                                     18

<210> SEQ ID NO 49
<211> LENGTH: 8
<212> TYPE: DNA
<213> ORGANISM: Artificial Sequence
<220> FEATURE:
<223> OTHER INFORMATION: Synthetic

<400> SEQUENCE: 49 ctccacca                                                                 8

<210> SEQ ID NO 50
<211> LENGTH: 21
<212> TYPE: DNA
<213> ORGANISM: Artificial Sequence
<220> FEATURE:
<223> OTHER INFORMATION: Synthetic

<400> SEQUENCE: 50
accagctgta gctgaacgtc t                                                 21

<210> SEQ ID NO 51
<211> LENGTH: 21
<212> TYPE: DNA
<213> ORGANISM: Artificial Sequence
<220> FEATURE:
<223> OTHER INFORMATION: Synthetic

<400> SEQUENCE: 51
catatctcca cgtgtgtcca g                                                 21

<210> SEQ ID NO 52
<211> LENGTH: 8
<212> TYPE: DNA
<213> ORGANISM: Artificial Sequence
<220> FEATURE:
<223> OTHER INFORMATION: Synthetic

<400> SEQUENCE: 52 tcctgctg                                                                 8

<210> SEQ ID NO 53
<211> LENGTH: 21
<212> TYPE: DNA
<213> ORGANISM: Artificial Sequence
<220> FEATURE:
<223> OTHER INFORMATION: Synthetic

<400> SEQUENCE: 53
gtccaagatc acaaagctgg t                                                 21

<210> SEQ ID NO 54
<211> LENGTH: 19
<212> TYPE: DNA
<213> ORGANISM: Artificial Sequence
<220> FEATURE:
<223> OTHER INFORMATION: Synthetic

<400> SEQUENCE: 54
```

```
ccgcactcct ccagacttc                                                    19

<210> SEQ ID NO 55
<211> LENGTH: 8
<212> TYPE: DNA
<213> ORGANISM: Artificial Sequence
<220> FEATURE:
<223> OTHER INFORMATION: Synthetic

<400> SEQUENCE: 55 cttcctcc                                                                 8

<210> SEQ ID NO 56
<211> LENGTH: 21
<212> TYPE: DNA
<213> ORGANISM: Artificial Sequence
<220> FEATURE:
<223> OTHER INFORMATION: Synthetic

<400> SEQUENCE: 56
tggaccctac ctacatcctg a                                                 21

<210> SEQ ID NO 57
<211> LENGTH: 20
<212> TYPE: DNA
<213> ORGANISM: Artificial Sequence
<220> FEATURE:
<223> OTHER INFORMATION: Synthetic

<400> SEQUENCE: 57
ggcccttgtt gtttttctca                                                   20

<210> SEQ ID NO 58
<211> LENGTH: 8
<212> TYPE: DNA
<213> ORGANISM: Artificial Sequence
<220> FEATURE:
<223> OTHER INFORMATION: Synthetic

<400> SEQUENCE: 58 tggtgatg                                                                 8

<210> SEQ ID NO 59
<211> LENGTH: 20
<212> TYPE: DNA
<213> ORGANISM: Artificial Sequence
<220> FEATURE:
<223> OTHER INFORMATION: Synthetic

<400> SEQUENCE: 59
tcactgatac ccggaaggac                                                   20

<210> SEQ ID NO 60
<211> LENGTH: 21
<212> TYPE: DNA
<213> ORGANISM: Artificial Sequence
<220> FEATURE:
<223> OTHER INFORMATION: Synthetic

<400> SEQUENCE: 60
ttcaagtcat tctccgagag c                                                 21

<210> SEQ ID NO 61
<211> LENGTH: 8
<212> TYPE: DNA
```

```
<213> ORGANISM: Artificial Sequence
<220> FEATURE:
<223> OTHER INFORMATION: Synthetic

<400> SEQUENCE: 61 agctggag                                                                    8

<210> SEQ ID NO 62
<211> LENGTH: 20
<212> TYPE: DNA
<213> ORGANISM: Artificial Sequence
<220> FEATURE:
<223> OTHER INFORMATION: Synthetic

<400> SEQUENCE: 62
cctgaatgac atcggggtaa                                                      20

<210> SEQ ID NO 63
<211> LENGTH: 19
<212> TYPE: DNA
<213> ORGANISM: Artificial Sequence
<220> FEATURE:
<223> OTHER INFORMATION: Synthetic

<400> SEQUENCE: 63
gtccaggatg ccatcttca                                                       19

<210> SEQ ID NO 64
<211> LENGTH: 8
<212> TYPE: DNA
<213> ORGANISM: Artificial Sequence
<220> FEATURE:
<223> OTHER INFORMATION: Synthetic

<400> SEQUENCE: 64 cctggagc                                                                    8

<210> SEQ ID NO 65
<211> LENGTH: 20
<212> TYPE: DNA
<213> ORGANISM: Artificial Sequence
<220> FEATURE:
<223> OTHER INFORMATION: Synthetic

<400> SEQUENCE: 65
agaggcaggt gtcattggag                                                      20

<210> SEQ ID NO 66
<211> LENGTH: 18
<212> TYPE: DNA
<213> ORGANISM: Artificial Sequence
<220> FEATURE:
<223> OTHER INFORMATION: Synthetic

<400> SEQUENCE: 66
ctggtcctgc ctttccag                                                        18

<210> SEQ ID NO 67
<211> LENGTH: 8
<212> TYPE: DNA
<213> ORGANISM: Artificial Sequence
<220> FEATURE:
<223> OTHER INFORMATION: Synthetic

<400> SEQUENCE: 67 cttcccca                                                                    8
```

<210> SEQ ID NO 68
<211> LENGTH: 19
<212> TYPE: DNA
<213> ORGANISM: Artificial Sequence
<220> FEATURE:
<223> OTHER INFORMATION: Synthetic

<400> SEQUENCE: 68
agccacatcg ctcagacac                                                  19

<210> SEQ ID NO 69
<211> LENGTH: 19
<212> TYPE: DNA
<213> ORGANISM: Artificial Sequence
<220> FEATURE:
<223> OTHER INFORMATION: Synthetic

<400> SEQUENCE: 69
gcccaatacg accaaatcc                                                  19

<210> SEQ ID NO 70
<211> LENGTH: 8
<212> TYPE: DNA
<213> ORGANISM: Artificial Sequence
<220> FEATURE:
<223> OTHER INFORMATION: Synthetic

<400> SEQUENCE: 70 tcctgctg                                                               8

<210> SEQ ID NO 71
<211> LENGTH: 20
<212> TYPE: DNA
<213> ORGANISM: Artificial Sequence
<220> FEATURE:
<223> OTHER INFORMATION: Synthetic

<400> SEQUENCE: 71
agatgcaacc aatcctgctt                                                 20

<210> SEQ ID NO 72
<211> LENGTH: 18
<212> TYPE: DNA
<213> ORGANISM: Artificial Sequence
<220> FEATURE:
<223> OTHER INFORMATION: Synthetic

<400> SEQUENCE: 72
catgtccccc gatgatct                                                   18

<210> SEQ ID NO 73
<211> LENGTH: 8
<212> TYPE: DNA
<213> ORGANISM: Artificial Sequence
<220> FEATURE:
<223> OTHER INFORMATION: Synthetic

<400> SEQUENCE: 73 ccagccag                                                               8

<210> SEQ ID NO 74
<211> LENGTH: 18
<212> TYPE: DNA
<213> ORGANISM: Artificial Sequence
<220> FEATURE:

<223> OTHER INFORMATION: Synthetic

<400> SEQUENCE: 74
ggtcgtgtgc ttggagga                                                                             18

<210> SEQ ID NO 75
<211> LENGTH: 20
<212> TYPE: DNA
<213> ORGANISM: Artificial Sequence
<220> FEATURE:
<223> OTHER INFORMATION: Synthetic

<400> SEQUENCE: 75
ggtaccattc ccaatgctga                                                                           20

<210> SEQ ID NO 76
<211> LENGTH: 8
<212> TYPE: DNA
<213> ORGANISM: Artificial Sequence
<220> FEATURE:
<223> OTHER INFORMATION: Synthetic

<400> SEQUENCE: 76 tccagtgt                                                                                         8

<210> SEQ ID NO 77
<211> LENGTH: 18
<212> TYPE: DNA
<213> ORGANISM: Artificial Sequence
<220> FEATURE:
<223> OTHER INFORMATION: Synthetic

<400> SEQUENCE: 77
ctcttcgcag tggggaca                                                                             18

<210> SEQ ID NO 78
<211> LENGTH: 19
<212> TYPE: DNA
<213> ORGANISM: Artificial Sequence
<220> FEATURE:
<223> OTHER INFORMATION: Synthetic

<400> SEQUENCE: 78
cccagatgtc tgcgtgttc                                                                            19

<210> SEQ ID NO 79
<211> LENGTH: 8
<212> TYPE: DNA
<213> ORGANISM: Artificial Sequence
<220> FEATURE:
<223> OTHER INFORMATION: Synthetic

<400> SEQUENCE: 79 ccacctcc                                                                                         8

<210> SEQ ID NO 80
<211> LENGTH: 19
<212> TYPE: DNA
<213> ORGANISM: Artificial Sequence
<220> FEATURE:
<223> OTHER INFORMATION: Synthetic

<400> SEQUENCE: 80
gtagccgagg aggaagcat                                                                            19

```
<210> SEQ ID NO 81
<211> LENGTH: 18
<212> TYPE: DNA
<213> ORGANISM: Artificial Sequence
<220> FEATURE:
<223> OTHER INFORMATION: Synthetic

<400> SEQUENCE: 81
actggtcagc acgcctct                                                       18

<210> SEQ ID NO 82
<211> LENGTH: 8
<212> TYPE: DNA
<213> ORGANISM: Artificial Sequence
<220> FEATURE:
<223> OTHER INFORMATION: Synthetic

<400> SEQUENCE: 82 tggtgatg                                                                   8

<210> SEQ ID NO 83
<211> LENGTH: 20
<212> TYPE: DNA
<213> ORGANISM: Artificial Sequence
<220> FEATURE:
<223> OTHER INFORMATION: Synthetic

<400> SEQUENCE: 83
gcttttgagg acccagatgt                                                     20

<210> SEQ ID NO 84
<211> LENGTH: 20
<212> TYPE: DNA
<213> ORGANISM: Artificial Sequence
<220> FEATURE:
<223> OTHER INFORMATION: Synthetic

<400> SEQUENCE: 84
aggcacttta cctccacgag                                                     20

<210> SEQ ID NO 85
<211> LENGTH: 8
<212> TYPE: DNA
<213> ORGANISM: Artificial Sequence
<220> FEATURE:
<223> OTHER INFORMATION: Synthetic

<400> SEQUENCE: 85 caggcagc                                                                   8

<210> SEQ ID NO 86
<211> LENGTH: 19
<212> TYPE: DNA
<213> ORGANISM: Artificial Sequence
<220> FEATURE:
<223> OTHER INFORMATION: Synthetic

<400> SEQUENCE: 86
gctgtcccca caaaaagtg                                                      19

<210> SEQ ID NO 87
<211> LENGTH: 18
<212> TYPE: DNA
<213> ORGANISM: Artificial Sequence
<220> FEATURE:
<223> OTHER INFORMATION: Synthetic
```

```
<400> SEQUENCE: 87
ccggaaggtc acgttgaa                                                    18

<210> SEQ ID NO 88
<211> LENGTH: 8
<212> TYPE: DNA
<213> ORGANISM: Artificial Sequence
<220> FEATURE:
<223> OTHER INFORMATION: Synthetic

<400> SEQUENCE: 88 ctgggaga                                                                8

<210> SEQ ID NO 89
<211> LENGTH: 19
<212> TYPE: DNA
<213> ORGANISM: Artificial Sequence
<220> FEATURE:
<223> OTHER INFORMATION: Synthetic

<400> SEQUENCE: 89
atcaactggg tgcagcgta                                                   19

<210> SEQ ID NO 90
<211> LENGTH: 25
<212> TYPE: DNA
<213> ORGANISM: Artificial Sequence
<220> FEATURE:
<223> OTHER INFORMATION: Synthetic

<400> SEQUENCE: 90
tcagctgagt agtacaaggt ttgaa                                            25

<210> SEQ ID NO 91
<211> LENGTH: 8
<212> TYPE: DNA
<213> ORGANISM: Artificial Sequence
<220> FEATURE:
<223> OTHER INFORMATION: Synthetic

<400> SEQUENCE: 91 ttcccagt                                                                8

<210> SEQ ID NO 92
<211> LENGTH: 22
<212> TYPE: DNA
<213> ORGANISM: Artificial Sequence
<220> FEATURE:
<223> OTHER INFORMATION: Synthetic

<400> SEQUENCE: 92
tgcccaaaca tctcaactta ca                                               22

<210> SEQ ID NO 93
<211> LENGTH: 21
<212> TYPE: DNA
<213> ORGANISM: Artificial Sequence
<220> FEATURE:
<223> OTHER INFORMATION: Synthetic

<400> SEQUENCE: 93
aataccattc acggttccag a                                                21

<210> SEQ ID NO 94
<211> LENGTH: 8
```

```
<212> TYPE: DNA
<213> ORGANISM: Artificial Sequence
<220> FEATURE:
<223> OTHER INFORMATION: Synthetic

<400> SEQUENCE: 94 tctggagc                                                              8

<210> SEQ ID NO 95
<211> LENGTH: 19
<212> TYPE: DNA
<213> ORGANISM: Artificial Sequence
<220> FEATURE:
<223> OTHER INFORMATION: Synthetic

<400> SEQUENCE: 95
gaaaaccttc gcctcaagc                                                 19

<210> SEQ ID NO 96
<211> LENGTH: 20
<212> TYPE: DNA
<213> ORGANISM: Artificial Sequence
<220> FEATURE:
<223> OTHER INFORMATION: Synthetic

<400> SEQUENCE: 96
tgaaaccttt gcccttgttc                                                20

<210> SEQ ID NO 97
<211> LENGTH: 8
<212> TYPE: DNA
<213> ORGANISM: Artificial Sequence
<220> FEATURE:
<223> OTHER INFORMATION: Synthetic

<400> SEQUENCE: 97 ttcctctg                                                              8

<210> SEQ ID NO 98
<211> LENGTH: 19
<212> TYPE: DNA
<213> ORGANISM: Artificial Sequence
<220> FEATURE:
<223> OTHER INFORMATION: Synthetic

<400> SEQUENCE: 98
ttggcaccca acactccta                                                 19

<210> SEQ ID NO 99
<211> LENGTH: 20
<212> TYPE: DNA
<213> ORGANISM: Artificial Sequence
<220> FEATURE:
<223> OTHER INFORMATION: Synthetic

<400> SEQUENCE: 99
ccagggcttt gtttatccag                                                20

<210> SEQ ID NO 100
<211> LENGTH: 8
<212> TYPE: DNA
<213> ORGANISM: Artificial Sequence
<220> FEATURE:
<223> OTHER INFORMATION: Synthetic

<400> SEQUENCE: 100
```

```
cctggaga                                                              8

<210> SEQ ID NO 101
<211> LENGTH: 18
<212> TYPE: DNA
<213> ORGANISM: Artificial Sequence
<220> FEATURE:
<223> OTHER INFORMATION: Synthetic

<400> SEQUENCE: 101
agtctgcctg tggcatgg                                                  18

<210> SEQ ID NO 102
<211> LENGTH: 20
<212> TYPE: DNA
<213> ORGANISM: Artificial Sequence
<220> FEATURE:
<223> OTHER INFORMATION: Synthetic

<400> SEQUENCE: 102
gctgtgcaga tggatgagac                                                20

<210> SEQ ID NO 103
<211> LENGTH: 8
<212> TYPE: DNA
<213> ORGANISM: Artificial Sequence
<220> FEATURE:
<223> OTHER INFORMATION: Synthetic

<400> SEQUENCE: 103 aggagctg                                                              8

<210> SEQ ID NO 104
<211> LENGTH: 22
<212> TYPE: DNA
<213> ORGANISM: Artificial Sequence
<220> FEATURE:
<223> OTHER INFORMATION: Synthetic

<400> SEQUENCE: 104
ttggatgtag gacaatggaa ga                                             22

<210> SEQ ID NO 105
<211> LENGTH: 20
<212> TYPE: DNA
<213> ORGANISM: Artificial Sequence
<220> FEATURE:
<223> OTHER INFORMATION: Synthetic

<400> SEQUENCE: 105
cctttctgga atgctgatcc                                                20

<210> SEQ ID NO 106
<211> LENGTH: 8
<212> TYPE: DNA
<213> ORGANISM: Artificial Sequence
<220> FEATURE:
<223> OTHER INFORMATION: Synthetic

<400> SEQUENCE: 106 tcctgctg                                                              8

<210> SEQ ID NO 107
<211> LENGTH: 20
<212> TYPE: DNA
<213> ORGANISM: Artificial Sequence
```

```
<220> FEATURE:
<223> OTHER INFORMATION: Synthetic

<400> SEQUENCE: 107
gaccgcagac atgaaacttg                                                      20

<210> SEQ ID NO 108
<211> LENGTH: 18
<212> TYPE: DNA
<213> ORGANISM: Artificial Sequence
<220> FEATURE:
<223> OTHER INFORMATION: Synthetic

<400> SEQUENCE: 108
gccagccaga cacagtcc                                                        18

<210> SEQ ID NO 109
<211> LENGTH: 8
<212> TYPE: DNA
<213> ORGANISM: Artificial Sequence
<220> FEATURE:
<223> OTHER INFORMATION: Synthetic

<400> SEQUENCE: 109 ttcctctg                                                                    8

<210> SEQ ID NO 110
<211> LENGTH: 22
<212> TYPE: DNA
<213> ORGANISM: Artificial Sequence
<220> FEATURE:
<223> OTHER INFORMATION: Synthetic

<400> SEQUENCE: 110
aatgcatctg atgtctggaa ga                                                   22

<210> SEQ ID NO 111
<211> LENGTH: 22
<212> TYPE: DNA
<213> ORGANISM: Artificial Sequence
<220> FEATURE:
<223> OTHER INFORMATION: Synthetic

<400> SEQUENCE: 111
ccataagagt tcccatctct gg                                                   22

<210> SEQ ID NO 112
<211> LENGTH: 8
<212> TYPE: DNA
<213> ORGANISM: Artificial Sequence
<220> FEATURE:
<223> OTHER INFORMATION: Synthetic

<400> SEQUENCE: 112 ccagccag                                                                    8

<210> SEQ ID NO 113
<211> LENGTH: 18
<212> TYPE: DNA
<213> ORGANISM: Artificial Sequence
<220> FEATURE:
<223> OTHER INFORMATION: Synthetic

<400> SEQUENCE: 113
cctgctgggc tttgagaa                                                        18
```

<210> SEQ ID NO 114
<211> LENGTH: 20
<212> TYPE: DNA
<213> ORGANISM: Artificial Sequence
<220> FEATURE:
<223> OTHER INFORMATION: Synthetic

<400> SEQUENCE: 114
gacaggtcct gccatttcac                                               20

<210> SEQ ID NO 115
<211> LENGTH: 8
<212> TYPE: DNA
<213> ORGANISM: Artificial Sequence
<220> FEATURE:
<223> OTHER INFORMATION: Synthetic

<400> SEQUENCE: 115 ctgcttcc                                                             8

<210> SEQ ID NO 116
<211> LENGTH: 19
<212> TYPE: DNA
<213> ORGANISM: Artificial Sequence
<220> FEATURE:
<223> OTHER INFORMATION: Synthetic

<400> SEQUENCE: 116
aaaatcgaca aggcgatgg                                                19

<210> SEQ ID NO 117
<211> LENGTH: 20
<212> TYPE: DNA
<213> ORGANISM: Artificial Sequence
<220> FEATURE:
<223> OTHER INFORMATION: Synthetic

<400> SEQUENCE: 117
gggatcacca ctggctcata                                               20

<210> SEQ ID NO 118
<211> LENGTH: 8
<212> TYPE: DNA
<213> ORGANISM: Artificial Sequence
<220> FEATURE:
<223> OTHER INFORMATION: Synthetic

<400> SEQUENCE: 118 cccagcag                                                             8

<210> SEQ ID NO 119
<211> LENGTH: 19
<212> TYPE: DNA
<213> ORGANISM: Artificial Sequence
<220> FEATURE:
<223> OTHER INFORMATION: Synthetic

<400> SEQUENCE: 119
gcgagactct ccacctgct                                                19

<210> SEQ ID NO 120
<211> LENGTH: 20
<212> TYPE: DNA
<213> ORGANISM: Artificial Sequence
<220> FEATURE:
<223> OTHER INFORMATION: Synthetic

```
<400> SEQUENCE: 120
catccggaag ctgttcaaag                                                 20

<210> SEQ ID NO 121
<211> LENGTH: 8
<212> TYPE: DNA
<213> ORGANISM: Artificial Sequence
<220> FEATURE:
<223> OTHER INFORMATION: Synthetic

<400> SEQUENCE: 121 ccgccgcc                                                               8

<210> SEQ ID NO 122
<211> LENGTH: 18
<212> TYPE: DNA
<213> ORGANISM: Artificial Sequence
<220> FEATURE:
<223> OTHER INFORMATION: Synthetic

<400> SEQUENCE: 122
ccacttgtcc gcttcaca                                                   18

<210> SEQ ID NO 123
<211> LENGTH: 20
<212> TYPE: DNA
<213> ORGANISM: Artificial Sequence
<220> FEATURE:
<223> OTHER INFORMATION: Synthetic

<400> SEQUENCE: 123
tcttggggtc accttgattt                                                 20

<210> SEQ ID NO 124
<211> LENGTH: 8
<212> TYPE: DNA
<213> ORGANISM: Artificial Sequence
<220> FEATURE:
<223> OTHER INFORMATION: Synthetic

<400> SEQUENCE: 124 ctccatcc                                                               8

<210> SEQ ID NO 125
<211> LENGTH: 21
<212> TYPE: DNA
<213> ORGANISM: Artificial Sequence
<220> FEATURE:
<223> OTHER INFORMATION: Synthetic

<400> SEQUENCE: 125
tcacagccaa aatcaattca a                                               21

<210> SEQ ID NO 126
<211> LENGTH: 20
<212> TYPE: DNA
<213> ORGANISM: Artificial Sequence
<220> FEATURE:
<223> OTHER INFORMATION: Synthetic

<400> SEQUENCE: 126
gccgtgcaat acaaatcaga                                                 20

<210> SEQ ID NO 127
```

```
<211> LENGTH: 8
<212> TYPE: DNA
<213> ORGANISM: Artificial Sequence
<220> FEATURE:
<223> OTHER INFORMATION: Synthetic

<400> SEQUENCE: 127 ctctgcct                                                                 8

<210> SEQ ID NO 128
<211> LENGTH: 19
<212> TYPE: DNA
<213> ORGANISM: Artificial Sequence
<220> FEATURE:
<223> OTHER INFORMATION: Synthetic

<400> SEQUENCE: 128
agctgcctga cacatctgg                                                    19

<210> SEQ ID NO 129
<211> LENGTH: 20
<212> TYPE: DNA
<213> ORGANISM: Artificial Sequence
<220> FEATURE:
<223> OTHER INFORMATION: Synthetic

<400> SEQUENCE: 129
ggagcttgga agagcttggt                                                   20

<210> SEQ ID NO 130
<211> LENGTH: 8
<212> TYPE: DNA
<213> ORGANISM: Artificial Sequence
<220> FEATURE:
<223> OTHER INFORMATION: Synthetic

<400> SEQUENCE: 130 cccagccc                                                                 8

<210> SEQ ID NO 131
<211> LENGTH: 22
<212> TYPE: DNA
<213> ORGANISM: Artificial Sequence
<220> FEATURE:
<223> OTHER INFORMATION: Synthetic

<400> SEQUENCE: 131
gagaatctct ttcgaggtgc tg                                                22

<210> SEQ ID NO 132
<211> LENGTH: 21
<212> TYPE: DNA
<213> ORGANISM: Artificial Sequence
<220> FEATURE:
<223> OTHER INFORMATION: Synthetic

<400> SEQUENCE: 132
caaggatctt ttgagctctc g                                                 21

<210> SEQ ID NO 133
<211> LENGTH: 8
<212> TYPE: DNA
<213> ORGANISM: Artificial Sequence
<220> FEATURE:
<223> OTHER INFORMATION: Synthetic

<400> SEQUENCE: 133
``` ctgccttc                                                             8

<210> SEQ ID NO 134
<211> LENGTH: 20
<212> TYPE: DNA
<213> ORGANISM: Artificial Sequence
<220> FEATURE:
<223> OTHER INFORMATION: Synthetic

<400> SEQUENCE: 134
tggatggatg ttagcctggt                                               20

<210> SEQ ID NO 135
<211> LENGTH: 19
<212> TYPE: DNA
<213> ORGANISM: Artificial Sequence
<220> FEATURE:
<223> OTHER INFORMATION: Synthetic

<400> SEQUENCE: 135
cttgtggctt gggtttgac                                                19

<210> SEQ ID NO 136
<211> LENGTH: 8
<212> TYPE: DNA
<213> ORGANISM: Artificial Sequence
<220> FEATURE:
<223> OTHER INFORMATION: Synthetic

<400> SEQUENCE: 136 ccagggcc                                                             8

<210> SEQ ID NO 137
<211> LENGTH: 20
<212> TYPE: DNA
<213> ORGANISM: Artificial Sequence
<220> FEATURE:
<223> OTHER INFORMATION: Synthetic

<400> SEQUENCE: 137
catgaccacc cagcagatag                                               20

<210> SEQ ID NO 138
<211> LENGTH: 18
<212> TYPE: DNA
<213> ORGANISM: Artificial Sequence
<220> FEATURE:
<223> OTHER INFORMATION: Synthetic

<400> SEQUENCE: 138
gccttgcttc caggagtg                                                 18

<210> SEQ ID NO 139
<211> LENGTH: 8
<212> TYPE: DNA
<213> ORGANISM: Artificial Sequence
<220> FEATURE:
<223> OTHER INFORMATION: Synthetic

<400> SEQUENCE: 139 cctggaga                                                             8

<210> SEQ ID NO 140
<211> LENGTH: 20
<212> TYPE: DNA

```
<213> ORGANISM: Artificial Sequence
<220> FEATURE:
<223> OTHER INFORMATION: Synthetic

<400> SEQUENCE: 140
gcccatcatg gtgactaagg                                               20

<210> SEQ ID NO 141
<211> LENGTH: 18
<212> TYPE: DNA
<213> ORGANISM: Artificial Sequence
<220> FEATURE:
<223> OTHER INFORMATION: Synthetic

<400> SEQUENCE: 141
cgttgatggc cacgatta                                                 18

<210> SEQ ID NO 142
<211> LENGTH: 8
<212> TYPE: DNA
<213> ORGANISM: Artificial Sequence
<220> FEATURE:
<223> OTHER INFORMATION: Synthetic

<400> SEQUENCE: 142 ctctgcct                                                             8

<210> SEQ ID NO 143
<211> LENGTH: 19
<212> TYPE: DNA
<213> ORGANISM: Artificial Sequence
<220> FEATURE:
<223> OTHER INFORMATION: Synthetic

<400> SEQUENCE: 143
tgtttccagg atgcctgtt                                                19

<210> SEQ ID NO 144
<211> LENGTH: 21
<212> TYPE: DNA
<213> ORGANISM: Artificial Sequence
<220> FEATURE:
<223> OTHER INFORMATION: Synthetic

<400> SEQUENCE: 144
ggacattagg tgtggatgtc g                                             21

<210> SEQ ID NO 145
<211> LENGTH: 8
<212> TYPE: DNA
<213> ORGANISM: Artificial Sequence
<220> FEATURE:
<223> OTHER INFORMATION: Synthetic

<400> SEQUENCE: 145 aggagctg                                                             8

<210> SEQ ID NO 146
<211> LENGTH: 21
<212> TYPE: DNA
<213> ORGANISM: Artificial Sequence
<220> FEATURE:
<223> OTHER INFORMATION: Synthetic

<400> SEQUENCE: 146
tcagtggcat tgggataaca t                                             21
```

<210> SEQ ID NO 147
<211> LENGTH: 22
<212> TYPE: DNA
<213> ORGANISM: Artificial Sequence
<220> FEATURE:
<223> OTHER INFORMATION: Synthetic

<400> SEQUENCE: 147
tgctgtctat gtcactgctg ag                                              22

<210> SEQ ID NO 148
<211> LENGTH: 8
<212> TYPE: DNA
<213> ORGANISM: Artificial Sequence
<220> FEATURE:
<223> OTHER INFORMATION: Synthetic

<400> SEQUENCE: 148 ttcctggc                                                               8

<210> SEQ ID NO 149
<211> LENGTH: 18
<212> TYPE: DNA
<213> ORGANISM: Artificial Sequence
<220> FEATURE:
<223> OTHER INFORMATION: Synthetic

<400> SEQUENCE: 149
ggggtggaca atgctctg                                                   18

<210> SEQ ID NO 150
<211> LENGTH: 20
<212> TYPE: DNA
<213> ORGANISM: Artificial Sequence
<220> FEATURE:
<223> OTHER INFORMATION: Synthetic

<400> SEQUENCE: 150
taagtccagc agtcggttcc                                                 20

<210> SEQ ID NO 151
<211> LENGTH: 8
<212> TYPE: DNA
<213> ORGANISM: Artificial Sequence
<220> FEATURE:
<223> OTHER INFORMATION: Synthetic

<400> SEQUENCE: 151 ctgccttc                                                               8

<210> SEQ ID NO 152
<211> LENGTH: 21
<212> TYPE: DNA
<213> ORGANISM: Artificial Sequence
<220> FEATURE:
<223> OTHER INFORMATION: Synthetic

<400> SEQUENCE: 152
actgtaagca gtctgggttg g                                               21

<210> SEQ ID NO 153
<211> LENGTH: 20
<212> TYPE: DNA
<213> ORGANISM: Artificial Sequence
<220> FEATURE:

<223> OTHER INFORMATION: Synthetic

<400> SEQUENCE: 153
gatggctatt tggcagttgg                                                    20

<210> SEQ ID NO 154
<211> LENGTH: 8
<212> TYPE: DNA
<213> ORGANISM: Artificial Sequence
<220> FEATURE:
<223> OTHER INFORMATION: Synthetic

<400> SEQUENCE: 154 tcctcagc                                                                  8

<210> SEQ ID NO 155
<211> LENGTH: 21
<212> TYPE: DNA
<213> ORGANISM: Artificial Sequence
<220> FEATURE:
<223> OTHER INFORMATION: Synthetic

<400> SEQUENCE: 155
gcttaaatac ggacgaggac a                                                  21

<210> SEQ ID NO 156
<211> LENGTH: 20
<212> TYPE: DNA
<213> ORGANISM: Artificial Sequence
<220> FEATURE:
<223> OTHER INFORMATION: Synthetic

<400> SEQUENCE: 156
acgagacaga agacggcatt                                                    20

<210> SEQ ID NO 157
<211> LENGTH: 8
<212> TYPE: DNA
<213> ORGANISM: Artificial Sequence
<220> FEATURE:
<223> OTHER INFORMATION: Synthetic

<400> SEQUENCE: 157 ctccagcc                                                                  8

<210> SEQ ID NO 158
<211> LENGTH: 20
<212> TYPE: DNA
<213> ORGANISM: Artificial Sequence
<220> FEATURE:
<223> OTHER INFORMATION: Synthetic

<400> SEQUENCE: 158
gggaacctgg gagtttcttc                                                    20

<210> SEQ ID NO 159
<211> LENGTH: 18
<212> TYPE: DNA
<213> ORGANISM: Artificial Sequence
<220> FEATURE:
<223> OTHER INFORMATION: Synthetic

<400> SEQUENCE: 159
acagccctgg gaaagctc                                                      18

```
<210> SEQ ID NO 160
<211> LENGTH: 8
<212> TYPE: DNA
<213> ORGANISM: Artificial Sequence
<220> FEATURE:
<223> OTHER INFORMATION: Synthetic

<400> SEQUENCE: 160 ctggtctc                                                                 8

<210> SEQ ID NO 161
<211> LENGTH: 20
<212> TYPE: DNA
<213> ORGANISM: Artificial Sequence
<220> FEATURE:
<223> OTHER INFORMATION: Synthetic

<400> SEQUENCE: 161
agaagacagc agaggggttg                                                   20

<210> SEQ ID NO 162
<211> LENGTH: 19
<212> TYPE: DNA
<213> ORGANISM: Artificial Sequence
<220> FEATURE:
<223> OTHER INFORMATION: Synthetic

<400> SEQUENCE: 162 cacttttttct gggggcatc                                                   19

<210> SEQ ID NO 163
<211> LENGTH: 8
<212> TYPE: DNA
<213> ORGANISM: Artificial Sequence
<220> FEATURE:
<223> OTHER INFORMATION: Synthetic

<400> SEQUENCE: 163 cagcaggt                                                                 8

<210> SEQ ID NO 164
<211> LENGTH: 22
<212> TYPE: DNA
<213> ORGANISM: Artificial Sequence
<220> FEATURE:
<223> OTHER INFORMATION: Synthetic

<400> SEQUENCE: 164
caaactgggg aataaagtcc ag                                                22

<210> SEQ ID NO 165
<211> LENGTH: 19
<212> TYPE: DNA
<213> ORGANISM: Artificial Sequence
<220> FEATURE:
<223> OTHER INFORMATION: Synthetic

<400> SEQUENCE: 165
cagctcctgc ttcatgctc                                                    19

<210> SEQ ID NO 166
<211> LENGTH: 8
<212> TYPE: DNA
<213> ORGANISM: Artificial Sequence
<220> FEATURE:
<223> OTHER INFORMATION: Synthetic
```

```
<400> SEQUENCE: 166 cttcctgc                                                                    8

<210> SEQ ID NO 167
<211> LENGTH: 18
<212> TYPE: DNA
<213> ORGANISM: Artificial Sequence
<220> FEATURE:
<223> OTHER INFORMATION: Synthetic

<400> SEQUENCE: 167
ggatggtggc aaagaagg                                                         18

<210> SEQ ID NO 168
<211> LENGTH: 20
<212> TYPE: DNA
<213> ORGANISM: Artificial Sequence
<220> FEATURE:
<223> OTHER INFORMATION: Synthetic

<400> SEQUENCE: 168
catctcccat ctgtcgaagg                                                       20

<210> SEQ ID NO 169
<211> LENGTH: 8
<212> TYPE: DNA
<213> ORGANISM: Artificial Sequence
<220> FEATURE:
<223> OTHER INFORMATION: Synthetic

<400> SEQUENCE: 169 tccaggtc                                                                    8

<210> SEQ ID NO 170
<211> LENGTH: 19
<212> TYPE: DNA
<213> ORGANISM: Artificial Sequence
<220> FEATURE:
<223> OTHER INFORMATION: Synthetic

<400> SEQUENCE: 170
ggacccatag gacgcgtta                                                        19

<210> SEQ ID NO 171
<211> LENGTH: 20
<212> TYPE: DNA
<213> ORGANISM: Artificial Sequence
<220> FEATURE:
<223> OTHER INFORMATION: Synthetic

<400> SEQUENCE: 171
cgtgacctaa gcccatcttc                                                       20

<210> SEQ ID NO 172
<211> LENGTH: 8
<212> TYPE: DNA
<213> ORGANISM: Artificial Sequence
<220> FEATURE:
<223> OTHER INFORMATION: Synthetic

<400> SEQUENCE: 172 cagcagcc                                                                    8

<210> SEQ ID NO 173
<211> LENGTH: 21
```

```
<212> TYPE: DNA
<213> ORGANISM: Artificial Sequence
<220> FEATURE:
<223> OTHER INFORMATION: Synthetic

<400> SEQUENCE: 173
acaggaagga tgaggaagac c                                              21

<210> SEQ ID NO 174
<211> LENGTH: 21
<212> TYPE: DNA
<213> ORGANISM: Artificial Sequence
<220> FEATURE:
<223> OTHER INFORMATION: Synthetic

<400> SEQUENCE: 174
ctgcccctct ttcagttcat a                                              21

<210> SEQ ID NO 175
<211> LENGTH: 8
<212> TYPE: DNA
<213> ORGANISM: Artificial Sequence
<220> FEATURE:
<223> OTHER INFORMATION: Synthetic

<400> SEQUENCE: 175 ctgggaga                                                              8

<210> SEQ ID NO 176
<211> LENGTH: 20
<212> TYPE: DNA
<213> ORGANISM: Artificial Sequence
<220> FEATURE:
<223> OTHER INFORMATION: Synthetic

<400> SEQUENCE: 176
cctgagccag aaggtgaaaa                                                20

<210> SEQ ID NO 177
<211> LENGTH: 21
<212> TYPE: DNA
<213> ORGANISM: Artificial Sequence
<220> FEATURE:
<223> OTHER INFORMATION: Synthetic

<400> SEQUENCE: 177
gggtcatgag gtggtagatc a                                              21

<210> SEQ ID NO 178
<211> LENGTH: 8
<212> TYPE: DNA
<213> ORGANISM: Artificial Sequence
<220> FEATURE:
<223> OTHER INFORMATION: Synthetic

<400> SEQUENCE: 178 tccaggtc                                                              8

<210> SEQ ID NO 179
<211> LENGTH: 20
<212> TYPE: DNA
<213> ORGANISM: Artificial Sequence
<220> FEATURE:
<223> OTHER INFORMATION: Synthetic

<400> SEQUENCE: 179
```
cttctggaag accagccaac                                                    20

<210> SEQ ID NO 180
<211> LENGTH: 20
<212> TYPE: DNA
<213> ORGANISM: Artificial Sequence
<220> FEATURE:
<223> OTHER INFORMATION: Synthetic

<400> SEQUENCE: 180
gaagctcaaa gccgaacttg                                                    20

<210> SEQ ID NO 181
<211> LENGTH: 8
<212> TYPE: DNA
<213> ORGANISM: Artificial Sequence
<220> FEATURE:
<223> OTHER INFORMATION: Synthetic

<400> SEQUENCE: 181 tgctgtcc                                                                  8

<210> SEQ ID NO 182
<211> LENGTH: 20
<212> TYPE: DNA
<213> ORGANISM: Artificial Sequence
<220> FEATURE:
<223> OTHER INFORMATION: Synthetic

<400> SEQUENCE: 182 gtttcccta aaccgctagg                                                     20

<210> SEQ ID NO 183
<211> LENGTH: 18
<212> TYPE: DNA
<213> ORGANISM: Artificial Sequence
<220> FEATURE:
<223> OTHER INFORMATION: Synthetic

<400> SEQUENCE: 183
agcgagagtg gcagagga                                                      18

<210> SEQ ID NO 184
<211> LENGTH: 8
<212> TYPE: DNA
<213> ORGANISM: Artificial Sequence
<220> FEATURE:
<223> OTHER INFORMATION: Synthetic

<400> SEQUENCE: 184 cccagcag                                                                  8

<210> SEQ ID NO 185
<211> LENGTH: 19
<212> TYPE: DNA
<213> ORGANISM: Artificial Sequence
<220> FEATURE:
<223> OTHER INFORMATION: Synthetic

<400> SEQUENCE: 185
ggagctcagc agacaccag                                                     19

<210> SEQ ID NO 186
<211> LENGTH: 18
<212> TYPE: DNA
<213> ORGANISM: Artificial Sequence

```
<220> FEATURE:
<223> OTHER INFORMATION: Synthetic

<400> SEQUENCE: 186
ccaatgccaa tggagagc                                                        18

<210> SEQ ID NO 187
<211> LENGTH: 8
<212> TYPE: DNA
<213> ORGANISM: Artificial Sequence
<220> FEATURE:
<223> OTHER INFORMATION: Synthetic

<400> SEQUENCE: 187 ctgggcaa                                                                    8

<210> SEQ ID NO 188
<211> LENGTH: 20
<212> TYPE: DNA
<213> ORGANISM: Artificial Sequence
<220> FEATURE:
<223> OTHER INFORMATION: Synthetic

<400> SEQUENCE: 188
atgtagccat ccaggcagtt                                                      20

<210> SEQ ID NO 189
<211> LENGTH: 22
<212> TYPE: DNA
<213> ORGANISM: Artificial Sequence
<220> FEATURE:
<223> OTHER INFORMATION: Synthetic

<400> SEQUENCE: 189
gatgagggag agaaaagcct tc                                                   22

<210> SEQ ID NO 190
<211> LENGTH: 8
<212> TYPE: DNA
<213> ORGANISM: Artificial Sequence
<220> FEATURE:
<223> OTHER INFORMATION: Synthetic

<400> SEQUENCE: 190 ctccacct                                                                    8

<210> SEQ ID NO 191
<211> LENGTH: 20
<212> TYPE: DNA
<213> ORGANISM: Artificial Sequence
<220> FEATURE:
<223> OTHER INFORMATION: Synthetic

<400> SEQUENCE: 191
ttcgagaatc ccaaacaagg                                                      20

<210> SEQ ID NO 192
<211> LENGTH: 20
<212> TYPE: DNA
<213> ORGANISM: Artificial Sequence
<220> FEATURE:
<223> OTHER INFORMATION: Synthetic

<400> SEQUENCE: 192
ctggattcca cagggattgt                                                      20
```

```
<210> SEQ ID NO 193
<211> LENGTH: 8
<212> TYPE: DNA
<213> ORGANISM: Artificial Sequence
<220> FEATURE:
<223> OTHER INFORMATION: Synthetic

<400> SEQUENCE: 193 ctgcttcc                                                                 8

<210> SEQ ID NO 194
<211> LENGTH: 21
<212> TYPE: DNA
<213> ORGANISM: Artificial Sequence
<220> FEATURE:
<223> OTHER INFORMATION: Synthetic

<400> SEQUENCE: 194
gacaagatgg ctgaactctg g                                                 21

<210> SEQ ID NO 195
<211> LENGTH: 23
<212> TYPE: DNA
<213> ORGANISM: Artificial Sequence
<220> FEATURE:
<223> OTHER INFORMATION: Synthetic

<400> SEQUENCE: 195
tgtccatcct ctttagtcca ctt                                               23

<210> SEQ ID NO 196
<211> LENGTH: 8
<212> TYPE: DNA
<213> ORGANISM: Artificial Sequence
<220> FEATURE:
<223> OTHER INFORMATION: Synthetic

<400> SEQUENCE: 196 ctccacct                                                                 8

<210> SEQ ID NO 197
<211> LENGTH: 22
<212> TYPE: DNA
<213> ORGANISM: Artificial Sequence
<220> FEATURE:
<223> OTHER INFORMATION: Synthetic

<400> SEQUENCE: 197
gcaactagcc tgtgagattc ag                                                22

<210> SEQ ID NO 198
<211> LENGTH: 23
<212> TYPE: DNA
<213> ORGANISM: Artificial Sequence
<220> FEATURE:
<223> OTHER INFORMATION: Synthetic

<400> SEQUENCE: 198
cgctgctaca gtgtaagtga aag                                               23

<210> SEQ ID NO 199
<211> LENGTH: 8
<212> TYPE: DNA
<213> ORGANISM: Artificial Sequence
<220> FEATURE:
<223> OTHER INFORMATION: Synthetic
```

```
<400> SEQUENCE: 199 cctggagc                                                              8

<210> SEQ ID NO 200
<211> LENGTH: 20
<212> TYPE: DNA
<213> ORGANISM: Artificial Sequence
<220> FEATURE:
<223> OTHER INFORMATION: Synthetic

<400> SEQUENCE: 200
tgtctgtctg caatgggatg                                                20

<210> SEQ ID NO 201
<211> LENGTH: 26
<212> TYPE: DNA
<213> ORGANISM: Artificial Sequence
<220> FEATURE:
<223> OTHER INFORMATION: Synthetic

<400> SEQUENCE: 201
gaataattgt tggttcagaa aattca                                         26

<210> SEQ ID NO 202
<211> LENGTH: 8
<212> TYPE: DNA
<213> ORGANISM: Artificial Sequence
<220> FEATURE:
<223> OTHER INFORMATION: Synthetic

<400> SEQUENCE: 202 caggcagc                                                              8

<210> SEQ ID NO 203
<211> LENGTH: 20
<212> TYPE: DNA
<213> ORGANISM: Artificial Sequence
<220> FEATURE:
<223> OTHER INFORMATION: Synthetic

<400> SEQUENCE: 203
caccaagagt caggcagtga                                                20

<210> SEQ ID NO 204
<211> LENGTH: 22
<212> TYPE: DNA
<213> ORGANISM: Artificial Sequence
<220> FEATURE:
<223> OTHER INFORMATION: Synthetic

<400> SEQUENCE: 204
agagatgagc accttcaaga ca                                             22

<210> SEQ ID NO 205
<211> LENGTH: 8
<212> TYPE: DNA
<213> ORGANISM: Artificial Sequence
<220> FEATURE:
<223> OTHER INFORMATION: Synthetic

<400> SEQUENCE: 205 tggctgtg                                                              8

<210> SEQ ID NO 206
```

<211> LENGTH: 21
<212> TYPE: DNA
<213> ORGANISM: Artificial Sequence
<220> FEATURE:
<223> OTHER INFORMATION: Synthetic

<400> SEQUENCE: 206
aatgatttgg tggtcagctt g                                    21

<210> SEQ ID NO 207
<211> LENGTH: 20
<212> TYPE: DNA
<213> ORGANISM: Artificial Sequence
<220> FEATURE:
<223> OTHER INFORMATION: Synthetic

<400> SEQUENCE: 207
gcttggcagt gtaggcaaac                                      20

<210> SEQ ID NO 208
<211> LENGTH: 8
<212> TYPE: DNA
<213> ORGANISM: Artificial Sequence
<220> FEATURE:
<223> OTHER INFORMATION: Synthetic

<400> SEQUENCE: 208 ccagccag                                                    8

<210> SEQ ID NO 209
<211> LENGTH: 21
<212> TYPE: DNA
<213> ORGANISM: Artificial Sequence
<220> FEATURE:
<223> OTHER INFORMATION: Synthetic

<400> SEQUENCE: 209
ccagaaggtg gtctgtgaga a                                    21

<210> SEQ ID NO 210
<211> LENGTH: 20
<212> TYPE: DNA
<213> ORGANISM: Artificial Sequence
<220> FEATURE:
<223> OTHER INFORMATION: Synthetic

<400> SEQUENCE: 210
catagctctg tggggtgttg                                      20

<210> SEQ ID NO 211
<211> LENGTH: 8
<212> TYPE: DNA
<213> ORGANISM: Artificial Sequence
<220> FEATURE:
<223> OTHER INFORMATION: Synthetic

<400> SEQUENCE: 211 cagaggag                                                    8

<210> SEQ ID NO 212
<211> LENGTH: 20
<212> TYPE: DNA
<213> ORGANISM: Artificial Sequence
<220> FEATURE:
<223> OTHER INFORMATION: Synthetic

<400> SEQUENCE: 212
ggctttggca tctatgaggt                                                  20

<210> SEQ ID NO 213
<211> LENGTH: 20
<212> TYPE: DNA
<213> ORGANISM: Artificial Sequence
<220> FEATURE:
<223> OTHER INFORMATION: Synthetic

<400> SEQUENCE: 213
gctgaggtgg atgttggtct                                                  20

<210> SEQ ID NO 214
<211> LENGTH: 8
<212> TYPE: DNA
<213> ORGANISM: Artificial Sequence
<220> FEATURE:
<223> OTHER INFORMATION: Synthetic

<400> SEQUENCE: 214 tctggagc                                                                8

<210> SEQ ID NO 215
<211> LENGTH: 19
<212> TYPE: DNA
<213> ORGANISM: Artificial Sequence
<220> FEATURE:
<223> OTHER INFORMATION: Synthetic

<400> SEQUENCE: 215
gaagatgctg gcgtgacat                                                   19

<210> SEQ ID NO 216
<211> LENGTH: 20
<212> TYPE: DNA
<213> ORGANISM: Artificial Sequence
<220> FEATURE:
<223> OTHER INFORMATION: Synthetic

<400> SEQUENCE: 216
gctgcctcca cctctaagtc                                                  20

<210> SEQ ID NO 217
<211> LENGTH: 8
<212> TYPE: DNA
<213> ORGANISM: Artificial Sequence
<220> FEATURE:
<223> OTHER INFORMATION: Synthetic

<400> SEQUENCE: 217 cctcagcc                                                                8

<210> SEQ ID NO 218
<211> LENGTH: 18
<212> TYPE: DNA
<213> ORGANISM: Artificial Sequence
<220> FEATURE:
<223> OTHER INFORMATION: Synthetic

<400> SEQUENCE: 218
tccaaaccct tcgctgac                                                    18

<210> SEQ ID NO 219
<211> LENGTH: 18
<212> TYPE: DNA

<213> ORGANISM: Artificial Sequence
<220> FEATURE:
<223> OTHER INFORMATION: Synthetic

<400> SEQUENCE: 219
tggcctccag catctcac                                                       18

<210> SEQ ID NO 220
<211> LENGTH: 8
<212> TYPE: DNA
<213> ORGANISM: Artificial Sequence
<220> FEATURE:
<223> OTHER INFORMATION: Synthetic

<400> SEQUENCE: 220 ctccagcc                                                                   8

<210> SEQ ID NO 221
<211> LENGTH: 20
<212> TYPE: DNA
<213> ORGANISM: Artificial Sequence
<220> FEATURE:
<223> OTHER INFORMATION: Synthetic

<400> SEQUENCE: 221
gaggttgagg tgtccgtgtt                                                     20

<210> SEQ ID NO 222
<211> LENGTH: 18
<212> TYPE: DNA
<213> ORGANISM: Artificial Sequence
<220> FEATURE:
<223> OTHER INFORMATION: Synthetic

<400> SEQUENCE: 222
cttcgtggga ggacctga                                                       18

<210> SEQ ID NO 223
<211> LENGTH: 8
<212> TYPE: DNA
<213> ORGANISM: Artificial Sequence
<220> FEATURE:
<223> OTHER INFORMATION: Synthetic

<400> SEQUENCE: 223 ctccatcc                                                                   8

<210> SEQ ID NO 224
<211> LENGTH: 22
<212> TYPE: DNA
<213> ORGANISM: Artificial Sequence
<220> FEATURE:
<223> OTHER INFORMATION: Synthetic

<400> SEQUENCE: 224
cactcagaca atagcaccaa gg                                                  22

<210> SEQ ID NO 225
<211> LENGTH: 21
<212> TYPE: DNA
<213> ORGANISM: Artificial Sequence
<220> FEATURE:
<223> OTHER INFORMATION: Synthetic

<400> SEQUENCE: 225
cgtgccattt ataccacaac a                                                   21

<210> SEQ ID NO 226
<211> LENGTH: 8
<212> TYPE: DNA
<213> ORGANISM: Artificial Sequence
<220> FEATURE:
<223> OTHER INFORMATION: Synthetic

<400> SEQUENCE: 226 tgctggag                                                              8

<210> SEQ ID NO 227
<211> LENGTH: 20
<212> TYPE: DNA
<213> ORGANISM: Artificial Sequence
<220> FEATURE:
<223> OTHER INFORMATION: Synthetic

<400> SEQUENCE: 227
tcagctttgg attcatgcag                                                20

<210> SEQ ID NO 228
<211> LENGTH: 20
<212> TYPE: DNA
<213> ORGANISM: Artificial Sequence
<220> FEATURE:
<223> OTHER INFORMATION: Synthetic

<400> SEQUENCE: 228
gagccgagaa tgtccactgt                                                20

<210> SEQ ID NO 229
<211> LENGTH: 8
<212> TYPE: DNA
<213> ORGANISM: Artificial Sequence
<220> FEATURE:
<223> OTHER INFORMATION: Synthetic

<400> SEQUENCE: 229 ctccatcc                                                              8

<210> SEQ ID NO 230
<211> LENGTH: 19
<212> TYPE: DNA
<213> ORGANISM: Artificial Sequence
<220> FEATURE:
<223> OTHER INFORMATION: Synthetic

<400> SEQUENCE: 230
acggtctcct gggtcaagt                                                 19

<210> SEQ ID NO 231
<211> LENGTH: 19
<212> TYPE: DNA
<213> ORGANISM: Artificial Sequence
<220> FEATURE:
<223> OTHER INFORMATION: Synthetic

<400> SEQUENCE: 231
ccctgaggtg gtcttcctg                                                 19

<210> SEQ ID NO 232
<211> LENGTH: 8
<212> TYPE: DNA
<213> ORGANISM: Artificial Sequence
<220> FEATURE:

<223> OTHER INFORMATION: Synthetic

<400> SEQUENCE: 232 cagcccag                                                                8

<210> SEQ ID NO 233
<211> LENGTH: 21
<212> TYPE: DNA
<213> ORGANISM: Artificial Sequence
<220> FEATURE:
<223> OTHER INFORMATION: Synthetic

<400> SEQUENCE: 233
gggaacatga gtgaattttg g                                                21

<210> SEQ ID NO 234
<211> LENGTH: 20
<212> TYPE: DNA
<213> ORGANISM: Artificial Sequence
<220> FEATURE:
<223> OTHER INFORMATION: Synthetic

<400> SEQUENCE: 234
cggtcaatcc gtcttctctt                                                  20

<210> SEQ ID NO 235
<211> LENGTH: 8
<212> TYPE: DNA
<213> ORGANISM: Artificial Sequence
<220> FEATURE:
<223> OTHER INFORMATION: Synthetic

<400> SEQUENCE: 235 ctctgcct                                                                8

<210> SEQ ID NO 236
<211> LENGTH: 22
<212> TYPE: DNA
<213> ORGANISM: Artificial Sequence
<220> FEATURE:
<223> OTHER INFORMATION: Synthetic

<400> SEQUENCE: 236
tgtaccagaa tatgggcatc tg                                               22

<210> SEQ ID NO 237
<211> LENGTH: 18
<212> TYPE: DNA
<213> ORGANISM: Artificial Sequence
<220> FEATURE:
<223> OTHER INFORMATION: Synthetic

<400> SEQUENCE: 237
ggggctccag tttcacaa                                                    18

<210> SEQ ID NO 238
<211> LENGTH: 8
<212> TYPE: DNA
<213> ORGANISM: Artificial Sequence
<220> FEATURE:
<223> OTHER INFORMATION: Synthetic

<400> SEQUENCE: 238 ctctgcct                                                                8

```
<210> SEQ ID NO 239
<211> LENGTH: 20
<212> TYPE: DNA
<213> ORGANISM: Artificial Sequence
<220> FEATURE:
<223> OTHER INFORMATION: Synthetic

<400> SEQUENCE: 239
atgtgggcaa tgtcatcaaa                                              20

<210> SEQ ID NO 240
<211> LENGTH: 22
<212> TYPE: DNA
<213> ORGANISM: Artificial Sequence
<220> FEATURE:
<223> OTHER INFORMATION: Synthetic

<400> SEQUENCE: 240
aagcacttgc tacctcttgc tc                                           22

<210> SEQ ID NO 241
<211> LENGTH: 8
<212> TYPE: DNA
<213> ORGANISM: Artificial Sequence
<220> FEATURE:
<223> OTHER INFORMATION: Synthetic

<400> SEQUENCE: 241 ctcctcca                                                            8

<210> SEQ ID NO 242
<211> LENGTH: 20
<212> TYPE: DNA
<213> ORGANISM: Artificial Sequence
<220> FEATURE:
<223> OTHER INFORMATION: Synthetic

<400> SEQUENCE: 242
ctggagatct gcctgaagga                                              20

<210> SEQ ID NO 243
<211> LENGTH: 19
<212> TYPE: DNA
<213> ORGANISM: Artificial Sequence
<220> FEATURE:
<223> OTHER INFORMATION: Synthetic

<400> SEQUENCE: 243
gagacgaccg ggtcagatt                                               19

<210> SEQ ID NO 244
<211> LENGTH: 8
<212> TYPE: DNA
<213> ORGANISM: Artificial Sequence
<220> FEATURE:
<223> OTHER INFORMATION: Synthetic

<400> SEQUENCE: 244 tgctgtcc                                                            8

<210> SEQ ID NO 245
<211> LENGTH: 20
<212> TYPE: DNA
<213> ORGANISM: Artificial Sequence
<220> FEATURE:
<223> OTHER INFORMATION: Synthetic
```

<400> SEQUENCE: 245
ccttcctgtt ggatttggag                                            20

<210> SEQ ID NO 246
<211> LENGTH: 18
<212> TYPE: DNA
<213> ORGANISM: Artificial Sequence
<220> FEATURE:
<223> OTHER INFORMATION: Synthetic

<400> SEQUENCE: 246
ggccacaccg atacatgc                                              18

<210> SEQ ID NO 247
<211> LENGTH: 8
<212> TYPE: DNA
<213> ORGANISM: Artificial Sequence
<220> FEATURE:
<223> OTHER INFORMATION: Synthetic

<400> SEQUENCE: 247 ctgcttcc                                                          8

<210> SEQ ID NO 248
<211> LENGTH: 18
<212> TYPE: DNA
<213> ORGANISM: Artificial Sequence
<220> FEATURE:
<223> OTHER INFORMATION: Synthetic

<400> SEQUENCE: 248
gctggggaac gacaacat                                              18

<210> SEQ ID NO 249
<211> LENGTH: 20
<212> TYPE: DNA
<213> ORGANISM: Artificial Sequence
<220> FEATURE:
<223> OTHER INFORMATION: Synthetic

<400> SEQUENCE: 249
cctcaaagtc caccaggtct                                            20

<210> SEQ ID NO 250
<211> LENGTH: 8
<212> TYPE: DNA
<213> ORGANISM: Artificial Sequence
<220> FEATURE:
<223> OTHER INFORMATION: Synthetic

<400> SEQUENCE: 250 agctggag                                                          8

<210> SEQ ID NO 251
<211> LENGTH: 20
<212> TYPE: DNA
<213> ORGANISM: Artificial Sequence
<220> FEATURE:
<223> OTHER INFORMATION: Synthetic

<400> SEQUENCE: 251
cttctccaac gacatcatgc                                            20

<210> SEQ ID NO 252
<211> LENGTH: 18

```
<212> TYPE: DNA
<213> ORGANISM: Artificial Sequence
<220> FEATURE:
<223> OTHER INFORMATION: Synthetic

<400> SEQUENCE: 252
acagctctgg tccgcttg                                                          18

<210> SEQ ID NO 253
<211> LENGTH: 8
<212> TYPE: DNA
<213> ORGANISM: Artificial Sequence
<220> FEATURE:
<223> OTHER INFORMATION: Synthetic

<400> SEQUENCE: 253 cctggagc                                                                      8

<210> SEQ ID NO 254
<211> LENGTH: 22
<212> TYPE: DNA
<213> ORGANISM: Artificial Sequence
<220> FEATURE:
<223> OTHER INFORMATION: Synthetic

<400> SEQUENCE: 254
tggaaaaacg gtactgatga aa                                                     22

<210> SEQ ID NO 255
<211> LENGTH: 21
<212> TYPE: DNA
<213> ORGANISM: Artificial Sequence
<220> FEATURE:
<223> OTHER INFORMATION: Synthetic

<400> SEQUENCE: 255
aaccctcgaa cttgaacaca a                                                      21

<210> SEQ ID NO 256
<211> LENGTH: 8
<212> TYPE: DNA
<213> ORGANISM: Artificial Sequence
<220> FEATURE:
<223> OTHER INFORMATION: Synthetic

<400> SEQUENCE: 256 ccagggca                                                                      8

<210> SEQ ID NO 257
<211> LENGTH: 20
<212> TYPE: DNA
<213> ORGANISM: Artificial Sequence
<220> FEATURE:
<223> OTHER INFORMATION: Synthetic

<400> SEQUENCE: 257
acaaccccca gtctcaaatg                                                        20

<210> SEQ ID NO 258
<211> LENGTH: 19
<212> TYPE: DNA
<213> ORGANISM: Artificial Sequence
<220> FEATURE:
<223> OTHER INFORMATION: Synthetic

<400> SEQUENCE: 258
```

```
tgccgtcgtt actgtggag                                                    19

<210> SEQ ID NO 259
<211> LENGTH: 8
<212> TYPE: DNA
<213> ORGANISM: Artificial Sequence
<220> FEATURE:
<223> OTHER INFORMATION: Synthetic

<400> SEQUENCE: 259 ctgcttcc                                                                 8

<210> SEQ ID NO 260
<211> LENGTH: 19
<212> TYPE: DNA
<213> ORGANISM: Artificial Sequence
<220> FEATURE:
<223> OTHER INFORMATION: Synthetic

<400> SEQUENCE: 260
ggactgtgca cttgctggt                                                    19

<210> SEQ ID NO 261
<211> LENGTH: 18
<212> TYPE: DNA
<213> ORGANISM: Artificial Sequence
<220> FEATURE:
<223> OTHER INFORMATION: Synthetic

<400> SEQUENCE: 261
attgctgagg gggctctt                                                     18

<210> SEQ ID NO 262
<211> LENGTH: 8
<212> TYPE: DNA
<213> ORGANISM: Artificial Sequence
<220> FEATURE:
<223> OTHER INFORMATION: Synthetic

<400> SEQUENCE: 262 ctccttcc                                                                 8

<210> SEQ ID NO 263
<211> LENGTH: 23
<212> TYPE: DNA
<213> ORGANISM: Artificial Sequence
<220> FEATURE:
<223> OTHER INFORMATION: Synthetic

<400> SEQUENCE: 263
ggagaaaaga gtctaacctg caa                                               23

<210> SEQ ID NO 264
<211> LENGTH: 27
<212> TYPE: DNA
<213> ORGANISM: Artificial Sequence
<220> FEATURE:
<223> OTHER INFORMATION: Synthetic

<400> SEQUENCE: 264
gatgtattaa atgtcaccac aaagtca                                           27

<210> SEQ ID NO 265
<211> LENGTH: 8
<212> TYPE: DNA
<213> ORGANISM: Artificial Sequence
```

<220> FEATURE:
<223> OTHER INFORMATION: Synthetic

<400> SEQUENCE: 265 ctcctcca                                                                 8

<210> SEQ ID NO 266
<211> LENGTH: 20
<212> TYPE: DNA
<213> ORGANISM: Artificial Sequence
<220> FEATURE:
<223> OTHER INFORMATION: Synthetic

<400> SEQUENCE: 266
cagcaatgtg gtccaactca                                                    20

<210> SEQ ID NO 267
<211> LENGTH: 18
<212> TYPE: DNA
<213> ORGANISM: Artificial Sequence
<220> FEATURE:
<223> OTHER INFORMATION: Synthetic

<400> SEQUENCE: 267
gagggcgttg tgatccag                                                      18

<210> SEQ ID NO 268
<211> LENGTH: 8
<212> TYPE: DNA
<213> ORGANISM: Artificial Sequence
<220> FEATURE:
<223> OTHER INFORMATION: Synthetic

<400> SEQUENCE: 268 tggctgtg                                                                 8

<210> SEQ ID NO 269
<211> LENGTH: 22
<212> TYPE: DNA
<213> ORGANISM: Artificial Sequence
<220> FEATURE:
<223> OTHER INFORMATION: Synthetic

<400> SEQUENCE: 269
cgttgcttca gaaaagactt ca                                                 22

<210> SEQ ID NO 270
<211> LENGTH: 26
<212> TYPE: DNA
<213> ORGANISM: Artificial Sequence
<220> FEATURE:
<223> OTHER INFORMATION: Synthetic

<400> SEQUENCE: 270
gaaaaatgac acagaatata ccatcc                                             26

<210> SEQ ID NO 271
<211> LENGTH: 8
<212> TYPE: DNA
<213> ORGANISM: Artificial Sequence
<220> FEATURE:
<223> OTHER INFORMATION: Synthetic

<400> SEQUENCE: 271 tccagtgt                                                                 8

<210> SEQ ID NO 272
<211> LENGTH: 21
<212> TYPE: DNA
<213> ORGANISM: Artificial Sequence
<220> FEATURE:
<223> OTHER INFORMATION: Synthetic

<400> SEQUENCE: 272
tgatctcctt gatcctgttg g                                     21

<210> SEQ ID NO 273
<211> LENGTH: 24
<212> TYPE: DNA
<213> ORGANISM: Artificial Sequence
<220> FEATURE:
<223> OTHER INFORMATION: Synthetic

<400> SEQUENCE: 273
ttcttcttgt gccattattc actt                                  24

<210> SEQ ID NO 274
<211> LENGTH: 8
<212> TYPE: DNA
<213> ORGANISM: Artificial Sequence
<220> FEATURE:
<223> OTHER INFORMATION: Synthetic

<400> SEQUENCE: 274 cccagcag                                                     8

<210> SEQ ID NO 275
<211> LENGTH: 18
<212> TYPE: DNA
<213> ORGANISM: Artificial Sequence
<220> FEATURE:
<223> OTHER INFORMATION: Synthetic

<400> SEQUENCE: 275
accacatccc gaccagtg                                         18

<210> SEQ ID NO 276
<211> LENGTH: 22
<212> TYPE: DNA
<213> ORGANISM: Artificial Sequence
<220> FEATURE:
<223> OTHER INFORMATION: Synthetic

<400> SEQUENCE: 276
ccttgtagcc accataggac tg                                    22

<210> SEQ ID NO 277
<211> LENGTH: 8
<212> TYPE: DNA
<213> ORGANISM: Artificial Sequence
<220> FEATURE:
<223> OTHER INFORMATION: Synthetic

<400> SEQUENCE: 277 ccagggca                                                     8

<210> SEQ ID NO 278
<211> LENGTH: 21
<212> TYPE: DNA
<213> ORGANISM: Artificial Sequence
<220> FEATURE:
<223> OTHER INFORMATION: Synthetic

<400> SEQUENCE: 278
aaccctcgag tcaatcattt g                                          21

<210> SEQ ID NO 279
<211> LENGTH: 24
<212> TYPE: DNA
<213> ORGANISM: Artificial Sequence
<220> FEATURE:
<223> OTHER INFORMATION: Synthetic

<400> SEQUENCE: 279
ttgatctttt catagagctg gaag                                       24

<210> SEQ ID NO 280
<211> LENGTH: 8
<212> TYPE: DNA
<213> ORGANISM: Artificial Sequence
<220> FEATURE:
<223> OTHER INFORMATION: Synthetic

<400> SEQUENCE: 280 cctggagc                                                          8

<210> SEQ ID NO 281
<211> LENGTH: 20
<212> TYPE: DNA
<213> ORGANISM: Artificial Sequence
<220> FEATURE:
<223> OTHER INFORMATION: Synthetic

<400> SEQUENCE: 281
gcagggagat accgctgtta                                            20

<210> SEQ ID NO 282
<211> LENGTH: 20
<212> TYPE: DNA
<213> ORGANISM: Artificial Sequence
<220> FEATURE:
<223> OTHER INFORMATION: Synthetic

<400> SEQUENCE: 282
tgagagggtg ggtttgttgt                                            20

<210> SEQ ID NO 283
<211> LENGTH: 8
<212> TYPE: DNA
<213> ORGANISM: Artificial Sequence
<220> FEATURE:
<223> OTHER INFORMATION: Synthetic

<400> SEQUENCE: 283 ccaccacc                                                          8

<210> SEQ ID NO 284
<211> LENGTH: 25
<212> TYPE: DNA
<213> ORGANISM: Artificial Sequence
<220> FEATURE:
<223> OTHER INFORMATION: Synthetic

<400> SEQUENCE: 284
caatatccag gagctcaatg tctac                                      25

<210> SEQ ID NO 285

```
<211> LENGTH: 20
<212> TYPE: DNA
<213> ORGANISM: Artificial Sequence
<220> FEATURE:
<223> OTHER INFORMATION: Synthetic

<400> SEQUENCE: 285
tgagctcatc caactgagca                                                   20

<210> SEQ ID NO 286
<211> LENGTH: 8
<212> TYPE: DNA
<213> ORGANISM: Artificial Sequence
<220> FEATURE:
<223> OTHER INFORMATION: Synthetic

<400> SEQUENCE: 286 ctctgcca                                                                 8

<210> SEQ ID NO 287
<211> LENGTH: 21
<212> TYPE: DNA
<213> ORGANISM: Artificial Sequence
<220> FEATURE:
<223> OTHER INFORMATION: Synthetic

<400> SEQUENCE: 287
tgtgtacact gcaggcaaat g                                                 21

<210> SEQ ID NO 288
<211> LENGTH: 20
<212> TYPE: DNA
<213> ORGANISM: Artificial Sequence
<220> FEATURE:
<223> OTHER INFORMATION: Synthetic

<400> SEQUENCE: 288
ggatcagggt cactgctttg                                                   20

<210> SEQ ID NO 289
<211> LENGTH: 8
<212> TYPE: DNA
<213> ORGANISM: Artificial Sequence
<220> FEATURE:
<223> OTHER INFORMATION: Synthetic

<400> SEQUENCE: 289 ctctgcca                                                                 8

<210> SEQ ID NO 290
<211> LENGTH: 20
<212> TYPE: DNA
<213> ORGANISM: Artificial Sequence
<220> FEATURE:
<223> OTHER INFORMATION: Synthetic

<400> SEQUENCE: 290
taagcctgat gacccctgtc                                                   20

<210> SEQ ID NO 291
<211> LENGTH: 24
<212> TYPE: DNA
<213> ORGANISM: Artificial Sequence
<220> FEATURE:
<223> OTHER INFORMATION: Synthetic

<400> SEQUENCE: 291
```

-continued

```
caattctttc tgcatggaat acct                                          24

<210> SEQ ID NO 292
<211> LENGTH: 8
<212> TYPE: DNA
<213> ORGANISM: Artificial Sequence
<220> FEATURE:
<223> OTHER INFORMATION: Synthetic

<400> SEQUENCE: 292 agctggga                                                             8

<210> SEQ ID NO 293
<211> LENGTH: 23
<212> TYPE: DNA
<213> ORGANISM: Artificial Sequence
<220> FEATURE:
<223> OTHER INFORMATION: Synthetic

<400> SEQUENCE: 293
ccgagatcta cgagttccat aaa                                           23

<210> SEQ ID NO 294
<211> LENGTH: 18
<212> TYPE: DNA
<213> ORGANISM: Artificial Sequence
<220> FEATURE:
<223> OTHER INFORMATION: Synthetic

<400> SEQUENCE: 294
ctgcccgtca aaccactt                                                 18

<210> SEQ ID NO 295
<211> LENGTH: 8
<212> TYPE: DNA
<213> ORGANISM: Artificial Sequence
<220> FEATURE:
<223> OTHER INFORMATION: Synthetic

<400> SEQUENCE: 295 ctggggct                                                             8

<210> SEQ ID NO 296
<211> LENGTH: 23
<212> TYPE: DNA
<213> ORGANISM: Artificial Sequence
<220> FEATURE:
<223> OTHER INFORMATION: Synthetic

<400> SEQUENCE: 296
caactacctt gaaccagttg agc                                           23

<210> SEQ ID NO 297
<211> LENGTH: 18
<212> TYPE: DNA
<213> ORGANISM: Artificial Sequence
<220> FEATURE:
<223> OTHER INFORMATION: Synthetic

<400> SEQUENCE: 297
atgtcggact gcggagag                                                 18

<210> SEQ ID NO 298
<211> LENGTH: 8
<212> TYPE: DNA
```

```
<213> ORGANISM: Artificial Sequence
<220> FEATURE:
<223> OTHER INFORMATION: Synthetic

<400> SEQUENCE: 298 agctggag                                                                    8

<210> SEQ ID NO 299
<211> LENGTH: 18
<212> TYPE: DNA
<213> ORGANISM: Artificial Sequence
<220> FEATURE:
<223> OTHER INFORMATION: Synthetic

<400> SEQUENCE: 299
gcagctccga gagcagag                                                        18

<210> SEQ ID NO 300
<211> LENGTH: 20
<212> TYPE: DNA
<213> ORGANISM: Artificial Sequence
<220> FEATURE:
<223> OTHER INFORMATION: Synthetic

<400> SEQUENCE: 300
ccgactgagg aggaagatca                                                      20

<210> SEQ ID NO 301
<211> LENGTH: 8
<212> TYPE: DNA
<213> ORGANISM: Artificial Sequence
<220> FEATURE:
<223> OTHER INFORMATION: Synthetic

<400> SEQUENCE: 301 cctggaga                                                                    8

<210> SEQ ID NO 302
<211> LENGTH: 24
<212> TYPE: DNA
<213> ORGANISM: Artificial Sequence
<220> FEATURE:
<223> OTHER INFORMATION: Synthetic

<400> SEQUENCE: 302
gtggatgtca gaattggtat gact                                                 24

<210> SEQ ID NO 303
<211> LENGTH: 20
<212> TYPE: DNA
<213> ORGANISM: Artificial Sequence
<220> FEATURE:
<223> OTHER INFORMATION: Synthetic

<400> SEQUENCE: 303
caaaccagtg agttccaacg                                                      20

<210> SEQ ID NO 304
<211> LENGTH: 8
<212> TYPE: DNA
<213> ORGANISM: Artificial Sequence
<220> FEATURE:
<223> OTHER INFORMATION: Synthetic

<400> SEQUENCE: 304 cagccacc                                                                    8
```

<210> SEQ ID NO 305
<211> LENGTH: 20
<212> TYPE: DNA
<213> ORGANISM: Artificial Sequence
<220> FEATURE:
<223> OTHER INFORMATION: Synthetic

<400> SEQUENCE: 305
tgagatcagg catgcaacag                                                    20

<210> SEQ ID NO 306
<211> LENGTH: 20
<212> TYPE: DNA
<213> ORGANISM: Artificial Sequence
<220> FEATURE:
<223> OTHER INFORMATION: Synthetic

<400> SEQUENCE: 306
gtacagttcc cgctgacgtt                                                    20

<210> SEQ ID NO 307
<211> LENGTH: 8
<212> TYPE: DNA
<213> ORGANISM: Artificial Sequence
<220> FEATURE:
<223> OTHER INFORMATION: Synthetic

<400> SEQUENCE: 307 ctggggct                                                                  8

<210> SEQ ID NO 308
<211> LENGTH: 19
<212> TYPE: DNA
<213> ORGANISM: Artificial Sequence
<220> FEATURE:
<223> OTHER INFORMATION: Synthetic

<400> SEQUENCE: 308
catcctgcct gcaaactca                                                     19

<210> SEQ ID NO 309
<211> LENGTH: 20
<212> TYPE: DNA
<213> ORGANISM: Artificial Sequence
<220> FEATURE:
<223> OTHER INFORMATION: Synthetic

<400> SEQUENCE: 309
cctcagttcc tgcctcatct                                                    20

<210> SEQ ID NO 310
<211> LENGTH: 8
<212> TYPE: DNA
<213> ORGANISM: Artificial Sequence
<220> FEATURE:
<223> OTHER INFORMATION: Synthetic

<400> SEQUENCE: 310 ctgcttcc                                                                  8

<210> SEQ ID NO 311
<211> LENGTH: 24
<212> TYPE: DNA
<213> ORGANISM: Artificial Sequence
<220> FEATURE:

-continued

<223> OTHER INFORMATION: Synthetic

<400> SEQUENCE: 311
tgttaacatc atccgtacat tcct                                    24

<210> SEQ ID NO 312
<211> LENGTH: 18
<212> TYPE: DNA
<213> ORGANISM: Artificial Sequence
<220> FEATURE:
<223> OTHER INFORMATION: Synthetic

<400> SEQUENCE: 312
ctttggcggt tgatcctc                                           18

<210> SEQ ID NO 313
<211> LENGTH: 8
<212> TYPE: DNA
<213> ORGANISM: Artificial Sequence
<220> FEATURE:
<223> OTHER INFORMATION: Synthetic

<400> SEQUENCE: 313 ctgcccca                                                       8

<210> SEQ ID NO 314
<211> LENGTH: 19
<212> TYPE: DNA
<213> ORGANISM: Artificial Sequence
<220> FEATURE:
<223> OTHER INFORMATION: Synthetic

<400> SEQUENCE: 314
gacggatgtt agcctgctg                                          19

<210> SEQ ID NO 315
<211> LENGTH: 18
<212> TYPE: DNA
<213> ORGANISM: Artificial Sequence
<220> FEATURE:
<223> OTHER INFORMATION: Synthetic

<400> SEQUENCE: 315
tggggatttg gtttggtg                                           18

<210> SEQ ID NO 316
<211> LENGTH: 8
<212> TYPE: DNA
<213> ORGANISM: Artificial Sequence
<220> FEATURE:
<223> OTHER INFORMATION: Synthetic

<400> SEQUENCE: 316 ctggtctc                                                       8

<210> SEQ ID NO 317
<211> LENGTH: 20
<212> TYPE: DNA
<213> ORGANISM: Artificial Sequence
<220> FEATURE:
<223> OTHER INFORMATION: Synthetic

<400> SEQUENCE: 317
aggctgcaca gacaacttga                                         20

```
<210> SEQ ID NO 318
<211> LENGTH: 19
<212> TYPE: DNA
<213> ORGANISM: Artificial Sequence
<220> FEATURE:
<223> OTHER INFORMATION: Synthetic

<400> SEQUENCE: 318
atggatgacg cttcccttc                                               19

<210> SEQ ID NO 319
<211> LENGTH: 8
<212> TYPE: DNA
<213> ORGANISM: Artificial Sequence
<220> FEATURE:
<223> OTHER INFORMATION: Synthetic

<400> SEQUENCE: 319 cctcagcc                                                            8

<210> SEQ ID NO 320
<211> LENGTH: 18
<212> TYPE: DNA
<213> ORGANISM: Artificial Sequence
<220> FEATURE:
<223> OTHER INFORMATION: Synthetic

<400> SEQUENCE: 320
ccagctcctt tcggctct                                                18

<210> SEQ ID NO 321
<211> LENGTH: 18
<212> TYPE: DNA
<213> ORGANISM: Artificial Sequence
<220> FEATURE:
<223> OTHER INFORMATION: Synthetic

<400> SEQUENCE: 321
gtgagctggg caagaagg                                                18

<210> SEQ ID NO 322
<211> LENGTH: 8
<212> TYPE: DNA
<213> ORGANISM: Artificial Sequence
<220> FEATURE:
<223> OTHER INFORMATION: Synthetic

<400> SEQUENCE: 322 tgctgtcc                                                            8

<210> SEQ ID NO 323
<211> LENGTH: 21
<212> TYPE: DNA
<213> ORGANISM: Artificial Sequence
<220> FEATURE:
<223> OTHER INFORMATION: Synthetic

<400> SEQUENCE: 323
tgggaaatag aagccagtga a                                            21

<210> SEQ ID NO 324
<211> LENGTH: 25
<212> TYPE: DNA
<213> ORGANISM: Artificial Sequence
<220> FEATURE:
<223> OTHER INFORMATION: Synthetic
```

-continued

<400> SEQUENCE: 324
cctttaggat ctttactgca acatc                                          25

<210> SEQ ID NO 325
<211> LENGTH: 8
<212> TYPE: DNA
<213> ORGANISM: Artificial Sequence
<220> FEATURE:
<223> OTHER INFORMATION: Synthetic

<400> SEQUENCE: 325 tctgctgc                                                              8

<210> SEQ ID NO 326
<211> LENGTH: 25
<212> TYPE: DNA
<213> ORGANISM: Artificial Sequence
<220> FEATURE:
<223> OTHER INFORMATION: Synthetic

<400> SEQUENCE: 326
tgaagaaaag accaaacttg gtaaa                                           25

<210> SEQ ID NO 327
<211> LENGTH: 19
<212> TYPE: DNA
<213> ORGANISM: Artificial Sequence
<220> FEATURE:
<223> OTHER INFORMATION: Synthetic

<400> SEQUENCE: 327
agttgggcag ccaaagagt                                                 19

<210> SEQ ID NO 328
<211> LENGTH: 8
<212> TYPE: DNA
<213> ORGANISM: Artificial Sequence
<220> FEATURE:
<223> OTHER INFORMATION: Synthetic

<400> SEQUENCE: 328 ctggggcc                                                              8

<210> SEQ ID NO 329
<211> LENGTH: 19
<212> TYPE: DNA
<213> ORGANISM: Artificial Sequence
<220> FEATURE:
<223> OTHER INFORMATION: Synthetic

<400> SEQUENCE: 329
gccccagtgt cagtttgtg                                                 19

<210> SEQ ID NO 330
<211> LENGTH: 21
<212> TYPE: DNA
<213> ORGANISM: Artificial Sequence
<220> FEATURE:
<223> OTHER INFORMATION: Synthetic

<400> SEQUENCE: 330
ccaaagggtg agtacagtcc a                                              21

<210> SEQ ID NO 331
<211> LENGTH: 8

```
<212> TYPE: DNA
<213> ORGANISM: Artificial Sequence
<220> FEATURE:
<223> OTHER INFORMATION: Synthetic

<400> SEQUENCE: 331 cccagccc                                                               8

<210> SEQ ID NO 332
<211> LENGTH: 20
<212> TYPE: DNA
<213> ORGANISM: Artificial Sequence
<220> FEATURE:
<223> OTHER INFORMATION: Synthetic

<400> SEQUENCE: 332
ttagttggac cggaagtggt                                                 20

<210> SEQ ID NO 333
<211> LENGTH: 19
<212> TYPE: DNA
<213> ORGANISM: Artificial Sequence
<220> FEATURE:
<223> OTHER INFORMATION: Synthetic

<400> SEQUENCE: 333
caggtgctga cactgcaca                                                  19

<210> SEQ ID NO 334
<211> LENGTH: 8
<212> TYPE: DNA
<213> ORGANISM: Artificial Sequence
<220> FEATURE:
<223> OTHER INFORMATION: Synthetic

<400> SEQUENCE: 334 tggtgatg                                                               8

<210> SEQ ID NO 335
<211> LENGTH: 21
<212> TYPE: DNA
<213> ORGANISM: Artificial Sequence
<220> FEATURE:
<223> OTHER INFORMATION: Synthetic

<400> SEQUENCE: 335
gcacctggaa aatgaactca c                                               21

<210> SEQ ID NO 336
<211> LENGTH: 21
<212> TYPE: DNA
<213> ORGANISM: Artificial Sequence
<220> FEATURE:
<223> OTHER INFORMATION: Synthetic

<400> SEQUENCE: 336
gggtaaatgt aagctggcag a                                               21

<210> SEQ ID NO 337
<211> LENGTH: 8
<212> TYPE: DNA
<213> ORGANISM: Artificial Sequence
<220> FEATURE:
<223> OTHER INFORMATION: Synthetic

<400> SEQUENCE: 337
```

-continued tccaggtc                                                            8

<210> SEQ ID NO 338
<211> LENGTH: 20
<212> TYPE: DNA
<213> ORGANISM: Artificial Sequence
<220> FEATURE:
<223> OTHER INFORMATION: Synthetic

<400> SEQUENCE: 338
tggagacatg agcgatgaga                                              20

<210> SEQ ID NO 339
<211> LENGTH: 20
<212> TYPE: DNA
<213> ORGANISM: Artificial Sequence
<220> FEATURE:
<223> OTHER INFORMATION: Synthetic

<400> SEQUENCE: 339
gactcctggc aacgaaactg                                              20

<210> SEQ ID NO 340
<211> LENGTH: 8
<212> TYPE: DNA
<213> ORGANISM: Artificial Sequence
<220> FEATURE:
<223> OTHER INFORMATION: Synthetic

<400> SEQUENCE: 340 cccagcag                                                            8

<210> SEQ ID NO 341
<211> LENGTH: 19
<212> TYPE: DNA
<213> ORGANISM: Artificial Sequence
<220> FEATURE:
<223> OTHER INFORMATION: Synthetic

<400> SEQUENCE: 341
ggtcgcagtt caacaagga                                               19

<210> SEQ ID NO 342
<211> LENGTH: 20
<212> TYPE: DNA
<213> ORGANISM: Artificial Sequence
<220> FEATURE:
<223> OTHER INFORMATION: Synthetic

<400> SEQUENCE: 342
gtccaggaca ccatcaaacc                                              20

<210> SEQ ID NO 343
<211> LENGTH: 8
<212> TYPE: DNA
<213> ORGANISM: Artificial Sequence
<220> FEATURE:
<223> OTHER INFORMATION: Synthetic

<400> SEQUENCE: 343 cttcctcc                                                            8

<210> SEQ ID NO 344
<211> LENGTH: 19
<212> TYPE: DNA
<213> ORGANISM: Artificial Sequence
<220> FEATURE:
<223> OTHER INFORMATION: Synthetic

<400> SEQUENCE: 344
tgcagctgaa ggccataga                                         19

<210> SEQ ID NO 345
<211> LENGTH: 18
<212> TYPE: DNA
<213> ORGANISM: Artificial Sequence
<220> FEATURE:
<223> OTHER INFORMATION: Synthetic

<400> SEQUENCE: 345
cgaattgctg ggacagga                                          18

<210> SEQ ID NO 346
<211> LENGTH: 8
<212> TYPE: DNA
<213> ORGANISM: Artificial Sequence
<220> FEATURE:
<223> OTHER INFORMATION: Synthetic

<400> SEQUENCE: 346 aggagctg                                                      8

<210> SEQ ID NO 347
<211> LENGTH: 20
<212> TYPE: DNA
<213> ORGANISM: Artificial Sequence
<220> FEATURE:
<223> OTHER INFORMATION: Synthetic

<400> SEQUENCE: 347
gtgtcggagg gaactaatgc                                        20

<210> SEQ ID NO 348
<211> LENGTH: 21
<212> TYPE: DNA
<213> ORGANISM: Artificial Sequence
<220> FEATURE:
<223> OTHER INFORMATION: Synthetic

<400> SEQUENCE: 348
tccacttgag gttgacgttc t                                      21

<210> SEQ ID NO 349
<211> LENGTH: 8
<212> TYPE: DNA
<213> ORGANISM: Artificial Sequence
<220> FEATURE:
<223> OTHER INFORMATION: Synthetic

<400> SEQUENCE: 349 ctcctcct                                                      8

<210> SEQ ID NO 350
<211> LENGTH: 27
<212> TYPE: DNA
<213> ORGANISM: Artificial Sequence
<220> FEATURE:
<223> OTHER INFORMATION: Synthetic

<400> SEQUENCE: 350
tgtctccatc aatacagtta cctatga                                27

<210> SEQ ID NO 351
<211> LENGTH: 20
<212> TYPE: DNA
<213> ORGANISM: Artificial Sequence
<220> FEATURE:
<223> OTHER INFORMATION: Synthetic

<400> SEQUENCE: 351
tccttgggta gcatctgcat                                               20

<210> SEQ ID NO 352
<211> LENGTH: 8
<212> TYPE: DNA
<213> ORGANISM: Artificial Sequence
<220> FEATURE:
<223> OTHER INFORMATION: Synthetic

<400> SEQUENCE: 352 cagcctcc                                                             8

<210> SEQ ID NO 353
<211> LENGTH: 25
<212> TYPE: DNA
<213> ORGANISM: Artificial Sequence
<220> FEATURE:
<223> OTHER INFORMATION: Synthetic

<400> SEQUENCE: 353
tctggactgt atcagtgtgt gatct                                         25

<210> SEQ ID NO 354
<211> LENGTH: 18
<212> TYPE: DNA
<213> ORGANISM: Artificial Sequence
<220> FEATURE:
<223> OTHER INFORMATION: Synthetic

<400> SEQUENCE: 354
ccaggggtcc ctgaaaaa                                                 18

<210> SEQ ID NO 355
<211> LENGTH: 8
<212> TYPE: DNA
<213> ORGANISM: Artificial Sequence
<220> FEATURE:
<223> OTHER INFORMATION: Synthetic

<400> SEQUENCE: 355 cagctccc                                                             8

<210> SEQ ID NO 356
<211> LENGTH: 20
<212> TYPE: DNA
<213> ORGANISM: Artificial Sequence
<220> FEATURE:
<223> OTHER INFORMATION: Synthetic

<400> SEQUENCE: 356
accttctcat ttgggccatt                                               20

<210> SEQ ID NO 357
<211> LENGTH: 18
<212> TYPE: DNA
<213> ORGANISM: Artificial Sequence
<220> FEATURE:
<223> OTHER INFORMATION: Synthetic

<400> SEQUENCE: 357
cgatgcagtc ctggctct					18

<210> SEQ ID NO 358
<211> LENGTH: 8
<212> TYPE: DNA
<213> ORGANISM: Artificial Sequence
<220> FEATURE:
<223> OTHER INFORMATION: Synthetic

<400> SEQUENCE: 358 cagcccag					8

<210> SEQ ID NO 359
<211> LENGTH: 20
<212> TYPE: DNA
<213> ORGANISM: Artificial Sequence
<220> FEATURE:
<223> OTHER INFORMATION: Synthetic

<400> SEQUENCE: 359
ttcgggttca gaagatcagg					20

<210> SEQ ID NO 360
<211> LENGTH: 20
<212> TYPE: DNA
<213> ORGANISM: Artificial Sequence
<220> FEATURE:
<223> OTHER INFORMATION: Synthetic

<400> SEQUENCE: 360
ggatccagga acgctaacat					20

<210> SEQ ID NO 361
<211> LENGTH: 8
<212> TYPE: DNA
<213> ORGANISM: Artificial Sequence
<220> FEATURE:
<223> OTHER INFORMATION: Synthetic

<400> SEQUENCE: 361 ctccacct					8

<210> SEQ ID NO 362
<211> LENGTH: 21
<212> TYPE: DNA
<213> ORGANISM: Artificial Sequence
<220> FEATURE:
<223> OTHER INFORMATION: Synthetic

<400> SEQUENCE: 362
gaccagctaa ccaacgacaa a					21

<210> SEQ ID NO 363
<211> LENGTH: 20
<212> TYPE: DNA
<213> ORGANISM: Artificial Sequence
<220> FEATURE:
<223> OTHER INFORMATION: Synthetic

<400> SEQUENCE: 363
gaagcatctc ctcctgcaat					20

<210> SEQ ID NO 364

```
<211> LENGTH: 8
<212> TYPE: DNA
<213> ORGANISM: Artificial Sequence
<220> FEATURE:
<223> OTHER INFORMATION: Synthetic

<400> SEQUENCE: 364 cctggagc                                                                   8

<210> SEQ ID NO 365
<211> LENGTH: 19
<212> TYPE: DNA
<213> ORGANISM: Artificial Sequence
<220> FEATURE:
<223> OTHER INFORMATION: Synthetic

<400> SEQUENCE: 365
gtgactacgt gcgccagac                                                      19

<210> SEQ ID NO 366
<211> LENGTH: 21
<212> TYPE: DNA
<213> ORGANISM: Artificial Sequence
<220> FEATURE:
<223> OTHER INFORMATION: Synthetic

<400> SEQUENCE: 366
cgtagcaatg agcttctcca c                                                   21

<210> SEQ ID NO 367
<211> LENGTH: 8
<212> TYPE: DNA
<213> ORGANISM: Artificial Sequence
<220> FEATURE:
<223> OTHER INFORMATION: Synthetic

<400> SEQUENCE: 367 cttccagc                                                                   8

<210> SEQ ID NO 368
<211> LENGTH: 18
<212> TYPE: DNA
<213> ORGANISM: Artificial Sequence
<220> FEATURE:
<223> OTHER INFORMATION: Synthetic

<400> SEQUENCE: 368
attggcaatg agcggttc                                                       18

<210> SEQ ID NO 369
<211> LENGTH: 21
<212> TYPE: DNA
<213> ORGANISM: Artificial Sequence
<220> FEATURE:
<223> OTHER INFORMATION: Synthetic

<400> SEQUENCE: 369
tgaaggtagt ttcgtggatg c                                                   21

<210> SEQ ID NO 370
<211> LENGTH: 8
<212> TYPE: DNA
<213> ORGANISM: Artificial Sequence
<220> FEATURE:
<223> OTHER INFORMATION: Synthetic

<400> SEQUENCE: 370
```

-continued caggcagc                                                               8

<210> SEQ ID NO 371
<211> LENGTH: 20
<212> TYPE: DNA
<213> ORGANISM: Artificial Sequence
<220> FEATURE:
<223> OTHER INFORMATION: Synthetic

<400> SEQUENCE: 371
ttggtgttgc tgaattgctt                                                  20

<210> SEQ ID NO 372
<211> LENGTH: 20
<212> TYPE: DNA
<213> ORGANISM: Artificial Sequence
<220> FEATURE:
<223> OTHER INFORMATION: Synthetic

<400> SEQUENCE: 372
accctccaga aagcacaatg                                                  20

<210> SEQ ID NO 373
<211> LENGTH: 8
<212> TYPE: DNA
<213> ORGANISM: Artificial Sequence
<220> FEATURE:
<223> OTHER INFORMATION: Synthetic

<400> SEQUENCE: 373 ctctgcca                                                               8

<210> SEQ ID NO 374
<211> LENGTH: 21
<212> TYPE: DNA
<213> ORGANISM: Artificial Sequence
<220> FEATURE:
<223> OTHER INFORMATION: Synthetic

<400> SEQUENCE: 374
tttattgtca accaccccaa g                                                21

<210> SEQ ID NO 375
<211> LENGTH: 20
<212> TYPE: DNA
<213> ORGANISM: Artificial Sequence
<220> FEATURE:
<223> OTHER INFORMATION: Synthetic

<400> SEQUENCE: 375
ccttagtctt cccggattgc                                                  20

<210> SEQ ID NO 376
<211> LENGTH: 8
<212> TYPE: DNA
<213> ORGANISM: Artificial Sequence
<220> FEATURE:
<223> OTHER INFORMATION: Synthetic

<400> SEQUENCE: 376 cttcctcc                                                               8

<210> SEQ ID NO 377
<211> LENGTH: 18
<212> TYPE: DNA

<213> ORGANISM: Artificial Sequence
<220> FEATURE:
<223> OTHER INFORMATION: Synthetic

<400> SEQUENCE: 377
cccagcactc ccatcaag                                                    18

<210> SEQ ID NO 378
<211> LENGTH: 20
<212> TYPE: DNA
<213> ORGANISM: Artificial Sequence
<220> FEATURE:
<223> OTHER INFORMATION: Synthetic

<400> SEQUENCE: 378
gtggcagcat cactgtcatc                                                  20

<210> SEQ ID NO 379
<211> LENGTH: 8
<212> TYPE: DNA
<213> ORGANISM: Artificial Sequence
<220> FEATURE:
<223> OTHER INFORMATION: Synthetic

<400> SEQUENCE: 379 tcctgctc                                                                8

<210> SEQ ID NO 380
<211> LENGTH: 22
<212> TYPE: DNA
<213> ORGANISM: Artificial Sequence
<220> FEATURE:
<223> OTHER INFORMATION: Synthetic

<400> SEQUENCE: 380
ggacaatcga acgtaaacaa ca                                               22

<210> SEQ ID NO 381
<211> LENGTH: 23
<212> TYPE: DNA
<213> ORGANISM: Artificial Sequence
<220> FEATURE:
<223> OTHER INFORMATION: Synthetic

<400> SEQUENCE: 381
tgaatttgtg aaacagatga agc                                              23

<210> SEQ ID NO 382
<211> LENGTH: 8
<212> TYPE: DNA
<213> ORGANISM: Artificial Sequence
<220> FEATURE:
<223> OTHER INFORMATION: Synthetic

<400> SEQUENCE: 382 caggcagc                                                                8

<210> SEQ ID NO 383
<211> LENGTH: 22
<212> TYPE: DNA
<213> ORGANISM: Artificial Sequence
<220> FEATURE:
<223> OTHER INFORMATION: Synthetic

<400> SEQUENCE: 383
gaaggatgta tcaaatgcag ga                                               22

<210> SEQ ID NO 384
<211> LENGTH: 21
<212> TYPE: DNA
<213> ORGANISM: Artificial Sequence
<220> FEATURE:
<223> OTHER INFORMATION: Synthetic

<400> SEQUENCE: 384
cttggagcca gatgttacca g				21

<210> SEQ ID NO 385
<211> LENGTH: 8
<212> TYPE: DNA
<213> ORGANISM: Artificial Sequence
<220> FEATURE:
<223> OTHER INFORMATION: Synthetic

<400> SEQUENCE: 385 ctcctcca				8

<210> SEQ ID NO 386
<211> LENGTH: 19
<212> TYPE: DNA
<213> ORGANISM: Artificial Sequence
<220> FEATURE:
<223> OTHER INFORMATION: Synthetic

<400> SEQUENCE: 386
ctgcaatggc atgaaaagg				19

<210> SEQ ID NO 387
<211> LENGTH: 20
<212> TYPE: DNA
<213> ORGANISM: Artificial Sequence
<220> FEATURE:
<223> OTHER INFORMATION: Synthetic

<400> SEQUENCE: 387
tgcagtcaag acacgaacaa				20

<210> SEQ ID NO 388
<211> LENGTH: 8
<212> TYPE: DNA
<213> ORGANISM: Artificial Sequence
<220> FEATURE:
<223> OTHER INFORMATION: Synthetic

<400> SEQUENCE: 388 ccaggagg				8

<210> SEQ ID NO 389
<211> LENGTH: 20
<212> TYPE: DNA
<213> ORGANISM: Artificial Sequence
<220> FEATURE:
<223> OTHER INFORMATION: Synthetic

<400> SEQUENCE: 389
cagtgagtcg tgtcctgtgc				20

<210> SEQ ID NO 390
<211> LENGTH: 24
<212> TYPE: DNA
<213> ORGANISM: Artificial Sequence
<220> FEATURE:

<223> OTHER INFORMATION: Synthetic

<400> SEQUENCE: 390
tgtgatttga tctacaggaa aagg                                        24

<210> SEQ ID NO 391
<211> LENGTH: 8
<212> TYPE: DNA
<213> ORGANISM: Artificial Sequence
<220> FEATURE:
<223> OTHER INFORMATION: Synthetic

<400> SEQUENCE: 391 tgggcagc                                                           8

<210> SEQ ID NO 392
<211> LENGTH: 19
<212> TYPE: DNA
<213> ORGANISM: Artificial Sequence
<220> FEATURE:
<223> OTHER INFORMATION: Synthetic

<400> SEQUENCE: 392
gatccaagcc atcatgcac                                              19

<210> SEQ ID NO 393
<211> LENGTH: 21
<212> TYPE: DNA
<213> ORGANISM: Artificial Sequence
<220> FEATURE:
<223> OTHER INFORMATION: Synthetic

<400> SEQUENCE: 393
tgatgaactc tggcaaggtc t                                           21

<210> SEQ ID NO 394
<211> LENGTH: 8
<212> TYPE: DNA
<213> ORGANISM: Artificial Sequence
<220> FEATURE:
<223> OTHER INFORMATION: Synthetic

<400> SEQUENCE: 394 ctggggct                                                           8

<210> SEQ ID NO 395
<211> LENGTH: 26
<212> TYPE: DNA
<213> ORGANISM: Artificial Sequence
<220> FEATURE:
<223> OTHER INFORMATION: Synthetic

<400> SEQUENCE: 395
caaaattatg gttgacatgc tagatt                                      26

<210> SEQ ID NO 396
<211> LENGTH: 23
<212> TYPE: DNA
<213> ORGANISM: Artificial Sequence
<220> FEATURE:
<223> OTHER INFORMATION: Synthetic

<400> SEQUENCE: 396
tcgtccagag aatgtagaac tcc                                         23

```
<210> SEQ ID NO 397
<211> LENGTH: 8
<212> TYPE: DNA
<213> ORGANISM: Artificial Sequence
<220> FEATURE:
<223> OTHER INFORMATION: Synthetic

<400> SEQUENCE: 397 tccaggtc                                                                 8

<210> SEQ ID NO 398
<211> LENGTH: 24
<212> TYPE: DNA
<213> ORGANISM: Artificial Sequence
<220> FEATURE:
<223> OTHER INFORMATION: Synthetic

<400> SEQUENCE: 398
aatgggaatt tataacccag tgag                                              24

<210> SEQ ID NO 399
<211> LENGTH: 21
<212> TYPE: DNA
<213> ORGANISM: Artificial Sequence
<220> FEATURE:
<223> OTHER INFORMATION: Synthetic

<400> SEQUENCE: 399
ggtgaatttc tgctccattc a                                                 21

<210> SEQ ID NO 400
<211> LENGTH: 8
<212> TYPE: DNA
<213> ORGANISM: Artificial Sequence
<220> FEATURE:
<223> OTHER INFORMATION: Synthetic

<400> SEQUENCE: 400 ctgcccca                                                                 8

<210> SEQ ID NO 401
<211> LENGTH: 27
<212> TYPE: DNA
<213> ORGANISM: Artificial Sequence
<220> FEATURE:
<223> OTHER INFORMATION: Synthetic

<400> SEQUENCE: 401
catcaacgaa ggaaatatag atcaaac                                           27

<210> SEQ ID NO 402
<211> LENGTH: 18
<212> TYPE: DNA
<213> ORGANISM: Artificial Sequence
<220> FEATURE:
<223> OTHER INFORMATION: Synthetic

<400> SEQUENCE: 402
ctcctggatg gggatggt                                                     18

<210> SEQ ID NO 403
<211> LENGTH: 8
<212> TYPE: DNA
<213> ORGANISM: Artificial Sequence
<220> FEATURE:
<223> OTHER INFORMATION: Synthetic
```

```
<400> SEQUENCE: 403 cccagccc                                                            8

<210> SEQ ID NO 404
<211> LENGTH: 19
<212> TYPE: DNA
<213> ORGANISM: Artificial Sequence
<220> FEATURE:
<223> OTHER INFORMATION: Synthetic

<400> SEQUENCE: 404
agcgtgacca gaaaggaca                                               19

<210> SEQ ID NO 405
<211> LENGTH: 19
<212> TYPE: DNA
<213> ORGANISM: Artificial Sequence
<220> FEATURE:
<223> OTHER INFORMATION: Synthetic

<400> SEQUENCE: 405
gaagcggaca ttgctgaac                                               19

<210> SEQ ID NO 406
<211> LENGTH: 8
<212> TYPE: DNA
<213> ORGANISM: Artificial Sequence
<220> FEATURE:
<223> OTHER INFORMATION: Synthetic

<400> SEQUENCE: 406 tggtgatg                                                            8

<210> SEQ ID NO 407
<211> LENGTH: 21
<212> TYPE: DNA
<213> ORGANISM: Artificial Sequence
<220> FEATURE:
<223> OTHER INFORMATION: Synthetic

<400> SEQUENCE: 407
tggtttcatt ccaatttcct g                                            21

<210> SEQ ID NO 408
<211> LENGTH: 19
<212> TYPE: DNA
<213> ORGANISM: Artificial Sequence
<220> FEATURE:
<223> OTHER INFORMATION: Synthetic

<400> SEQUENCE: 408
aggacatccc caacacctc                                               19

<210> SEQ ID NO 409
<211> LENGTH: 8
<212> TYPE: DNA
<213> ORGANISM: Artificial Sequence
<220> FEATURE:
<223> OTHER INFORMATION: Synthetic

<400> SEQUENCE: 409 cctggagc                                                            8

<210> SEQ ID NO 410
<211> LENGTH: 19
```

```
<212> TYPE: DNA
<213> ORGANISM: Artificial Sequence
<220> FEATURE:
<223> OTHER INFORMATION: Synthetic

<400> SEQUENCE: 410
gtccacctcg acctgctct                                                    19

<210> SEQ ID NO 411
<211> LENGTH: 19
<212> TYPE: DNA
<213> ORGANISM: Artificial Sequence
<220> FEATURE:
<223> OTHER INFORMATION: Synthetic

<400> SEQUENCE: 411
cactggggca ggagaaact                                                    19

<210> SEQ ID NO 412
<211> LENGTH: 8
<212> TYPE: DNA
<213> ORGANISM: Artificial Sequence
<220> FEATURE:
<223> OTHER INFORMATION: Synthetic

<400> SEQUENCE: 412 tggctctg                                                                 8

<210> SEQ ID NO 413
<211> LENGTH: 20
<212> TYPE: DNA
<213> ORGANISM: Artificial Sequence
<220> FEATURE:
<223> OTHER INFORMATION: Synthetic

<400> SEQUENCE: 413
acagagcgga gattgtcctg                                                   20

<210> SEQ ID NO 414
<211> LENGTH: 22
<212> TYPE: DNA
<213> ORGANISM: Artificial Sequence
<220> FEATURE:
<223> OTHER INFORMATION: Synthetic

<400> SEQUENCE: 414
ctctgtagcc gtgcaaactt ac                                                22

<210> SEQ ID NO 415
<211> LENGTH: 8
<212> TYPE: DNA
<213> ORGANISM: Artificial Sequence
<220> FEATURE:
<223> OTHER INFORMATION: Synthetic

<400> SEQUENCE: 415 cagcccag                                                                 8

<210> SEQ ID NO 416
<211> LENGTH: 25
<212> TYPE: DNA
<213> ORGANISM: Artificial Sequence
<220> FEATURE:
<223> OTHER INFORMATION: Synthetic

<400> SEQUENCE: 416
```
tctaggggct tatagctcca ataat                                      25

<210> SEQ ID NO 417
<211> LENGTH: 19
<212> TYPE: DNA
<213> ORGANISM: Artificial Sequence
<220> FEATURE:
<223> OTHER INFORMATION: Synthetic

<400> SEQUENCE: 417
ctggtagggg cagcatttc                                             19

<210> SEQ ID NO 418
<211> LENGTH: 8
<212> TYPE: DNA
<213> ORGANISM: Artificial Sequence
<220> FEATURE:
<223> OTHER INFORMATION: Synthetic

<400> SEQUENCE: 418 catcctcc                                                          8

<210> SEQ ID NO 419
<211> LENGTH: 18
<212> TYPE: DNA
<213> ORGANISM: Artificial Sequence
<220> FEATURE:
<223> OTHER INFORMATION: Synthetic

<400> SEQUENCE: 419
ctgggtgccc acaatcat                                              18

<210> SEQ ID NO 420
<211> LENGTH: 20
<212> TYPE: DNA
<213> ORGANISM: Artificial Sequence
<220> FEATURE:
<223> OTHER INFORMATION: Synthetic

<400> SEQUENCE: 420
gcactgtgag cttggtgatg                                            20

<210> SEQ ID NO 421
<211> LENGTH: 8
<212> TYPE: DNA
<213> ORGANISM: Artificial Sequence
<220> FEATURE:
<223> OTHER INFORMATION: Synthetic

<400> SEQUENCE: 421 cttctgcc                                                          8

<210> SEQ ID NO 422
<211> LENGTH: 21
<212> TYPE: DNA
<213> ORGANISM: Artificial Sequence
<220> FEATURE:
<223> OTHER INFORMATION: Synthetic

<400> SEQUENCE: 422
ccatgtaaga cttgcctgct t                                          21

<210> SEQ ID NO 423
<211> LENGTH: 25
<212> TYPE: DNA
<213> ORGANISM: Artificial Sequence
<220> FEATURE:
<223> OTHER INFORMATION: Synthetic

<400> SEQUENCE: 423
gaggcttaat agattcacag ttcca                                                    25

<210> SEQ ID NO 424
<211> LENGTH: 8
<212> TYPE: DNA
<213> ORGANISM: Artificial Sequence
<220> FEATURE:
<223> OTHER INFORMATION: Synthetic

<400> SEQUENCE: 424 tccagtgt                                                                        8

<210> SEQ ID NO 425
<211> LENGTH: 20
<212> TYPE: DNA
<213> ORGANISM: Artificial Sequence
<220> FEATURE:
<223> OTHER INFORMATION: Synthetic

<400> SEQUENCE: 425
gagcccatct accttgtgga                                                          20

<210> SEQ ID NO 426
<211> LENGTH: 20
<212> TYPE: DNA
<213> ORGANISM: Artificial Sequence
<220> FEATURE:
<223> OTHER INFORMATION: Synthetic

<400> SEQUENCE: 426
cctgttcaaa accccgtaga                                                          20

<210> SEQ ID NO 427
<211> LENGTH: 8
<212> TYPE: DNA
<213> ORGANISM: Artificial Sequence
<220> FEATURE:
<223> OTHER INFORMATION: Synthetic

<400> SEQUENCE: 427 ccagggcc                                                                        8

<210> SEQ ID NO 428
<211> LENGTH: 24
<212> TYPE: DNA
<213> ORGANISM: Artificial Sequence
<220> FEATURE:
<223> OTHER INFORMATION: Synthetic

<400> SEQUENCE: 428
tggagtaaca agaccaatga agaa                                                     24

<210> SEQ ID NO 429
<211> LENGTH: 19
<212> TYPE: DNA
<213> ORGANISM: Artificial Sequence
<220> FEATURE:
<223> OTHER INFORMATION: Synthetic

<400> SEQUENCE: 429
tggctatcag cttccgatg                                                           19

```
<210> SEQ ID NO 430
<211> LENGTH: 8
<212> TYPE: DNA
<213> ORGANISM: Artificial Sequence
<220> FEATURE:
<223> OTHER INFORMATION: Synthetic

<400> SEQUENCE: 430 ctctgcct                                                                8

<210> SEQ ID NO 431
<211> LENGTH: 25
<212> TYPE: DNA
<213> ORGANISM: Artificial Sequence
<220> FEATURE:
<223> OTHER INFORMATION: Synthetic

<400> SEQUENCE: 431
tgctaagtac aaatcattca aggtg                                             25

<210> SEQ ID NO 432
<211> LENGTH: 20
<212> TYPE: DNA
<213> ORGANISM: Artificial Sequence
<220> FEATURE:
<223> OTHER INFORMATION: Synthetic

<400> SEQUENCE: 432
ggcccgttag agaattaccc                                                   20

<210> SEQ ID NO 433
<211> LENGTH: 8
<212> TYPE: DNA
<213> ORGANISM: Artificial Sequence
<220> FEATURE:
<223> OTHER INFORMATION: Synthetic

<400> SEQUENCE: 433 ctggggct                                                                8

<210> SEQ ID NO 434
<211> LENGTH: 20
<212> TYPE: DNA
<213> ORGANISM: Artificial Sequence
<220> FEATURE:
<223> OTHER INFORMATION: Synthetic

<400> SEQUENCE: 434
gagtccactg gcgtcttcac                                                   20

<210> SEQ ID NO 435
<211> LENGTH: 20
<212> TYPE: DNA
<213> ORGANISM: Artificial Sequence
<220> FEATURE:
<223> OTHER INFORMATION: Synthetic

<400> SEQUENCE: 435
ttcacaccca tgacgaacat                                                   20

<210> SEQ ID NO 436
<211> LENGTH: 8
<212> TYPE: DNA
<213> ORGANISM: Artificial Sequence
<220> FEATURE:
<223> OTHER INFORMATION: Synthetic
```

```
<400> SEQUENCE: 436 ccagggca                                                             8

<210> SEQ ID NO 437
<211> LENGTH: 20
<212> TYPE: DNA
<213> ORGANISM: Artificial Sequence
<220> FEATURE:
<223> OTHER INFORMATION: Synthetic

<400> SEQUENCE: 437
gggggaccca gagattaaaa                                               20

<210> SEQ ID NO 438
<211> LENGTH: 21
<212> TYPE: DNA
<213> ORGANISM: Artificial Sequence
<220> FEATURE:
<223> OTHER INFORMATION: Synthetic

<400> SEQUENCE: 438
ccattgtttc gtccatagga g                                             21

<210> SEQ ID NO 439
<211> LENGTH: 8
<212> TYPE: DNA
<213> ORGANISM: Artificial Sequence
<220> FEATURE:
<223> OTHER INFORMATION: Synthetic

<400> SEQUENCE: 439 cttctccc                                                             8

<210> SEQ ID NO 440
<211> LENGTH: 20
<212> TYPE: DNA
<213> ORGANISM: Artificial Sequence
<220> FEATURE:
<223> OTHER INFORMATION: Synthetic

<400> SEQUENCE: 440
gctgtggtgc gtttacaaga                                               20

<210> SEQ ID NO 441
<211> LENGTH: 20
<212> TYPE: DNA
<213> ORGANISM: Artificial Sequence
<220> FEATURE:
<223> OTHER INFORMATION: Synthetic

<400> SEQUENCE: 441
gaggatggcc caaaaactct                                               20

<210> SEQ ID NO 442
<211> LENGTH: 8
<212> TYPE: DNA
<213> ORGANISM: Artificial Sequence
<220> FEATURE:
<223> OTHER INFORMATION: Synthetic

<400> SEQUENCE: 442 tcctgctg                                                             8

<210> SEQ ID NO 443
```

```
<211> LENGTH: 20
<212> TYPE: DNA
<213> ORGANISM: Artificial Sequence
<220> FEATURE:
<223> OTHER INFORMATION: Synthetic

<400> SEQUENCE: 443
gtggctatct ccacgtccac                                              20

<210> SEQ ID NO 444
<211> LENGTH: 19
<212> TYPE: DNA
<213> ORGANISM: Artificial Sequence
<220> FEATURE:
<223> OTHER INFORMATION: Synthetic

<400> SEQUENCE: 444
catggcttcc atttcaacg                                               19

<210> SEQ ID NO 445
<211> LENGTH: 8
<212> TYPE: DNA
<213> ORGANISM: Artificial Sequence
<220> FEATURE:
<223> OTHER INFORMATION: Synthetic

<400> SEQUENCE: 445 tgctggag                                                            8

<210> SEQ ID NO 446
<211> LENGTH: 21
<212> TYPE: DNA
<213> ORGANISM: Artificial Sequence
<220> FEATURE:
<223> OTHER INFORMATION: Synthetic

<400> SEQUENCE: 446
cggtcaaaga cattcacaac a                                            21

<210> SEQ ID NO 447
<211> LENGTH: 19
<212> TYPE: DNA
<213> ORGANISM: Artificial Sequence
<220> FEATURE:
<223> OTHER INFORMATION: Synthetic

<400> SEQUENCE: 447
gcgtcgtgga tgacacagt                                               19

<210> SEQ ID NO 448
<211> LENGTH: 8
<212> TYPE: DNA
<213> ORGANISM: Artificial Sequence
<220> FEATURE:
<223> OTHER INFORMATION: Synthetic

<400> SEQUENCE: 448 ttcctggc                                                            8

<210> SEQ ID NO 449
<211> LENGTH: 25
<212> TYPE: DNA
<213> ORGANISM: Artificial Sequence
<220> FEATURE:
<223> OTHER INFORMATION: Synthetic

<400> SEQUENCE: 449
```

```
aaagtttaa tgcacgatgt agctt                                            25

<210> SEQ ID NO 450
<211> LENGTH: 22
<212> TYPE: DNA
<213> ORGANISM: Artificial Sequence
<220> FEATURE:
<223> OTHER INFORMATION: Synthetic

<400> SEQUENCE: 450
tgtgctggat aaattcacat gc                                              22

<210> SEQ ID NO 451
<211> LENGTH: 8
<212> TYPE: DNA
<213> ORGANISM: Artificial Sequence
<220> FEATURE:
<223> OTHER INFORMATION: Synthetic

<400> SEQUENCE: 451 tcctgctg                                                               8

<210> SEQ ID NO 452
<211> LENGTH: 18
<212> TYPE: DNA
<213> ORGANISM: Artificial Sequence
<220> FEATURE:
<223> OTHER INFORMATION: Synthetic

<400> SEQUENCE: 452
gggactcaga gggctgct                                                   18

<210> SEQ ID NO 453
<211> LENGTH: 18
<212> TYPE: DNA
<213> ORGANISM: Artificial Sequence
<220> FEATURE:
<223> OTHER INFORMATION: Synthetic

<400> SEQUENCE: 453
ggcctgccac acactctc                                                   18

<210> SEQ ID NO 454
<211> LENGTH: 8
<212> TYPE: DNA
<213> ORGANISM: Artificial Sequence
<220> FEATURE:
<223> OTHER INFORMATION: Synthetic

<400> SEQUENCE: 454 aggagctg                                                               8

<210> SEQ ID NO 455
<211> LENGTH: 21
<212> TYPE: DNA
<213> ORGANISM: Artificial Sequence
<220> FEATURE:
<223> OTHER INFORMATION: Synthetic

<400> SEQUENCE: 455
ggactttaat tgcacccatg a                                               21

<210> SEQ ID NO 456
<211> LENGTH: 20
<212> TYPE: DNA
```

```
<213> ORGANISM: Artificial Sequence
<220> FEATURE:
<223> OTHER INFORMATION: Synthetic

<400> SEQUENCE: 456
aaccatcaaa gccaccacat                                                    20

<210> SEQ ID NO 457
<211> LENGTH: 8
<212> TYPE: DNA
<213> ORGANISM: Artificial Sequence
<220> FEATURE:
<223> OTHER INFORMATION: Synthetic

<400> SEQUENCE: 457 agctggag                                                                  8

<210> SEQ ID NO 458
<211> LENGTH: 20
<212> TYPE: DNA
<213> ORGANISM: Artificial Sequence
<220> FEATURE:
<223> OTHER INFORMATION: Synthetic

<400> SEQUENCE: 458
cgagatctgc agaccagaca                                                    20

<210> SEQ ID NO 459
<211> LENGTH: 26
<212> TYPE: DNA
<213> ORGANISM: Artificial Sequence
<220> FEATURE:
<223> OTHER INFORMATION: Synthetic

<400> SEQUENCE: 459
gagattttct ttccaaacaa tacaca                                             26

<210> SEQ ID NO 460
<211> LENGTH: 8
<212> TYPE: DNA
<213> ORGANISM: Artificial Sequence
<220> FEATURE:
<223> OTHER INFORMATION: Synthetic

<400> SEQUENCE: 460 ccaccacc                                                                  8

<210> SEQ ID NO 461
<211> LENGTH: 20
<212> TYPE: DNA
<213> ORGANISM: Artificial Sequence
<220> FEATURE:
<223> OTHER INFORMATION: Synthetic

<400> SEQUENCE: 461
cagccccagt ctccatacag                                                    20

<210> SEQ ID NO 462
<211> LENGTH: 18
<212> TYPE: DNA
<213> ORGANISM: Artificial Sequence
<220> FEATURE:
<223> OTHER INFORMATION: Synthetic

<400> SEQUENCE: 462
ggcggcgctg tagtcata                                                      18
```

<210> SEQ ID NO 463
<211> LENGTH: 8
<212> TYPE: DNA
<213> ORGANISM: Artificial Sequence
<220> FEATURE:
<223> OTHER INFORMATION: Synthetic

<400> SEQUENCE: 463 tggtggcc                                                              8

<210> SEQ ID NO 464
<211> LENGTH: 20
<212> TYPE: DNA
<213> ORGANISM: Artificial Sequence
<220> FEATURE:
<223> OTHER INFORMATION: Synthetic

<400> SEQUENCE: 464
gccttgattt ggcagctaat                                                20

<210> SEQ ID NO 465
<211> LENGTH: 22
<212> TYPE: DNA
<213> ORGANISM: Artificial Sequence
<220> FEATURE:
<223> OTHER INFORMATION: Synthetic

<400> SEQUENCE: 465
tttcattcac ccagttgaca at                                             22

<210> SEQ ID NO 466
<211> LENGTH: 8
<212> TYPE: DNA
<213> ORGANISM: Artificial Sequence
<220> FEATURE:
<223> OTHER INFORMATION: Synthetic

<400> SEQUENCE: 466 aggagcag                                                              8

<210> SEQ ID NO 467
<211> LENGTH: 20
<212> TYPE: DNA
<213> ORGANISM: Artificial Sequence
<220> FEATURE:
<223> OTHER INFORMATION: Synthetic

<400> SEQUENCE: 467
tggtcagaac ccagtgacct                                                20

<210> SEQ ID NO 468
<211> LENGTH: 20
<212> TYPE: DNA
<213> ORGANISM: Artificial Sequence
<220> FEATURE:
<223> OTHER INFORMATION: Synthetic

<400> SEQUENCE: 468
tgttttgtga cggactgagg                                                20

<210> SEQ ID NO 469
<211> LENGTH: 8
<212> TYPE: DNA
<213> ORGANISM: Artificial Sequence
<220> FEATURE:

<223> OTHER INFORMATION: Synthetic

<400> SEQUENCE: 469 cagccacc                                                                  8

<210> SEQ ID NO 470
<211> LENGTH: 19
<212> TYPE: DNA
<213> ORGANISM: Artificial Sequence
<220> FEATURE:
<223> OTHER INFORMATION: Synthetic

<400> SEQUENCE: 470
ggagaggtgt ttggtgcag                                                     19

<210> SEQ ID NO 471
<211> LENGTH: 23
<212> TYPE: DNA
<213> ORGANISM: Artificial Sequence
<220> FEATURE:
<223> OTHER INFORMATION: Synthetic

<400> SEQUENCE: 471
gaaaggtagt tttccaacac tgg                                                23

<210> SEQ ID NO 472
<211> LENGTH: 8
<212> TYPE: DNA
<213> ORGANISM: Artificial Sequence
<220> FEATURE:
<223> OTHER INFORMATION: Synthetic

<400> SEQUENCE: 472 ccaggagg                                                                  8

<210> SEQ ID NO 473
<211> LENGTH: 25
<212> TYPE: DNA
<213> ORGANISM: Artificial Sequence
<220> FEATURE:
<223> OTHER INFORMATION: Synthetic

<400> SEQUENCE: 473
ctaatctgaa aaagtgctca acctc                                              25

<210> SEQ ID NO 474
<211> LENGTH: 23
<212> TYPE: DNA
<213> ORGANISM: Artificial Sequence
<220> FEATURE:
<223> OTHER INFORMATION: Synthetic

<400> SEQUENCE: 474
gccatcttct tcggttttac ttc                                                23

<210> SEQ ID NO 475
<211> LENGTH: 8
<212> TYPE: DNA
<213> ORGANISM: Artificial Sequence
<220> FEATURE:
<223> OTHER INFORMATION: Synthetic

<400> SEQUENCE: 475 cagcccag                                                                  8

```
<210> SEQ ID NO 476
<211> LENGTH: 20
<212> TYPE: DNA
<213> ORGANISM: Artificial Sequence
<220> FEATURE:
<223> OTHER INFORMATION: Synthetic

<400> SEQUENCE: 476
tggatcggac tcttcagtca                                              20

<210> SEQ ID NO 477
<211> LENGTH: 21
<212> TYPE: DNA
<213> ORGANISM: Artificial Sequence
<220> FEATURE:
<223> OTHER INFORMATION: Synthetic

<400> SEQUENCE: 477
cagtcttcga gttgcccatt a                                            21

<210> SEQ ID NO 478
<211> LENGTH: 8
<212> TYPE: DNA
<213> ORGANISM: Artificial Sequence
<220> FEATURE:
<223> OTHER INFORMATION: Synthetic

<400> SEQUENCE: 478 ccacctcc                                                            8

<210> SEQ ID NO 479
<211> LENGTH: 18
<212> TYPE: DNA
<213> ORGANISM: Artificial Sequence
<220> FEATURE:
<223> OTHER INFORMATION: Synthetic

<400> SEQUENCE: 479
ctgcccacca agatctcc                                                18

<210> SEQ ID NO 480
<211> LENGTH: 22
<212> TYPE: DNA
<213> ORGANISM: Artificial Sequence
<220> FEATURE:
<223> OTHER INFORMATION: Synthetic

<400> SEQUENCE: 480
ttgggcatca agtatgtctc tg                                           22

<210> SEQ ID NO 481
<211> LENGTH: 8
<212> TYPE: DNA
<213> ORGANISM: Artificial Sequence
<220> FEATURE:
<223> OTHER INFORMATION: Synthetic

<400> SEQUENCE: 481 cttccagc                                                            8

<210> SEQ ID NO 482
<211> LENGTH: 22
<212> TYPE: DNA
<213> ORGANISM: Artificial Sequence
<220> FEATURE:
<223> OTHER INFORMATION: Synthetic
```

```
<400> SEQUENCE: 482
ggaaggggat ataatcctgg tg                                          22

<210> SEQ ID NO 483
<211> LENGTH: 19
<212> TYPE: DNA
<213> ORGANISM: Artificial Sequence
<220> FEATURE:
<223> OTHER INFORMATION: Synthetic

<400> SEQUENCE: 483
ccaccttccc tttgcactc                                              19

<210> SEQ ID NO 484
<211> LENGTH: 8
<212> TYPE: DNA
<213> ORGANISM: Artificial Sequence
<220> FEATURE:
<223> OTHER INFORMATION: Synthetic

<400> SEQUENCE: 484 cttcctcc                                                           8

<210> SEQ ID NO 485
<211> LENGTH: 20
<212> TYPE: DNA
<213> ORGANISM: Artificial Sequence
<220> FEATURE:
<223> OTHER INFORMATION: Synthetic

<400> SEQUENCE: 485
gtcaccccct tagggacatc                                             20

<210> SEQ ID NO 486
<211> LENGTH: 24
<212> TYPE: DNA
<213> ORGANISM: Artificial Sequence
<220> FEATURE:
<223> OTHER INFORMATION: Synthetic

<400> SEQUENCE: 486
gagctatgtc ctctctctgg aact                                        24

<210> SEQ ID NO 487
<211> LENGTH: 8
<212> TYPE: DNA
<213> ORGANISM: Artificial Sequence
<220> FEATURE:
<223> OTHER INFORMATION: Synthetic

<400> SEQUENCE: 487 ctccagcc                                                           8

<210> SEQ ID NO 488
<211> LENGTH: 20
<212> TYPE: DNA
<213> ORGANISM: Artificial Sequence
<220> FEATURE:
<223> OTHER INFORMATION: Synthetic

<400> SEQUENCE: 488
gaaattgagg gcagagcaat                                             20

<210> SEQ ID NO 489
<211> LENGTH: 22
```

```
<212> TYPE: DNA
<213> ORGANISM: Artificial Sequence
<220> FEATURE:
<223> OTHER INFORMATION: Synthetic

<400> SEQUENCE: 489
tgacaaacag agttttggat gg                                              22

<210> SEQ ID NO 490
<211> LENGTH: 8
<212> TYPE: DNA
<213> ORGANISM: Artificial Sequence
<220> FEATURE:
<223> OTHER INFORMATION: Synthetic

<400> SEQUENCE: 490 cccagcag                                                               8

<210> SEQ ID NO 491
<211> LENGTH: 20
<212> TYPE: DNA
<213> ORGANISM: Artificial Sequence
<220> FEATURE:
<223> OTHER INFORMATION: Synthetic

<400> SEQUENCE: 491
gcaaccagct ctcatccact                                                 20

<210> SEQ ID NO 492
<211> LENGTH: 20
<212> TYPE: DNA
<213> ORGANISM: Artificial Sequence
<220> FEATURE:
<223> OTHER INFORMATION: Synthetic

<400> SEQUENCE: 492
gacgtcagca aacacctgaa                                                 20

<210> SEQ ID NO 493
<211> LENGTH: 8
<212> TYPE: DNA
<213> ORGANISM: Artificial Sequence
<220> FEATURE:
<223> OTHER INFORMATION: Synthetic

<400> SEQUENCE: 493 cagcatcc                                                               8

<210> SEQ ID NO 494
<211> LENGTH: 21
<212> TYPE: DNA
<213> ORGANISM: Artificial Sequence
<220> FEATURE:
<223> OTHER INFORMATION: Synthetic

<400> SEQUENCE: 494
cactgtgtct gggtctggtt c                                               21

<210> SEQ ID NO 495
<211> LENGTH: 20
<212> TYPE: DNA
<213> ORGANISM: Artificial Sequence
<220> FEATURE:
<223> OTHER INFORMATION: Synthetic

<400> SEQUENCE: 495
```

```
tcttctccag ggcttcgata                                               20

<210> SEQ ID NO 496
<211> LENGTH: 8
<212> TYPE: DNA
<213> ORGANISM: Artificial Sequence
<220> FEATURE:
<223> OTHER INFORMATION: Synthetic

<400> SEQUENCE: 496 ctggctcc                                                            8

<210> SEQ ID NO 497
<211> LENGTH: 19
<212> TYPE: DNA
<213> ORGANISM: Artificial Sequence
<220> FEATURE:
<223> OTHER INFORMATION: Synthetic

<400> SEQUENCE: 497
cctgccttta atgcactgg                                                19

<210> SEQ ID NO 498
<211> LENGTH: 20
<212> TYPE: DNA
<213> ORGANISM: Artificial Sequence
<220> FEATURE:
<223> OTHER INFORMATION: Synthetic

<400> SEQUENCE: 498
atgagccctg cataaacctc                                               20

<210> SEQ ID NO 499
<211> LENGTH: 8
<212> TYPE: DNA
<213> ORGANISM: Artificial Sequence
<220> FEATURE:
<223> OTHER INFORMATION: Synthetic

<400> SEQUENCE: 499 cctggagc                                                            8

<210> SEQ ID NO 500
<211> LENGTH: 18
<212> TYPE: DNA
<213> ORGANISM: Artificial Sequence
<220> FEATURE:
<223> OTHER INFORMATION: Synthetic

<400> SEQUENCE: 500
gtgctgccag cctttgac                                                 18

<210> SEQ ID NO 501
<211> LENGTH: 21
<212> TYPE: DNA
<213> ORGANISM: Artificial Sequence
<220> FEATURE:
<223> OTHER INFORMATION: Synthetic

<400> SEQUENCE: 501
ggtcgacgta gacttgagag c                                             21

<210> SEQ ID NO 502
<211> LENGTH: 8
<212> TYPE: DNA
<213> ORGANISM: Artificial Sequence
```

```
<220> FEATURE:
<223> OTHER INFORMATION: Synthetic

<400> SEQUENCE: 502 ctgctgcc                                                                8

<210> SEQ ID NO 503
<211> LENGTH: 20
<212> TYPE: DNA
<213> ORGANISM: Artificial Sequence
<220> FEATURE:
<223> OTHER INFORMATION: Synthetic

<400> SEQUENCE: 503
aacaatgccc tggagtcaaa                                                  20

<210> SEQ ID NO 504
<211> LENGTH: 20
<212> TYPE: DNA
<213> ORGANISM: Artificial Sequence
<220> FEATURE:
<223> OTHER INFORMATION: Synthetic

<400> SEQUENCE: 504
aggctgagca tggtctaagg                                                  20

<210> SEQ ID NO 505
<211> LENGTH: 8
<212> TYPE: DNA
<213> ORGANISM: Artificial Sequence
<220> FEATURE:
<223> OTHER INFORMATION: Synthetic

<400> SEQUENCE: 505 ctccacca                                                                8

<210> SEQ ID NO 506
<211> LENGTH: 19
<212> TYPE: DNA
<213> ORGANISM: Artificial Sequence
<220> FEATURE:
<223> OTHER INFORMATION: Synthetic

<400> SEQUENCE: 506
gggctgaacc tgaagatgc                                                   19

<210> SEQ ID NO 507
<211> LENGTH: 19
<212> TYPE: DNA
<213> ORGANISM: Artificial Sequence
<220> FEATURE:
<223> OTHER INFORMATION: Synthetic

<400> SEQUENCE: 507
cctggtcttc ctcctgtcc                                                   19

<210> SEQ ID NO 508
<211> LENGTH: 8
<212> TYPE: DNA
<213> ORGANISM: Artificial Sequence
<220> FEATURE:
<223> OTHER INFORMATION: Synthetic

<400> SEQUENCE: 508 ctggggcc                                                                8
```

<210> SEQ ID NO 509
<211> LENGTH: 22
<212> TYPE: DNA
<213> ORGANISM: Artificial Sequence
<220> FEATURE:
<223> OTHER INFORMATION: Synthetic

<400> SEQUENCE: 509
ggttgaacaa cctactggct ct                                              22

<210> SEQ ID NO 510
<211> LENGTH: 20
<212> TYPE: DNA
<213> ORGANISM: Artificial Sequence
<220> FEATURE:
<223> OTHER INFORMATION: Synthetic

<400> SEQUENCE: 510
gggttgttat cctgcattcg                                                 20

<210> SEQ ID NO 511
<211> LENGTH: 8
<212> TYPE: DNA
<213> ORGANISM: Artificial Sequence
<220> FEATURE:
<223> OTHER INFORMATION: Synthetic

<400> SEQUENCE: 511 ctgccttc                                                               8

<210> SEQ ID NO 512
<211> LENGTH: 18
<212> TYPE: DNA
<213> ORGANISM: Artificial Sequence
<220> FEATURE:
<223> OTHER INFORMATION: Synthetic

<400> SEQUENCE: 512
acagcttgcc ccaaacaa                                                   18

<210> SEQ ID NO 513
<211> LENGTH: 22
<212> TYPE: DNA
<213> ORGANISM: Artificial Sequence
<220> FEATURE:
<223> OTHER INFORMATION: Synthetic

<400> SEQUENCE: 513
tggaagaata cgatcacctt ga                                              22

<210> SEQ ID NO 514
<211> LENGTH: 8
<212> TYPE: DNA
<213> ORGANISM: Artificial Sequence
<220> FEATURE:
<223> OTHER INFORMATION: Synthetic

<400> SEQUENCE: 514 cagtggca                                                               8

<210> SEQ ID NO 515
<211> LENGTH: 26
<212> TYPE: DNA
<213> ORGANISM: Artificial Sequence
<220> FEATURE:
<223> OTHER INFORMATION: Synthetic

<400> SEQUENCE: 515
tcaaatccta gtccaatatg tcaaaa                                          26

<210> SEQ ID NO 516
<211> LENGTH: 21
<212> TYPE: DNA
<213> ORGANISM: Artificial Sequence
<220> FEATURE:
<223> OTHER INFORMATION: Synthetic

<400> SEQUENCE: 516
cccagagaat gcagtaacca t                                               21

<210> SEQ ID NO 517
<211> LENGTH: 8
<212> TYPE: DNA
<213> ORGANISM: Artificial Sequence
<220> FEATURE:
<223> OTHER INFORMATION: Synthetic

<400> SEQUENCE: 517 tggctgtg                                                               8

<210> SEQ ID NO 518
<211> LENGTH: 21
<212> TYPE: DNA
<213> ORGANISM: Artificial Sequence
<220> FEATURE:
<223> OTHER INFORMATION: Synthetic

<400> SEQUENCE: 518
caaaaagatg atgggaaatg c                                               21

<210> SEQ ID NO 519
<211> LENGTH: 22
<212> TYPE: DNA
<213> ORGANISM: Artificial Sequence
<220> FEATURE:
<223> OTHER INFORMATION: Synthetic

<400> SEQUENCE: 519
catgggtgtt tatggaaacc tt                                              22

<210> SEQ ID NO 520
<211> LENGTH: 8
<212> TYPE: DNA
<213> ORGANISM: Artificial Sequence
<220> FEATURE:
<223> OTHER INFORMATION: Synthetic

<400> SEQUENCE: 520 cagaggag                                                               8

<210> SEQ ID NO 521
<211> LENGTH: 18
<212> TYPE: DNA
<213> ORGANISM: Artificial Sequence
<220> FEATURE:
<223> OTHER INFORMATION: Synthetic

<400> SEQUENCE: 521
aatggggctg acctctcc                                                   18

<210> SEQ ID NO 522

```
<211> LENGTH: 20
<212> TYPE: DNA
<213> ORGANISM: Artificial Sequence
<220> FEATURE:
<223> OTHER INFORMATION: Synthetic

<400> SEQUENCE: 522
gtcagcacag ccttatgcac                                            20

<210> SEQ ID NO 523
<211> LENGTH: 8
<212> TYPE: DNA
<213> ORGANISM: Artificial Sequence
<220> FEATURE:
<223> OTHER INFORMATION: Synthetic

<400> SEQUENCE: 523 ccaccacc                                                          8

<210> SEQ ID NO 524
<211> LENGTH: 23
<212> TYPE: DNA
<213> ORGANISM: Artificial Sequence
<220> FEATURE:
<223> OTHER INFORMATION: Synthetic

<400> SEQUENCE: 524
cgattctaaa tccattacca cca                                        23

<210> SEQ ID NO 525
<211> LENGTH: 21
<212> TYPE: DNA
<213> ORGANISM: Artificial Sequence
<220> FEATURE:
<223> OTHER INFORMATION: Synthetic

<400> SEQUENCE: 525
caccatagct gtcaatgtgg a                                          21

<210> SEQ ID NO 526
<211> LENGTH: 8
<212> TYPE: DNA
<213> ORGANISM: Artificial Sequence
<220> FEATURE:
<223> OTHER INFORMATION: Synthetic

<400> SEQUENCE: 526 cagcctgg                                                          8

<210> SEQ ID NO 527
<211> LENGTH: 20
<212> TYPE: DNA
<213> ORGANISM: Artificial Sequence
<220> FEATURE:
<223> OTHER INFORMATION: Synthetic

<400> SEQUENCE: 527
tcaacgtgtt gtcagccttc                                            20

<210> SEQ ID NO 528
<211> LENGTH: 18
<212> TYPE: DNA
<213> ORGANISM: Artificial Sequence
<220> FEATURE:
<223> OTHER INFORMATION: Synthetic

<400> SEQUENCE: 528
```
gggtgaggct ggtcaaag                                     18

<210> SEQ ID NO 529
<211> LENGTH: 8
<212> TYPE: DNA
<213> ORGANISM: Artificial Sequence
<220> FEATURE:
<223> OTHER INFORMATION: Synthetic

<400> SEQUENCE: 529 ctcctgcc                                                8

<210> SEQ ID NO 530
<211> LENGTH: 20
<212> TYPE: DNA
<213> ORGANISM: Artificial Sequence
<220> FEATURE:
<223> OTHER INFORMATION: Synthetic

<400> SEQUENCE: 530
ttttctggct accgaagtgg                                   20

<210> SEQ ID NO 531
<211> LENGTH: 18
<212> TYPE: DNA
<213> ORGANISM: Artificial Sequence
<220> FEATURE:
<223> OTHER INFORMATION: Synthetic

<400> SEQUENCE: 531
gttctccagg gccgtctt                                     18

<210> SEQ ID NO 532
<211> LENGTH: 8
<212> TYPE: DNA
<213> ORGANISM: Artificial Sequence
<220> FEATURE:
<223> OTHER INFORMATION: Synthetic

<400> SEQUENCE: 532 cagcctcc                                                8

<210> SEQ ID NO 533
<211> LENGTH: 19
<212> TYPE: DNA
<213> ORGANISM: Artificial Sequence
<220> FEATURE:
<223> OTHER INFORMATION: Synthetic

<400> SEQUENCE: 533
taatggcctt gcagggaac                                    19

<210> SEQ ID NO 534
<211> LENGTH: 22
<212> TYPE: DNA
<213> ORGANISM: Artificial Sequence
<220> FEATURE:
<223> OTHER INFORMATION: Synthetic

<400> SEQUENCE: 534
tctcactgct ctgaactttg ct                                22

<210> SEQ ID NO 535
<211> LENGTH: 8
<212> TYPE: DNA

```
<213> ORGANISM: Artificial Sequence
<220> FEATURE:
<223> OTHER INFORMATION: Synthetic

<400> SEQUENCE: 535 cccagcag                                                                  8

<210> SEQ ID NO 536
<211> LENGTH: 20
<212> TYPE: DNA
<213> ORGANISM: Artificial Sequence
<220> FEATURE:
<223> OTHER INFORMATION: Synthetic

<400> SEQUENCE: 536
ttcctggagg ggatagaagc                                                    20

<210> SEQ ID NO 537
<211> LENGTH: 23
<212> TYPE: DNA
<213> ORGANISM: Artificial Sequence
<220> FEATURE:
<223> OTHER INFORMATION: Synthetic

<400> SEQUENCE: 537
atactcagtt tgcagcaata gca                                                23

<210> SEQ ID NO 538
<211> LENGTH: 8
<212> TYPE: DNA
<213> ORGANISM: Artificial Sequence
<220> FEATURE:
<223> OTHER INFORMATION: Synthetic

<400> SEQUENCE: 538 ccagccag                                                                  8

<210> SEQ ID NO 539
<211> LENGTH: 26
<212> TYPE: DNA
<213> ORGANISM: Artificial Sequence
<220> FEATURE:
<223> OTHER INFORMATION: Synthetic

<400> SEQUENCE: 539
ttacaaatgt gacagatatc atcagg                                             26

<210> SEQ ID NO 540
<211> LENGTH: 22
<212> TYPE: DNA
<213> ORGANISM: Artificial Sequence
<220> FEATURE:
<223> OTHER INFORMATION: Synthetic

<400> SEQUENCE: 540
aagaccaggc tcttactcag ga                                                 22

<210> SEQ ID NO 541
<211> LENGTH: 8
<212> TYPE: DNA
<213> ORGANISM: Artificial Sequence
<220> FEATURE:
<223> OTHER INFORMATION: Synthetic

<400> SEQUENCE: 541 tccaggtc                                                                  8
```

<210> SEQ ID NO 542
<211> LENGTH: 21
<212> TYPE: DNA
<213> ORGANISM: Artificial Sequence
<220> FEATURE:
<223> OTHER INFORMATION: Synthetic

<400> SEQUENCE: 542
cgaggacatc agcaataagg t                                               21

<210> SEQ ID NO 543
<211> LENGTH: 18
<212> TYPE: DNA
<213> ORGANISM: Artificial Sequence
<220> FEATURE:
<223> OTHER INFORMATION: Synthetic

<400> SEQUENCE: 543
atggagcccg acctcttc                                                   18

<210> SEQ ID NO 544
<211> LENGTH: 8
<212> TYPE: DNA
<213> ORGANISM: Artificial Sequence
<220> FEATURE:
<223> OTHER INFORMATION: Synthetic

<400> SEQUENCE: 544 ccaccacc                                                               8

<210> SEQ ID NO 545
<211> LENGTH: 20
<212> TYPE: DNA
<213> ORGANISM: Artificial Sequence
<220> FEATURE:
<223> OTHER INFORMATION: Synthetic

<400> SEQUENCE: 545
atgcccctga gttcaagttc                                                 20

<210> SEQ ID NO 546
<211> LENGTH: 21
<212> TYPE: DNA
<213> ORGANISM: Artificial Sequence
<220> FEATURE:
<223> OTHER INFORMATION: Synthetic

<400> SEQUENCE: 546
actgcacatt gttgttgagg a                                               21

<210> SEQ ID NO 547
<211> LENGTH: 8
<212> TYPE: DNA
<213> ORGANISM: Artificial Sequence
<220> FEATURE:
<223> OTHER INFORMATION: Synthetic

<400> SEQUENCE: 547 ctctgcct                                                               8

<210> SEQ ID NO 548
<211> LENGTH: 20
<212> TYPE: DNA
<213> ORGANISM: Artificial Sequence
<220> FEATURE:

<223> OTHER INFORMATION: Synthetic

<400> SEQUENCE: 548
tacaggaagc tgctggaagg                                              20

<210> SEQ ID NO 549
<211> LENGTH: 20
<212> TYPE: DNA
<213> ORGANISM: Artificial Sequence
<220> FEATURE:
<223> OTHER INFORMATION: Synthetic

<400> SEQUENCE: 549
accagaggga gtgaatccag                                              20

<210> SEQ ID NO 550
<211> LENGTH: 8
<212> TYPE: DNA
<213> ORGANISM: Artificial Sequence
<220> FEATURE:
<223> OTHER INFORMATION: Synthetic

<400> SEQUENCE: 550 ctcctccc                                                            8

<210> SEQ ID NO 551
<211> LENGTH: 19
<212> TYPE: DNA
<213> ORGANISM: Artificial Sequence
<220> FEATURE:
<223> OTHER INFORMATION: Synthetic

<400> SEQUENCE: 551
gctgcacaag ttcctggtc                                               19

<210> SEQ ID NO 552
<211> LENGTH: 18
<212> TYPE: DNA
<213> ORGANISM: Artificial Sequence
<220> FEATURE:
<223> OTHER INFORMATION: Synthetic

<400> SEQUENCE: 552
tcatccccat ggacacct                                                18

<210> SEQ ID NO 553
<211> LENGTH: 71
<212> TYPE: DNA
<213> ORGANISM: Artificial Sequence
<220> FEATURE:
<223> OTHER INFORMATION: Synthetic

<400> SEQUENCE: 553
cactactggg ctcagggaaa gctgtgctgc cagatgtgtg agccaggaac attcctcgtg   60
aaggactgtg a                                                       71

<210> SEQ ID NO 554
<211> LENGTH: 21
<212> TYPE: DNA
<213> ORGANISM: Artificial Sequence
<220> FEATURE:
<223> OTHER INFORMATION: Synthetic

<400> SEQUENCE: 554
ttgtaaggag cacttcctga c                                            21

```
<210> SEQ ID NO 555
<211> LENGTH: 20
<212> TYPE: DNA
<213> ORGANISM: Artificial Sequence
<220> FEATURE:
<223> OTHER INFORMATION: Synthetic

<400> SEQUENCE: 555
aaggagcact tcctgacact                                              20

<210> SEQ ID NO 556
<211> LENGTH: 91
<212> TYPE: DNA
<213> ORGANISM: Artificial Sequence
<220> FEATURE:
<223> OTHER INFORMATION: Synthetic

<400> SEQUENCE: 556
cccagagagg cactactggg ctcagggaaa gctgtgctgc cagatgtgtg agccaggaac   60
attcctcgtg aaggactgtg accagcatag a                                 91
```

COMPOSITIONS AND METHODS FOR FUNCTIONAL QUALITY CONTROL FOR HUMAN BLOOD-BASED GENE EXPRESSION PRODUCTS

This application claims priority to U.S. Provisional Patent Application Ser. No. 61/570,257, filed Dec. 13, 2011, the disclosure of which is herein incorporated by reference in its entirety.

Pursuant to 35 U.S.C. § 202(c), it is acknowledged that the U.S. Government has rights in the invention described, which was made in part with funds from the National Institutes of Health, Grant Numbers, 5U24MH068457 (NIMH); 5U10 AA008401 (NIAAA); SN271200900012C (NIDA) and HHSN276201100016C (NIDDK).

FIELD OF THE INVENTION

This invention relates the fields of molecular biology and quality control maintenance of samples stored in biorepositories. More specifically, the methods of the invention provide a high-throughput, automatable process for assessing and characterizing the integrity of RNA samples utilized in large-scale gene expression studies or biorepositories, significantly limiting sample replicate variability and technical error.

BACKGROUND OF THE INVENTION

Several publications and patent documents are cited throughout the specification in order to describe the state of the art to which this invention pertains. Each of these citations is incorporated by reference herein as though set forth in full.

Gene expression measurements and analytical methods rest upon the assumption that a given messenger RNA sample provides a faithful representation of in vivo transcript levels at the time of extraction. In an ideal scenario, fully intact messenger RNA is reverse transcribed to high-quality cDNA for use in gene expression analysis studies, generating reliable and robust data. However, as a labile molecule, the integrity of RNA can be jeopardized at several points prior to, during, and post-extraction, adversely affecting the fidelity of gene expression measurements and hindering data interpretation and discovery. Accurately assessing RNA integrity prior to gene expression analysis on platforms such as microarrays and real-time quantitative PCR proves to be a critical step, requiring a highly sensitive and standardized RNA quality control method [1].

The current industry-standard technique for measuring RNA quality is microcapillary electrophoretic RNA separation, predominantly performed on the Agilent 2100 Bioanalyzer [2, 3]. The 'lab-on-a-chip' microfluidics technology and data visualization software offers multiple ways to visualize and evaluate RNA integrity, yet these broad-spectrum systems often lack sensitivity on the scale necessitated by RNA samples destined for gene expression analysis. While Bioanalyzer measurements provide a gross analytical assessment of RNA integrity, the proprietary RNA Integrity Number (RIN) scoring algorithm and visualization software has intrinsic limitations preventing in-depth RNA integrity profiles and cannot adequately predict the functional performance of RNA samples intended for gene expression analysis.

Clearly a need exists in the art for improved methods for assessing RNA integrity on a large scale.

SUMMARY OF THE INVENTION

In accordance with the present invention, a method for reproducibly assessing the integrity of an RNA sample in a high through put manner is provided. In one embodiment, the method for quantitatively evaluating the extent of RNA degradation in a RNA sample obtained from a tissue or blood specimen entails identifying a candidate gene set specific to said tissue or blood specimen, and determining an arbitrary expression score for each gene present in said set, and sorting said genes into at least two tiers based on said expression score. A plurality of amplification plots and $C\tau$ profiles from the set of candidate genes encoding RNAs exposed to differential degradation conditions are then generated, thereby providing a series of differentially weighted $C\tau$ profiles correlating to the degradation state of said RNA, said scores corresponding to intact and incrementally degraded RNAs. The test sample is subjected to qPCR, and an amplification plot and a $C\tau$, score generated. The $C\tau$ score of the sample is then correlated with those previously determined, thereby providing the degree of degradation of said sample.

In a preferred embodiment the candidate genes are isolated from whole blood. However, any sample type may be used. The term "sample" or "biological sample" as used herein is used in its broadest sense. A sample is derived from a specimen from any source that contains or may contain a molecule of interest (e.g., RNA), including any specimen that is collected from or is associated with a biological or environmental source, or which comprises or contains biological material, whether in whole or in part, and whether living or dead. Samples or biological samples may be plant or animal, including human, fluid (e.g., blood or blood fractions, urine, saliva, sputum, cerebral spinal fluid, pleural fluid, milk, lymph, or semen), swabs (e.g., buccal or cervical swabs), solid (e.g., stool), microbial cultures (e.g., plate or liquid cultures of bacteria, fungi, parasites, protozoans, or viruses), or cells or tissue (e.g., fresh or paraffin-embedded tissue sections, hair follicles, mouse tail snips, leaves, or parts of human, animal, plant, microbial, viral, or other cells, tissues, organs or whole organisms, including subcellular fractions or cell extracts), as well as liquid and solid food and feed products and ingredients such as dairy items, vegetables, meat and meat by-products, agricultural materials, and waste. Biological samples may be obtained from all of the various families of domestic plants or animals, as well as wild animals or plants. In some embodiments, the sample comprises or consists of one or more whole cells from a specimen, such as from a fixed or paraffin-embedded formalin-fixed ("FFPE") section, or cells, such as human, animal, plant, or microbial cells grown in culture (e.g., human, animal, or plant cells obtained by fluorescent-activated cell sorting ("FACS"), or replica-plated bacteria or yeast). Environmental samples include environmental material such as surface matter, soil, water, air, or industrial samples, as well as samples obtained from food and dairy processing instruments, apparatus, equipment, utensils, disposable and non-disposable items. These examples are not to be construed as limiting the sample types applicable to the present invention.

In an alternative embodiment the candidate genes are isolated from a tissue selected from the group consisting of breast tissue, colon tissue, lung tissue, kidney tissue, ovarian tissue, liver tissue, muscle tissue, brain tissue, and stomach tissue.

Also provided in accordance with the invention are novel class distinction algorithms which measure RNA quality as a function of the magnitude of deviation from an expected Cτ value. This approach enables the researcher to properly weigh or exclude subpar samples from subsequent analysis.

Further provided herein are systems and devices that carry out any of the methods described herein. In some embodiments, such systems or devices employ a computer processor employing a computer memory and/or computer readable medium. As used herein, the terms "processor" and "central processing unit" or "CPU" are used interchangeably and refer to a device that is able to read a program from a computer memory (e.g., ROM or other computer memory) and perform a set of steps according to the program. Devices include, but are not limited to desktop computers, hand-held computers (including pads, phones, and other similar devices), and scientific instruments (e.g., thermocyclers, detection devices, mass spectrometers, etc.). In some embodiments, the systems and devices employ software configured to carry out the data analysis approaches described herein. In some embodiments, the systems and devices further employ one or more databases or are in communication with such databases that are housed on a separate device or data storage system (e.g., cloud).

For example, in some embodiments, provided herein are methods for quantitatively evaluating the extent of RNA degradation in a sample, comprising; a) identifying a candidate gene set and determining an arbitrary expression score for each gene present in said set, said gene set being specifically expressed in said tissue or said blood specimen and sorting said genes into at least two tiers based on said expression score; b) generating a plurality of amplification plots and Cτ profiles from a set of candidate genes encoding RNAs exposed to differential degradation conditions thereby providing a series of differentially weighted Cτ profiles correlating to the degradation state of said RNA, said scores corresponding to intact and incrementally degraded RNAs; and c) subjecting RNA in said sample to quantitative amplification, thereby generating an amplification plot and a Cτ score; said Cτ score being correlated with those determined in step b) said score providing the degree of degradation of said sample. The sample can be of any type including environmental samples, samples obtained from a human, tissue samples, fluid samples, whole blood, and the like.

In some embodiments, the method is coupled with screening or diagnostic techniques for assessing any desired genotype or phenotype, including disease status and progression, general health status, and response to diet, therapeutics, or other stimuli. In some such embodiments, the method further comprises the step of d) analyzing a gene expression profile employing the sample. In some embodiments, the method further comprises the step of e) assessing disease status or progression using the gene expression profile. In some embodiments, the method further comprises the step of d) discarding the sample without conducting a gene expression profile analysis if the degree of degradation is unsuitable (e.g., is of a degree in which a screening or diagnostic test will lack the required or desired level of sensitivity or specificity).

As discussed above, further provided herein are systems and devices that can carry out one or more or all aspects of the methods. For example, in some embodiments, a system or device comprises a computer processor that generates the plurality of amplification plots and Cτ profiles. Such systems can include any component useful, necessary, or sufficient for processing the sample, detecting the sample, analyzing the data, and/or using the data. Such components, include, but are not limited to thermocyclers, sample processing components (e.g., that purify or isolate RNA from cells or tissues or other sample types), detection components (e.g., that mass, optical signals, heat, pH changes, radioactivity, or other detectable signals), and the like.

BRIEF DESCRIPTION OF THE DRAWINGS

FIG. 5: Roche UPL ProbeFinder assay design. ProbeFinder software designs UPL assays based on an input target gene; below is one possible assay design for the CD27 gene. ProbeFinder outputs forward (SEQ ID NO: 35) and reverse primer (SEQ ID NO: 36) sequences flanking the UPL probe of choice (SEQ ID NO: 556), shown in the 'Detailed view' as green and purple text, respectively. Amplicon generated is showing SEQ ID NO: 553. Image taken from the ProbeFinder website (www dot roche-applied-science dot com backslash sis backslash rtpcr backslash upl).

FIG. 6: Comparison of ideal and poor amplification plots. Figure on left: an ideal, tight amplification plot for the CAPN2 5' assay; limited expression variability exists between different subjects. Figure on right: a dispersed amplification plot for the TRPM2 3' assay; demonstrates great variability between different subjects.

FIGS. 7A-7F: RNA Extraction Quality Control Data. (A) Nanodrop ND-8000 RNA Yield Data, (B-F) LabChip 90 HT Microcapillary Electrophoresis RNA Quality Data for five samples.

FIGS. 8A-8F: cDNA synthesis and Amplification Quality Control Data. (A) Nanodrop ND-8000 cDNA Yield Data, (B-F) LabChip 90 HT Microcapillary Electrophoresis cDNA Quality Data for five samples.

FIGS. 10A-10D: (A-B) RNA quality data for freeze/thaw cycle treatment (lanes 1-5) and heat treatment (lanes 6-10), (C-D) RNA quality data for RNase A degradation treatment (lanes 1-7).

FIGS. 12A-12B: (A) Table showing Nanodrop ND-8000 manually extracted RNA Yield Data, (B) Images showing manually extracted RNA Bioanalyzer 2100 Data.

FIGS. 13A-13B: (A) Table showing Nanodrop ND-8000 RNase A Degradation and Column-Purified RNA Yield Data (B) Images showing RNase A Degradation and Column-Purified RNA Bioanalyzer 2100 Data.

FIGS. 14A-14E: RNA Degradation: cDNA Synthesis and Amplification Quality Control Data: (A) Table showing Nanodrop ND-8000 cDNA Yield Data, (B-E) Images showing LabChip 90 HT Microcapillary Electrophoresis cDNA Quality Data.

SEQUENCE LISTING

Figure 1:
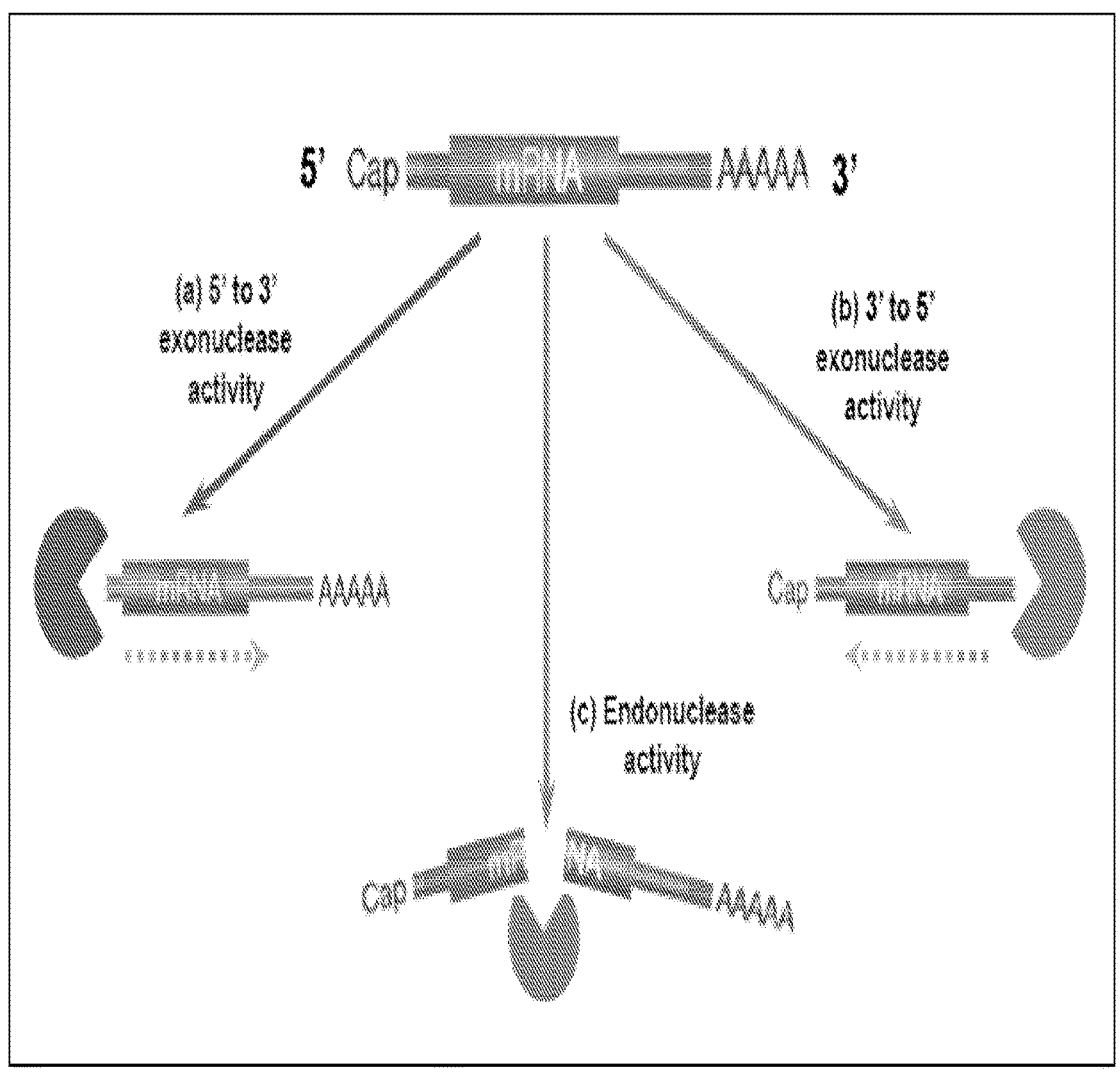
FIG. 1: Mechanisms of messenger RNA degradation by RNases. (a) 5' to 3' exonuclease activity removes the 7-methyl guanosine cap and degrades RNA in a 5' to 3' direction, (b) 3' to 5' exonuclease activity removes the poly-A tail and degrades RNA in a 3' to 5' direction, and (c) endonucleases attack at specific sites within the molecule and endonucleolytically cleaves the RNA. Modified image from Newbury 2006 [9].

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file in the form of the file named "seq listing rna.txt" (~104 kb), which was created on Jan. 8, 2018, and which is incorporated by reference herein.

SEQ ID NOS: 1-552 are PCR primers for amplification of the genes listed in Appendix II.

SEQ ID NO: 553 is a CD27 amplicon sequence generated using SEQ ID NOS: 35 and 36.

SEQ ID NO: 554 is a PCR primer sequence.

SEQ ID NO: 555 is the reverse of SEQ ID NO: 36.

SEQ ID NO: 556 is a portion of a CD27 gene sequence.

DETAILED DESCRIPTION OF THE INVENTION

Sample quality control is central to applied, and clinical genomic analyses. Most sample processing is decentralized, which leads to differential results between laboratories. Thus, in accordance with the present invention, an efficient protocol for QC of each unique sample has been developed and standardized. While QC of RNA from whole blood samples is exemplified herein, the methods described can be applied to a variety of sample sources. The research to develop such a technology is best developed in a biorepository setting where thousands of samples are processed every month. The Rutgers University Cell and DNA Repository currently employs a QC protocol for all human genomic DNA samples that uses a custom-designed SNP genotyping assay panel to determine gender, ethnicity, uniqueness, and sample quality. A similar approach has been developed for RNA given the labile nature of this nucleic acid and the variability associated with extraction and purification thus providing a metric for comparing samples extracted at different sites. This functional QC gene expression panel has commercial applications in terms of qualifying samples for diagnostic and clinical applications.

Real-time quantitative polymerase chain reaction (qPCR) assays offer a more sensitive, modifiable method for quantitatively evaluating the extent of RNA degradation. Fluorescent probe-based assays can be customized to a specific tissue type or field of research by modifying the target genes. Additionally, this method offers a high-throughput, automatable solution for large-scale gene expression studies or biorepositories, significantly limiting sample replicate variability and technical error. By exploiting the regional degradation patterns of RNA, algorithms have been developed to compare gene expression measurements, $C_T$ values, of a test sample to those of an intact RNA control sample and synthetic/empirically degraded RNA samples. Based on the differentially weighted $C_T$ profiles for all assays in the panel, an overall quality constant is assigned to a given RNA sample, allowing researchers to properly normalize or exclude any given sample during gene expression data analysis and interpretation.

The following work describes the de novo development and validation of a novel functional quality control method for RNA samples extracted from human whole blood, comprised of a custom gene expression assay panel and complementary algorithms.

RNA Degradation Mechanisms In Vivo

While RNA degradation is a hindrance to gene expression research, it is a ubiquitous and controlled activity in vivo. Within the cell, active RNA degradation systems are in place to regulate RNA production and decay in order to maintain a steady-state level of RNA messages and their successive proteins. Misfolded or otherwise defective RNA molecules are rapidly degraded by cellular surveillance machinery [4]. In addition, it has been suggested that RNA-degrading enzymes, RNases, can confer protection from viruses by reducing viral replication and protein synthesis [5, 6]. Intact cells tightly control the essential activities of RNases, but when cells are disrupted during sample collection and RNA extraction, these endogenous cellular RNases are immediately released and can begin to break down RNA molecules.

Identified by the direction of degradation along an RNA molecule, three major classes of RNases exist in eukaryotes: (1) 5' to 3' exonucleases, (2) 3' to 5' exonucleases, and (3) endonucleases, which cleave RNA internally [7]. During the transcription process, nascent messenger RNA molecules are modified with protective structures on both ends that serve to maintain stability as mature messenger RNA is translated to protein. As messenger RNA is transcribed, a methylated guanine cap is added to the 5' end of the molecule and a stretch of 150-200 adenine residues is added to the 3' end of the molecule, forming the poly-A tail [$]. Exoribonucleases target the 5' cap or 3' poly-A tail as points of entry, while endoribonucleases can initiate degradation at specific sites within the molecule. FIG. 1 depicts three mechanisms of messenger RNA degradation by RNases.

Sources of RNA Degradation Ex Vivo

As many gene expression studies are clinically based, subject sample collection and processing pose the challenge of stabilizing and maintaining RNA integrity in an ex vivo environment. First and foremost, biospecimen collection methods must be considered when controlling for RNA degradation. Dependent upon tissue type, samples can be collected or stored in a variety of ways, all of which introduce inherent risk of RNA degradation. Formalin-fixed paraffin-embedded (FFPE) tissue samples are routinely used for disease diagnosis and provide a long-term sample storage solution. As archived collections of these samples grow, so does the appeal of extracting RNA for large-scale gene expression studies. However, RNA extracted from fresh, frozen, or archival FFPE specimens is extensively degraded due to the fixation process and length of storage [10]. Alternatively, fresh samples can be collected from tissue biopsies or whole blood drawings for immediate processing, eliminating the fixation and storage limitations of FFPE tissue samples. However, these samples must be immediately and adequately stabilized by immersion in a proprietary reagent that protects RNA from endogenous ribonuclease degradation and minimizes post-collection gene induction [11].

Regardless of the collection method chosen, variability in RNA extraction techniques and mishandling by technicians further introduces opportunities for RNA degradation. The latency period and conditions between collection and processing, conditions of the extraction process such as time lapse and temperature, and inadvertent contamination with ubiquitous RNases present on lab surfaces, gloves, and skin are common sources of RNA degradation [4, 12]. Post-extraction handling, such as freeze/thaw cycles, heat, and pH fluctuations are also potential sources of RNA degradation [13-15]. The first line of defense against RNA degradation is tightly controlling the variables associated with its collection and processing, however, not all samples in a collection will be handled properly and some degree of RNA degradation is inevitable. When paired with the costly venture of biospecimen procurement and storage, it becomes financially and analytically advantageous to include all viable samples in a gene expression study, including data derived from variably degraded RNA [13, 14]. Due to the propensity for RNA degradation, quality control methods become of paramount importance to ensure the reliability and reproducibility of downstream gene expression analysis and data interpretation.

Compounding the issue of RNA degradation is that prior to running an RNA sample on a gene expression platform, it must first be reverse transcribed to stable complementary DNA (cDNA). cDNA is synthesized from a messenger RNA template and serves as the input molecule for gene expression analysis platforms. Demonstrating a ripple-effect, if the messenger RNA template is degraded and of low quality, the cDNA synthesized from it will follow suit, resulting in skewed gene expression data that does not accurately portray the gene expression products present within a given sample at the time of RNA extraction. Numerous platforms exist for measuring gene expression, each with varied applications, multiplexing capability, and throughput. For the purposes of this discussion, the effect of RNA degradation on real-time quantitative PCR data will be considered.

RNA Degradation and Effects on Real-Time Quantitative PCR Measurements

Real-time quantitative PCR (qPCR) is considered a routine, 'gold standard' RNA quantification method. Due to the relatively low cost, speed, and reliability of performing qPCR assays, they are also often used to validate gene expression data generated by other methods, as is the case with expression microarrays[16, 17]. Designing qPCR assays is a flexible and customizable process, allowing for the design of highly specific assay panels. For high-throughput studies or processes, the reaction set up can be fully automated for more accurate results and more consistent technical replicates. The qPCR workflow consists of three steps: (1) the reverse transcriptase-mediated conversion of labile RNA to stable cDNA, (2) the amplification of cDNA using the polymerase chain reaction (PCR), and (3) the real-time detection and quantification of amplification products [18].

Individual qPCR reactions consist of or comprise the following components: (1) cDNA template, (2) gene expression master mix, (3) forward and reverse primers, (4) a fluorescent probe, and (5) DNase/RNase-free water. Master mix contains the components necessary for the DNA synthesis machinery, primarily thermo-stable DNA polymerase. Primers are short, specific oligonucleotides which hybridize to a DNA template and serve as a start point for DNA synthesis. Forward and reverse primers are used for amplification of both DNA template strands and can be designed to target a specific region for amplification. The probe is a short oligonucleotide labeled with a fluorescent reporter at one end and a fluorescence quencher at the opposite end. The probe hybridizes to the complementary sequence of the DNA template, proximal to and downstream of one of the hybridized primers. Due to the close proximity of the fluorescent moiety and quencher, a fluorescent signal is dampened until the amplification process begins. As the target PCR product is synthesized, the probe is cleaved by the 5' to 3' exonuclease activity of DNA polymerase. Breaking the close proximity of the fluorophore and quencher emits a detectable fluorescent signal upon excitation by a laser within the PCR instrument[19].

Figure 2:
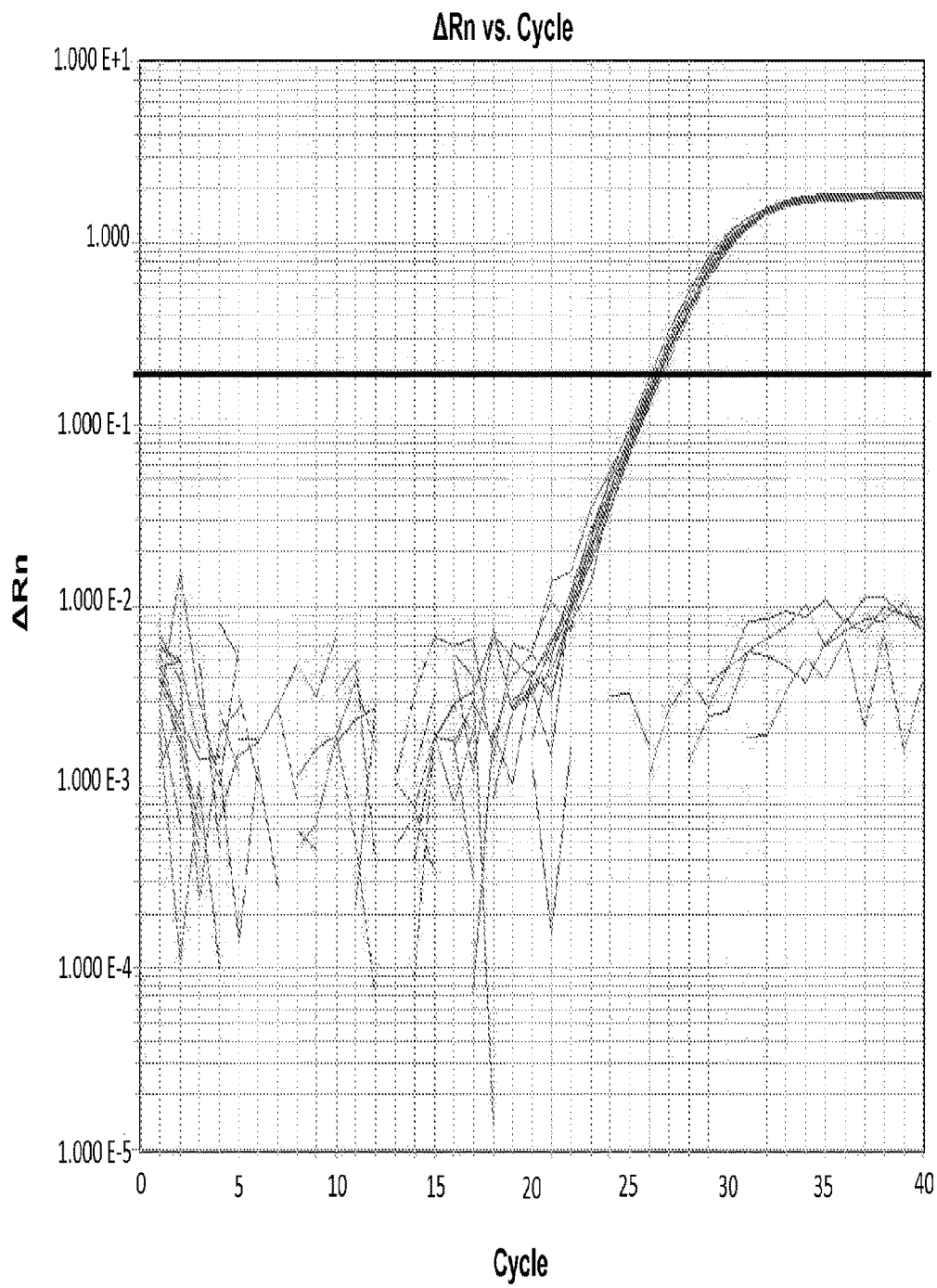
FIG. 2: Typical qPCR amplification plot, ΔRn vs. Cycle. A measure of accumulating PCR products, the magnitude of fluorescence (ΔRn) is plotted against the PCR amplification cycle number (Cycle). The threshold line, in red, is set at the middle of the linear phase of the plot, defining the $C_T$ value for a given qPCR reaction.

During the PCR thermal cycling course, as the target amplicons accumulate, a proportional amount of fluorescent signal accumulates. The magnitude of fluorescence emitted by individual reactions, and thereby the amount of accumulated PCR product, is quantified by a cycle threshold ($C_T$) value. $C_T$ values are determined by a threshold line, which is set at the midpoint of the linear phase of an amplification plot and defines the PCR cycle iteration at which a measurable fluorescence level first surpasses the background fluorescence threshold. $C_T$ values are inversely related to the level of gene expression of the target gene: the greater the amount of target sequence present in the starting cDNA, the earlier the cycle at which fluorescence intensity surpasses the threshold, generating a lower $C_T$ value [18]. Once generated, depending upon the application and objectives of the study, $C_T$ values are then analyzed with established statistical methods. FIG. 2 depicts a typical qPCR amplification plot and threshold line.

qPCR offers sensitive and reliable gene expression quantification, yet it is not without potential drawbacks stemming from lack of standardization at steps within the workflow. Among the variables to consider when planning and executing qPCR assays, RNA sample quality is arguably the most important, followed by assay design efficiency, choice of chemistry, linearity during reverse transcription, and threshold determination [18, 20, 21]. For the purposes of this discussion, assays will henceforth be defined as a primer set/probe pairing. The variables of sample quality and assay design go hand-in-hand when considering the effects of degraded starting material on gene expression quantification. For instance, RNase activity is dictated by a directionally-driven mechanism: RNases move in a 5' to 3' direction, 3' to 5' direction, or attack at specific sequences of a transcript and cleave the molecule at that point. Depending on the entry point of ribonuclease attack and the extent of degradation or fragmentation, a given transcript may no longer contain the region for which an assay was designed, thus under-representing expression level of the target gene. This under-representation corresponds to a higher $C_T$ value, as the amount of starting material is smaller and the threshold takes longer to surpass.

In terms of designing effective assays, the location of the primer and probe sequences is critical. Assays designed proximal to the 3' or 5' ends of the molecule will be at greater risk for failure as they are the entry points for exoribonucleases, whereas assays designed in the middle region are prone to failure due to endoribonuclease degradation activity. Multiple assays per gene should be designed in order to compare regional efficacy. To choose optimal assays from a large candidate pool, a validation study must be conducted to eliminate assays that fail due to poor primer/probe hybridization, large variations in $C_T$ between RNA samples from different subjects, or significant expression level inconsistencies between regional assays of the same target gene. Studies have indicated that a certain threshold of RNA degradation is tolerated without significantly impacting gene expression data, yet beyond which gene expression analysis is adversely impacted by sample degeneration [13, 14, 22, 23]. The hallmark $C_T$ increase for a degraded sample, as compared to an expected $C_T$ value of a control sample, can potentially be used to weight the reliability of gene expression data for a given sample and allow for appropriate inclusion or exclusion of variably degraded RNA samples in a study.

Current RNA Integrity Assessment Methods

Existing RNA integrity assessment tools each have inherent strengths and weaknesses, and each looks at different RNA structural features to determine quality. The three most common methods used to evaluate RNA integrity will be discussed for comparison: (1) Ratio method: measuring the ratio between the 28S and 18S ribosomal RNA (rRNA) subunit electrophoresis bands, (2) Manual method: subjective evaluation of an electropherogram, and (3) RNA Integrity Number (RIN): objective evaluation of an electropherogram [2]. All of these methods rely on measurements generated by an electrophoretic RNA separation system, such as the Agilent 2100 Bioanalyzer and corresponding RNA 6000 LabChip® kit. The Bioanalyzer combines disposable microfluidic chips, voltage-induced size separation, and laser-induced fluorescence quantification on a small scale, with the capacity to process 12 samples in approximately 30 minutes [24, 25]. Data is visualized within the software as electropherograms and simulated gel electrophoresis images, while RNA concentration, RNA area, and 28S/18S ratios are quantitatively reported.

Figure 3:
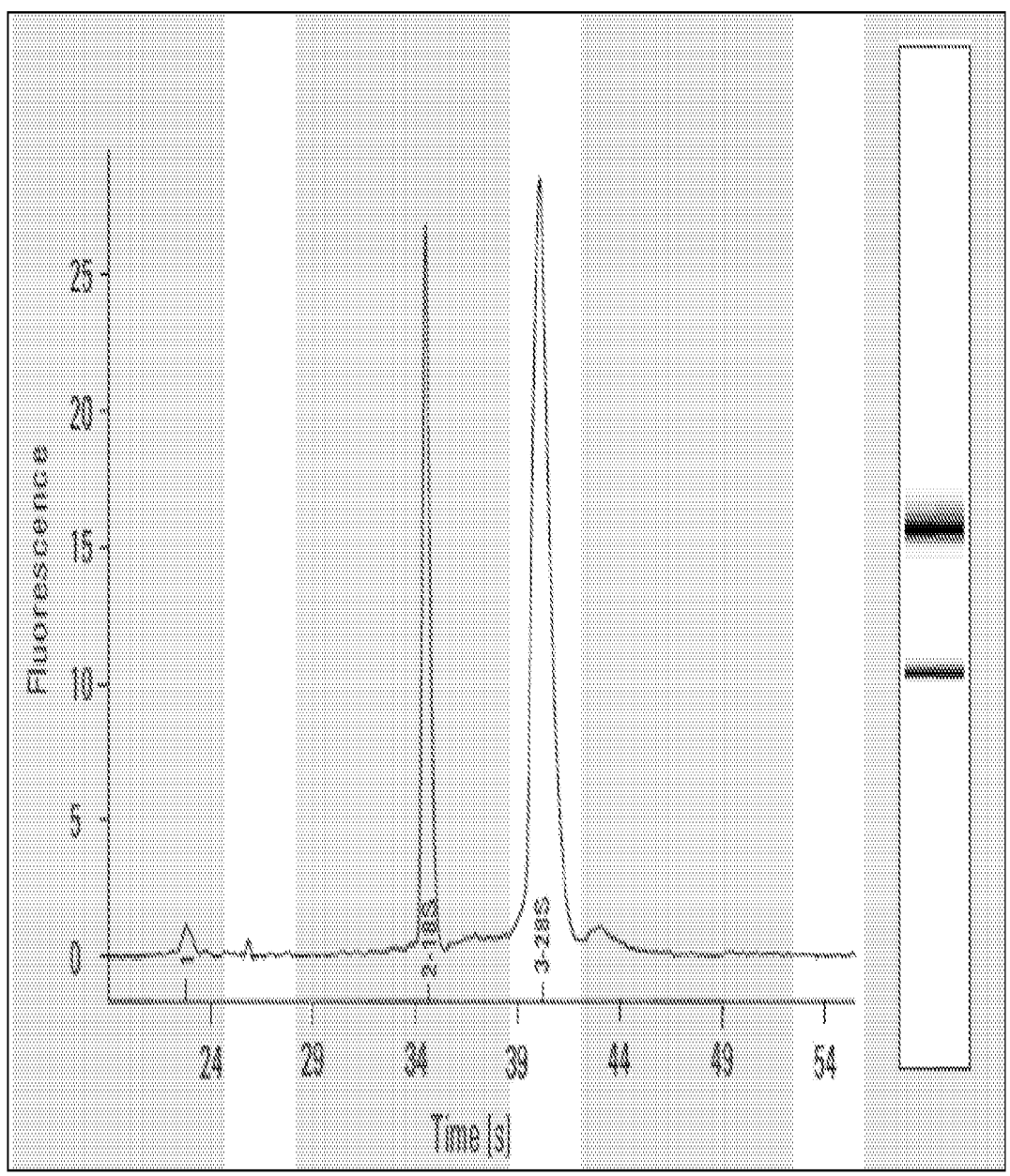
FIG. 3: Visualizing 28S and 18S ribosomal subunits on gels and electropherograms. The image on the left represents a typical electropherogram: the right peak depicts the 28S ribosomal subunit and the left peak depicts the 18S ribosomal subunit. The image on the right is a corresponding gel image, the top band depicting the 28S subunit and the bottom band depicting the 18S subunit. Image taken from Kuschel 2000 [25].

Traditionally used to evaluate RNA integrity, the 28S/18S rRNA ratio method uses agarose gel electrophoresis stained with ethidium bromide to produce a banding pattern representing the 28S and 18S ribosomal RNA species [3]. More recently, physical gels have been replaced by microfluidics chips. Though the concept remains the same, Bioanalyzer software generates simulated gel images and electropherograms from the data it collects during RNA separation. The intensities of the 28S and 18S bands are used to calculate a ratio reflecting RNA integrity. Band intensity and electropherogram peak amplitude are based on the size of the ribosomal subunit; the larger the molecule, the more intercalating dyes bind to it, hence a stronger intensity displayed by the larger 28S subunit. FIG. 3 depicts typical 28S and 18S visualizations on both a gel and an electropherogram. On a gel or gel image, a ratio of 2.0 or greater indicates good to high quality RNA, while an electropherogram peak ratio of ≥0.65 is considered high quality [2, 3]. The determination of a 28S/18S ratio via physical gel electrophoresis has been largely replaced by microcapillary gel electrophoresis due to the subjectivity involved with determining band intensity ratios. Furthermore, the large amount of input RNA required and the variability associated with electrophoresis conditions make physical gel analysis an unreliable RNA degradation indicator [26]. While Bioanalyzer digital ratio calculation removes subjectivity, it also has drawbacks. Bioanalyzer calculation of the 28S/18S ratio is based on peak area measurements that are heavily dependent on exact definition of the start and end points of the peak, and even accurate determination of this ratio is not sufficient to detect RNA degradation [27].

The manual method of evaluating RNA integrity involves visual inspection of an electropherogram, specifically looking at the 28S and 18S peaks of an electropherogram. A high quality RNA sample is characterized by distinct 28S and 18S peaks and a flat baseline. With increased degradation, there is a decrease in the 18S to 28S ribosomal band ratio and an increase in the baseline signal between the two ribosomal peaks and the lower marker, while additional peaks begin to appear in the small RNA range as short degradation products accumulate [27, 28]. Much like the 28S/18S ratio used with physical gels, this method is subjective and prone to variability, but may have utility if used in conjunction with a secondary validation method to determine the extent of RNA degradation.

In order to standardize the subjective process of RNA integrity assessment, the RNA Integrity Number (RIN) algorithm was later developed and integrated into the Bioanalyzer software. The RIN algorithm is based on a selection of features that contribute different information about RNA quality, taking into account that a single feature is insufficient to universally evaluate RNA degradation. Specifically, the features incorporated into the RIN algorithm are: (1) the fraction of area beneath the 28S and 18S peaks as compared to total area, reflecting the proportion of large molecules compared to smaller ones, (2) the amplitude of the 28S peak, which correlates with the onset of degradation, (3) the 'fast area' ratio, referring to the degradation peaks observed between the marker and 18S peaks of increasingly degraded RNA, and (4) marker height, an indicator for accumulation of short degradation products [3]. While providing a much more comprehensive evaluation of RNA integrity than the other two methods, the RIN algorithm cannot predict the quality of downstream gene expression data without prior validation work; that is, an RNA sample might be too degraded for use in a microarray study, but might deliver good qPCR data [28, 29]. The inadequate predictive utility of the RIN algorithm, in terms of forecasting sample performance on a range of gene expression platforms, limits its value as an RNA quality control method and creates a niche in the market for a more sensitive quality control analytical tool.

Real-Time Quantitative PCR as a Functional RNA Quality Control Method

While instruments such as the Bioanalyzer offer a comprehensive method of determining RNA quality, to appropriately evaluate the functional potential of a given sample, 'like' must be compared with 'like'. In order to gauge the reliability of a given RNA sample during downstream gene expression analysis, functional performance must be measured as opposed to static evaluation within a system that solely considers structural features of the molecule. Furthermore, the sensitivity of these tools falls off quickly when analyzing RNA samples of increasingly lower quality and yield, sacrificing scoring linearity at the lower boundary of RNA quality [30, 31]. The limiting threshold of sensitivity inherent to lab-on-a-chip solutions is surpassed by a functional expression assay.

If all variables are controlled for, qPCR assays offer a highly sensitive, reproducible, and customizable quality control method. Already used to confirm and validate gene expression data generated by microarrays, using qPCR as a means to evaluate both RNA integrity and functional potential in one concerted effort is a natural extension of the technology [16, 32]. qPCR assays are highly customizable and assay panels can be specifically designed based on tissue type or area of research based on the target genes chosen. Reaction setup can be automated to eliminate human pipetting error, ensure reproducibility, and allow for high-throughput quality control screening. Additionally, a qPCR quality control method addresses the needs of high-throughput laboratories by eliminating the need for additional costly instruments, consumables, and kits necessitated by other technologies.

With growing incentive to include all samples of a collection in a gene expression study, sample exclusion based on poor RNA integrity can potentially be countered by annotating expression data with sample quality metrics. The generally predictable nature of RNA degradation suggests that correlations may be drawn between transcript integrity and gene expression level for a target gene, as compared to an expected expression baseline. By exploiting the direction and magnitude of $C_T$ shift between a control RNA sample and a test sample, assay-centric class distinction algorithms can be developed and collectively considered to quantify the quality of RNA samples. The following work describes the development of a novel functional quality control method for RNA samples extracted from human whole blood, consisting of a custom gene expression assay panel and complementary class distinction algorithms.

Assay Development
Literature and Database Search for Candidate Genes

A pool of over 1,400 genes expressed in human whole blood was generated from literature and public database searches, primarily genome-wide analysis studies and the Weizmann Institute's GeneCards® online database (www dot genecards dot org) [33-35]. Providing a complete summary for each gene, the GeneCards® human gene database acquires and compiles transcriptomic, genetic, proteomic, and functional information from relevant publications and public databases, including Weizmann Institute's own tissue-specific microarray expression data. Candidate genes were selected from the pool based on adherence to the following criteria: (1) the gene must be measurably expressed in human whole blood cells, (2) the gene must be expressed in a non-disease state, with limited potential for expression variability between whole blood samples from different donors, and (3) the gene must be central to blood cell structure or function (i.e. not an immediate early gene) [36]. For use as a universal RNA quality control method, the final assay panel must be suited to accommodate samples from a broad range of subjects, controlling for disease states, immune challenge, and expression variability between subjects. Taking these variables into account, candidate genes were limited to normal-state, non-transient genes involved in white blood cell structure or function, as indicated by the GeneCards® database.

Expression Profiles for Candidate Genes

Figure 4:
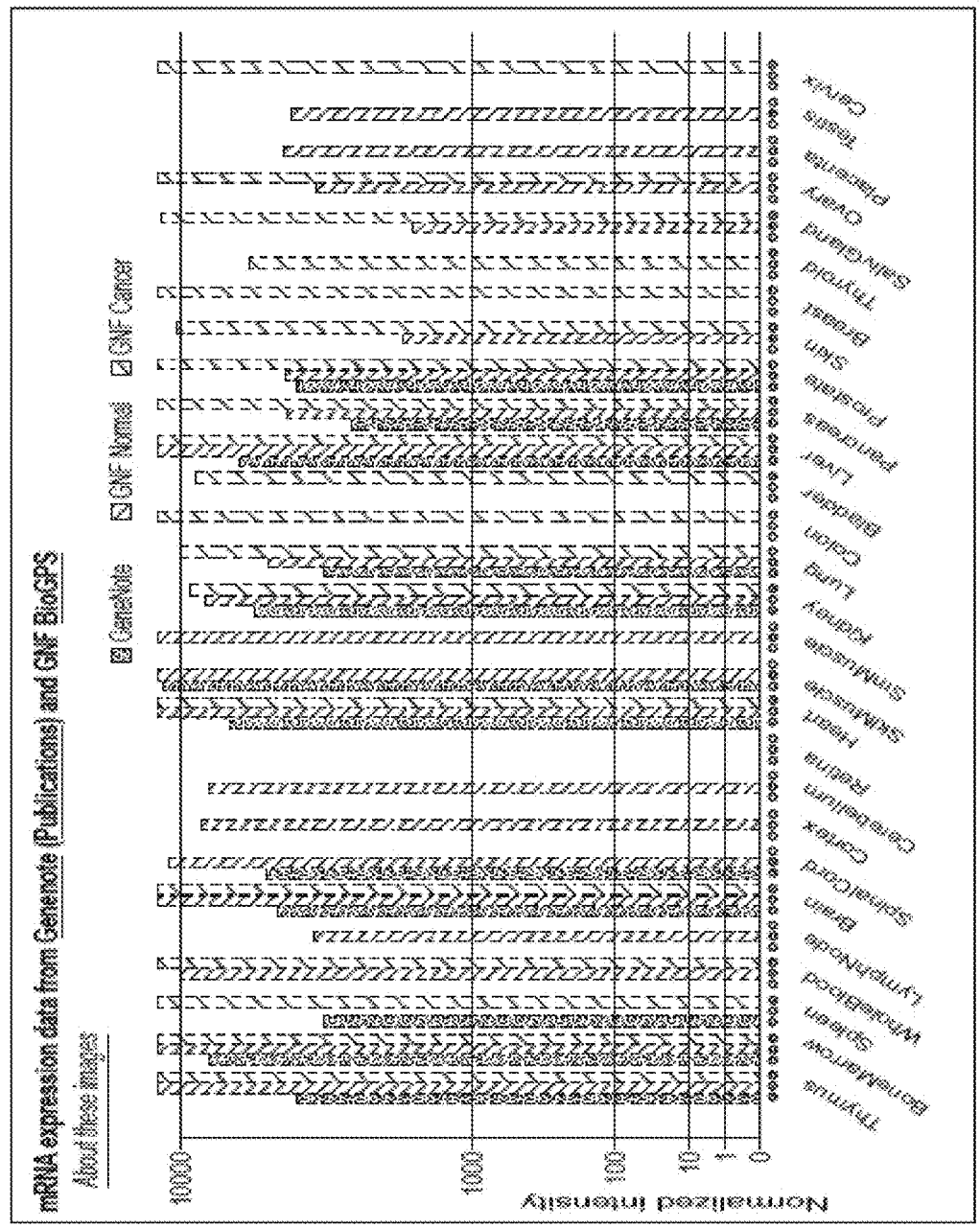
FIG. 4: GeneNote and BioGPS expression data. A representative gene expression data plot generated for numerous experimental tissue vectors. The example shown below represents the GAPDH gene. Image taken from the GeneCards® website (www dot genecards dot org).
Figure 7F:
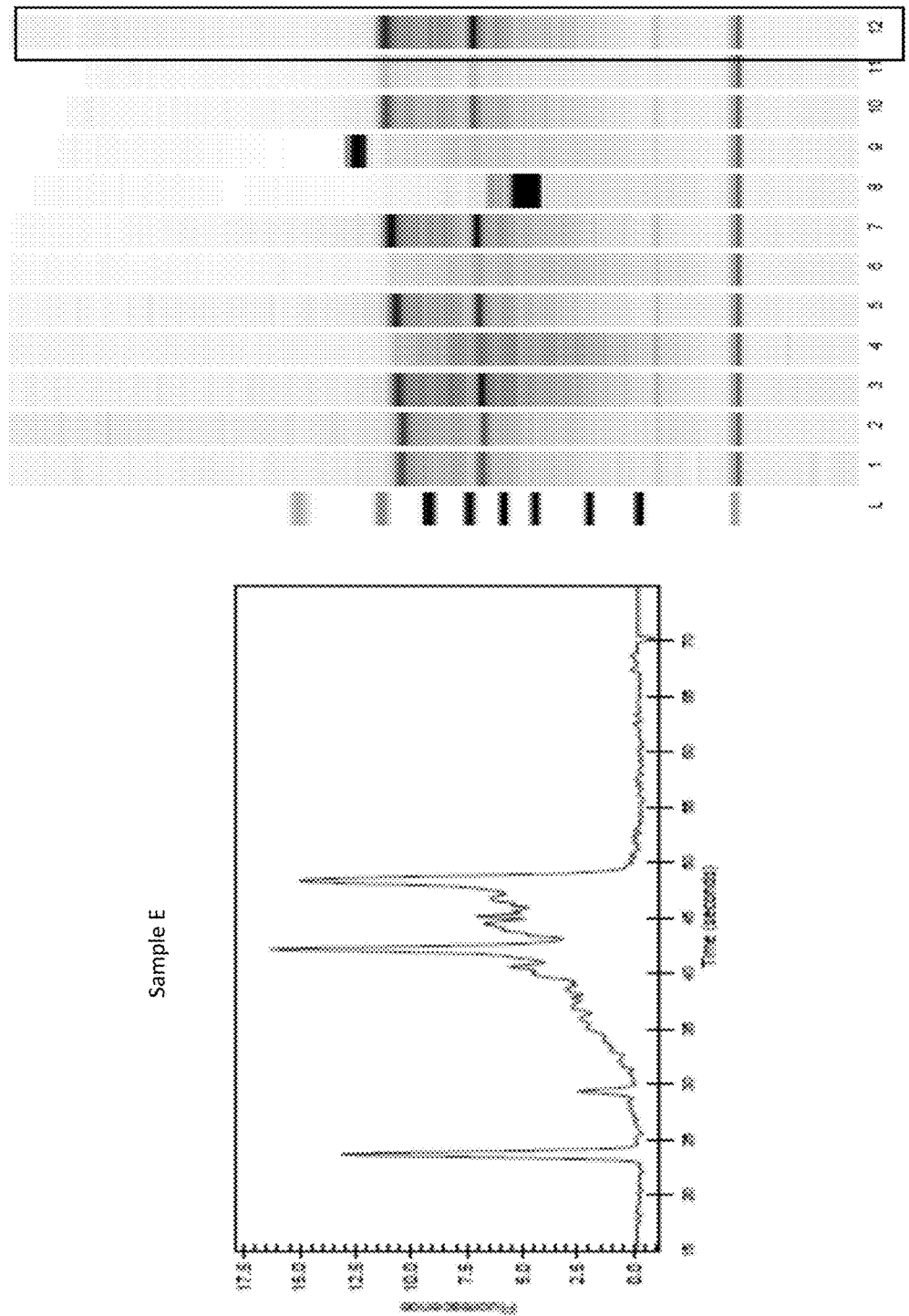

Using public microarray data provided by the GeneCards® gene expression database, GeneNote, an arbitrary expression score (0-10,000) was assigned to each gene on the candidate list. GeneNote data was compiled from two sources: Weizmann Institute high-density DNA microarray data and BioGPS, a gene annotation portal (biogps dot gnf dot org) [37-39]. Expression data is presented within GeneNote as a log-scale plot of normalized expression intensity across a range of healthy human tissues, as depicted in FIG. 4. Primarily based on Weizmann Institute array experiments performed on the Affymetrix GeneChip® HG-U95 set A-E, consisting of 62,839 probesets representing the full human genome, all expression data was normalized in a tissue-specific manner for comparison on a single plot [37, 38].

GeneNote plots the normalized intensity for each tissue type run in microarray experiments on a scale of 0-10,000 without providing the exact intensity score so approximated expression scores were noted for each gene on the candidate list. Based on the expression score assigned, candidate genes were sorted into six tiers: (1a) 150-449, (1b) 450-749, (1c) 750-999, (2) 1000-3332, (3) 3333-6665, and (4) 6666-10,000. As lower-expressing genes can often serve as good class discriminators, genes exhibiting significantly different expression levels between two groups, the low expression group was further stratified for weighted representation in the assay validation experiments [40, 41].

Selection of Genes for Assay Design

A comprehensive master list was compiled of all candidate genes, their functions as provided by the GeneCards®, Entrez Gene, and UniProtKB/Swiss-Prot databases, and expression scores provided by the GeneNote database. The list was ordered by expression score and a total of 62 genes, 10 from each expression tier and 2 control genes, were chosen for the assay design phase, as presented in Appendix I. The decision to include a gene in the design phase was primarily determined by gene function. Genes with a role in cell structure or function were highly preferred over genes with speculative functional roles or genes expressed during periods of immune system challenge or disease, as they are less variably expressed between individuals and are temporally stable.

Assay Design

Based on ease of design and cost effectiveness, Roche Universal ProbeLibrary assays were chosen for the assay validation phase. Within the online Universal ProbeLibrary Assay Design Center, ProbeFinder software (v2.45, human) was used to design region-specific real-time qPCR assays targeting the 62 genes of interest (www dot roche-applied-science dot com backslash sis backslash rtpcr backslashupl). ProbeFinder is a web-based software tool that designs optimal primer set/probe pairings for a user-defined gene of interest. Using 165 proprietary Universal ProbeLibrary (UPL)fluorescent probes, 8- and 9-mer motifs that are highly prevalent in the transcriptome, the software computes all possible primer/probe combinations around the probe hybridization sequences present within the gene of interest. To gauge the efficacy of individual assays, the software performs in silico PCR reactions to predict amplicon fidelity and minimize the risk of false assay signals [42]. FIG. 5 depicts an example of a ProbeFinder UPL assay design.

A total of 184 intron-spanning assays were designed with ProbeFinder: three designs per 60 genes of interest and two designs per 2 control genes. For each gene of interest, an optimal assay was designed for the 5', middle, and 3' regions. For control genes, ACTB and GAPDH, optimal assays were designed only for the 5' and 3' regions. Assay designs, consisting of forward and reverse primers and the corresponding UPL probe, were exported from the software and are presented in Appendix II. Primers were custom ordered from Sigma according to the following specifications: shipment in a 96-well plate format, purification by standard desalting, and lyophilized forward and reverse primer sets (20 nM each) were to be combined in a single well.

Assay Validation
Primer Preparation

The lyophilized primer sets, 20 nM each of both forward and reverse primers per assay design, were reconstituted with 200 µl DNase/RNase-free water for a standard stock solution of 100 µM. From the stock solution, working 1:5 dilutions were prepared on a Biomek FX liquid handling instrument (Beckman Coulter) for use in subsequent qPCR reactions.

Sample Collection and Automated RNA Extraction

Fresh human whole blood samples were collected in PAXgene® Blood RNA tubes (Qiagen/PreAnalytiX), according to manufacturer specifications. PAXgene® Blood RNA tubes contain a proprietary RNA stabilization reagent that protects RNA molecules from RNase degradation during cell lysis and minimizes gene induction post-collection [43]. Blood samples were drawn from five healthy donors, totaling two PAXgene® Blood RNA tubes per subject, with 2.5 ml of whole blood drawn per collection tube. Tube sets were labeled A-E to ensure donor anonymity. One set of donor tubes was stored at −20° C. for later extraction while the remaining set of tubes was processed immediately.

According to manufacturer specifications, the PAXgene® tubes were incubated for two hours at room temperature then stored overnight at 4° C. to adequately lyse the blood cells and stabilize the RNA. Once lysed, total RNA was extracted and purified using the PAXgene® Blood RNA MDx Kit on the BioRobot Universal instrument (Qiagen), according to the manufacturer's protocol. Total RNA yield and purity was assessed using Nanodrop ND-8000 spectrophotometric measurements (Thermo Fisher). Total RNA integrity was assessed with LabChip 90 HT RNA electropherogram and gel electrophoresis images (Caliper Life Sciences). Total RNA quality data is presented in FIGS. 7A-7F.

cDNA Synthesis and Amplification

In a two-step process, extracted RNA was reverse transcribed to cDNA, which was then amplified using the Ovation Pico WTA System (NuGEN) on a Biomek FX liquid handling instrument according to the manufacturer's protocol. cDNA yield and purity was assessed using Nanodrop ND-8000 spectrophotometric measurements. cDNA integrity was assessed with LabChip 90 HT RNA electropherogram and gel electrophoresis images. cDNA quality data is presented in FIGS. 8A-8F. Working dilutions of 1:200 cDNA were prepared with DNase/RNase-free water for use in subsequent qPCR reactions.

Assay Validation: Real-Time Quantitative PCR

Real-time qPCR reactions were run for 184 assays against 4 cDNA samples generated from intact RNA on a 7900HT Real-Time PCR System (Applied Biosystems). Three technical sample replicates and one no template control (NTC) were run for each assay. A general reaction plate map is presented in Table 1. Single 10 μl reactions consisted of a gene-specific forward/reverse primer set (Sigma), corresponding Universal ProbeLibrary probe (Roche), TaqMan®Gene Expression Master Mix (Applied Biosystems), DNase/RNase-free water, and 1:5 dilution cDNA template. To ensure accuracy and produce reliable gene expression data, all qPCR reaction plates were prepared in 384-well PCR plates on a Biomek FX liquid handling instrument.

TABLE 1

Assay validation phase: qPCR 384 well general plate map for assay validation qPCR reactions
Numbers refer to unique assays
'NTC' stands for No Template Control; these wells contain only assay master mix but no cDNA sample

|   |   | 1 | 2 | 3 | 4 | 5 | 6 | 7 | 8 | 9 | 10 | 11 | 12 | 13 | 14 | 15 | 16 | 17 | 18 |
|---|---|---|---|---|---|---|---|---|---|---|----|----|----|----|----|----|----|----|----|
| A | A | 1 | 1 | 2 | 2 | 3 | 3 | 4 | 4 | 5 | 5 | 6 | 6 | 7 | 7 | 8 | 8 | 9 | 9 |
|   | B | 1 | NTC | 2 | NTC | 3 | NTC | 4 | NTC | 5 | NTC | 6 | NTC | 7 | NTC | 8 | NTC | 9 | NTC |
| B | C | 1 | 1 | 2 | 2 | 3 | 3 | 4 | 4 | 5 | 5 | 6 | 6 | 7 | 7 | 8 | 8 | 9 | 9 |
|   | D | 1 | NTC | 2 | NTC | 3 | NTC | 4 | NTC | 5 | NTC | 6 | NTC | 7 | NTC | 8 | NTC | 9 | NTC |
| C | E | 1 | 1 | 2 | 2 | 3 | 3 | 4 | 4 | 5 | 5 | 6 | 6 | 7 | 7 | 8 | 8 | 9 | 9 |
|   | F | 1 | NTC | 2 | NTC | 3 | NTC | 4 | NTC | 5 | NTC | 6 | NTC | 7 | NTC | 8 | NTC | 9 | NTC |
| D | G | 1 | 1 | 2 | 2 | 3 | 3 | 4 | 4 | 5 | 5 | 6 | 6 | 7 | 7 | 8 | 8 | 9 | 9 |
|   | H | 1 | NTC | 2 | NTC | 3 | NTC | 4 | NTC | 5 | NTC | 6 | NTC | 7 | NTC | 8 | NTC | 9 | NTC |
| A | I | 13 | 13 | 14 | 14 | 15 | 15 | 16 | 16 | 17 | 17 | 18 | 18 | 19 | 19 | 20 | 20 | 21 | 21 |
|   | J | 13 | NTC | 14 | NTC | 15 | NTC | 16 | NTC | 17 | NTC | 18 | NTC | 19 | NTC | 20 | NTC | 21 | NTC |
| B | K | 13 | 13 | 14 | 14 | 15 | 15 | 16 | 16 | 17 | 17 | 18 | 18 | 19 | 19 | 20 | 20 | 21 | 21 |
|   | L | 13 | NTC | 14 | NTC | 15 | NTC | 16 | NTC | 17 | NTC | 18 | NTC | 19 | NTC | 20 | NTC | 21 | NTC |
| C | M | 13 | 13 | 14 | 14 | 15 | 15 | 16 | 16 | 17 | 17 | 18 | 18 | 19 | 19 | 20 | 20 | 21 | 21 |
|   | N | 13 | NTC | 14 | NTC | 15 | NTC | 16 | NTC | 17 | NTC | 18 | NTC | 19 | NTC | 20 | NTC | 21 | NTC |
| D | O | 13 | 13 | 14 | 14 | 15 | 15 | 16 | 16 | 17 | 17 | 18 | 18 | 19 | 19 | 20 | 20 | 21 | 21 |
|   | P | 13 | NTC | 14 | NTC | 15 | NTC | 16 | NTC | 17 | NTC | 18 | NTC | 19 | NTC | 20 | NW | 21 | NTC |

|   |   | 19 | 20 | 21 | 22 | 23 | 24 |
|---|---|----|----|----|----|----|----|
| A | A | 10 | 10 | 11 | 11 | 12 | 12 |
|   | B | 10 | NTC | 11 | NTC | 12 | NTC |
| B | C | 10 | 10 | 11 | 11 | 12 | 12 |
|   | D | 10 | NTC | 11 | NTC | 12 | NTC |
| C | E | 10 | 10 | 11 | 11 | 12 | 12 |
|   | F | 10 | NTC | 11 | NTC | 12 | NTC |
| D | G | 10 | 10 | 11 | 11 | 12 | 12 |
|   | H | 10 | NTC | 11 | NTC | 12 | NTC |
| A | I | 22 | 22 | 23 | 23 | 24 | 24 |
|   | J | 22 | NTC | 23 | NTC | 24 | NTC |
| B | K | 22 | 22 | 23 | 23 | 24 | 24 |
|   | L | 22 | NTC | 23 | NTC | 24 | NTC |
| C | M | 22 | 22 | 23 | 23 | 24 | 24 |
|   | N | 22 | NTC | 23 | NTC | 24 | NTC |
| D | O | 22 | 22 | 23 | 23 | 24 | 24 |
|   | P | 22 | NTC | 23 | NTC | 24 | NTC |

Results

Assay Performance Analysis and Scoring

For each of the assay validation reactions, RQ Manager version 1.2 software (Applied Biosystems) plotted the magnitude of fluorescence (ΔRn) against the PCR amplification cycle number. A comprehensive logarithmic amplification plot was generated and a threshold line was manually set at the midpoint of the linear phase of each plot, intersecting to define an individual $C_T$ value for each reaction well of a given assay. Individual $C_T$ values and amplification plots were exported for qualitative and descriptive statistical analyses.

$C_T$ values were grouped by assay then sub-grouped by sample for descriptive statistical analysis. For each assay, the statistical average and standard deviation of triplicate $C_T$ values per sample was calculated. Additionally, for each assay, a statistical average and standard deviation of $C_T$ values per all samples was calculated, as presented in Table 2.

TABLE 2

Assay Validation Phase: Expression Data and Descriptive Statistics

| Detector | Threshold | Avg $C_T$ A | StDev A | Avg $C_T$ E | StDev E | Avg $C_T$ C | StDev C | Avg $C_T$ D | StDev D | Overall Avg $C_T$ | Overall StDev |
|---|---|---|---|---|---|---|---|---|---|---|---|
| ACTB_L | 0.042 | 24 | 0.2 | 23.9 | 0.16 | 24.24 | 0.43 | 23.63 | 0.21 | 23.94 | 0.33 |
| ACTB_R | 0.062 | 21.18 | 0.17 | 21.22 | 0.07 | 20.91 | 0.1 | 20.91 | 0.07 | 21.05 | 0.18 |
| ACTR2_L | 0.091 | 22.72 | 0.16 | 22.68 | 0.1 | 22.76 | 0.23 | 22.72 | 0.34 | 22.72 | 0.19 |
| ACTR2_M | 0.082 | 25.84 | 0.14 | 25.63 | 0.07 | 25.52 | 0.14 | 25.4 | 0.14 | 25.6 | 0.2 |
| ACTR2_R | 0.066 | 23.27 | 0.23 | 22.99 | 0.06 | 23.13 | 0.08 | 23.28 | 0.15 | 23.17 | 0.17 |
| ADAR_L | 0.042 | 25.42 | 0.62 | 25.5 | 0.1 | 25.56 | 0.26 | 25.94 | 0.1 | 25.6 | 0.36 |
| ADAR_M | 0.042 | 24.38 | 0.24 | 24.9 | 0.04 | 23.81 | 0.17 | 24.57 | 0.1 | 24.41 | 0.43 |
| ADAR_R | 0.03 | 25.84 | 0.31 | 26.21 | 0.09 | 26.09 | 0.22 | 26.08 | 0.11 | 26.06 | 0.22 |
| ADD1_L | 0.035 | 29.52 | 0.22 | 29.72 | 0.18 | 29.18 | 0.48 | 29.31 | 0.15 | 29.43 | 0.33 |
| ADD1_M | 0.044 | 27.05 | 0.03 | 26.3 | 0.11 | 26.71 | 0.1 | 27.1 | 0.05 | 26.79 | 0.34 |
| ADD1_R | 0.09 | 26.18 | 0.21 | 25.05 | 0.17 | 25.12 | 0.19 | 25.35 | 0.26 | 25.43 | 0.51 |
| ADD3_L | 0.056 | 28.41 | 0.2 | 28.94 | 0.1 | 28.36 | 0.12 | 28.38 | 0.12 | 28.52 | 0.28 |
| ADD3_M | 0.088 | 27.49 | 0.14 | 27.92 | 0.13 | 27.23 | 0.11 | 27.45 | 0.21 | 27.52 | 0.29 |
| ADD3_R | 0.047 | 24.2 | 0.14 | 24.06 | 0.05 | 24.15 | 0.03 | 24.28 | 0.18 | 24.17 | 0.13 |
| AIM1_L | 0.043 | 30.55 | 0.3 | 29.47 | 0.17 | 30.39 | 0.07 | 30.93 | 0.06 | 30.33 | 0.58 |
| AIM1_M | 0.091 | 30.69 | 0.14 | 30.25 | 0.22 | 30.15 | 0.24 | 30.7 | 0.23 | 30.45 | 0.32 |
| AlM1_R | 0.132 | 26.05 | 0.08 | 25.74 | 0.18 | 25.76 | 0.08 | 25.91 | 0.21 | 25.87 | 0.18 |
| ARPC5_L | 0.063 | 22.06 | 0.54 | 22.2 | 0.16 | 21.85 | 0.11 | 21.86 | 0.05 | 21.99 | 0.29 |
| ARPC5_M | 0.077 | 21.25 | 0.1 | 21.2 | 0.02 | 20.74 | 0.1 | 20.62 | 0.16 | 20.95 | 0.3 |
| ARPC5_R | 0.057 | 22.39 | 0.41 | 22.17 | 0.16 | 21.7 | 0.15 | 21.57 | 0.17 | 21.96 | 0.41 |
| BACH2_L | 0.091 | 36.88 | 0.88 | 34.1 | 0.21 | 33.06 | 0.25 | 33.75 | 0.47 | 34.45 | 1.58 |
| BACH2_M | 0.035 | Undet. | Undet. | 27.64 | 0.17 | 27.54 | 0.28 | 26.92 | 0.2 | 27.36 | 0.39 |
| BACH2_R | 0.053 | 31.36 | 0.25 | 30.01 | 0.14 | 31.82 | 0.16 | 30.5 | 0.53 | 30.93 | 0.79 |
| C1orf38_L | 0.067 | 27.51 | 0.4 | 27.46 | 0.16 | 27.22 | 0.02 | 27.76 | 0.16 | 27.49 | 0.28 |
| C1orf38_M | 0.071 | 28.85 | 0.06 | 27.89 | 0.13 | 28.02 | 0.05 | 28.69 | 0.19 | 28.36 | 0.44 |
| C1orf38_R | 0.08 | 35.5 | 1.08 | 31.88 | 0.44 | 32 | 0.4 | 31.9 | 0.1 | 32.82 | 1.7 |
| CAPN2_L | 0.086 | 28.17 | 0.07 | 27.95 | 0.1 | 28.69 | 0.19 | 27.34 | 0.05 | 28.04 | 0.51 |
| CAPN2_M | 0.088 | 24.1 | 0.19 | 23.74 | 0.1 | 23.77 | 0.12 | 23.89 | 0.16 | 23.88 | 0.19 |
| CAPN2_R | 0.093 | 25.12 | 0.1 | 25.06 | 0.14 | 25.11 | 0.08 | 25.32 | 0.13 | 25.15 | 0.14 |
| CD163_L | 0.019 | 30.25 | 0.49 | 30.01 | 0.07 | 30.2 | 0.19 | 30.19 | 0.16 | 30.16 | 0.26 |
| CD163_M | 0.046 | 28.2 | 0.61 | 28.91 | 0.87 | 28.64 | 0.35 | 28.06 | 0.09 | 28.45 | 0.6 |
| CD163_R | 0.082 | 27.76 | 0.05 | 27.71 | 0.1 | 27.97 | 0.02 | 27.86 | 0.08 | 27.83 | 0.12 |
| CD27_L | 0.032 | 28.74 | 0.17 | 28.73 | 0.21 | 30.11 | 0.11 | 29.14 | 0.25 | 29.18 | 0.61 |
| CD27_M | 0.028 | 31.83 | 0.06 | 32.55 | 0.26 | 31.96 | 0.27 | 32.81 | 0.07 | 32.29 | 0.45 |
| CD27_R | 0.05 | 30.1 | 0.13 | 30.03 | 0.37 | 30.66 | 0.33 | 30.72 | 0.12 | 30.38 | 0.4 |
| CD300C_L | 0.031 | 32.8 | 0.26 | 32.61 | 0.13 | 34.07 | 0.39 | 31.06 | 0.21 | 32.63 | 1.14 |
| CD300C_M | 0.083 | 30.52 | 0.2 | 29.52 | 0.11 | 31.47 | 0.26 | 30.09 | 0.25 | 30.4 | 0.77 |
| CD300C_R | 0.066 | 30 | 0.39 | 30.03 | 0.33 | 31.18 | 0.34 | 29.69 | 0.11 | 30.23 | 0.65 |
| CD53_L | 0.022 | 23.2 | 0.28 | 23.35 | 0.59 | 23.6 | 0.65 | 23.27 | 0.3 | 23.36 | 0.44 |
| CD53_M | 0.061 | 24.94 | 0.21 | 24.71 | 0.12 | 24.85 | 0.22 | 24.69 | 0.13 | 24.8 | 0.19 |
| CD53_R | 0.023 | 26.16 | 0.21 | 25.93 | 0.41 | 25.88 | 0.25 | 25.63 | 0.29 | 25.9 | 0.33 |
| CD68_L | 0.04 | 22.1 | 0.09 | 21.45 | 0.04 | 21.89 | 0.18 | 21.58 | 0.08 | 21.75 | 0.28 |
| CD68_M | 0.059 | 27.48 | 0.2 | 27.34 | 0.69 | 27.15 | 0.23 | 28.61 | 0.23 | 27.65 | 0.69 |
| CD68_R | 0.132 | 26.55 | 0.08 | 25.54 | 0.07 | 26.09 | 0.12 | 25.95 | 0.2 | 26.03 | 0.39 |
| CD83_L | 0.036 | Undet. | Undet. | 36.28 | 0.41 | 37.07 | Undet. | 36.94 | 1.05 | 36.63 | 0.66 |
| CD83_M | 0.061 | 33.21 | 0.22 | 34.6 | 0.97 | 36.34 | 2.97 | 37.32 | Undet. | 34.82 | 1.92 |
| CD83_R | 0.095 | 30.81 | 0.34 | 29.83 | 0.15 | 30.34 | 0.17 | 31.5 | 0.17 | 30.62 | 0.67 |
| CDC42SE1_L | 0.04 | 29.85 | 0.19 | 30.36 | 0.16 | 31.55 | 0.47 | 31.67 | 0.49 | 30.86 | 0.86 |
| CDC42SE1_M | 0.076 | 24.79 | 0.12 | 24.95 | 0.3 | 24.42 | 0.22 | 24.68 | 0.16 | 24.71 | 0.27 |
| CDC42SE1_R | 0.058 | 24.34 | 0.05 | 24.09 | 0.3 | 23.97 | 0.09 | 23.51 | 0.18 | 23.98 | 0.35 |
| CSF3R_L | 0.028 | 26.03 | 0.18 | 26.58 | 0.51 | 25.76 | 0.63 | 25.92 | 0.31 | 26.1 | 0.47 |
| CSF3R_M | 0.06 | 28.29 | 0.08 | 28.59 | 0.15 | 27.67 | 0.13 | 28.03 | 0.09 | 28.15 | 0.37 |
| CSF3R_R | 0.056 | 24.39 | 0.23 | 24.65 | 0.31 | 24.38 | 0.24 | 24.51 | 0.17 | 24.48 | 0.24 |
| DDX58_L | 0.062 | 27.34 | 0.58 | 28.48 | 0.2 | 27.41 | 0.07 | 27.82 | 0.18 | 27.76 | 0.55 |
| DDX58_M | 0.04 | 26.45 | 0.9 | 26.3 | 0.09 | 25.88 | 0.32 | 26.28 | 0.25 | 26.23 | 0.48 |
| DDX58_R | 0.056 | 27.79 | 0.1 | 27.63 | 0.08 | 27.4 | 0.19 | 28.35 | 0.33 | 27.8 | 0.41 |
| EEF2_L | 0.01 | 28.23 | 0.84 | 27.96 | Undet. | 28.62 | 0.08 | 28.59 | 0.28 | 28.43 | 0.43 |
| EEF2_M | 0.062 | 24.29 | 0.1 | 24.13 | 0.14 | 24.15 | 0.34 | 24.28 | 0.07 | 24.21 | 0.18 |
| EEF2_R | 0.026 | 25.61 | 0.14 | 25.73 | 0.34 | 25.25 | 0.23 | 25.9 | 0.28 | 25.62 | 0.33 |
| F13A1_L | 0.06 | 27.91 | 0.11 | 27.31 | 0.14 | 26.29 | 0.09 | 26.96 | 0.12 | 27.12 | 0.62 |
| F13A1_M | 0.077 | 26.95 | 0.26 | 26.47 | 0.09 | 25.29 | 0.08 | 26.42 | 0.12 | 26.28 | 0.65 |
| F13A1_R | 0.085 | 27.85 | 0.15 | 26.89 | 0.16 | 26.01 | 0.11 | 27.52 | 0.23 | 27.07 | 0.75 |
| FCN1_L | 0.134 | 25.52 | 0.13 | 24.63 | 0.26 | 25.01 | 0.4 | 25.33 | 0.09 | 25.12 | 0.41 |
| FCN1_M | 0.054 | 29.98 | 0.33 | 23.7 | 0.42 | 23.81 | 0.49 | 24.68 | 0.14 | 25.54 | 2.72 |
| FCN1_R | 0.051 | 25.08 | 0.07 | 24.47 | 0.11 | 24.67 | 0.11 | 25.03 | 0.07 | 24.81 | 0.28 |

TABLE 2-continued

Assay Validation Phase: Expression Data and Descriptive Statistics

| Detector | Threshold | Avg $C_T$ A | StDev A | Avg $C_T$ E | StDev E | Avg $C_T$ C | StDev C | Avg $C_T$ D | StDev D | Overall Avg $C_T$ | Overall StDev |
|---|---|---|---|---|---|---|---|---|---|---|---|
| GAPDH_L | 0.08 | 24.43 | 0.12 | 24.55 | 0.13 | 25.37 | 0.09 | 25.07 | 0.18 | 24.86 | 0.42 |
| GAPDH_R | 0.122 | 27.22 | 0.19 | 26.7 | 0.2 | 26.81 | 0.22 | 27.16 | 0.23 | 26.97 | 0.29 |
| GZMB_L | 0.006 | 28.71 | Undet. | 30.31 | 0.53 | 29.97 | Undet. | 29.06 | 0.24 | 29.68 | 0.77 |
| GZMB_M | 0.06 | 33.12 | 0.92 | 26.79 | 0.14 | 25.95 | 0.24 | 26.24 | 0.13 | 28.02 | 3.11 |
| GZMB_R | 0.06 | 26.7 | 0.1 | 25.74 | 0.22 | 26.19 | 0.2 | 25.73 | 0.04 | 26.09 | 0.44 |
| IL10RB_L | 0.056 | 30.73 | 0.07 | 30.23 | 0.17 | 29.77 | 0.17 | 30.35 | 0.07 | 30.27 | 0.37 |
| IL10RB_M | 0.055 | 31.71 | 0.43 | 30.91 | 0.26 | 31.04 | 0.11 | 30.57 | 0.3 | 31.06 | 0.5 |
| IL10RB_R | 0.053 | 29.69 | 0.15 | 29.33 | 0.09 | 29.18 | 0.11 | 28.96 | 0.09 | 29.29 | 0.29 |
| IL15RA_L | 0.031 | 37.37 | Undet. | 34.24 | 0.12 | 35.93 | 0.86 | 34.67 | 0.26 | 35.19 | 1.13 |
| IL15RA_M | 0.104 | 30.26 | 0.13 | 28.23 | 0.18 | 29.76 | 0.24 | 29.29 | 0.31 | 29.39 | 0.81 |
| IL15RA_R | 0.01 | 35.18 | 0.53 | 36.73 | 1.36 | 36.08 | 0.37 | 34.81 | 0.48 | 35.75 | 1.06 |
| IL6R_L | 0.066 | 33.22 | 0.29 | 34.2 | 0.22 | 33.69 | 0.38 | 33.91 | 0.33 | 33.75 | 0.46 |
| IL6R_M | 0.041 | 28.03 | 0.42 | 28.57 | 0.17 | 28.34 | 0.02 | 27.54 | 0.28 | 28.1 | 0.48 |
| IL6R_R | 0.076 | 25.43 | 0.19 | 25.48 | 0.09 | 25.42 | 0.02 | 25.58 | 0.22 | 25.48 | 0.15 |
| IL7R_L | 0.022 | 26.88 | 0.16 | Undet. | Undet. | 27.26 | 0.2 | Undet. | Undet. | 27.07 | 0.26 |
| IL7R_M | 0.06 | 28.11 | 1.02 | 28.96 | 0.11 | 28.82 | 0.13 | 28.92 | 0.08 | 28.7 | 0.57 |
| IL7R_R | 0.033 | 25.03 | 0.23 | 26.06 | 0.07 | 25.62 | 0.4 | 26.28 | 0.03 | 25.75 | 0.54 |
| ITGB2_L | 0.061 | 25.49 | 0.22 | 25.25 | 0.11 | 25.48 | 0.09 | 25.3 | 0.11 | 25.38 | 0.17 |
| ITGB2_M | 0.042 | 25.97 | 0.45 | 25.81 | 0.32 | 26.18 | 0.29 | 26.25 | 0.3 | 26.05 | 0.35 |
| ITGB2_R | 0.018 | 26.96 | 0.35 | 26.6 | 0.28 | 26.86 | 0.27 | 27.34 | 0.57 | 26.94 | 0.43 |
| IVNS1ABP_L | 0.069 | 27.76 | 0.19 | 27.56 | 0.29 | 26.79 | 0.07 | 27.15 | 0.19 | 27.32 | 0.43 |
| IVNS1ABP_M | 0.029 | 27.82 | 0.62 | 27.43 | 0.66 | 28.16 | 0.23 | 27.58 | 0 | 27.75 | 0.49 |
| IVNS1ABP_R | 0.035 | 27.12 | 0.13 | 27.55 | 0.1 | 26.72 | 0.32 | 26.75 | 0.18 | 27.04 | 0.39 |
| KLRF1_L | 0.03 | 34.22 | 0.29 | 32.9 | 0.18 | 32.51 | 0.23 | 32.89 | 0.24 | 33.13 | 0.71 |
| KLRF1_M | 0.021 | 34.32 | 0.51 | 34.07 | 0.62 | 35.22 | 2.32 | 34.41 | 0.3 | 34.44 | 0.92 |
| KLRF1_R | 0.05 | 33.06 | 0.28 | 33.5 | 0.37 | 33.64 | 0.06 | 34.94 | 0.45 | 33.78 | 0.79 |
| LASP1_L | 0.062 | 25.45 | 0.23 | 24.98 | 0.08 | 25.45 | 0.08 | 24.91 | 0.15 | 25.2 | 0.29 |
| LASP1_M | 0.059 | 25.62 | 0.26 | 25.31 | 0.15 | 24.89 | 0.15 | 24.82 | 0.09 | 25.16 | 0.37 |
| LASP1_R | 0.067 | 27.69 | 0.22 | 27.22 | 0.09 | 26.85 | 0.04 | 26.97 | 0.04 | 27.18 | 0.36 |
| LCP1_L | 0.015 | 21.57 | 0.33 | 21.54 | 0.37 | 21.63 | 0.16 | 21.17 | 0.36 | 21.5 | 0.32 |
| LCP1_M | 0.088 | 20.78 | 0.22 | 20.32 | 0.17 | 20.94 | 0.05 | 20.52 | 0.13 | 20.64 | 0.28 |
| LCP1_R | 0.033 | 25.34 | 0.21 | 25.06 | 0.24 | 25.1 | 0.57 | 25.08 | 0.11 | 25.14 | 0.3 |
| LILRA5_L | 0.025 | 31.01 | 0.24 | 30.99 | 0.08 | 32.35 | 0.25 | 30.95 | 0.07 | 31.33 | 0.64 |
| LILRA5_M | 0.112 | 29.65 | 0.29 | 29.39 | 0.25 | 31.21 | 0.11 | 30.2 | 0.33 | 30.11 | 0.76 |
| LILRA5_R | 0.067 | 28.1 | 0.05 | 27.59 | 0.2 | 29.03 | 0.19 | 27.68 | 0.17 | 28.1 | 0.61 |
| LPXN_L | 0.038 | 31.96 | 0.17 | 31.18 | 0.3 | 31.89 | 0.36 | 31.51 | 0.27 | 31.64 | 0.4 |
| LPXN_M | 0.08 | 29.41 | 0.14 | 29.76 | 0.2 | 29.76 | 0.07 | 29.57 | 0.06 | 29.63 | 0.19 |
| LPXN_R | 0.068 | 32.11 | 0.15 | 32.09 | 0.25 | 32.48 | 0.22 | 31.69 | 0.44 | 32.09 | 0.38 |
| LTF_L | 0.022 | 36.81 | 0.62 | 37.05 | 0.47 | 35.13 | 0.2 | 34.3 | 0.23 | 35.73 | 1.26 |
| LTF_M | 0.037 | 28.75 | 0.09 | 27.63 | 0.03 | 27.73 | 0.11 | 29.08 | 0.07 | 28.3 | 0.66 |
| LTF_R | 0.08 | 27.4 | 0.15 | 25.74 | 0.09 | 26.25 | 0.06 | 26.95 | 0.11 | 26.59 | 0.67 |
| LY75_L | 0.024 | 31.12 | 0.22 | 31.33 | 0.29 | 32.26 | 0.33 | 30.8 | 0.21 | 31.38 | 0.61 |
| LY75_M | 0.029 | 29.13 | 0.09 | 29.32 | 0.18 | 28.7 | 0.58 | 28.87 | 0.17 | 29.01 | 0.37 |
| LY75_R | 0.069 | 29.27 | 0.29 | 30.01 | 0.3 | 29.29 | 0.23 | 28.64 | 0.19 | 29.3 | 0.55 |
| NCF1_L | 0.061 | 24.76 | 0.51 | 24.93 | 0.13 | 24.38 | 0.06 | 24.39 | 0.19 | 24.62 | 0.35 |
| NCF1_M | 0.063 | 26.14 | 0.02 | 26.2 | 0.26 | 25.21 | 0.28 | 25.44 | 0.17 | 25.75 | 0.48 |
| NCF1_R | 0.064 | 23.91 | 0.04 | 24.06 | 0.15 | 23.69 | 0.24 | 23.74 | 0.22 | 23.85 | 0.22 |
| NCF2_L | 0.059 | 24.44 | 0.1 | 24.81 | 0.15 | 24.4 | 0.1 | 24.24 | 0.12 | 24.47 | 0.24 |
| NCF2_M | 0.093 | 23.09 | 0.17 | 23.54 | 0.19 | 23.45 | 0.1 | 23.27 | 0.17 | 23.34 | 0.23 |
| NCF2_R | 0.042 | 24.63 | 0.1 | 24.88 | 0.08 | 24.66 | 0.04 | 24.52 | 0.22 | 24.67 | 0.17 |
| NCF4_L | 0.052 | 27.47 | 0.38 | 28.01 | 0.1 | 27.61 | 0.04 | 27.35 | 0.13 | 27.61 | 0.31 |
| NCF4_M | 0.075 | 26.74 | 0.2 | 26.76 | 0.11 | 27.05 | 0.16 | 27.02 | 0.2 | 26.89 | 0.21 |
| NCF4_R | 0.147 | 31.07 | 0.18 | 31.03 | 0.26 | 32.49 | 0.37 | 31.71 | 0.08 | 31.58 | 0.65 |
| NCL_L | 0.057 | 25.74 | 0.15 | 25.55 | 0.19 | 25.82 | 0.15 | 26.23 | 0.08 | 25.84 | 0.29 |
| NCL_M | 0.03 | 24.31 | 0.11 | 23.83 | 0.2 | 24.39 | 0.22 | 24.41 | 0.12 | 24.24 | 0.29 |
| NCL_R | 0.059 | 23.42 | 0.16 | 23.46 | 0.21 | 23.19 | 0.11 | 23.47 | 0.01 | 23.39 | 0.17 |
| NCOA1_L | 0.049 | 25.09 | 0.35 | 24.7 | 0.14 | 24.37 | 0.22 | 24.64 | 0.15 | 24.7 | 0.33 |
| NCOA1_M | 0.058 | 24.79 | 0.16 | 25.08 | 0.09 | 24.61 | 0.1 | 24.49 | 0.14 | 24.74 | 0.26 |
| NCOA1_R | 0.096 | 27.8 | 0.2 | 28.47 | 0.06 | 28.04 | 0.11 | 27.9 | 0.1 | 28.05 | 0.29 |
| NLRP1_L | 0.06 | 26.98 | 0.13 | 27.55 | 0.23 | 27.16 | 0.33 | 27.05 | 0.09 | 27.19 | 0.3 |
| NLRP1_M | 0.129 | 28.39 | 0.21 | 28.58 | 0.23 | 28.25 | 0.11 | 28.5 | 0.18 | 28.43 | 0.21 |
| NLRP1_R | 0.032 | 28.86 | 0.11 | 29.05 | 0.21 | 28.96 | 0.25 | 28.57 | 0.23 | 28.86 | 0.26 |
| OAS2_L | 0.132 | 29.98 | 0.09 | 30.12 | 0.13 | 30.02 | 0.09 | 29.76 | 0.15 | 29.97 | 0.17 |
| OAS2_M | 0.051 | 27.4 | 0.14 | 26.76 | 0.08 | 27.4 | 0.1 | 27.34 | 0.15 | 27.23 | 0.3 |
| OAS2_R | 0.096 | 27.06 | 0.14 | 26.86 | 0.11 | 27.24 | 0.16 | 27.14 | 0.24 | 27.08 | 0.2 |
| OAS3_L | 0.068 | 29.73 | 0.2 | 31.92 | 0.14 | 34.05 | 0.87 | 31.36 | 0.1 | 31.77 | 1.66 |
| OAS3_M | 0.059 | 29.46 | 0.17 | 28.16 | 0.04 | 29.42 | 0.2 | 28.41 | 0.2 | 28.86 | 0.63 |
| OAS3_R | 0.08 | 28.09 | 0.22 | 29.69 | 0.22 | 29.04 | 0.13 | 28.94 | 0.06 | 28.94 | 0.61 |
| PDLIM1_L | 0.079 | 33.66 | 0.42 | 32.15 | 0.16 | 31.19 | 0.21 | 30.83 | 0.26 | 31.95 | 1.17 |
| PDLIM1_M | 0.093 | 28.86 | 0.33 | 28.01 | 0.19 | 27.86 | 0.06 | 28.06 | 0.15 | 28.2 | 0.45 |
| PDLIM1_R | 0.037 | 27.9 | 0.16 | 28.97 | 0.29 | 28.1 | 0.18 | 29.01 | 0.19 | 28.5 | 0.55 |
| PDLIM2_L | 0.041 | 30.35 | 0.07 | 31.38 | 0.62 | 30.44 | 0.24 | 30.85 | 0.2 | 30.75 | 0.52 |
| PDLIM2_M | 0.034 | 32.18 | 0.17 | 31.72 | 0.11 | 32.13 | 0.19 | 32.47 | 0.36 | 32.12 | 0.34 |
| PDLIM2_R | 0.012 | Undet. | Undet. | Undet. | Undet. | 38.02 | Undet. | Undet. | Undet. | 38.02 | Undet. |
| RAF1_L | 0.047 | 30.25 | 0.11 | 29.6 | 0.2 | 29.67 | 0.15 | 29.62 | 0.23 | 29.79 | 0.32 |

TABLE 2-continued

Assay Validation Phase: Expression Data and Descriptive Statistics

| Detector | Threshold | Avg $C_T$ A | StDev A | Avg $C_T$ E | StDev E | Avg $C_T$ C | StDev C | Avg $C_T$ D | StDev D | Overall Avg $C_T$ | Overall StDev |
|---|---|---|---|---|---|---|---|---|---|---|---|
| RAF1_M | 0.067 | 30.28 | 0.16 | 30.76 | 0.11 | 30.62 | 0.39 | 30.23 | 0.03 | 30.47 | 0.3 |
| RAF1_R | 0.082 | 27.46 | 0.04 | 27.02 | 0.07 | 26.97 | 0.11 | 26.69 | 0.1 | 27.03 | 0.29 |
| ROCK2_L | 0.038 | 23.79 | 0.1 | 23.8 | 0.2 | 23.88 | 0.28 | 23.77 | 0.12 | 23.81 | 0.17 |
| ROCK2_M | 0.013 | 31.41 | 0.25 | 30.43 | 0.09 | 30.37 | 0.46 | 31.01 | 0.18 | 30.81 | 0.51 |
| ROCK2_R | 0.083 | 30.54 | 0.15 | 29.61 | 0.1 | 30.95 | 0.11 | 30.98 | 0.25 | 30.52 | 0.59 |
| SELL_L | 0.045 | 23.28 | 0.2 | 24.06 | 0.11 | 23.8 | 0.12 | 22.65 | 0.26 | 23.45 | 0.59 |
| SELL_M | 0.17 | 24.4 | 0.16 | 24.58 | 0.27 | 24.99 | 0.14 | 23.96 | 0.08 | 24.48 | 0.41 |
| SELL_R | 0.039 | 26.91 | 0.14 | 27.37 | 0.17 | 27.33 | 0.39 | 26.68 | 0.1 | 27.05 | 0.36 |
| SELP_L | 0.104 | 35.34 | 0.55 | 30.57 | 0.07 | 28.75 | 0.03 | 30.61 | 0.15 | 31.32 | 2.56 |
| SELP_M | 0.072 | 33.18 | 0.3 | 30.78 | 0.23 | 31.87 | 0.17 | 32.78 | 0.9 | 32.15 | 1.05 |
| SELP_R | 0.027 | Undet. | Undet. | 35.1 | 0.38 | 33.06 | 0.43 | 37.31 | 0.07 | 35.16 | 1.86 |
| SERPINA1_L | 0.064 | 25.82 | 0.25 | 24.34 | 0.02 | 23.83 | 0.15 | 24.52 | 0.16 | 24.63 | 0.78 |
| SERPINA1_M | 0.03 | 26.43 | 0.49 | 24.44 | 0.22 | 24.66 | 0.2 | 25.34 | 0.23 | 25.22 | 0.85 |
| SERPINA1_R | 0.112 | 22.34 | 0.05 | 21.23 | 1.08 | 21.97 | 0.16 | 22.58 | 0.16 | 22.03 | 0.71 |
| SORL1_L | 0.093 | 24.57 | 0.15 | 24.68 | 0.12 | 24.96 | 0.07 | 24.48 | 0.16 | 24.67 | 0.22 |
| SORL1_M | 0.075 | 26.1 | 0.22 | 26.36 | 0.02 | 25.87 | 0.19 | 25.93 | 0.19 | 26.09 | 0.24 |
| SORL1_R | 0.086 | 23.63 | 0.17 | 23.59 | 0.07 | 23.68 | 0.2 | 23.44 | 0.19 | 23.58 | 0.17 |
| STAT6_L | 0.08 | 24.4 | 0.04 | 24.27 | 0.25 | 24.39 | 0.29 | 24.2 | 0.1 | 24.32 | 0.19 |
| STAT6_M | 0.082 | 25.79 | 0.16 | 25.68 | 0.14 | 25.43 | 0.11 | 25.38 | 0.15 | 25.57 | 0.21 |
| STAT6_R | 0.05 | 27.44 | 0.06 | 28.55 | 0.43 | 27.94 | 0.28 | 27.98 | 0.21 | 27.98 | 0.47 |
| STX4_L | 0.072 | 25.77 | 0.25 | 25.22 | 0.11 | 25.69 | 0.08 | 25.71 | 0.21 | 25.6 | 0.28 |
| STX4_M | 0.076 | 29.93 | 0.18 | 29.66 | 0.38 | 32.2 | 0.46 | 29.9 | 0.22 | 30.42 | 1.12 |
| STX4_R | 0.082 | 29.09 | 0.16 | 28.54 | 0.21 | 28.76 | 0.08 | 28.55 | 0.12 | 28.74 | 0.26 |
| SYNE2_L | 0.06 | 28.25 | 0.36 | 28.18 | 0.22 | 28.98 | 0.13 | 27.76 | 0.1 | 28.29 | 0.5 |
| SYNE2_M | 0.057 | 25.26 | 0.27 | 25.63 | 0.12 | 25.57 | 0.17 | 25.5 | 0.09 | 25.49 | 0.21 |
| SYNEZ_R | 0.062 | 33.43 | 1.08 | 32.01 | 0.08 | 31.27 | 0.09 | 33.01 | 0.34 | 32.43 | 1.01 |
| TES_L | 0.098 | 24.37 | 0.12 | 24.81 | 0.17 | 23.76 | 0.2 | 23.97 | 0.21 | 24.23 | 0.45 |
| TES_M | 0.095 | 28.53 | 0.06 | 28.77 | 0.17 | 28.96 | 0.02 | 28.19 | 0.05 | 28.61 | 0.31 |
| TES_R | 0.041 | 28.15 | 0.07 | 28.32 | 0.14 | 28.33 | 0.22 | 27.97 | 0.18 | 28.19 | 0.21 |
| TREM1_L | 0.053 | 29.88 | 0.1 | 29.54 | 0.03 | 29.54 | 0.16 | 29.57 | 0.24 | 29.63 | 0.2 |
| TREM1_M | 0.076 | 27.95 | 0.24 | 26.87 | 0.06 | 27.35 | 0.16 | 28.22 | 0.12 | 27.6 | 0.56 |
| TREM1_R | 0.05 | 26.72 | 0.01 | 26.38 | 0.12 | 26.72 | 0.13 | 27.21 | 0.18 | 26.76 | 0.33 |
| TRPM2_L | 0.069 | 30.54 | 0.16 | 35.71 | 0.59 | 35.65 | 0.98 | 31.57 | 0.3 | 33.37 | 2.5 |
| TRPM2_M | 0.075 | 34.13 | 0.92 | 32.99 | 0.51 | 33.32 | 0.14 | 34.05 | 0.69 | 33.62 | 0.74 |
| TRPM2_R | 0.091 | 35.71 | Undet. | 37.02 | 1.16 | 33.16 | 0.49 | 33.83 | 0.31 | 34.77 | 1.82 |
| TXNIP_L | 0.086 | 20.51 | 0.07 | 20.32 | 0.1 | 20.15 | 0.2 | 19.81 | 0.12 | 20.2 | 0.29 |
| TXNIP_M | 0.057 | 21.78 | 0.04 | 21.78 | 0.23 | 21.63 | 0.21 | 21.37 | 0.21 | 21.64 | 0.24 |
| TXNIP_R | 0.11 | 23.83 | 0.15 | 23.94 | 0.13 | 23.62 | 0.13 | 23.59 | 0.18 | 23.75 | 0.2 |
| VIM_L | 0.057 | 35.4 | 0.28 | 37.37 | 0.98 | 35.47 | 0.21 | 37.63 | 0.84 | 36.39 | 1.17 |
| VIM_M | 0.051 | 25.59 | 0.12 | 25.56 | 0.19 | 25.88 | 0.36 | 25.96 | 0.12 | 25.75 | 0.26 |
| VIM_R | 0.056 | 23.23 | 0.12 | 23.03 | 0.02 | 23.28 | 0.15 | 23.45 | 0.16 | 23.24 | 0.19 |
| ZAP70_L | 0.054 | 37.11 | 1.17 | 36.46 | 0.94 | 36.35 | 0.1 | 36.41 | 0.89 | 36.56 | 0.76 |
| ZAP70_M | 0.106 | 31.13 | 0.11 | 31.28 | 0.24 | 31.43 | 0.18 | 31.48 | 0.01 | 31.33 | 0.2 |
| ZAP70_R | 0.091 | 30.35 | 0.05 | 30.92 | 0.3 | 29.93 | 0.33 | 30.51 | 0.25 | 30.42 | 0.43 |

Figure 9A:
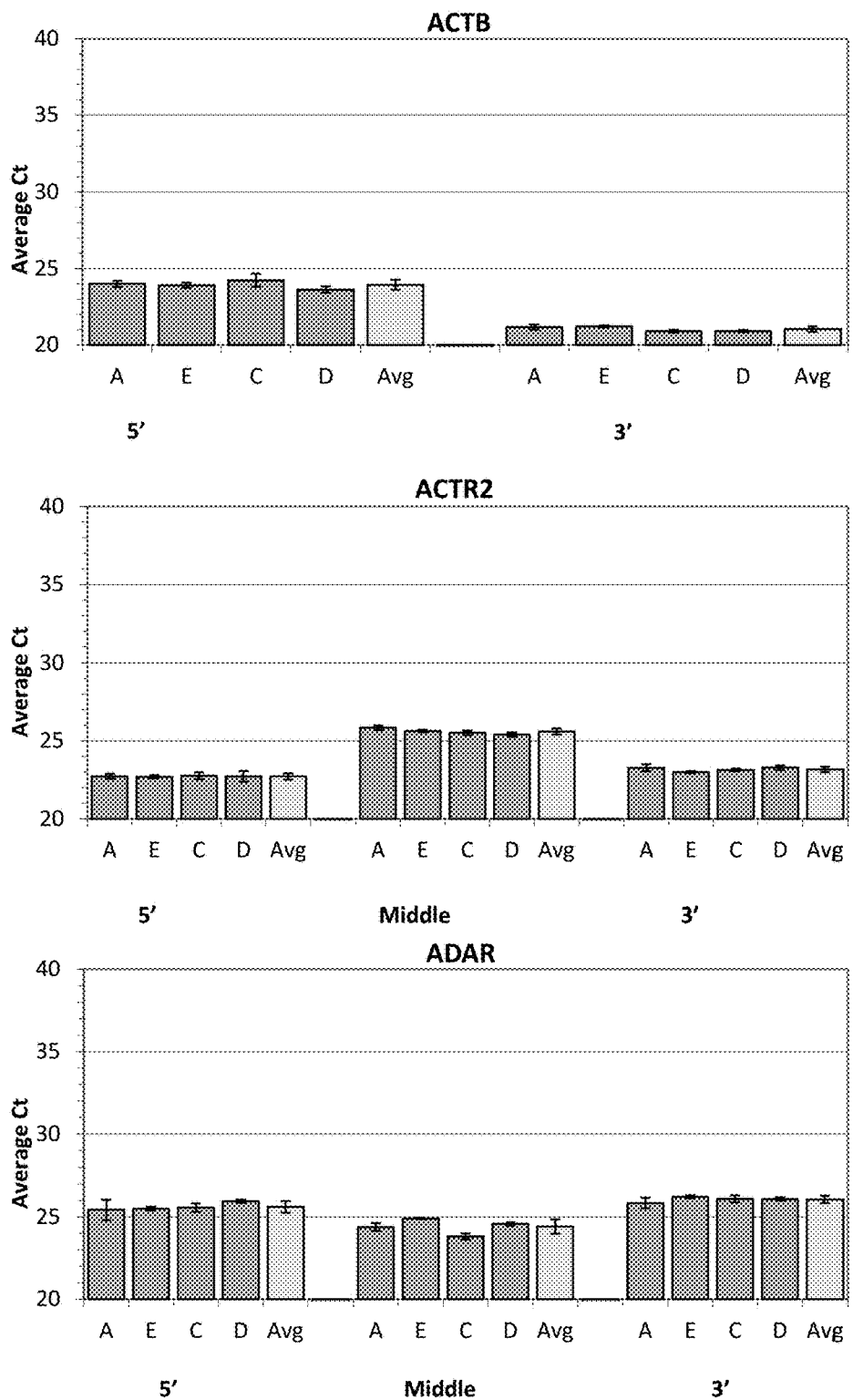
FIGS. 9A-9U: Assay Validation Histograms: Sample average and overall average Cτ values of regional assays.
Figure 9B:
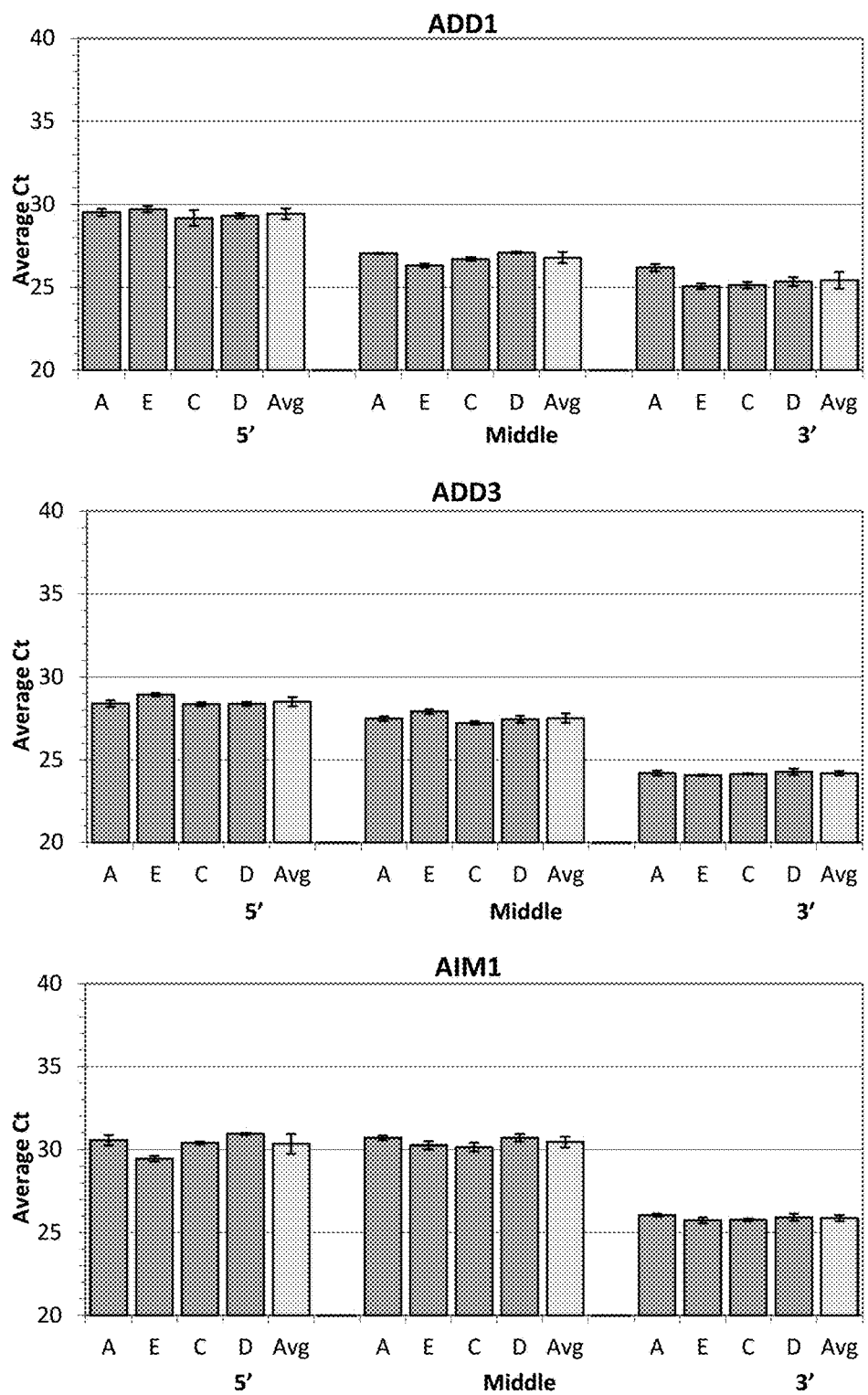
Figure 9C:
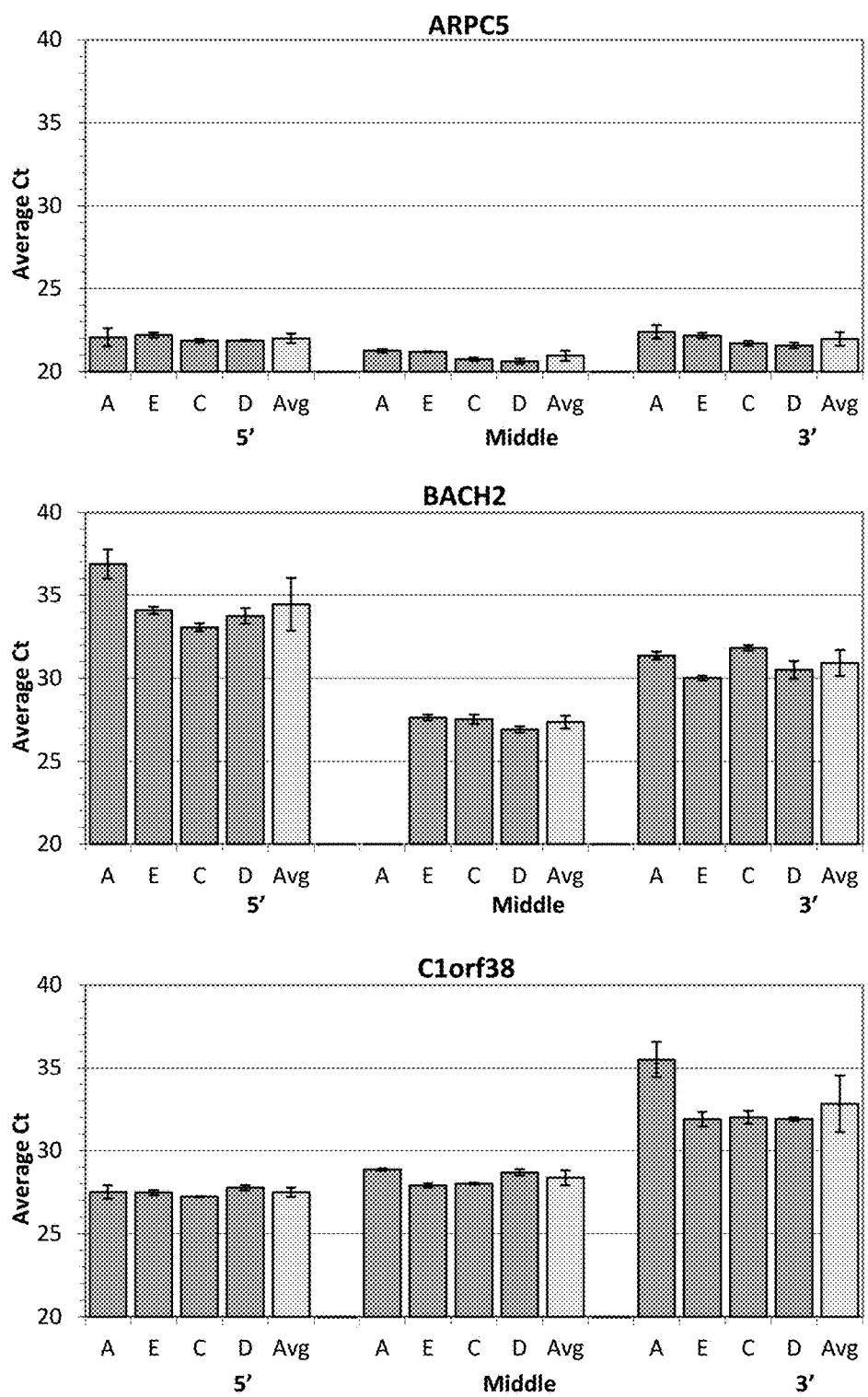
Figure 9D:
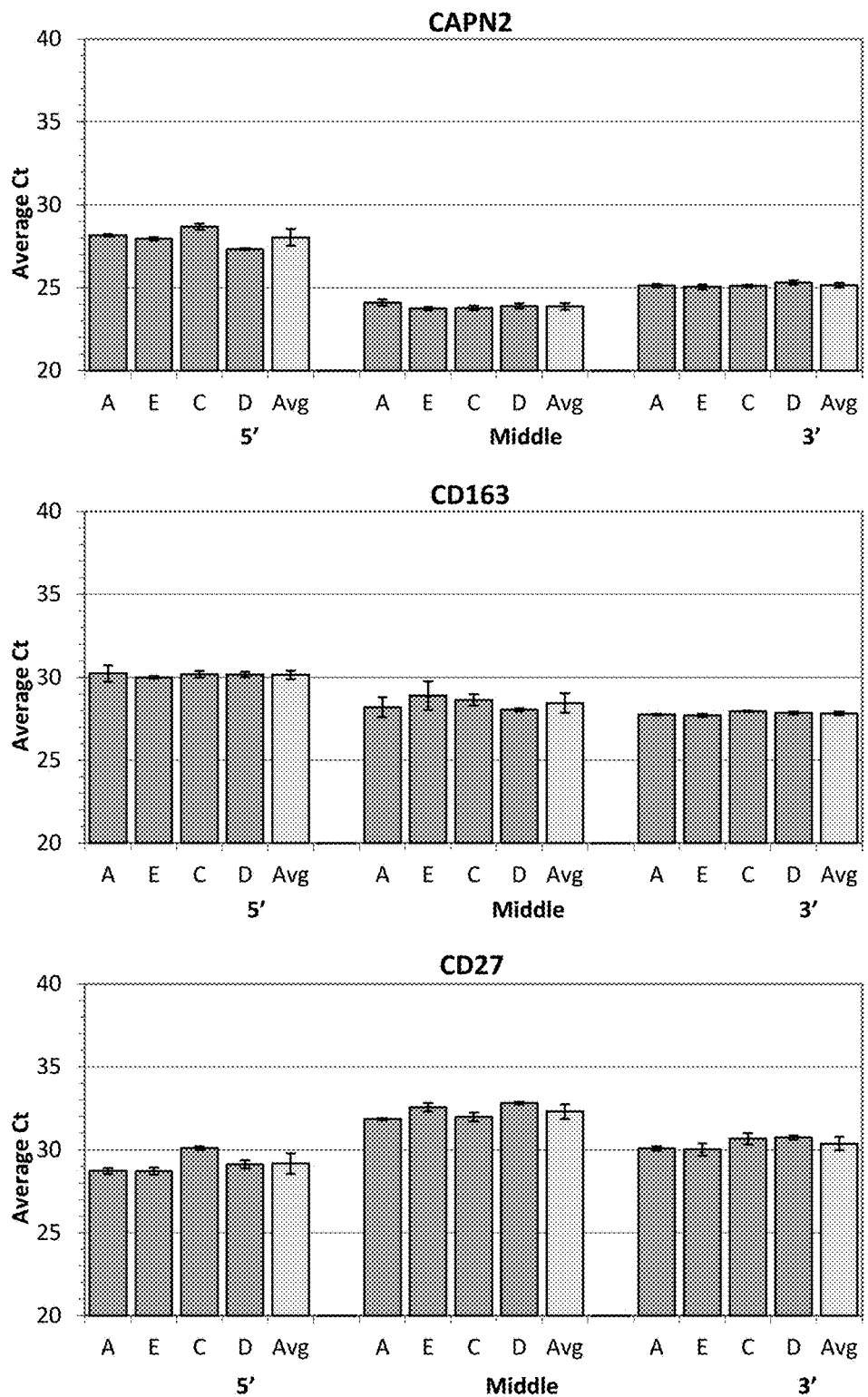
Figure 9E:
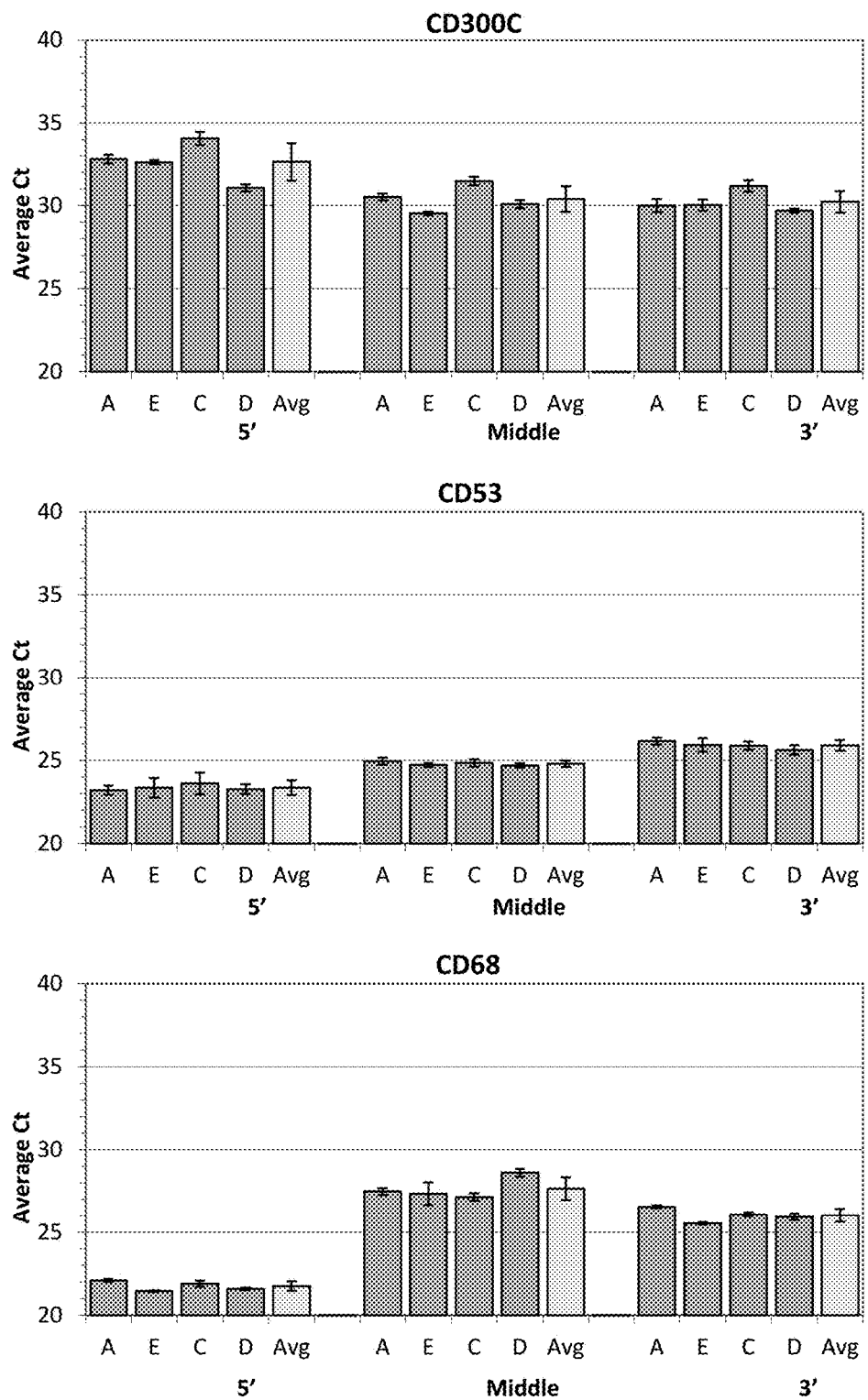
Figure 9F:
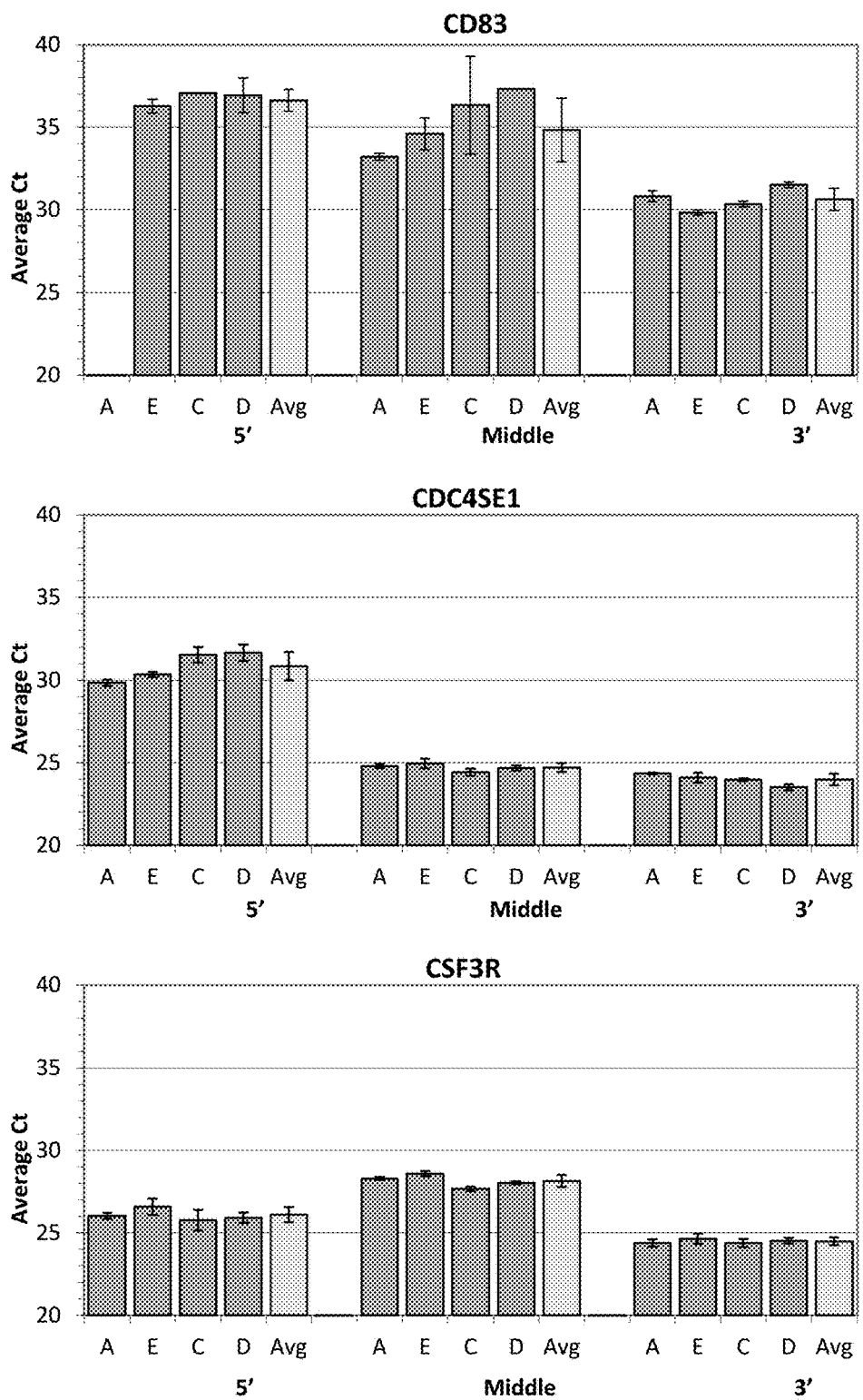
Figure 9G:
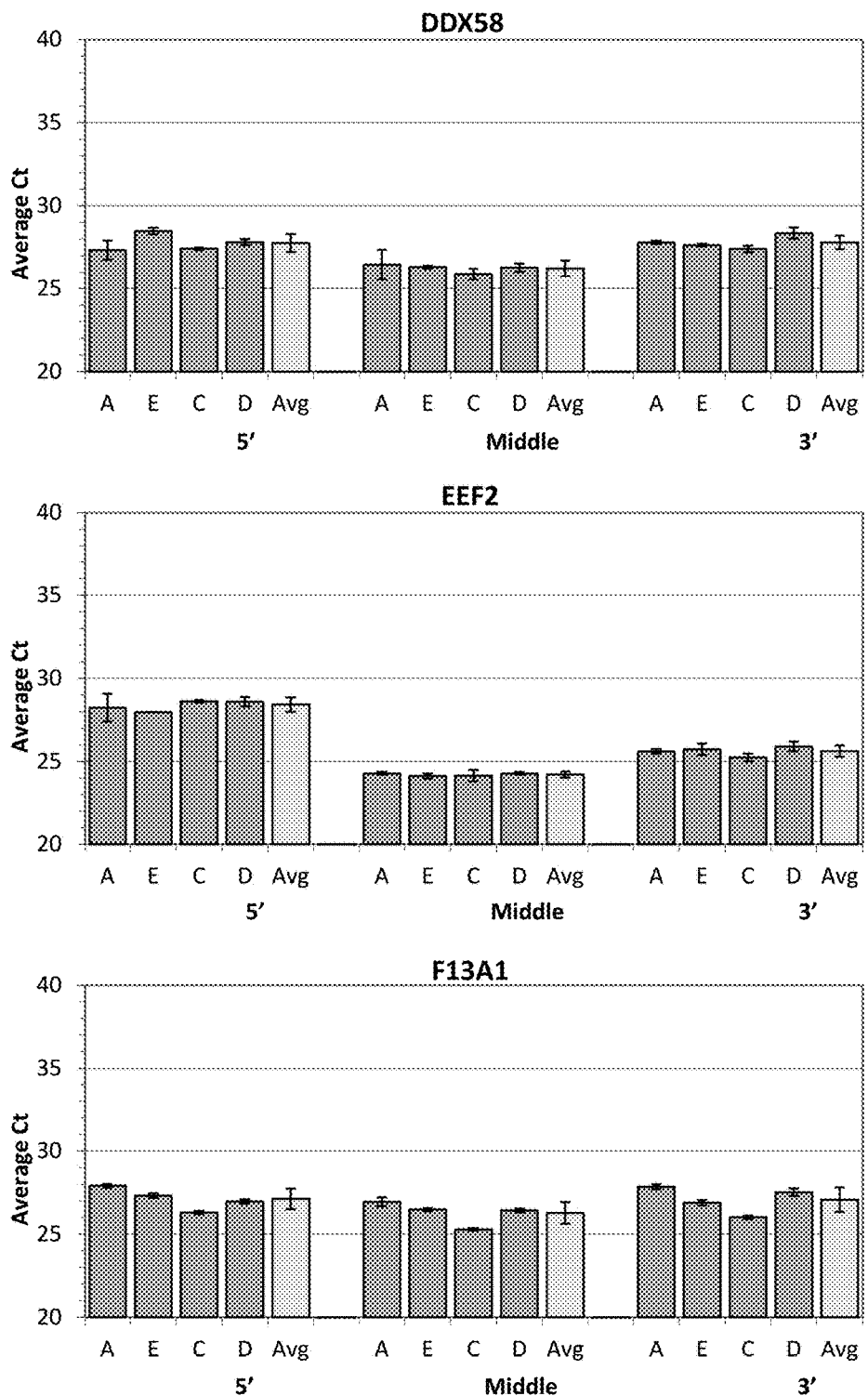
Figure 9H:
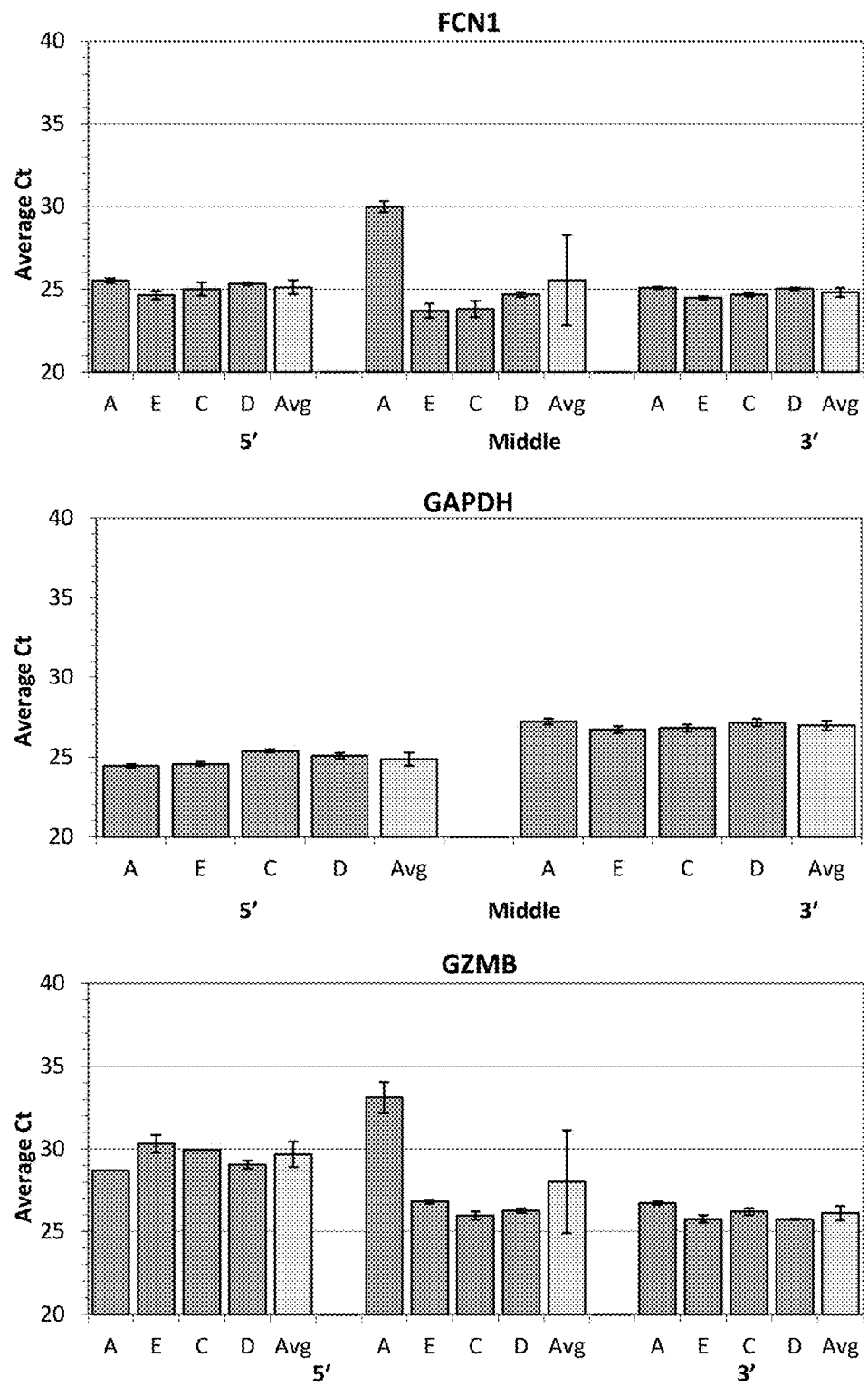
Figure 9I:
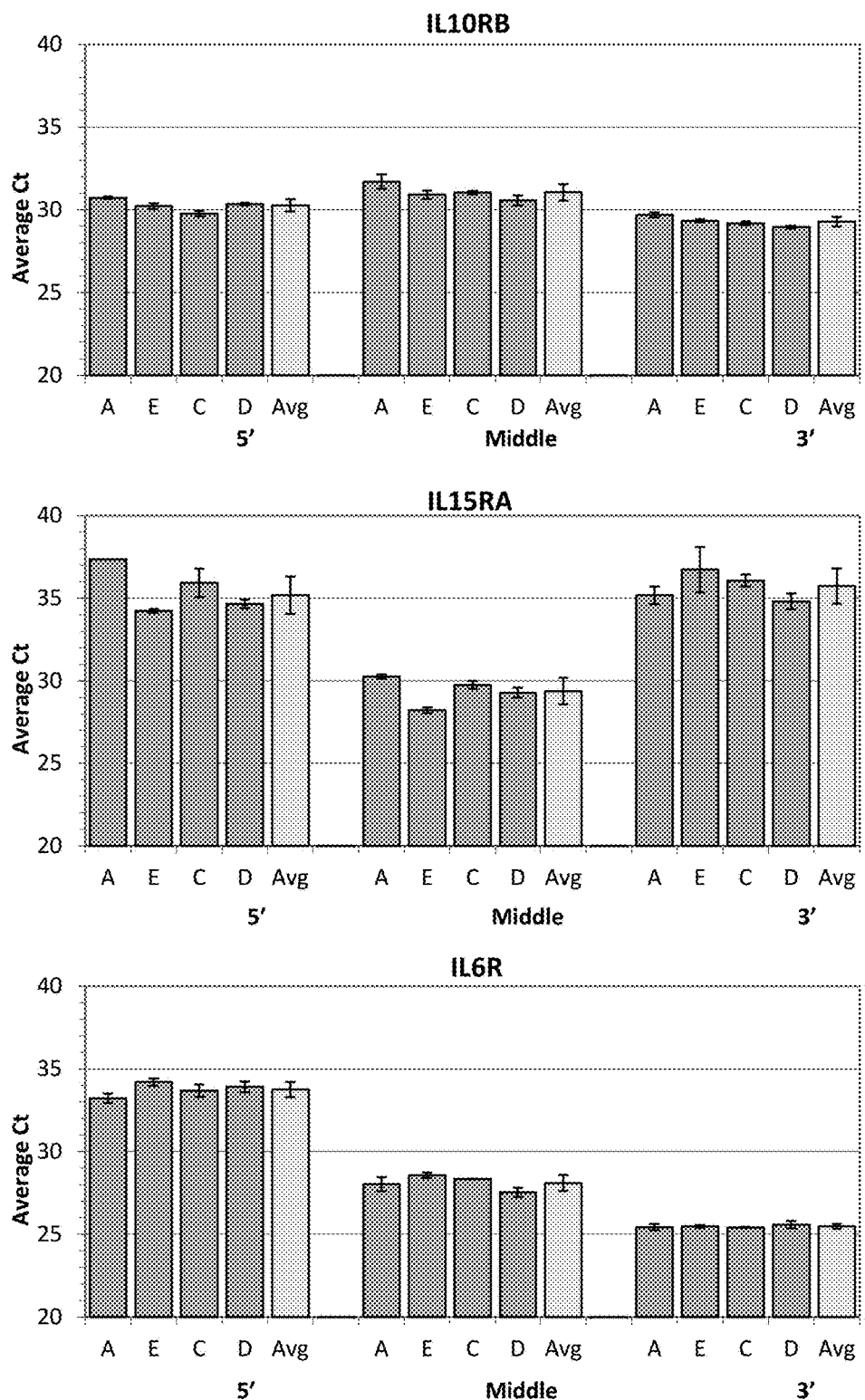
Figure 9J:
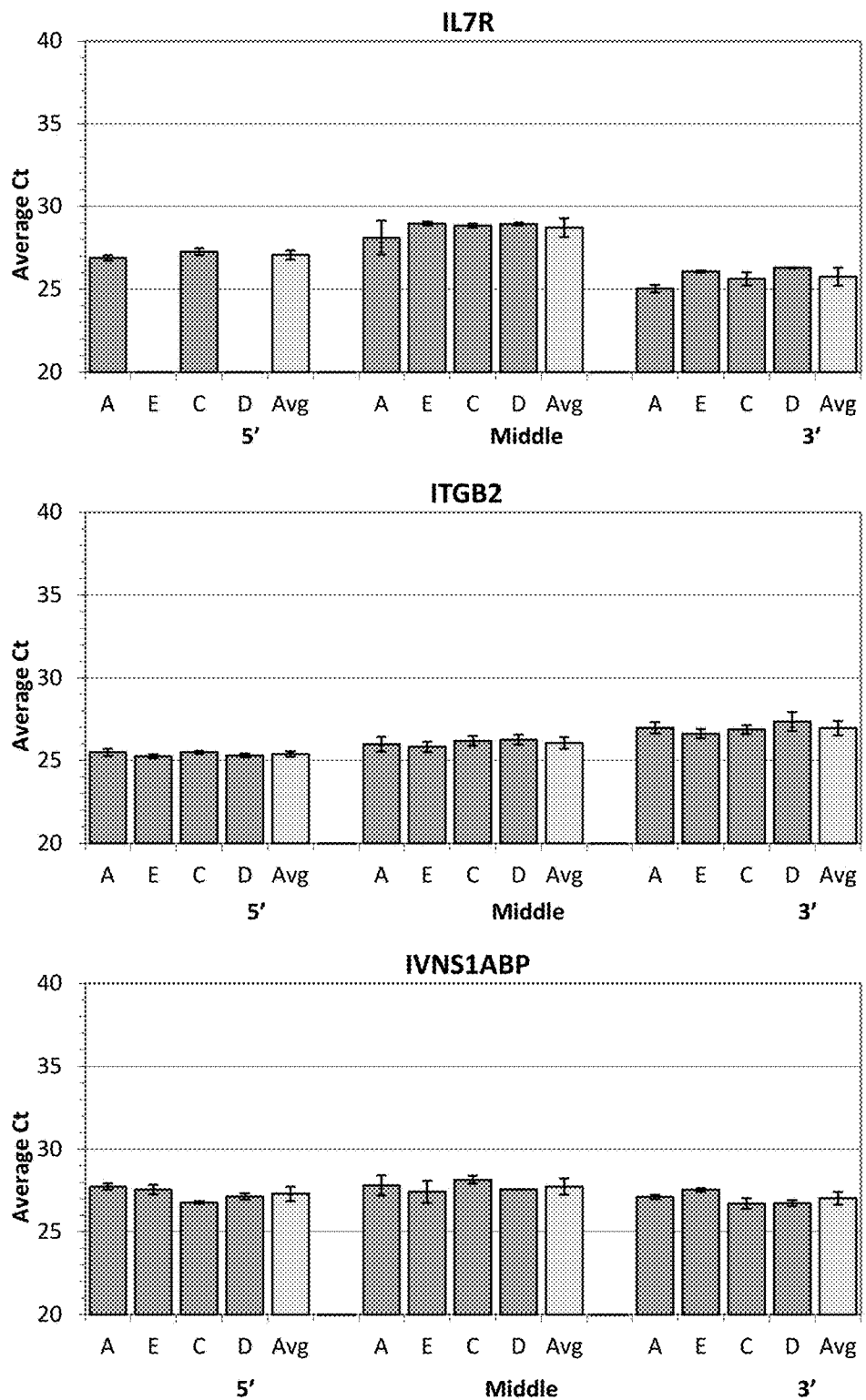
Figure 9K:
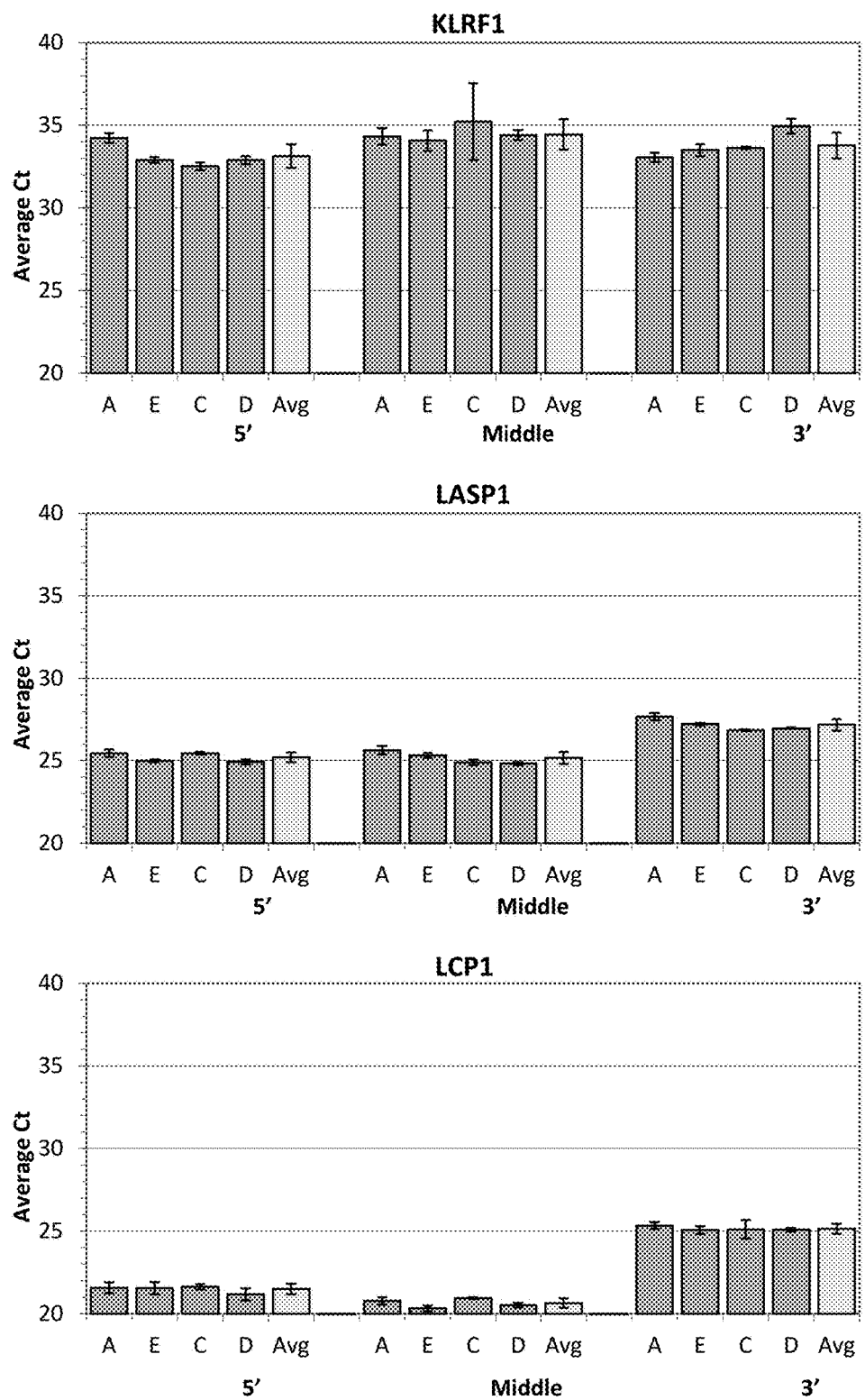
Figure 9L:
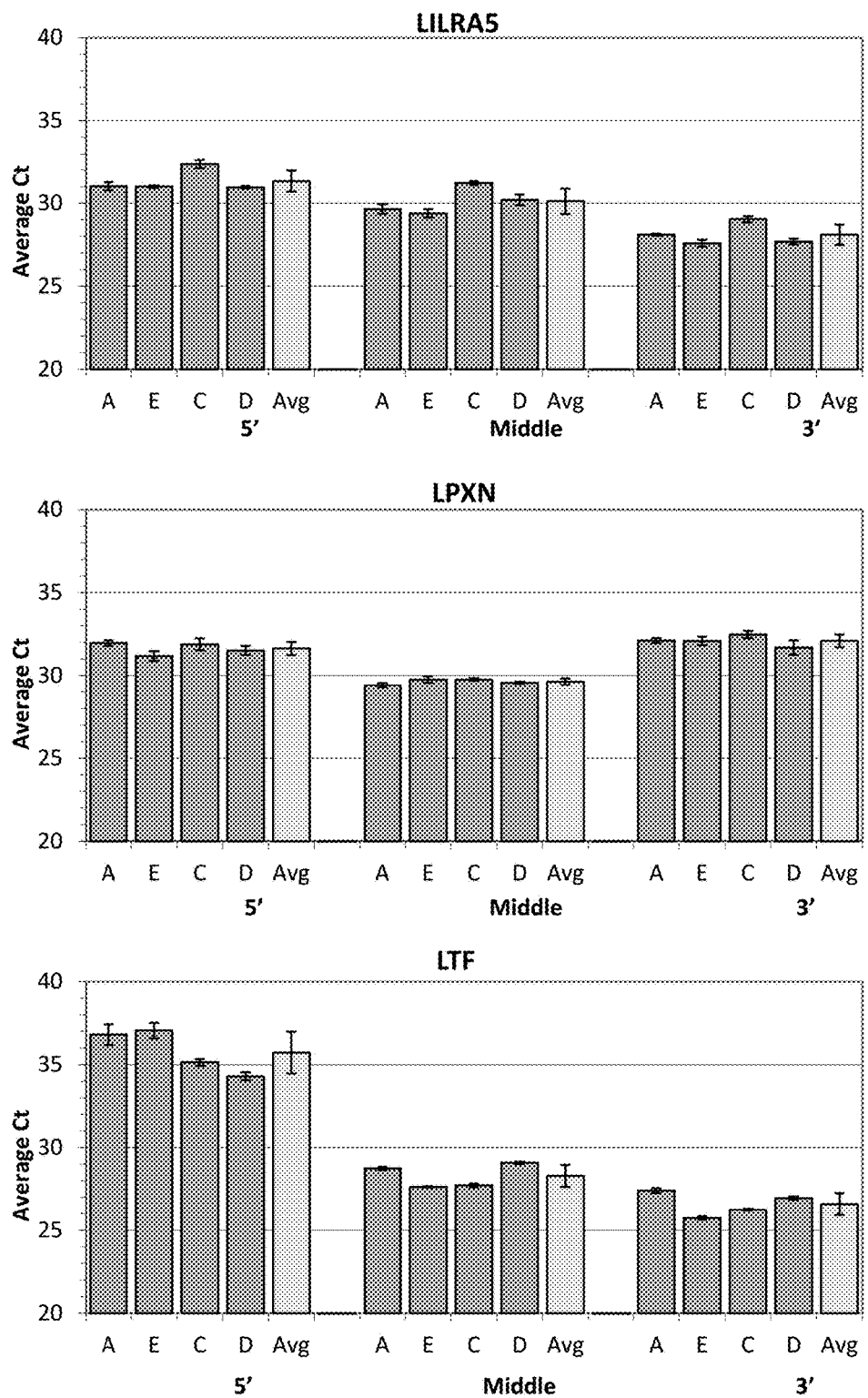
Figure 9M:
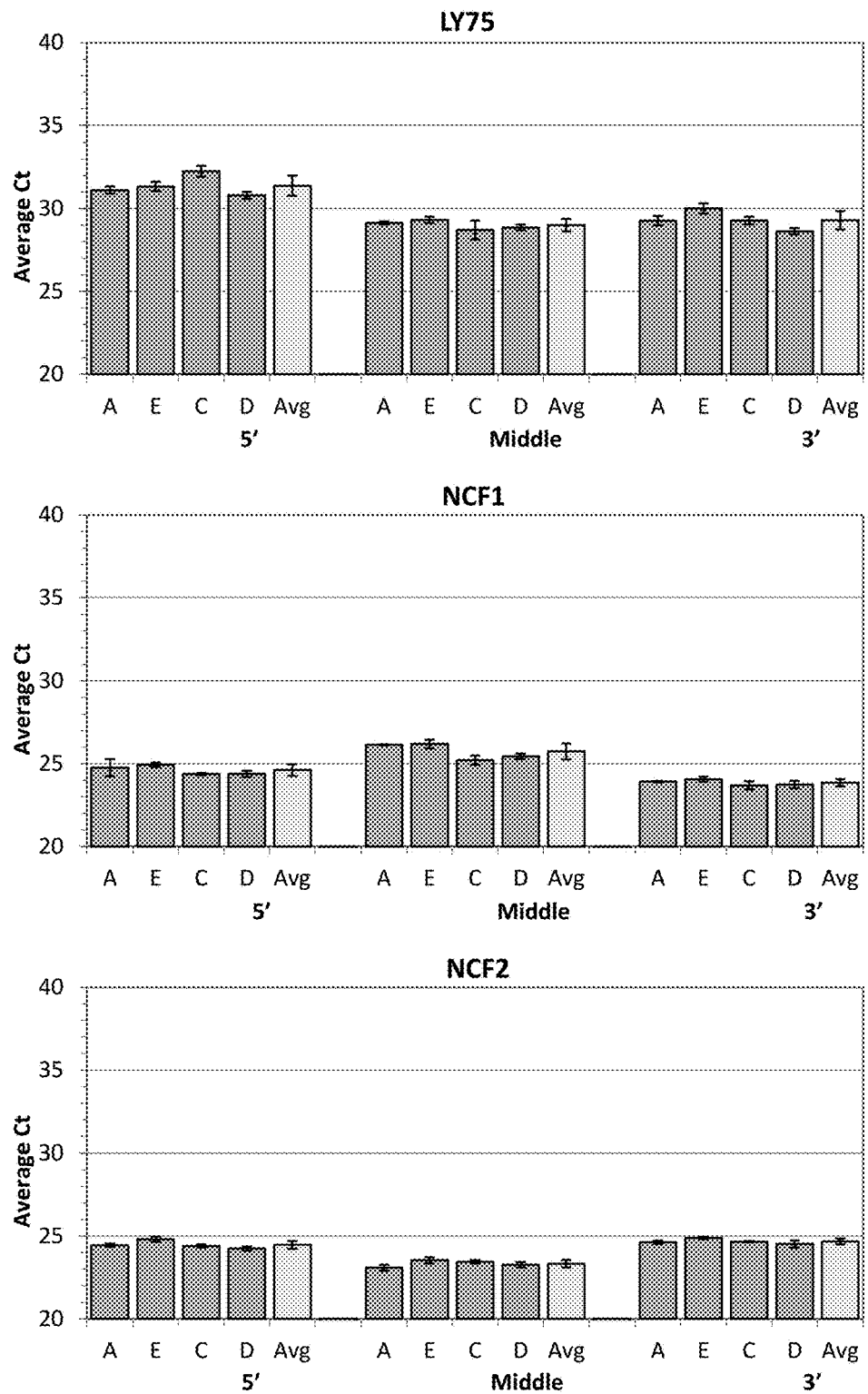
Figure 9N:
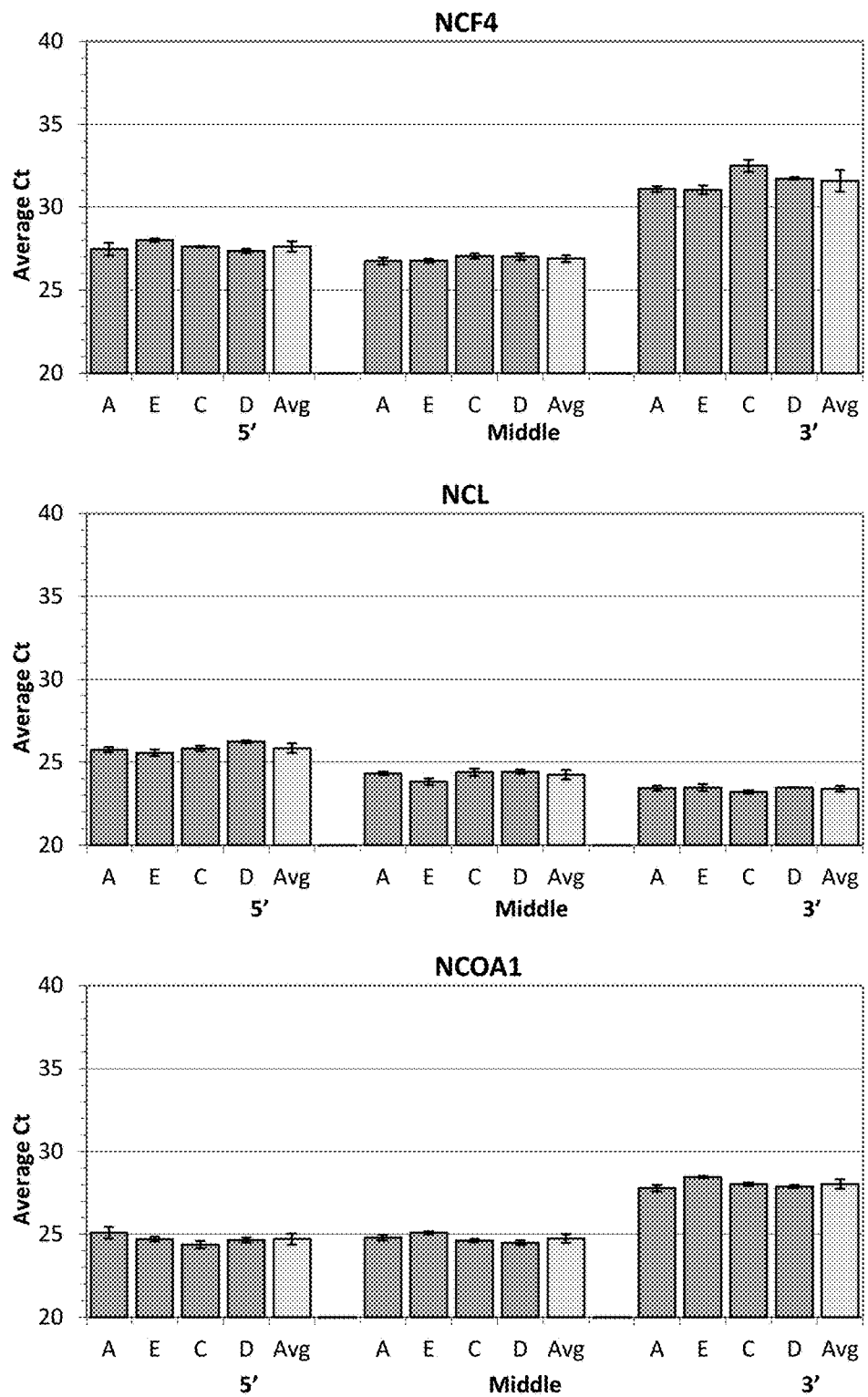
Figure 9O:
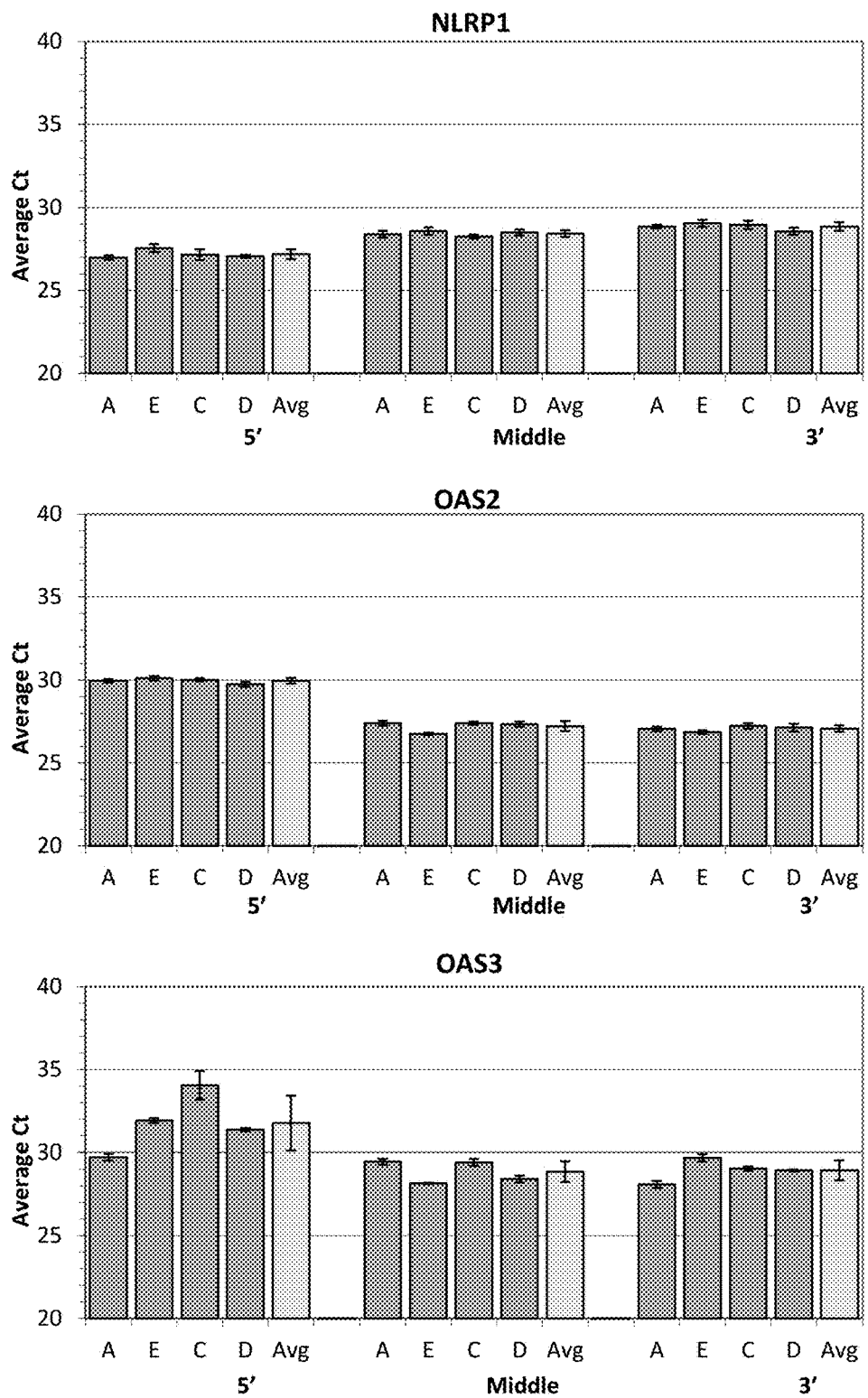
Figure 9R:
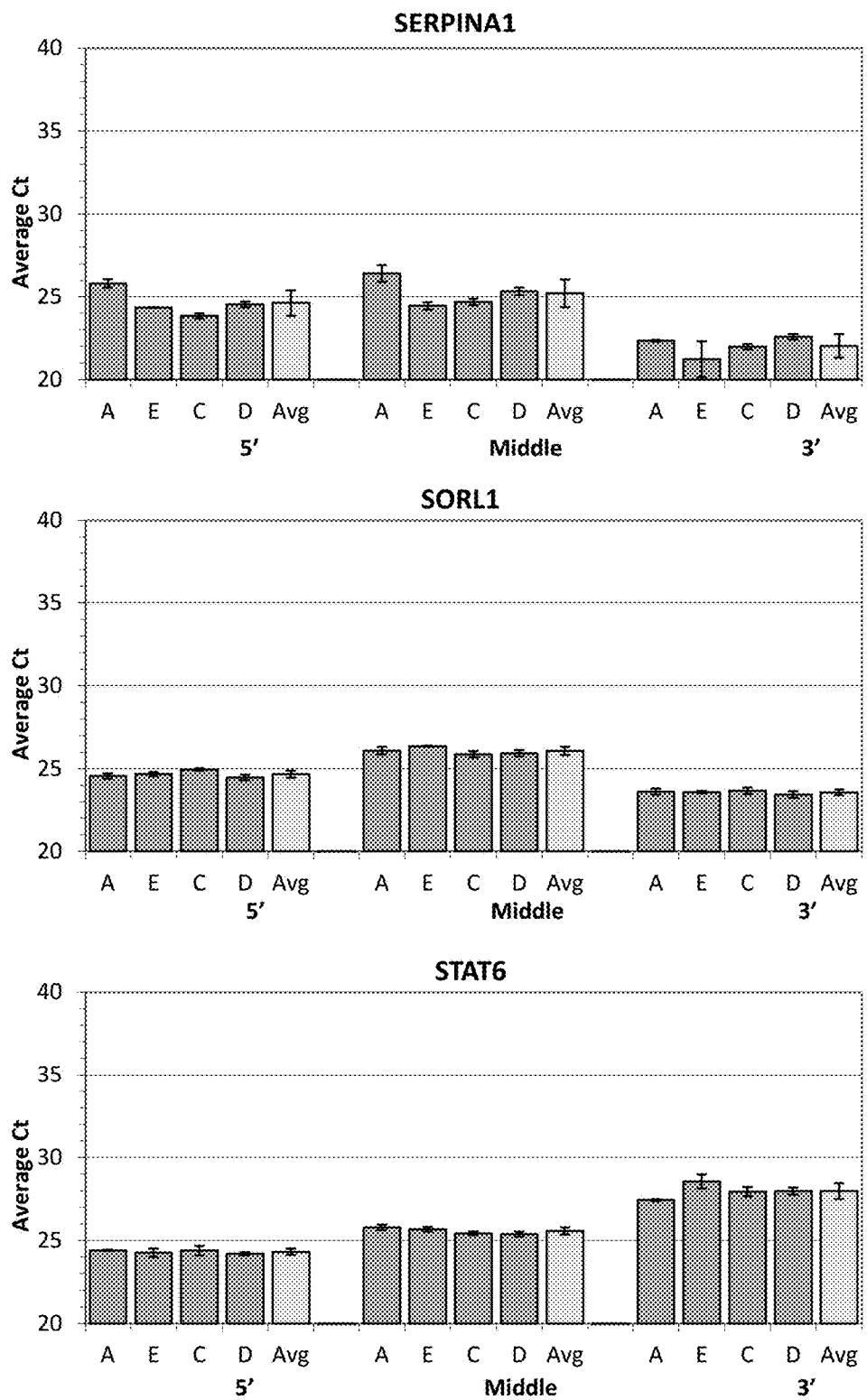
Figure 9S:
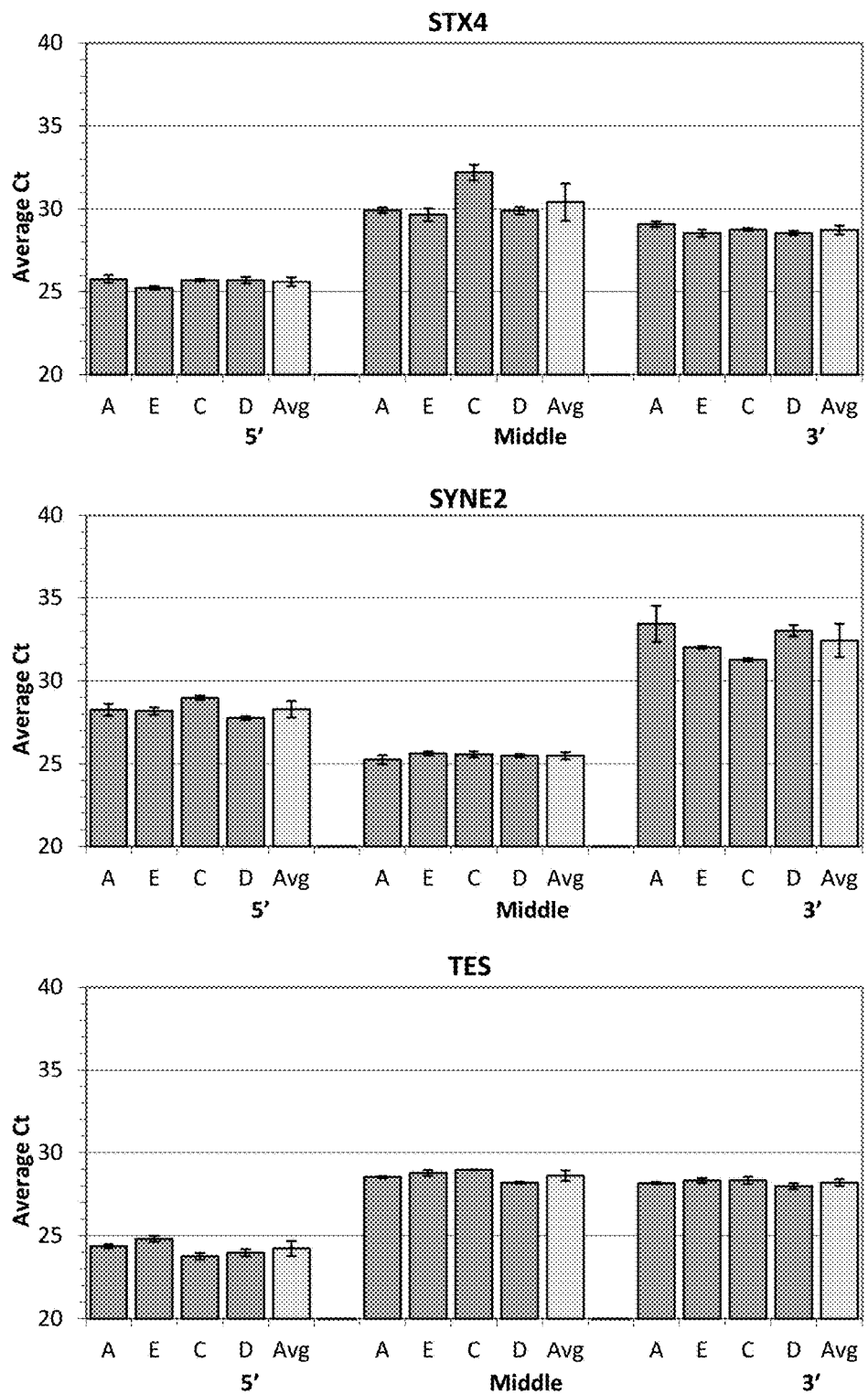
Figure 9T:
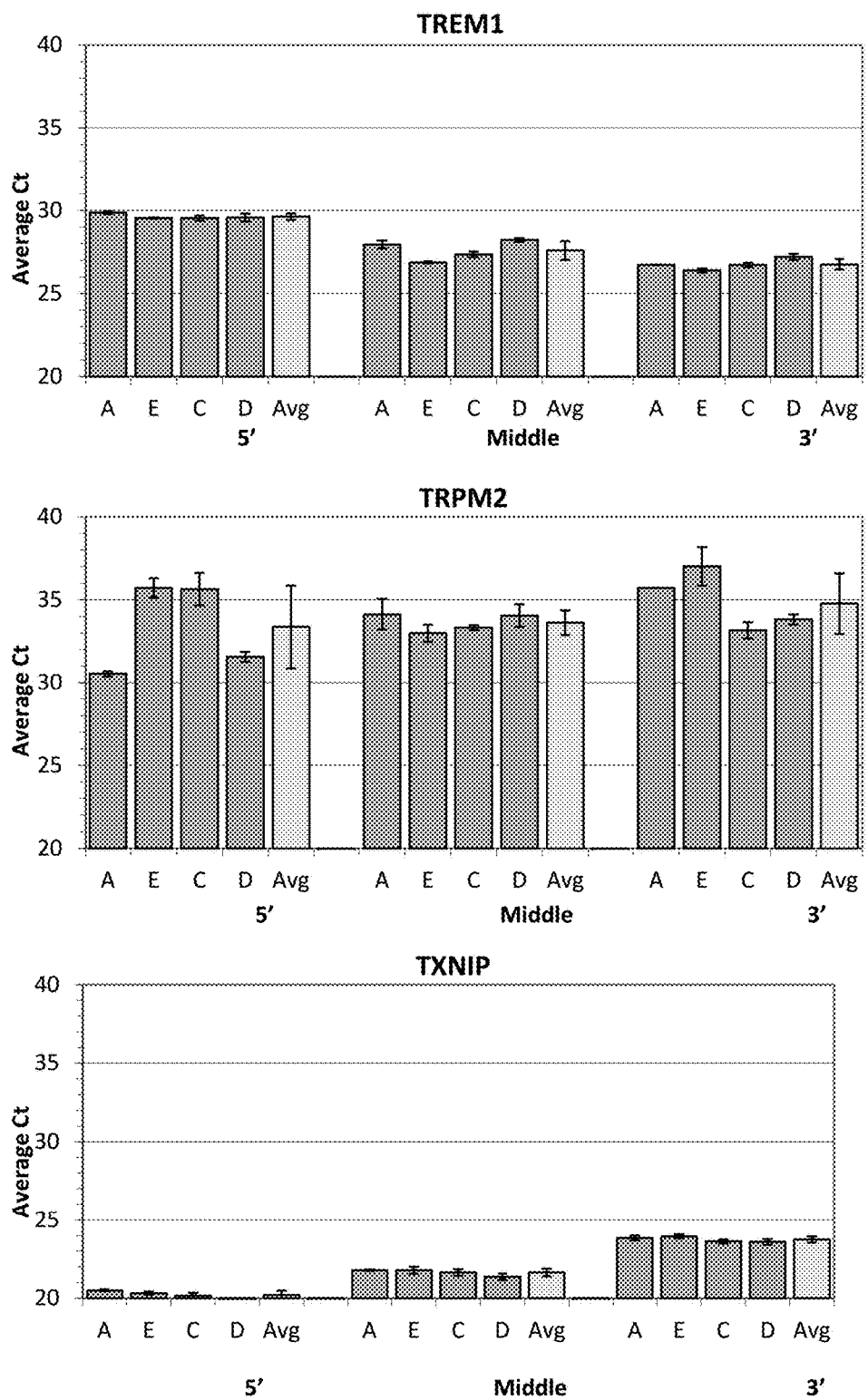
Figure 9U:
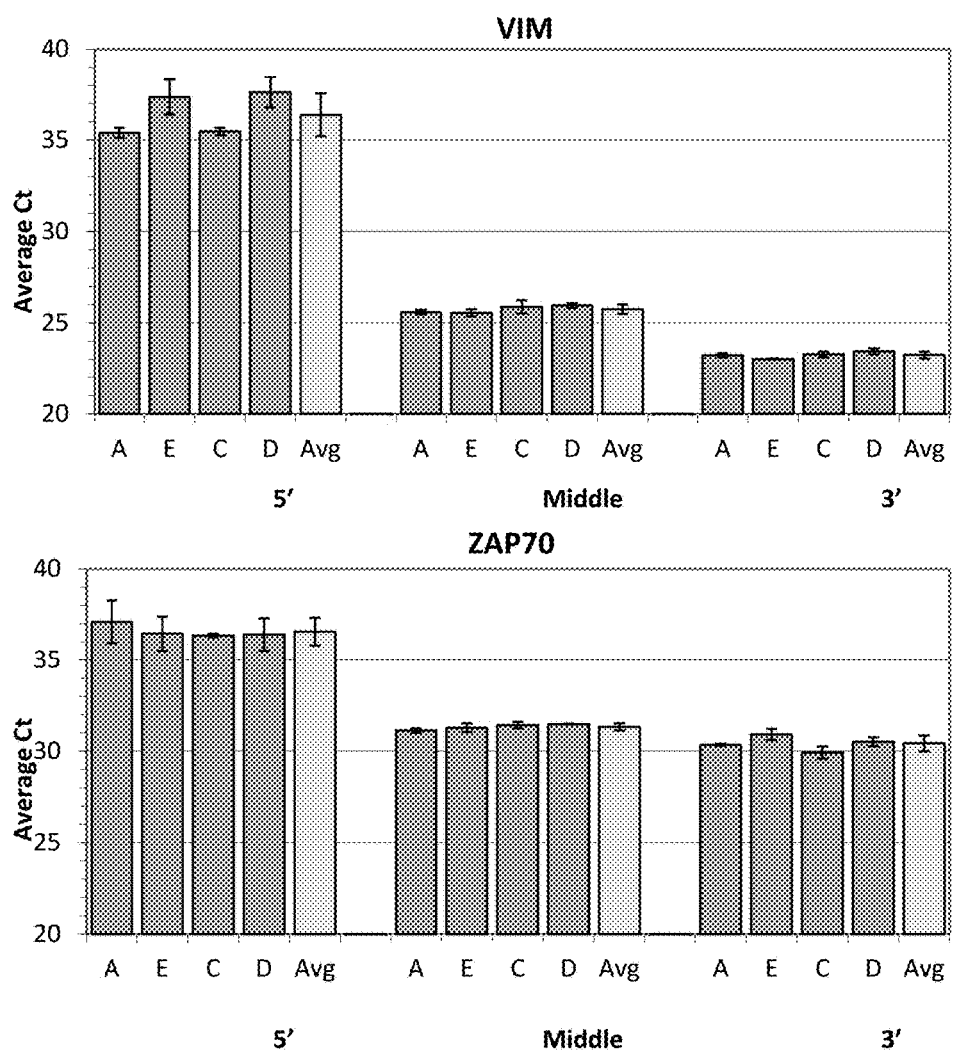
Figure 10B:
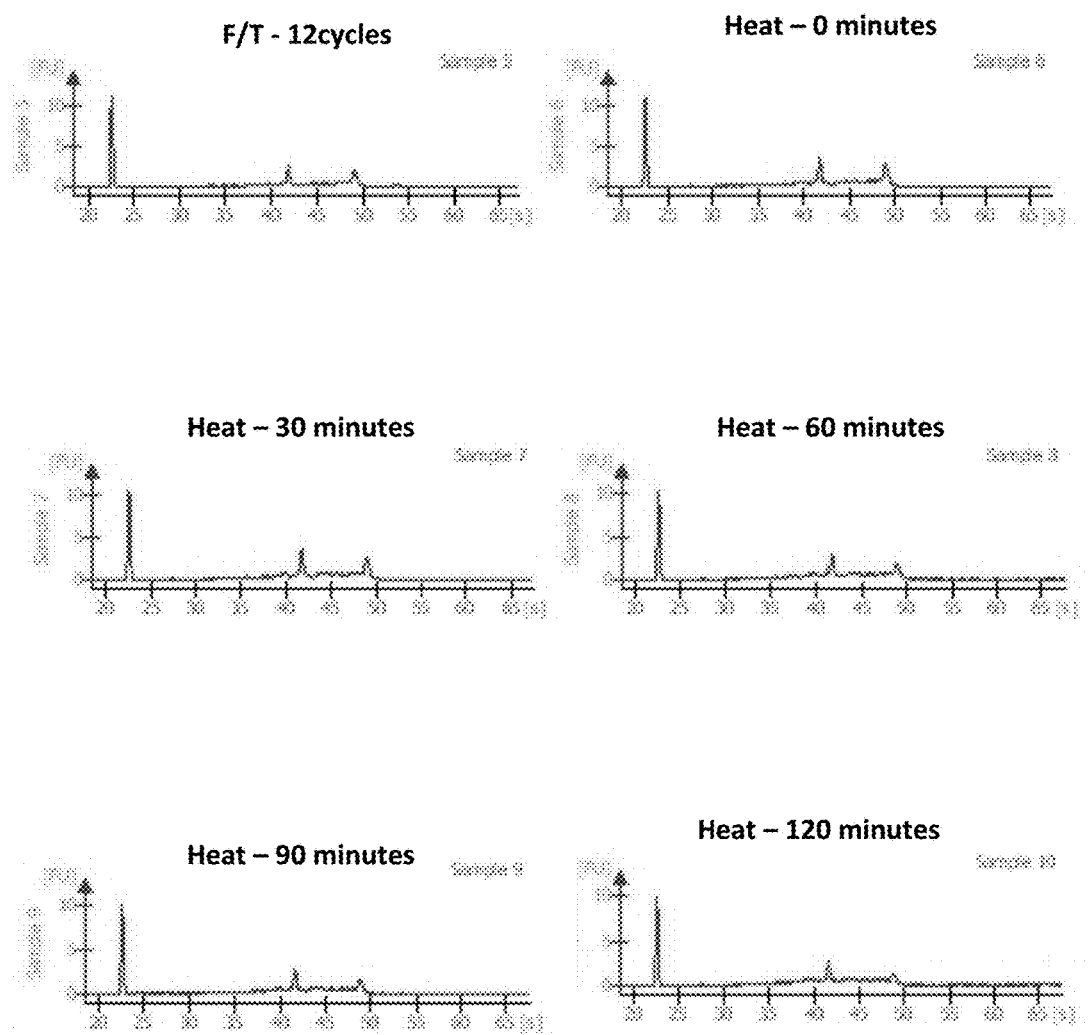
Figure 10D:
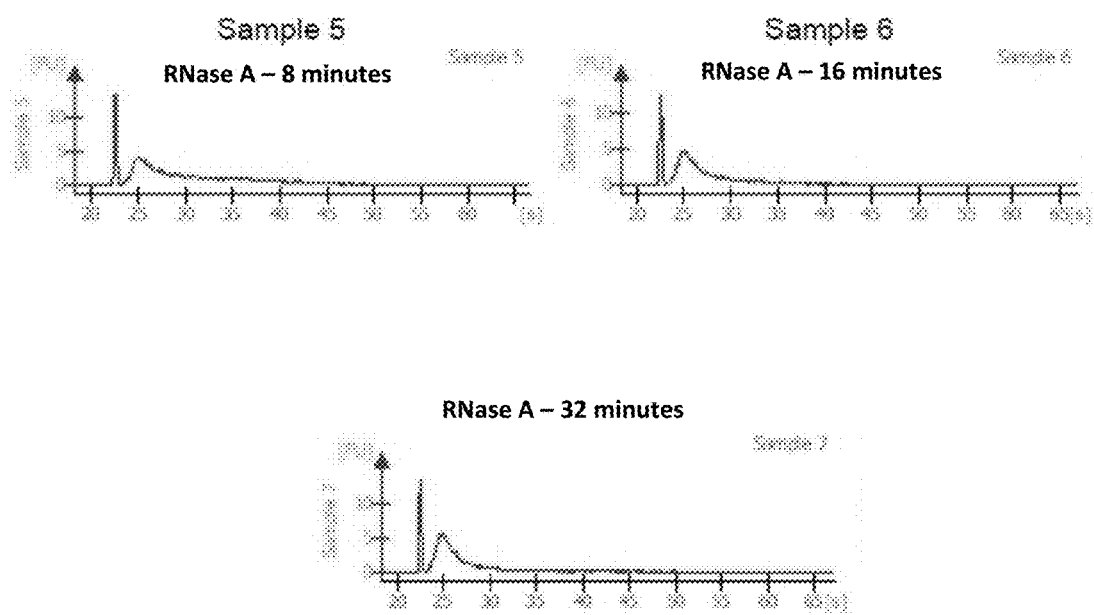

Average $C_T$ is the average of three technical replicates
Overall Average $C_T$ is the average of three technical replicates of all four samples
'Undet.' indicates that the $C_T$ value was undetermined for that sample Outlying $C_T$ values below 15 and above 38.5 were excluded from all calculations due to experimental error or assay failure, and NTC $C_T$ values were checked for evidence of contamination. To better evaluate assay performance, the descriptive statistical data was visualized with histogram plots. Histograms were plotted to compare assay performance between individual samples per given assay; all regional assays for a given gene were plotted on the same histogram to reveal local biases, as presented in FIGS. 9A-9U. To compare performance across all 184 assays, the overall average $C_T$ value and overall standard deviation of all four samples per given assay were plotted on a single histogram. Histogram plots were used to determine gene expression consistency across regional assay designs for a given gene.

Three criteria were used to score assay performance: (1) expression level consistency across all regional assays of a given gene, (2) amplification plot uniformity and $C_T$ value standard deviation, and (3) conformity to expected expression levels, as determined by GeneNote public microarray data. Expression level consistency among regional assays designed for the same gene served as an indicator that there were no biases stemming from location of the assay design within the gene, important for establishing a reliable baseline for algorithm development and mitigating performance variability. Uniformity among individual reaction amplification plots and corresponding $C_T$ value standard deviations served as indicators of how similarly a given assay would perform between samples from different subjects, important for clinical applications and utility as a universal quality control method. Conformity to the expected expression level reported by the GeneNote database served to validate expression data and was indicative of high-quality input RNA, important for assay validation.

Based on these three criteria, two performance lists were generated, one placing emphasis on regional consistency and the other placing emphasis on amplification plot and $C_T$ value uniformity among different samples, as presented in Table 3. While regional consistency is important for algorithm generation and assay performance predictability, just as important is the consistency between different samples within the same assay. When compared, most of the best-performing assays were found at the top of both lists, so they were combined when choosing the subset of assays for use in the experimental degradation phase of the project.

TABLE 3

Assay Performance, Regional Consistency weighted most heavily. In 'Assay' column:
L = 5' design, M = Middle design, R = 3' design

| Performance Order | Assay | Regional Consistency | Amp. Plot Consistency | Matches Expression Expectation | Assay Avg. $C_T$ | Expected Expression Score |
|---|---|---|---|---|---|---|
| 1 | ADAR_M | 3 | Y | Y | 24.41 | 4500 |
| 2 | ARPC5_L | 3 | Y | Y | 21.99 | 5500 |
| 3 | ARPC5_M | 3 | Y | Y | 20.95 | 5500 |
| 4 | ARPC5_R | 3 | Y | Y | 21.96 | 5500 |
| 5 | F13A1_L | 3 | Y | Y | 27.12 | 2300 |
| 6 | F13A1_M | 3 | Y | Y | 26.28 | 2300 |
| 7 | F13A1_R | 3 | Y | Y | 27.07 | 2300 |
| 8 | FCN1_R | 3 | Y | Y | 24.81 | 9000 |
| 9 | IL10RB_L | 3 | Y | Y | 30.27 | 850 |
| 10 | IL10RB_M | 3 | Y | Y | 31.06 | 850 |
| 11 | NCF1_L | 3 | Y | Y | 24.62 | 5500 |
| 12 | NCF1_R | 3 | Y | Y | 23.85 | 5500 |
| 13 | NCF2_L | 3 | Y | Y | 24.47 | 8500 |
| 14 | NCF2_M | 3 | Y | Y | 23.34 | 8500 |
| 15 | NCF2_R | 3 | Y | Y | 24.67 | 8500 |
| 16 | ADAR_R | 3 | Y | Borderline | 26.06 | 4500 |
| 17 | FCN1_L | 3 | Y | Borderline | 25.12 | 9000 |
| 18 | IL10RB_R | 3 | Y | Borderline | 29.29 | 850 |
| 19 | ITGB2_L | 3 | Y | Borderline | 25.38 | 10000 |
| 20 | ITGB2_M | 3 | Y | Borderline | 26.05 | 10000 |
| 21 | NCF1_M | 3 | Y | Borderline | 25.75 | 5500 |
| 22 | DDX58_L | 3 | Y | N | 27.76 | 350 |
| 23 | DDX58_M | 3 | Y | N | 26.23 | 350 |
| 24 | ITGB2_R | 3 | Y | N | 26.94 | 10000 |
| 25 | IVNS1ABP_L | 3 | Y | N | 27.32 | 750 |
| 26 | IVNS1ABP_M | 3 | Y | N | 27.75 | 750 |
| 27 | IVNS1ABP_R | 3 | Y | N | 27.04 | 750 |
| 28 | NLRP1_L | 3 | Y | N | 27.19 | 600 |
| 29 | NLRP1_M | 3 | Y | N | 28.43 | 600 |
| 30 | NLRP1_R | 3 | Y | N | 28.86 | 600 |
| 31 | KLRF1_L | 3 | N | Y | 33.13 | 650 |
| 32 | KLRF1_M | 3 | N | Y | 34.44 | 650 |
| 33 | KLRF1_R | 3 | N | Y | 33.78 | 650 |
| 34 | TRPM2_L | 3 | N | Y | 33.37 | 400 |
| 35 | TRPM2_M | 3 | N | Y | 33.62 | 400 |
| 36 | TRPM2_R | 3 | N | Y | 34.77 | 400 |
| 37 | ADAR_L | 3 | N | Borderline | 25.6 | 4500 |
| 38 | FCN1_M | 3 | N | Borderline | 25.54 | 9000 |
| 39 | DDX58_R | 3 | N | N | 27.8 | 350 |
| 40 | ACTR2_M | 2 | Y | Y | 25.6 | 2000 |
| 41 | ADD3_L | 2 | Y | Y | 28.52 | 1500 |
| 42 | ADD3_M | 2 | Y | Y | 27.52 | 1500 |
| 43 | AIM1_R | 2 | Y | Y | 25.87 | 1000 |
| 44 | C1orf38_M | 2 | Y | Y | 28.36 | 3000 |
| 45 | CD53_M | 2 | Y | Y | 24.8 | 8000 |
| 46 | CDC42SE1_M | 2 | Y | Y | 24.71 | 5000 |
| 47 | CDC42SE1_R | 2 | Y | Y | 23.98 | 5000 |
| 48 | EEF2_M | 2 | Y | Y | 24.21 | 7000 |
| 49 | IL7R_M | 2 | Y | Y | 28.7 | 3500 |
| 50 | IL7R_R | 2 | Y | Y | 25.75 | 3500 |
| 51 | LCP1_L | 2 | Y | Y | 21.5 | 6500 |
| 52 | LCP1_M | 2 | Y | Y | 20.64 | 6500 |
| 53 | LPXN_M | 2 | Y | Y | 29.63 | 1100 |
| 54 | NCL_L | 2 | Y | Y | 25.84 | 2000 |
| 55 | PDLIM2_M | 2 | Y | Y | 32.12 | 950 |
| 56 | RAF1_L | 2 | Y | Y | 29.79 | 3000 |
| 57 | RAF1_R | 2 | Y | Y | 27.03 | 3000 |
| 58 | ROCK2_R | 2 | Y | Y | 30.52 | 200 |
| 59 | SERPINA1_R | 2 | Y | Y | 22.03 | 7500 |
| 60 | ZAP70_M | 2 | Y | Y | 31.33 | 650 |
| 61 | ZAP70_R | 2 | Y | Y | 30.42 | 650 |
| 62 | ADD1_L | 2 | Y | Borderline | 29.43 | 750 |
| 63 | AIM1_M | 2 | Y | Borderline | 30.45 | 1000 |
| 64 | CD53_R | 2 | Y | Borderline | 25.9 | 8000 |
| 65 | EEF2_R | 2 | Y | Borderline | 25.62 | 7000 |
| 66 | LASP1_L | 2 | Y | Borderline | 25.2 | 4500 |
| 67 | LASP1_M | 2 | Y | Borderline | 25.16 | 4500 |
| 68 | LASP1_R | 2 | Y | Borderline | 27.18 | 4500 |
| 69 | LCP1_R | 2 | Y | Borderline | 25.14 | 6500 |
| 70 | LPXN_L | 2 | Y | Borderline | 31.64 | 1100 |
| 71 | LPXN_R | 2 | Y | Borderline | 32.09 | 1100 |
| 72 | LY75_M | 2 | Y | Borderline | 29.01 | 800 |
| 73 | LY75_R | 2 | Y | Borderline | 29.3 | 800 |

TABLE 3-continued

Assay Performance, Regional Consistency weighted most heavily. In 'Assay' column:
L = 5' design, M = Middle design, R = 3' design

| | | | | | | |
|---|---|---|---|---|---|---|
| 74 | NCF4_L | 2 | Y | Borderline | 27.61 | 4500 |
| 75 | NCF4_M | 2 | Y | Borderline | 26.89 | 4500 |
| 76 | OAS2_L | 2 | Y | Borderline | 29.97 | 500 |
| 77 | PDLIM1_R | 2 | Y | Borderline | 28.5 | 900 |
| 78 | RAF1_M | 2 | Y | Borderline | 30.47 | 3000 |
| 79 | TREM1_L | 2 | Y | Borderline | 29.63 | 4500 |
| 80 | TREM1_M | 2 | Y | Borderline | 27.6 | 4500 |
| 81 | TREM1_R | 2 | Y | Borderline | 26.76 | 4500 |
| 82 | ACTR2_L | 2 | Y | N | 22.72 | 2000 |
| 83 | ACTR2_R | 2 | Y | N | 23.17 | 2000 |
| 84 | ADD1_M | 2 | Y | N | 26.79 | 750 |
| 85 | ADD1_R | 2 | Y | N | 25.43 | 750 |
| 86 | ADD3_R | 2 | Y | N | 24.17 | 1500 |
| 87 | CAPN2_L | 2 | Y | N | 28.04 | 750 |
| 88 | CAPN2_M | 2 | Y | N | 23.88 | 750 |
| 89 | CAPN2_R | 2 | Y | N | 25.15 | 750 |
| 90 | CD163_R | 2 | Y | N | 27.83 | 200 |
| 91 | CD68_L | 2 | Y | N | 21.75 | 250 |
| 92 | CD68_R | 2 | Y | N | 26.03 | 250 |
| 93 | LTF_R | 2 | Y | N | 26.59 | 200 |
| 94 | NCF4_R | 2 | Y | N | 31.58 | 4500 |
| 95 | NCL_M | 2 | Y | N | 24.24 | 2000 |
| 96 | NCL_R | 2 | Y | N | 23.39 | 2000 |
| 97 | NCOA1_L | 2 | Y | N | 24.7 | 850 |
| 98 | NCOA1_M | 2 | Y | N | 24.74 | 850 |
| 99 | NCOA1_R | 2 | Y | N | 28.05 | 850 |
| 100 | OAS2_M | 2 | Y | N | 27.23 | 500 |
| 101 | OAS2_R | 2 | Y | N | 27.08 | 500 |
| 102 | OAS3_M | 2 | Y | N | 28.86 | 650 |
| 103 | OAS3_R | 2 | Y | N | 28.94 | 650 |
| 104 | PDLIM1_M | 2 | Y | N | 28.2 | 900 |
| 105 | ROCK2_L | 2 | Y | N | 23.81 | 200 |
| 106 | TES_L | 2 | Y | N | 24.23 | 750 |
| 107 | TES_M | 2 | Y | N | 28.61 | 750 |
| 108 | TES_R | 2 | Y | N | 28.19 | 750 |
| 109 | C1orf38_L | 2 | N | Y | 27.49 | 3000 |
| 110 | CD163_L | 2 | N | Y | 30.16 | 200 |
| 111 | CD27_M | 2 | N | Y | 32.29 | 650 |
| 112 | CD27_R | 2 | N | Y | 30.38 | 650 |
| 113 | CD300C_L | 2 | N | Y | 32.63 | 500 |
| 114 | CD300C_M | 2 | N | Y | 30.4 | 500 |
| 115 | CD300C_R | 2 | N | Y | 30.23 | 500 |
| 116 | CD53_L | 2 | N | Y | 23.36 | 8000 |
| 117 | CD83_L | 2 | N | Y | 36.63 | 150 |
| 118 | CD83_M | 2 | N | Y | 34.82 | 150 |
| 119 | CD83_R | 2 | N | Y | 30.62 | 150 |
| 120 | IL15RA_L | 2 | N | Y | 35.19 | 300 |
| 121 | IL15RA_R | 2 | N | Y | 35.75 | 300 |
| 122 | IL7R_L | 2 | N | Y | 27.07 | 3500 |
| 123 | LTF_L | 2 | N | Y | 35.73 | 200 |
| 124 | LY75_L | 2 | N | Y | 31.38 | 800 |
| 125 | OAS3_L | 2 | N | Y | 31.77 | 650 |
| 126 | PDLIM1_L | 2 | N | Y | 31.95 | 900 |
| 127 | PDLIM2_L | 2 | N | Y | 30.75 | 950 |
| 128 | PDLIM2_R | 2 | N | Y | 38.02 | 950 |
| 129 | ROCK2_M | 2 | N | Y | 30.81 | 200 |
| 130 | SERPINA1_L | 2 | N | Y | 24.63 | 7500 |
| 131 | ZAP70_L | 2 | N | Y | 36.56 | 650 |
| 132 | AIM1_L | 2 | N | Borderline | 30.33 | 1000 |
| 133 | C1orf38_R | 2 | N | Borderline | 32.82 | 3000 |
| 134 | SERPINA1_M | 2 | N | Borderline | 25.22 | 7500 |
| 135 | CD163_M | 2 | N | N | 28.45 | 200 |
| 136 | CD27_L | 2 | N | N | 29.18 | 650 |
| 137 | CD68_M | 2 | N | N | 27.65 | 250 |
| 138 | CDC42SE1_L | 2 | N | N | 30.86 | 5000 |
| 139 | EEF2_L | 2 | N | N | 28.43 | 7000 |
| 140 | IL15RA_M | 2 | N | N | 29.39 | 300 |
| 141 | LTF_M | 2 | N | N | 28.3 | 200 |
| 142 | ACTB_L | 0 | Y | Y | 23.94 | 10,000 |
| 143 | ACTB_R | 0 | Y | Y | 21.05 | 10,000 |
| 144 | CSF3R_R | 0 | Y | Y | 24.48 | 6500 |
| 145 | GAPDH_L | 0 | Y | Y | 24.86 | 10,000 |
| 146 | GZMB_R | 0 | Y | Y | 26.09 | 1500 |
| 147 | IL6R_L | 0 | Y | Y | 33.75 | 500 |
| 148 | LILRA5_L | 0 | Y | Y | 31.33 | 900 |
| 149 | SELL_L | 0 | Y | Y | 23.45 | 8500 |
| 150 | SELL_M | 0 | Y | Y | 24.48 | 8500 |

TABLE 3-continued

Assay Performance, Regional Consistency weighted most heavily. In 'Assay' column:
L = 5' design, M = Middle design, R = 3' design

| | | | | | | |
|---|---|---|---|---|---|---|
| 151 | SORL1_L | 0 | Y | Y | 24.67 | 7500 |
| 152 | SORL1_R | 0 | Y | Y | 23.58 | 7500 |
| 153 | STAT6_M | 0 | Y | Y | 25.57 | 1000 |
| 154 | STAT6_R | 0 | Y | Y | 27.98 | 1000 |
| 155 | TXNIP_L | 0 | Y | Y | 20.2 | 8000 |
| 156 | TXNIP_M | 0 | Y | Y | 21.64 | 8000 |
| 157 | TXNIP_R | 0 | Y | Y | 23.75 | 8000 |
| 158 | VIM_R | 0 | Y | Y | 23.24 | 9500 |
| 159 | LILRA5_R | 0 | Y | Borderline | 28.1 | 900 |
| 160 | SORL1_M | 0 | Y | Borderline | 26.09 | 7500 |
| 161 | VIM_M | 0 | Y | Borderline | 25.75 | 9500 |
| 162 | CSF3R_M | 0 | Y | N | 28.15 | 6500 |
| 163 | GAPDH_R | 0 | Y | N | 26.97 | 10,000 |
| 164 | IL6R_M | 0 | Y | N | 28.1 | 500 |
| 165 | IL6R_R | 0 | Y | N | 25.48 | 500 |
| 166 | SELL_R | 0 | Y | N | 27.05 | 8500 |
| 167 | STAT6_L | 0 | Y | N | 24.32 | 1000 |
| 168 | STX4_L | 0 | Y | N | 25.6 | 600 |
| 169 | STX4_R | 0 | Y | N | 28.74 | 600 |
| 170 | SYNE2_L | 0 | Y | N | 28.29 | 400 |
| 171 | SYNE2_M | 0 | Y | N | 25.49 | 400 |
| 172 | BACH2_L | 0 | N | Y | 34.45 | 150 |
| 173 | BACH2_R | 0 | N | Y | 30.93 | 150 |
| 174 | GZMB_L | 0 | N | Y | 29.68 | 1500 |
| 175 | GZMB_M | 0 | N | Y | 28.02 | 1500 |
| 176 | LILRA5_M | 0 | N | Y | 30.11 | 900 |
| 177 | SELP_L | 0 | N | Y | 31.32 | 700 |
| 178 | SELP_M | 0 | N | Y | 32.15 | 700 |
| 179 | SELP_R | 0 | N | Y | 35.16 | 700 |
| 180 | STX4_M | 0 | N | Y | 30.42 | 600 |
| 181 | SYNE2_R | 0 | N | Y | 32.43 | 400 |
| 182 | CSF3R_L | 0 | N | Borderline | 26.1 | 6500 |
| 183 | BACH2_M | 0 | N | N | 27.36 | 150 |
| 184 | VIM_L | 0 | N | N | 36.39 | 9500 |

| Performance Order | Assay | Amp. Plot Consistency | Regional Consistency | Matches Expression Expectation | Assay Avg $C_T$ | Expected Expression Score |
|---|---|---|---|---|---|---|
| 1 | ADAR_M | Y | 3 | Y | 24.41 | 4500 |
| 2 | ARPC5_L | Y | 3 | Y | 21.99 | 5500 |
| 3 | ARPC5_M | Y | 3 | Y | 20.95 | 5500 |
| 4 | ARPC5_R | Y | 3 | Y | 21.96 | 5500 |
| 5 | F13A1_L | Y | 3 | Y | 27.12 | 2300 |
| 6 | F13A1_M | Y | 3 | Y | 26.28 | 2300 |
| 7 | F13A1_R | Y | 3 | Y | 27.07 | 2300 |
| 8 | FCN1_R | Y | 3 | Y | 24.81 | 9000 |
| 9 | IL10RB_L | Y | 3 | Y | 30.27 | 850 |
| 10 | IL10RB_M | Y | 3 | Y | 31.06 | 850 |
| 11 | NCF1_L | Y | 3 | Y | 24.62 | 5500 |
| 12 | NCF1_R | Y | 3 | Y | 23.85 | 5500 |
| 13 | NCF2_L | Y | 3 | Y | 24.47 | 8500 |
| 14 | NCF2_M | Y | 3 | Y | 23.34 | 8500 |
| 15 | NCF2_R | Y | 3 | Y | 24.67 | 8500 |
| 16 | ADAR_R | Y | 3 | Borderline | 26.06 | 4500 |
| 17 | FCN1_L | Y | 3 | Borderline | 25.12 | 9000 |
| 18 | IL10RB_R | Y | 3 | Borderline | 29.29 | 850 |
| 19 | ITGB2_L | Y | 3 | Borderline | 25.38 | 10000 |
| 20 | ITGB2_M | Y | 3 | Borderline | 26.05 | 10000 |
| 21 | NCF1_M | Y | 3 | Borderline | 25.75 | 5500 |
| 22 | DDX58_L | Y | 3 | N | 27.76 | 350 |
| 23 | DDX58_M | Y | 3 | N | 26.23 | 350 |
| 24 | ITGB2_R | Y | 3 | N | 26.94 | 10000 |
| 25 | IVNS1ABP_L | Y | 3 | N | 27.32 | 750 |
| 26 | IVNS1ABP_M | Y | 3 | N | 27.75 | 750 |
| 27 | IVNS1ABP_R | Y | 3 | N | 27.04 | 750 |
| 28 | NLRP1_L | Y | 3 | N | 27.19 | 600 |
| 29 | NLRP1_M | Y | 3 | N | 28.43 | 600 |
| 30 | NLRP1_R | Y | 3 | N | 28.86 | 600 |
| 31 | ACTR2_M | Y | 2 | Y | 25.6 | 2000 |
| 32 | ADD3_L | Y | 2 | Y | 28.52 | 1500 |
| 33 | ADD3_M | Y | 2 | Y | 27.52 | 1500 |
| 34 | AIM1_R | Y | 2 | Y | 25.87 | 1000 |
| 35 | C1orf38_M | Y | 2 | Y | 28.36 | 3000 |
| 36 | CD163_L | Y | 2 | Y | 30.16 | 200 |
| 37 | CD27_R | Y | 2 | Y | 30.38 | 650 |
| 38 | CD300C_R | Y | 2 | Y | 30.23 | 500 |

TABLE 3-continued

Assay Performance, Regional Consistency weighted most heavily. In 'Assay' column:
L = 5' design, M = Middle design, R = 3' design

| | | | | | | |
|---|---|---|---|---|---|---|
| 39 | CD53_M | Y | 2 | Y | 24.8 | 8000 |
| 40 | CD83_R | Y | 2 | Y | 30.62 | 150 |
| 41 | CDC42SE1_M | Y | 2 | Y | 24.71 | 5000 |
| 42 | CDC42SE1_R | Y | 2 | Y | 23.98 | 5000 |
| 43 | EEF2_M | Y | 2 | Y | 24.21 | 7000 |
| 44 | IL7R_M | Y | 2 | Y | 28.7 | 3500 |
| 45 | IL7R_R | Y | 2 | Y | 25.75 | 3500 |
| 46 | LCP1_L | Y | 2 | Y | 21.5 | 6500 |
| 47 | LCP1_M | Y | 2 | Y | 20.64 | 6500 |
| 48 | LPXN_M | Y | 2 | Y | 29.63 | 1100 |
| 49 | NCL_L | Y | 2 | Y | 25.84 | 2000 |
| 50 | PDLIM2_M | Y | 2 | Y | 32.12 | 950 |
| 51 | RAF1_L | Y | 2 | Y | 29.79 | 3000 |
| 52 | RAF1_R | Y | 2 | Y | 27.03 | 3000 |
| 53 | ROCK2_R | Y | 2 | Y | 30.52 | 200 |
| 54 | SERPINA1_R | Y | 2 | Y | 22.03 | 7500 |
| 55 | ZAP70_M | Y | 2 | Y | 31.33 | 650 |
| 56 | ZAP70_R | Y | 2 | Y | 30.42 | 650 |
| 57 | ADD1_L | Y | 2 | Borderline | 29.43 | 750 |
| 58 | AIM1_M | Y | 2 | Borderline | 30.45 | 1000 |
| 59 | CD53_R | Y | 2 | Borderline | 25.9 | 8000 |
| 60 | EEF2_R | Y | 2 | Borderline | 25.62 | 7000 |
| 61 | LASP1_L | Y | 2 | Borderline | 25.2 | 4500 |
| 62 | LASP1_M | Y | 2 | Borderline | 25.16 | 4500 |
| 63 | LASP1_R | Y | 2 | Borderline | 27.18 | 4500 |
| 64 | LCP1_R | Y | 2 | Borderline | 25.14 | 6500 |
| 65 | LPXN_L | Y | 2 | Borderline | 31.64 | 1100 |
| 66 | LPXN_R | Y | 2 | Borderline | 32.09 | 1100 |
| 67 | LY75_M | Y | 2 | Borderline | 29.01 | 800 |
| 68 | LY75_R | Y | 2 | Borderline | 29.3 | 800 |
| 69 | NCF4_L | Y | 2 | Borderline | 27.61 | 4500 |
| 70 | NCF4_M | Y | 2 | Borderline | 26.89 | 4500 |
| 71 | OAS2_L | Y | 2 | Borderline | 29.97 | 500 |
| 72 | PDLIM1_R | Y | 2 | Borderline | 28.5 | 900 |
| 73 | RAF1_M | Y | 2 | Borderline | 30.47 | 3000 |
| 74 | TREM1_L | Y | 2 | Borderline | 29.63 | 4500 |
| 75 | TREM1_M | Y | 2 | Borderline | 27.6 | 4500 |
| 76 | TREM1_R | Y | 2 | Borderline | 26.76 | 4500 |
| 77 | ACTR2_L | Y | 2 | N | 22.72 | 2000 |
| 78 | ACTR2_R | Y | 2 | N | 23.17 | 2000 |
| 79 | ADD1_M | Y | 2 | N | 26.79 | 750 |
| 80 | ADD1_R | Y | 2 | N | 25.43 | 750 |
| 81 | ADD3_R | Y | 2 | N | 24.17 | 1500 |
| 82 | CAPN2_L | Y | 2 | N | 28.04 | 750 |
| 83 | CAPN2_M | Y | 2 | N | 23.88 | 750 |
| 84 | CAPN2_R | Y | 2 | N | 25.15 | 750 |
| 85 | CD163_R | Y | 2 | N | 27.83 | 200 |
| 86 | CD68_L | Y | 2 | N | 21.75 | 250 |
| 87 | CD68_R | Y | 2 | N | 26.03 | 250 |
| 88 | LTF_R | Y | 2 | N | 26.59 | 200 |
| 89 | NCF4_R | Y | 2 | N | 31.58 | 4500 |
| 90 | NCL_M | Y | 2 | N | 24.24 | 2000 |
| 91 | NCL_R | Y | 2 | N | 23.39 | 2000 |
| 92 | NCOA1_L | Y | 2 | N | 24.7 | 850 |
| 93 | NCOA1_M | Y | 2 | N | 24.74 | 850 |
| 94 | NCOA1_R | Y | 2 | N | 28.05 | 850 |
| 95 | OAS2_M | Y | 2 | N | 27.23 | 500 |
| 96 | OAS2_R | Y | 2 | N | 27.08 | 500 |
| 97 | OAS3_M | Y | 2 | N | 28.86 | 650 |
| 98 | OAS3_R | Y | 2 | N | 28.94 | 650 |
| 99 | PDLIM1_M | Y | 2 | N | 28.2 | 900 |
| 100 | ROCK2_L | Y | 2 | N | 23.81 | 200 |
| 101 | TES_L | Y | 2 | N | 24.23 | 750 |
| 102 | TES_M | Y | 2 | N | 28.61 | 750 |
| 103 | TES_R | Y | 2 | N | 28.19 | 750 |
| 104 | ACTB_L | Y | 0 | Y | 23.94 | 10,000 |
| 105 | ACTB_R | Y | 0 | Y | 21.05 | 10,000 |
| 106 | CSF3R_R | Y | 0 | Y | 24.48 | 6500 |
| 107 | GAPDH_L | Y | 0 | Y | 24.86 | 10,000 |
| 108 | GZMB_R | Y | 0 | Y | 26.09 | 1500 |
| 109 | IL6R_L | Y | 0 | Y | 33.75 | 500 |
| 110 | LILRA5_L | Y | 0 | Y | 31.33 | 900 |
| 111 | SELL_L | Y | 0 | Y | 23.45 | 8500 |
| 112 | SELL_M | Y | 0 | Y | 24.48 | 8500 |
| 113 | SORL1_L | Y | 0 | Y | 24.67 | 7500 |
| 114 | SORL1_R | Y | 0 | Y | 23.58 | 7500 |
| 115 | STAT6_M | Y | 0 | Y | 25.57 | 1000 |

TABLE 3-continued

Assay Performance, Regional Consistency weighted most heavily. In 'Assay' column:
L = 5' design, M = Middle design, R = 3' design

| | | | | | | |
|---|---|---|---|---|---|---|
| 116 | STAT6_R | Y | 0 | Y | 27.98 | 1000 |
| 117 | TXNIP_L | Y | 0 | Y | 20.2 | 8000 |
| 118 | TXNIP_M | Y | 0 | Y | 21.64 | 8000 |
| 119 | TXNIP_R | Y | 0 | Y | 23.75 | 8000 |
| 120 | VIM_R | Y | 0 | Y | 23.24 | 9500 |
| 121 | LILRA5_R | Y | 0 | Borderline | 28.1 | 900 |
| 122 | SORL1_M | Y | 0 | Borderline | 26.09 | 7500 |
| 123 | VIM_M | Y | 0 | Borderline | 25.75 | 9500 |
| 124 | CSF3R_M | Y | 0 | N | 28.15 | 6500 |
| 125 | GAPDH_R | Y | 0 | N | 26.97 | 10,000 |
| 126 | IL6R_M | Y | 0 | N | 28.1 | 500 |
| 127 | IL6R_R | Y | 0 | N | 25.48 | 500 |
| 128 | SELL_R | Y | 0 | N | 27.05 | 8500 |
| 129 | STAT6_L | Y | 0 | N | 24.32 | 1000 |
| 130 | STX4_L | Y | 0 | N | 25.6 | 600 |
| 131 | STX4_R | Y | 0 | N | 28.74 | 600 |
| 132 | SYNE2_L | Y | 0 | N | 28.29 | 400 |
| 133 | SYNE2_M | Y | 0 | N | 25.49 | 400 |
| 134 | KLRF1_L | N | 3 | Y | 33.13 | 650 |
| 135 | KLRF1_M | N | 3 | Y | 34.44 | 650 |
| 136 | KLRF1_R | N | 3 | Y | 33.78 | 650 |
| 137 | TRPM2_L | N | 3 | Y | 33.37 | 400 |
| 138 | TRPM2_M | N | 3 | Y | 33.62 | 400 |
| 139 | TRPM2_R | N | 3 | Y | 34.77 | 400 |
| 140 | ADAR_L | N | 3 | Borderline | 25.6 | 4500 |
| 141 | FCN1_M | N | 3 | Borderline | 25.54 | 9000 |
| 142 | DDX58_R | N | 3 | N | 27.8 | 350 |
| 143 | C1orf38_L | N | 2 | Y | 27.49 | 3000 |
| 144 | CD27_M | N | 2 | Y | 32.29 | 650 |
| 145 | CD300C_L | N | 2 | Y | 32.63 | 500 |
| 146 | CD300C_M | N | 2 | Y | 30.4 | 500 |
| 147 | CD53_L | N | 2 | Y | 23.36 | 8000 |
| 148 | CD83_L | N | 2 | Y | 36.63 | 150 |
| 149 | CD83_M | N | 2 | Y | 34.82 | 150 |
| 150 | IL15RA_L | N | 2 | Y | 35.19 | 300 |
| 151 | IL15RA_R | N | 2 | Y | 35.75 | 300 |
| 152 | IL7R_L | N | 2 | Y | 27.07 | 3500 |
| 153 | LTF_L | N | 2 | Y | 35.73 | 200 |
| 154 | LY75_L | N | 2 | Y | 31.38 | 800 |
| 155 | OAS3_L | N | 2 | Y | 31.77 | 650 |
| 156 | PDLIM1_L | N | 2 | Y | 31.95 | 900 |
| 157 | PDLIM2_L | N | 2 | Y | 30.75 | 950 |
| 158 | PDLIM2_R | N | 2 | Y | 38.02 | 950 |
| 159 | ROCK2_M | N | 2 | Y | 30.81 | 200 |
| 160 | SERPINA1_L | N | 2 | Y | 24.63 | 7500 |
| 161 | ZAP70_L | N | 2 | Y | 36.56 | 650 |
| 162 | AIM1_L | N | 2 | Borderline | 30.33 | 1000 |
| 163 | C1orf38_R | N | 2 | Borderline | 32.82 | 3000 |
| 164 | SERPINA1_M | N | 2 | Borderline | 25.22 | 7500 |
| 165 | CD163_M | N | 2 | N | 28.45 | 200 |
| 166 | CD27_L | N | 2 | N | 29.18 | 650 |
| 167 | CD68_M | N | 2 | N | 27.65 | 250 |
| 168 | CDC42SE1_L | N | 2 | N | 30.86 | 5000 |
| 169 | EEF2_L | N | 2 | N | 28.43 | 7000 |
| 170 | IL15RA_M | N | 2 | N | 29.39 | 300 |
| 171 | LTF_M | N | 2 | N | 28.3 | 200 |
| 172 | BACH2_L | N | 0 | Y | 34.45 | 150 |
| 173 | BACH2_R | N | 0 | Y | 30.93 | 150 |
| 174 | GZMB_L | N | 0 | Y | 29.68 | 1500 |
| 175 | GZMB_M | N | 0 | Y | 28.02 | 1500 |
| 176 | LILRA5_M | N | 0 | Y | 30.11 | 900 |
| 177 | SELP_L | N | 0 | Y | 31.32 | 700 |
| 178 | SELP_M | N | 0 | Y | 32.15 | 700 |
| 179 | SELP_R | N | 0 | Y | 35.16 | 700 |
| 180 | STX4_M | N | 0 | Y | 30.42 | 600 |
| 181 | SYNE2_R | N | 0 | Y | 32.43 | 400 |
| 182 | CSF3R_L | N | 0 | Borderline | 26.1 | 6500 |
| 183 | BACH2_M | N | 0 | N | 27.36 | 150 |
| 184 | VIM_L | N | 0 | N | 36.39 | 9500 |

Experimental RNA Degradation and Assay Performance
Materials and Methods
Experimental RNA Degradation Conditions To determine the best method for experimentally degrading RNA samples, multiple degradation conditions were evaluated [2, 13-15, 44, 45]. Aliquots of native RNA were either subjected to repeat freeze/thaw cycles, heat treatments, or exposure to an endoribonuclease, RNase A. Freeze/thaw cycling consisted of flash-freezing native RNA aliquots on dry ice for 2 minutes, followed by a complete thaw on wet ice for 7.5 minutes. Five 6 µl RNA aliquots were exposed to 3, 6, 9, and 12 freeze/thaw cycles, respectively. RNA integrity was assessed for each aliquot using the RNA 6000 Nano LabChip® kit on a Bioanalyzer 2100 instrument (Agilent); electropherogram and gel electrophoresis images are presented in FIGS. 10A-10D.

Heat treatments consisted of exposing native RNA aliquots to high heat over a time continuum. Five 7 µl RNA aliquots were incubated in a 60° C. Mastercycler® Ep thermal cycler heat block (Eppendorf) for 30, 60, 90, and 120 minutes, respectively. After each 30-minute time interval, a single aliquot tube was removed from the heat block and frozen immediately on dry ice. RNA integrity was assessed for each aliquot using the RNA 6000 Nano LabChip® kit on a Bioanalyzer 2100 instrument; electropherogram and gel electrophoresis images are presented in FIGS. 10A-10D.

RNase A treatments consisted of exposing native RNA aliquots to an optimal dilution of stock RNase A solution (Qiagen). The enzymatic reaction was stopped at set time points with optimally diluted SUPERase-In (Ambion), a multiple RNase inhibitor. Several attempts to optimize dilutions and exposure periods resulted in completely degraded RNA before a final RNase A dilution of 1:5,000,000 and SUPERase-In dilution of 1:2 produced measurable, incrementally degraded RNA [46, 47]. For eight 6 µl. RNA aliquots, 1 µl of 1:5,000,000 diluted RNase A was added and tubes were incubated in a 37° C. Mastercycler® Ep thermal cycler heat block. At time points 0.5, 1, 2, 4, 8, 16, and 32 minutes, a single tube was taken off the heat block and 1 µl of 1:2 diluted SUPERase-In was added, thoroughly mixed, and the tube was immediately frozen on dry ice. RNA integrity was assessed for each aliquot using the RNA 6000 Nano LabChip® kit on a Bioanalyzer 2100 instrument; electropherogram and gel electrophoresis images are presented in FIGS. 10A-10D.

Based on the graded degradation patterns produced by the RNase A treatment, this method was chosen for subsequent degradation testing. Since production of RNase inhibitors involves co-purification with RNases which can potentially contaminate stock solutions, a concern arose about reintroducing unwanted RNases during the supposed inactivation step. To address this concern in subsequent RNase experiments, a second RNA purification step was performed after the RNase inactivation step to ensure the degradation process would not continue to fragment the RNA beyond the desired inactivation time point. To stabilize the RNA during the purification step, ten volumes of TRIzol® reagent (Invitrogen) and two volumes of chloroform (Invitrogen) were added to each RNA aliquot in a phase lock gel heavy tube (5 Prime), shaken vigorously, incubated at room temperature for 3 minutes, then centrifuged at 12,000×g and 4° C. for 15 minutes. TRIzol® reagent, containing phenol and guanidine isothiocyanate, is often used prior to RNA extraction and purification protocols to maintain RNA integrity during the extraction process [48]. The aqueous layer, containing stabilized RNA, was transferred to a fresh microfuge tube and purified with an RNeasy Mini Kit (Qiagen), according to the manufacturer's protocol. The RNeasy Mini Kit is a system for RNA extraction and purification that binds RNA to a silica-membrane spin column, purifying the bound RNA through a series of buffer washes and centrifugation steps [49].

Figure 11A:
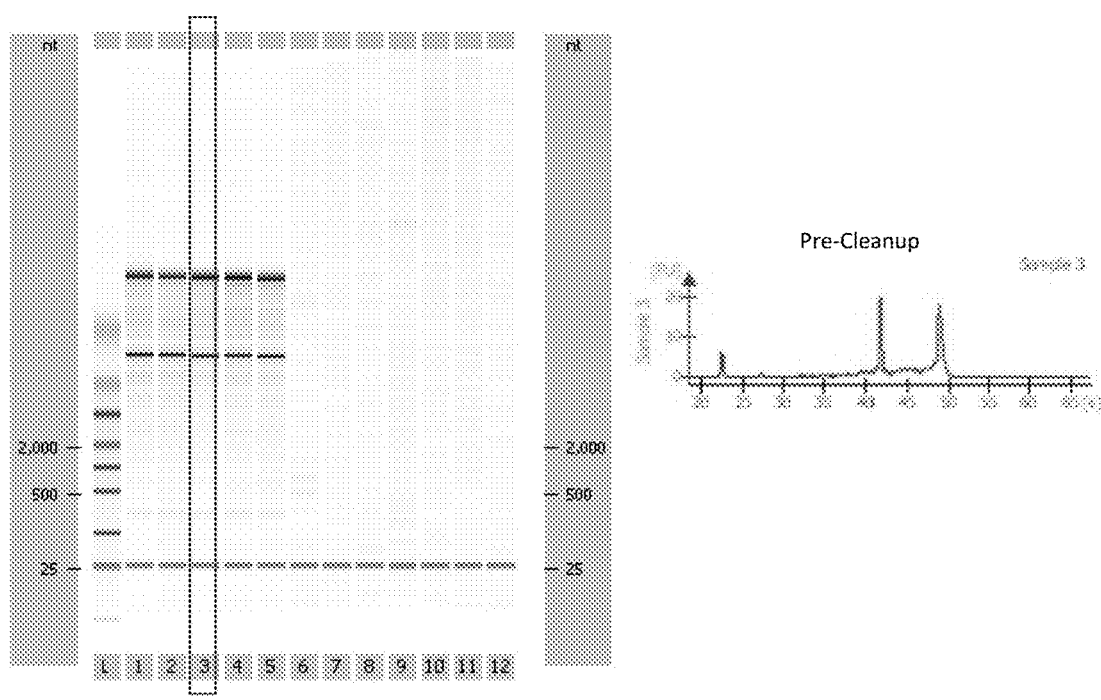
FIGS. 11A-11B: (A) Table showing Nanodrop ND-8000 Native RNA Yield Data and imagines showing Pre-Cleanup Bioanalyzer 2100 Data, (B) Images showing Post-Cleanup Bioanalyzer 2100 Data.
Figure 11B:
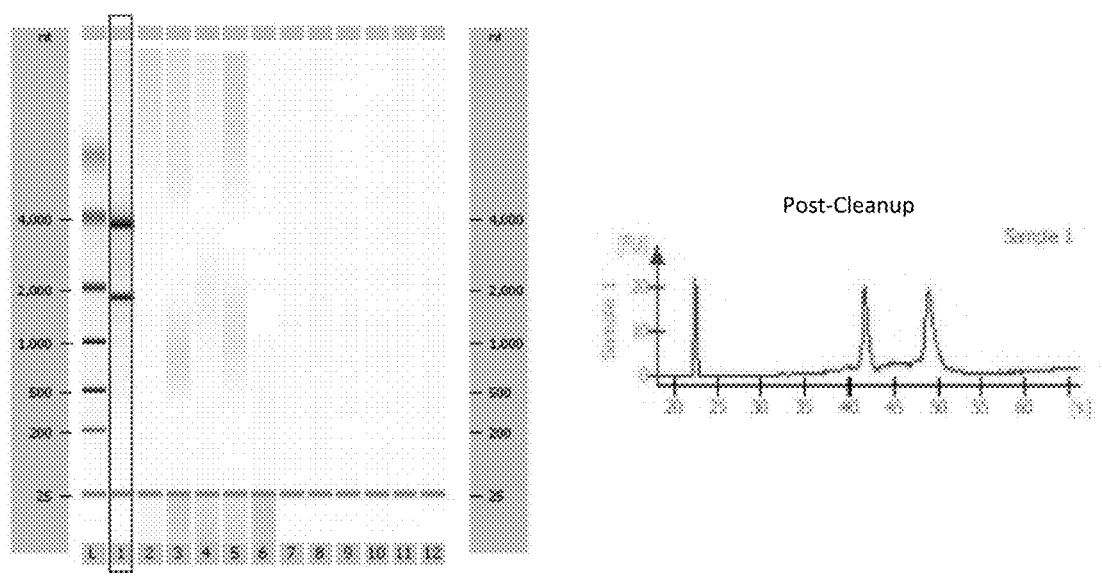
Figure 14B:
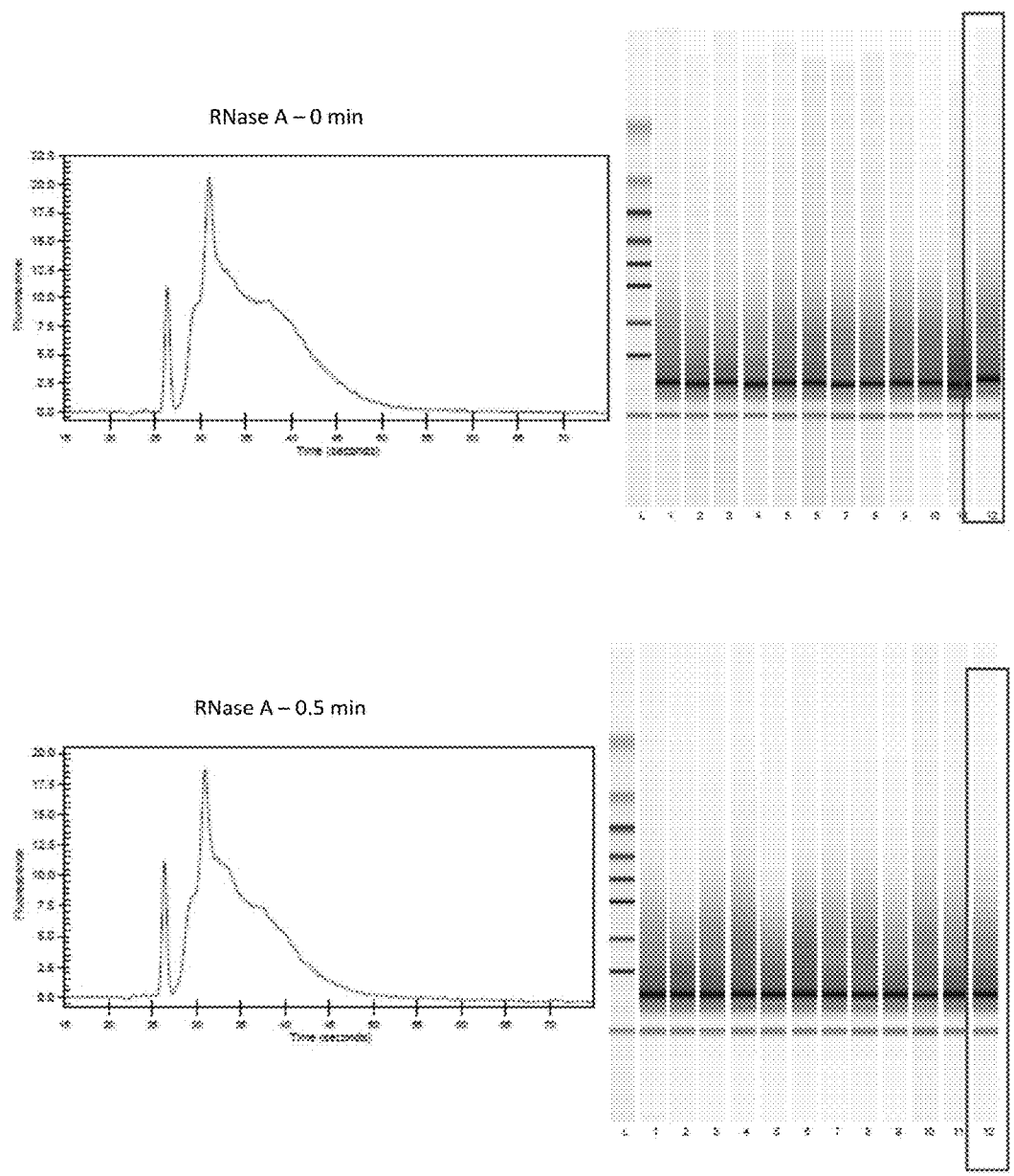
Figure 14C:
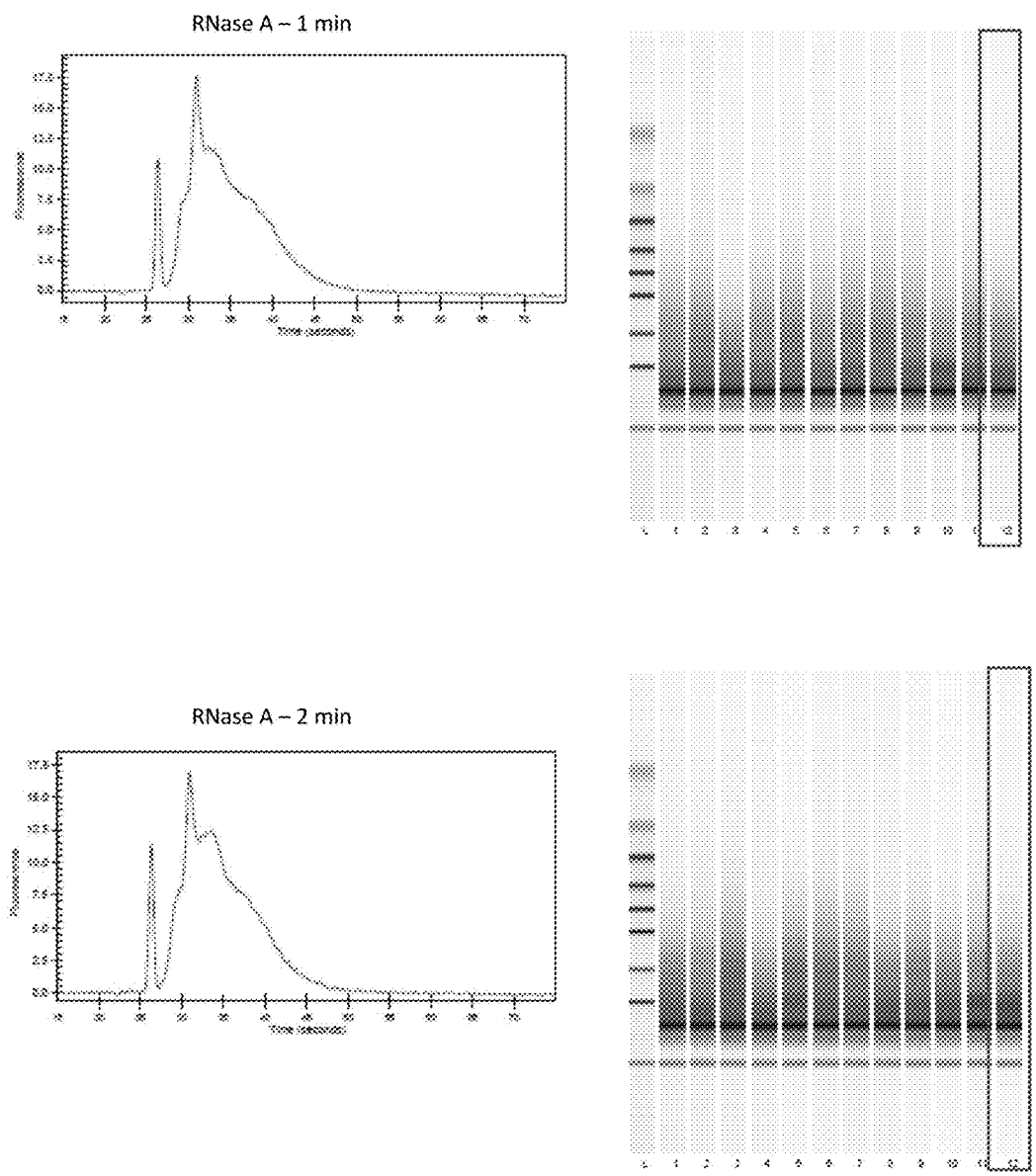
Figure 14E:
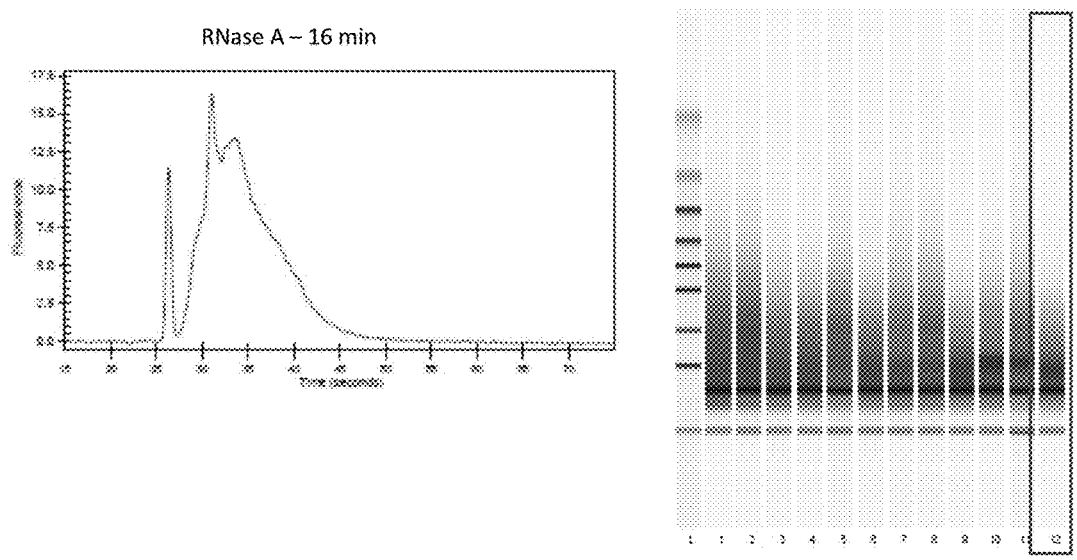

To gauge the amount of RNA yield net loss to be expected as a result of adding an additional purification step, the secondary RNase inactivation step was performed on native RNA. Once satisfied that RNA yield would not be compromised, the RNase A treatment of samples was followed by the secondary RNase inactivation step described previously for all subsequent testing. Nanodrop ND-8000 (Thermo Fisher) and Bioanalyzer 2100 yield and quality data are presented in FIGS. 11A-11B.

Manual RNA Extraction and Experimental Degradation

Once the combined RNase A treatment and purification step was defined as the optimal experimental degradation method, RNA was manually extracted from the second set of frozen blood samples using a PAXgene® Blood RNA Kit (Qiagen), according to the manufacturer's protocol. As opposed to the automated method, manually extracting the RNA provided a greater overall yield, necessary for running multiple degradation conditions and subsequent qPCR reactions. RNA yield and purity was assessed using Nanodrop ND-8000 spectrophotometric measurements. RNA integrity was assessed for each sample with electropherogram and gel electrophoresis images on a Bioanalyzer 2100, as presented in FIGS. 12A-12B.

Manually extracted RNA sample 'D' was arbitrarily chosen for experimental degradation by RNase A according to the optimized two-step method previously outlined. Seven 10 µl RNA aliquots were treated and purified according to plan for time points 0, 0.5, 1, 2, 4, 8, and 16 minutes. RNA yield and purity was assessed using Nanodrop ND-8000 spectrophotometric measurements. RNA integrity was assessed for each aliquot with electropherogram and gel electrophoresis images on a Bioanalyzer 2100, as presented in FIGS. 13A-13B.

cDNA Synthesis and Amplification

In a two-step process, the seven variably-degraded RNA aliquots were reverse transcribed to cDNA, which was then amplified using the Ovation Pico WTA System (NuGEN) on a Biomek FX liquid handling instrument according to the manufacturer's protocol. cDNA yield and purity was assessed using Nanodrop ND-8000 spectrophotometric measurements. cDNA integrity was assessed with LabChip 90 HT RNA electropherogram and gel electrophoresis images (Caliper Life Sciences). cDNA quality data is presented in FIGS. 14A-14E. Working dilutions of 1:200 cDNA were prepared with DNase/RNase-free water for use in subsequent qPCR reactions.

Incrementally Degraded RNA: Real-Time Quantitative PCR

Real-time qPCR reactions were run for 71 of the top-performing assays, as identified by the assay validation phase, against 7 cDNA samples generated from increasingly degraded RNA on a 7900HT Real-Time PCR System (Applied Biosystems). Three technical sample replicates and one no template control (NTC) were run for each assay. A general reaction plate map is presented in Table 4. Single 10 µl reactions consisted of a gene-specific forward/reverse primer set (Sigma), corresponding Universal ProbeLibrary probe (Roche), TaqMan® Gene Expression Master Mix (Applied Biosystems), DNase/RNase-free water, and 1:5 dilution cDNA template. To ensure accuracy and produce reliable gene expression data, all qPCR reaction plates were prepared in 384-well PCR plates on a Biomek FX liquid handling instrument.

Figure 15B:
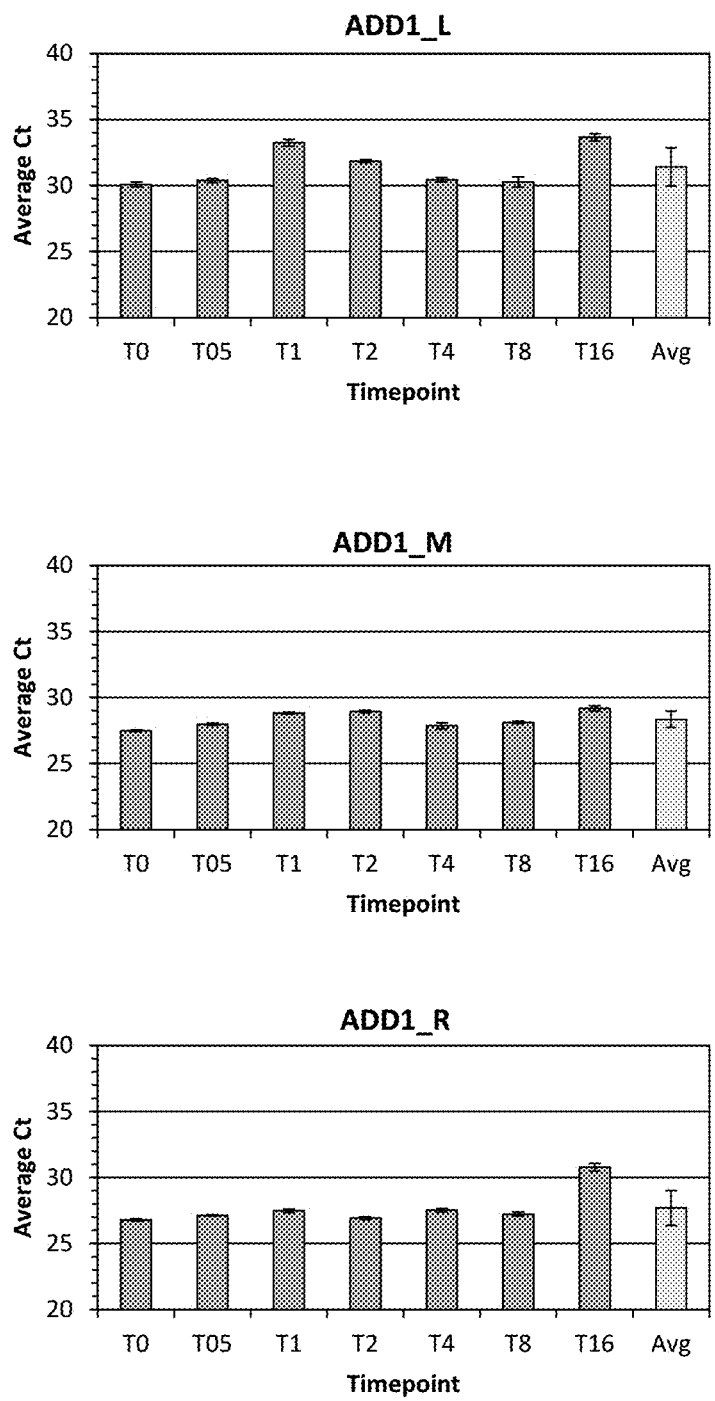
FIGS. 15A-15X: RNA Degradation Assay Histograms: Sample Average and Overall Average CT Values.
Figure 15D:
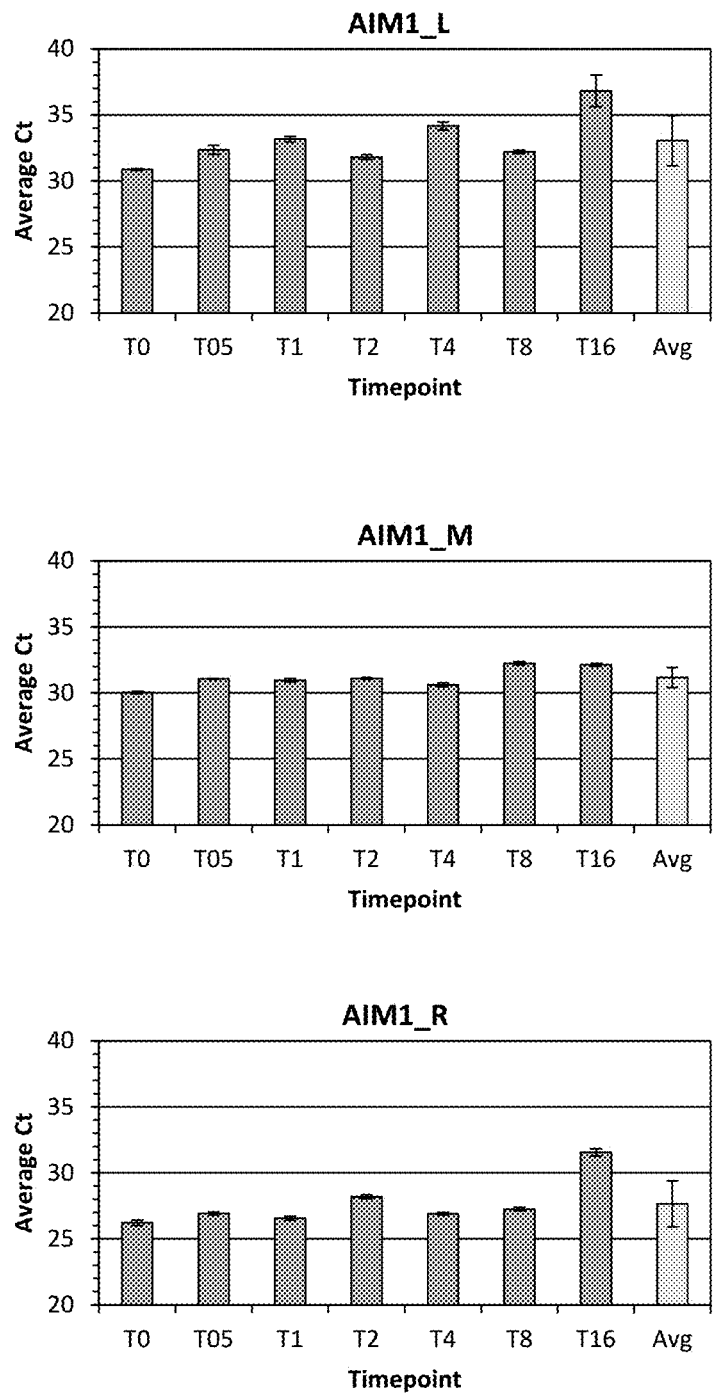
Figure 15F:
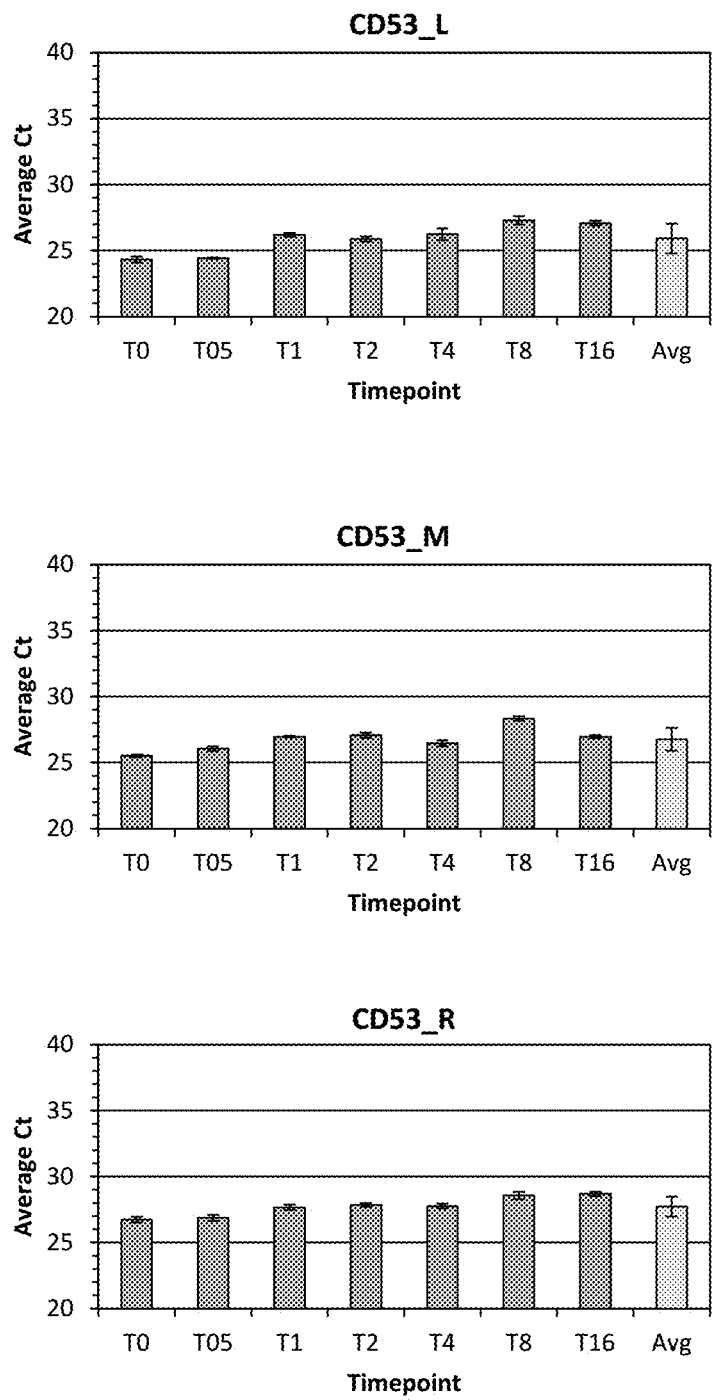
Figure 15G:
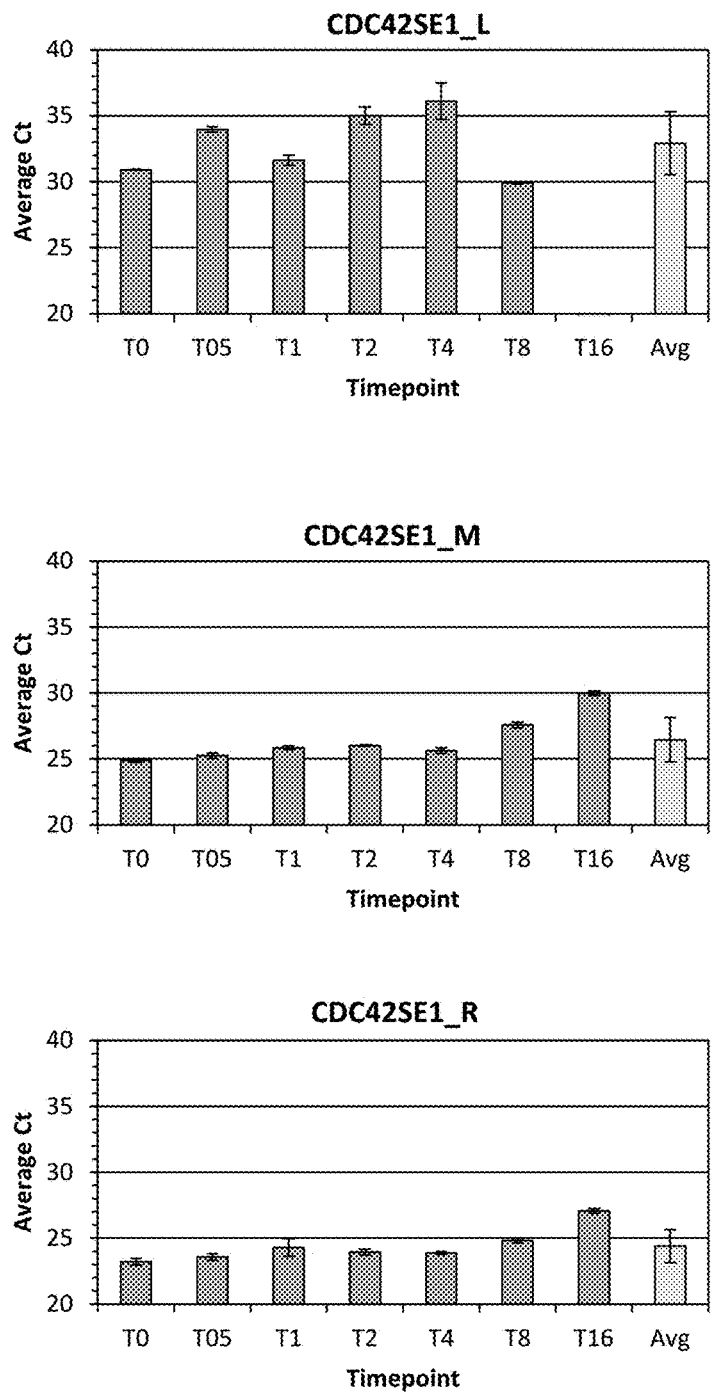
Figure 15I:
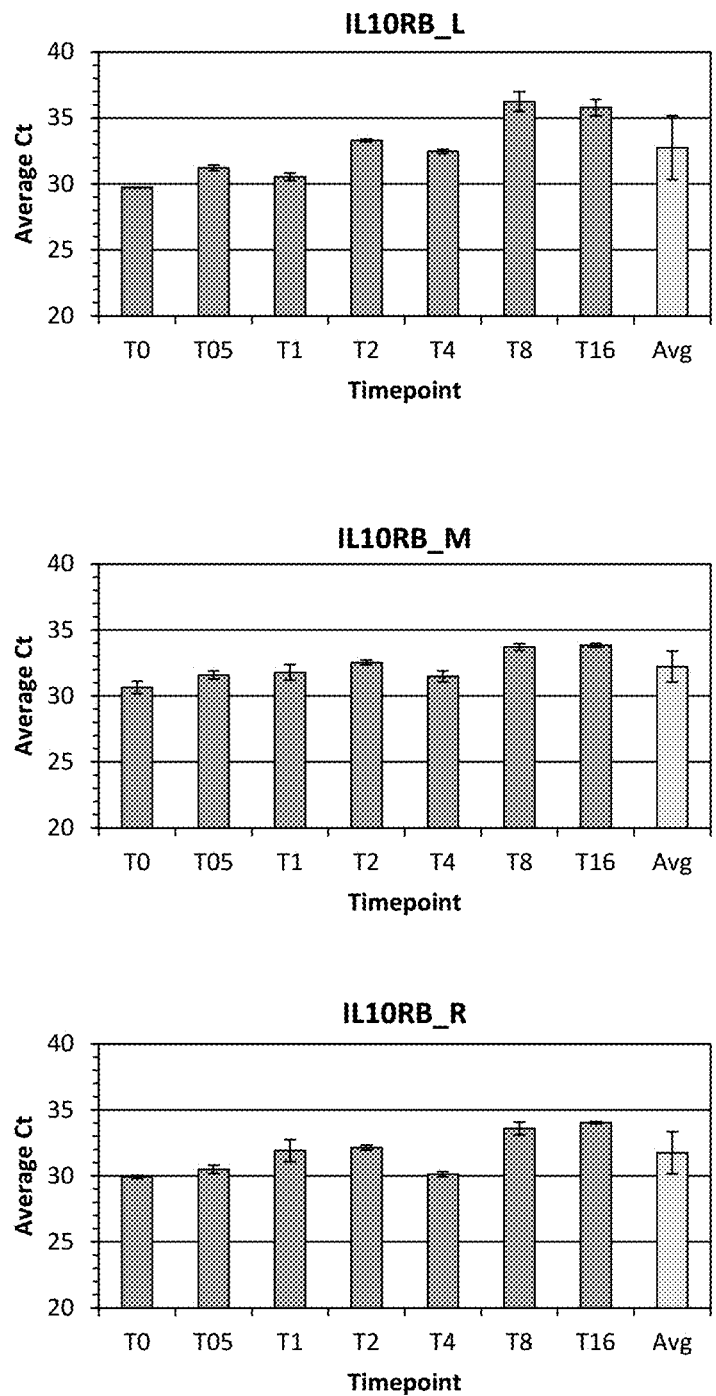
Figure 15K:
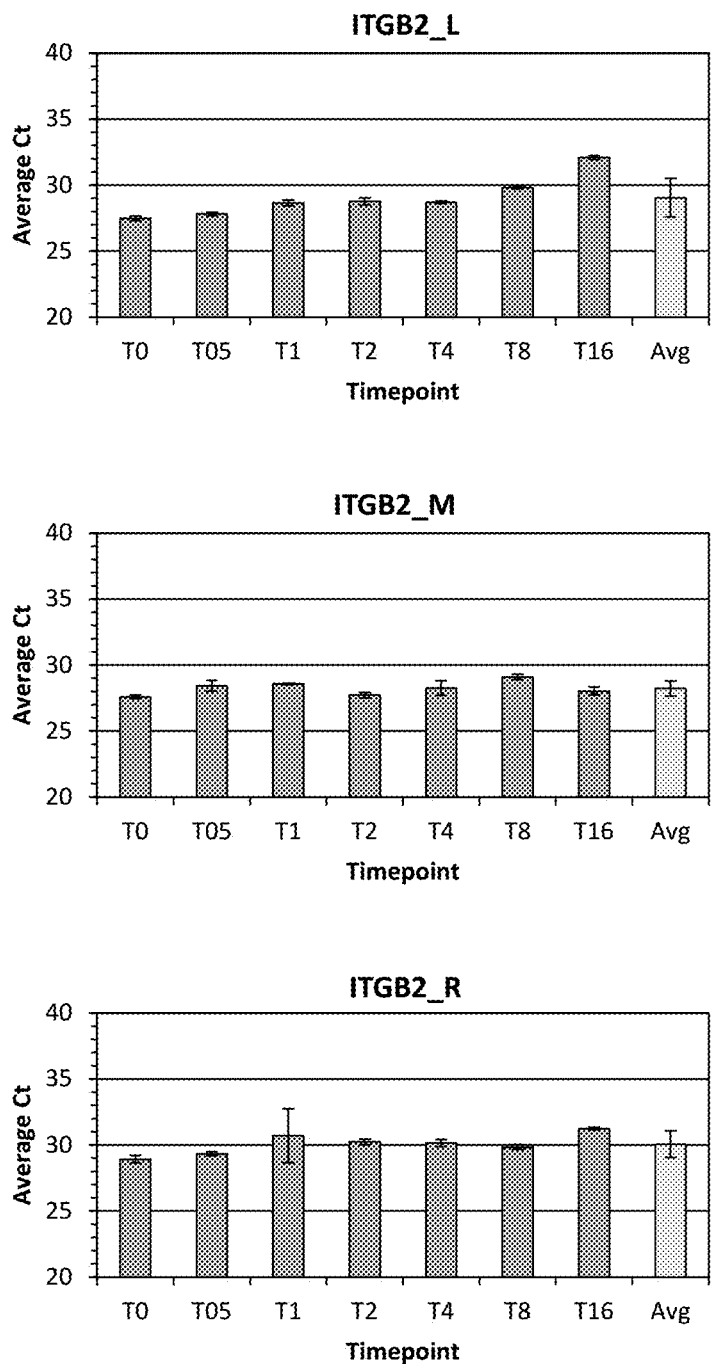
Figure 15L:
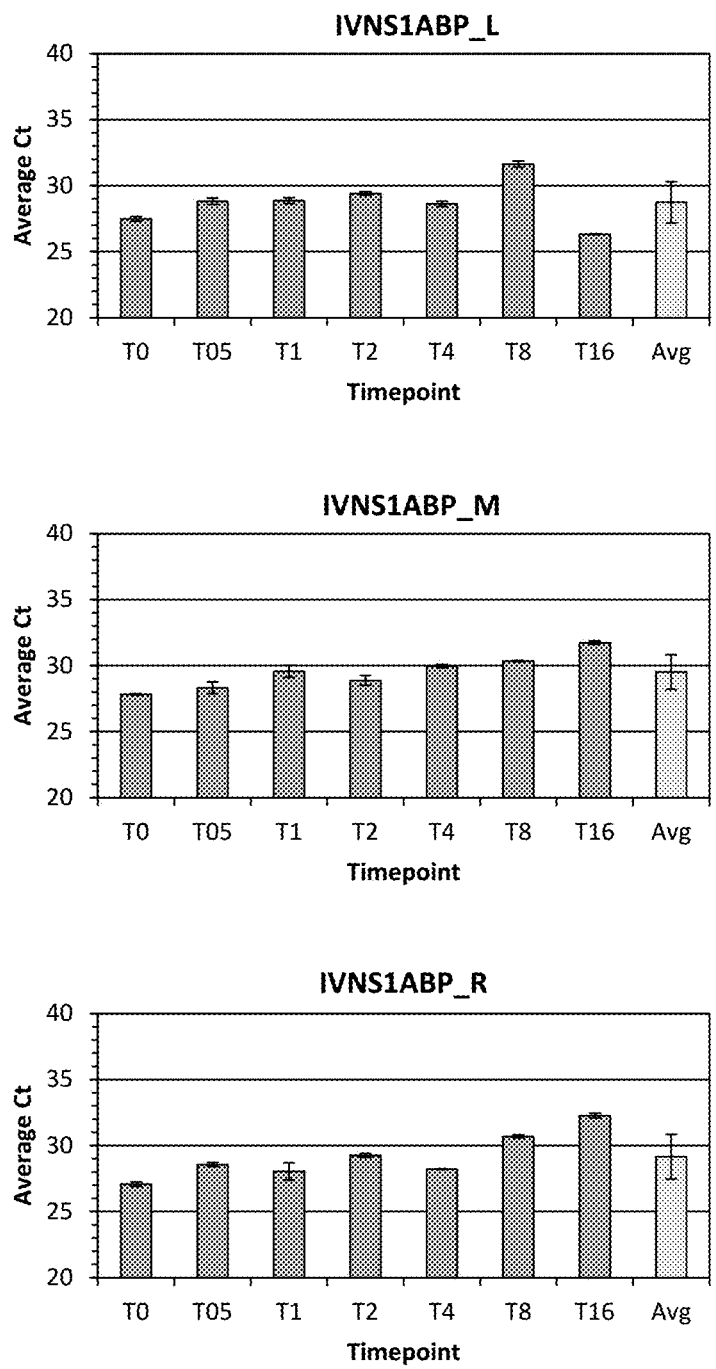
Figure 15M:
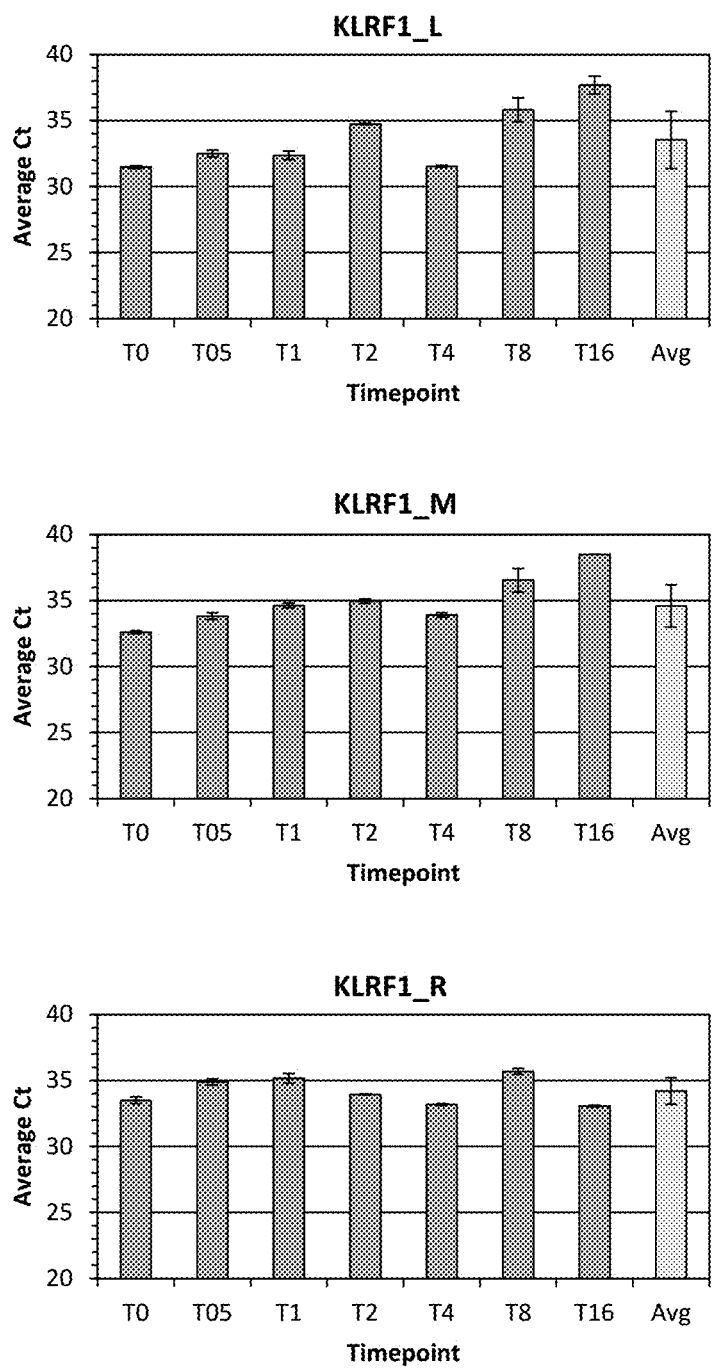
Figure 15N:
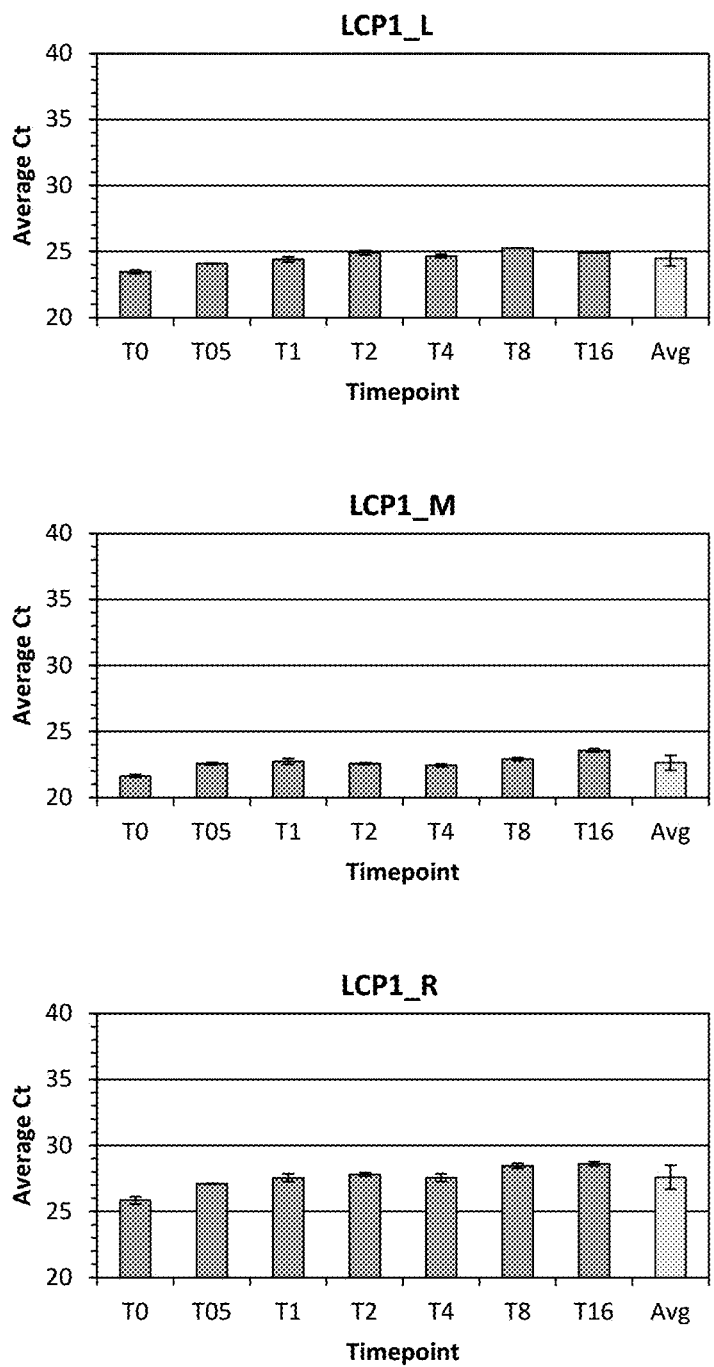
Figure 15O:
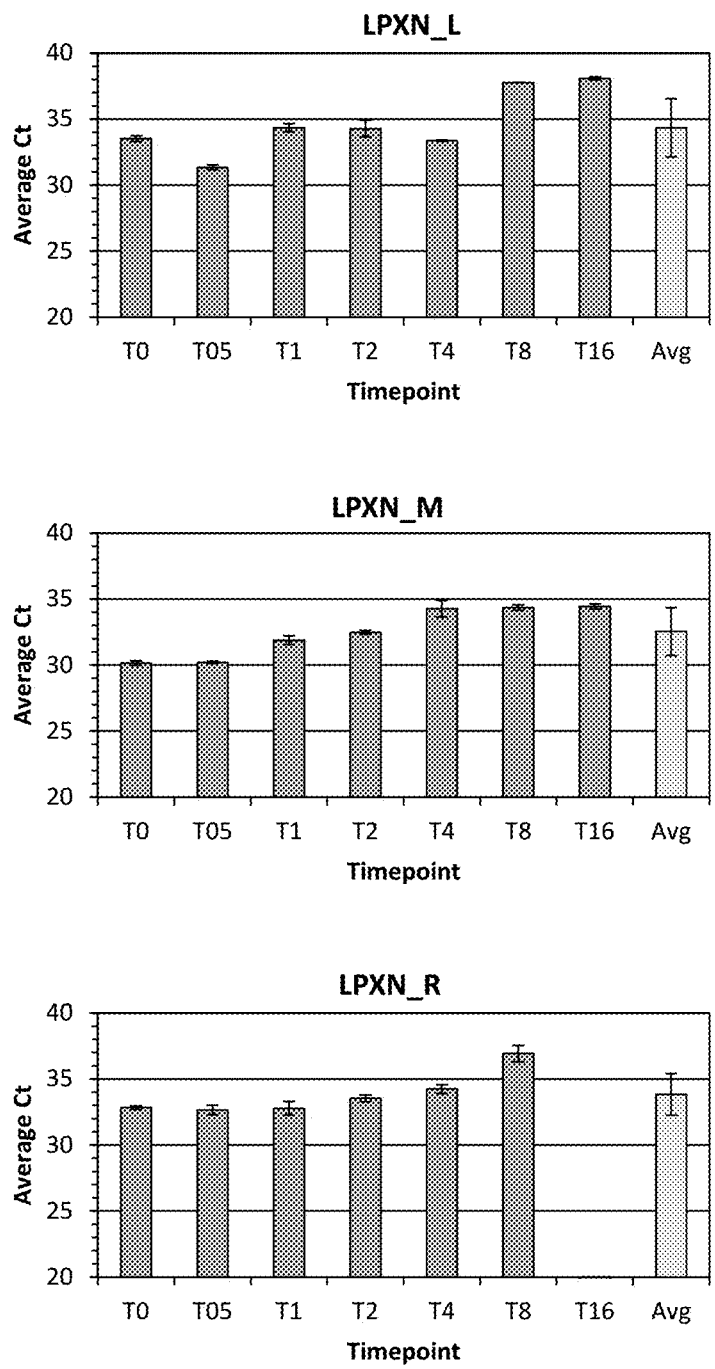
Figure 15Q:
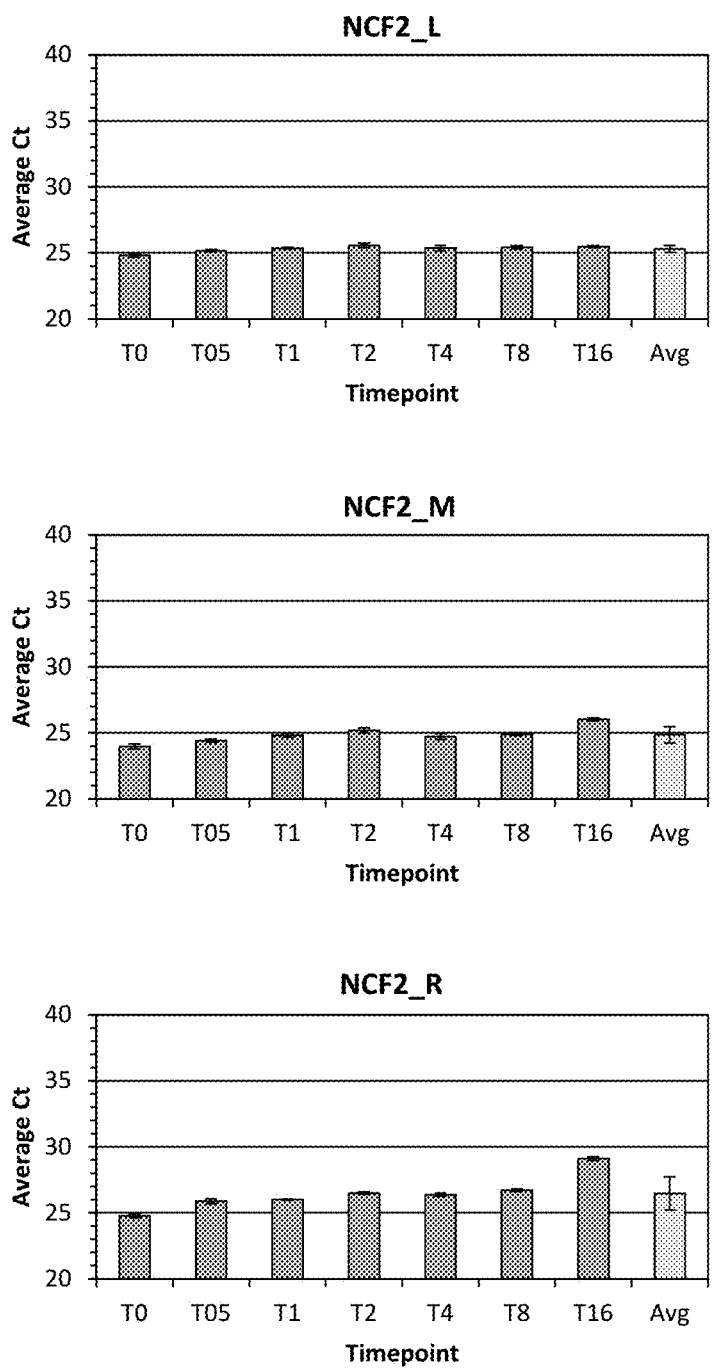
Figure 15S:
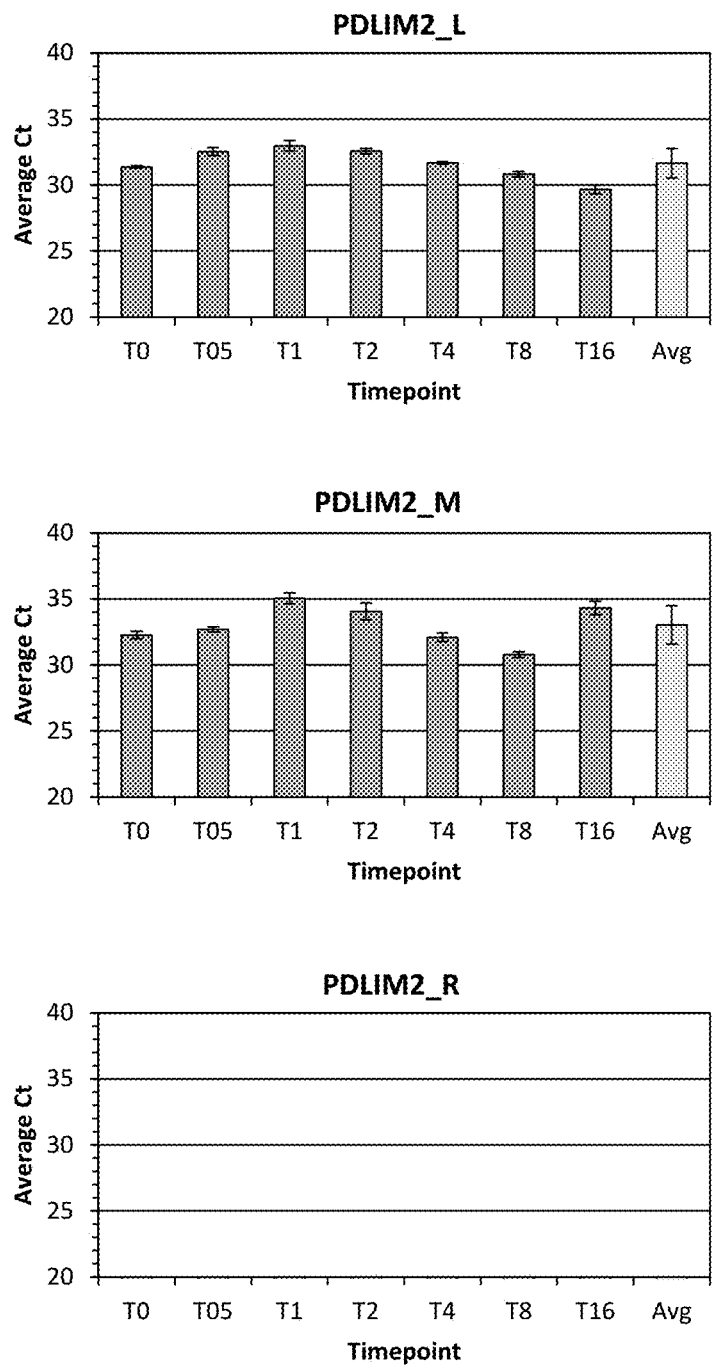
Figure 15T:
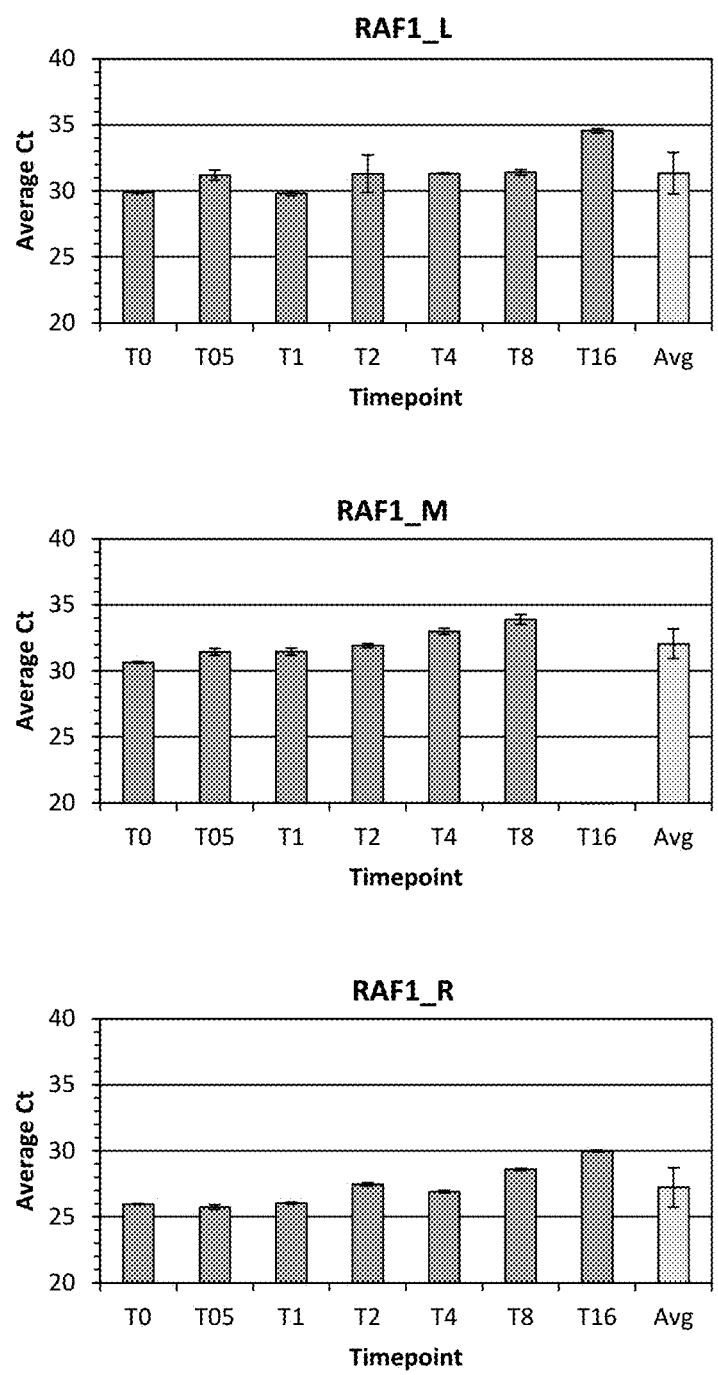
Figure 15U:
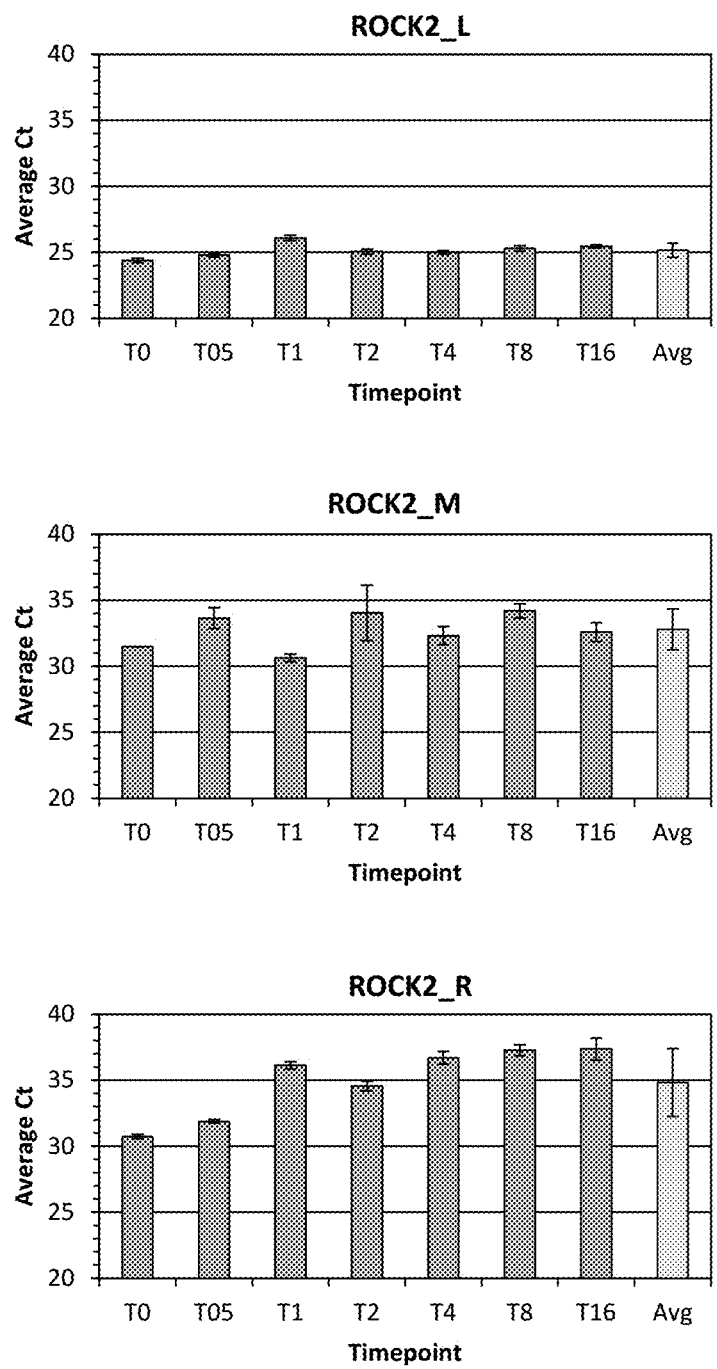
Figure 15V:
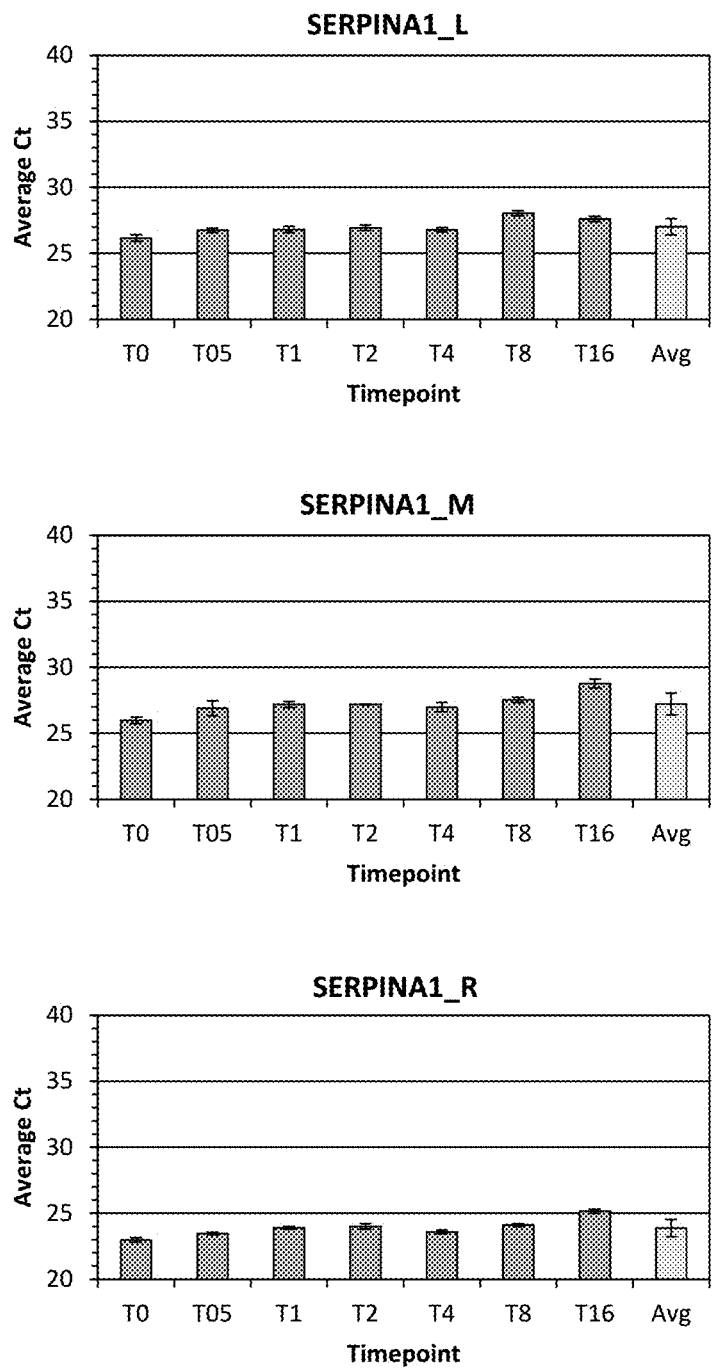
Figure 15W:
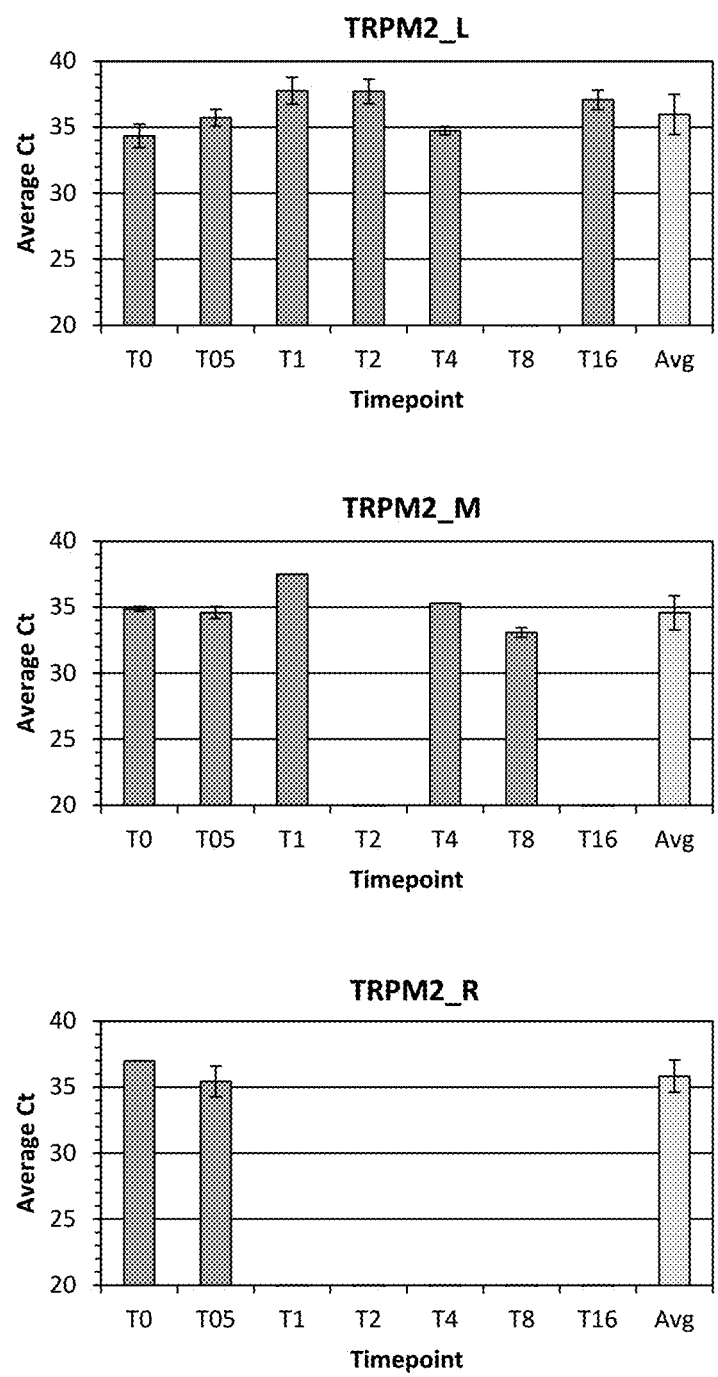
Figure 15X:
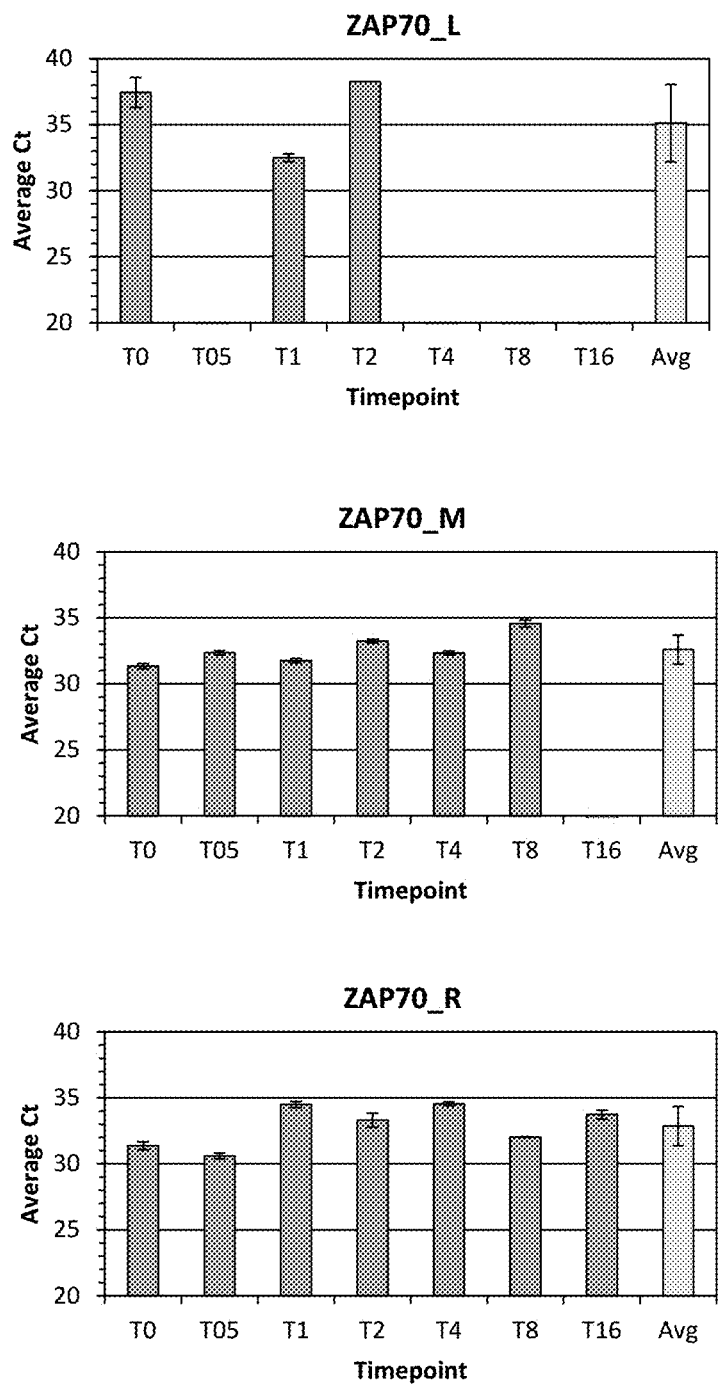

$C_T$ values were grouped by assay then sub-grouped by sample for descriptive statistical analysis. For each assay, the statistical average and standard deviation of triplicate $C_T$ values per sample was calculated. Additionally, for each assay, a statistical average and standard deviation of $C_T$ values per all samples was calculated, as presented in Table 5. Outlying $C_T$ values below 15 and above 38.5 were excluded from all calculations due to experimental error or assay failure, and NTC $C_T$ values were checked for evidence of contamination. To better evaluate assay performance, the descriptive statistical data was visualized with histogram plots. Histograms were plotted to compare assay performance between individual samples per given assay; all regional assays for a given gene were plotted on the same histogram to reveal local biases, as presented in FIGS. 15A-15X. To compare performance across all 71 assays, the

TABLE 4

General Plate Map for Degraded RNA qPCR Reactions
Numbers refer to unique assays
'NTC' stands for
No Template Control: these wells contain only assay master mix but no cDNA sample

|     |   | 1 | 2   | 3 | 4   | 5 | 6   | 7 | 8   | 9 | 10  | 11 | 12  |
|-----|---|---|-----|---|-----|---|-----|---|-----|---|-----|----|-----|
| 0   | A | 1 | 1   | 2 | 2   | 3 | 3   | 4 | 4   | 5 | 5   | 6  | 6   |
|     | B | 1 | NTC | 2 | NTC | 3 | NTC | 4 | NTC | 5 | NTC | 6  | NTC |
| 0.5 | C | 1 | 1   | 2 | 2   | 3 | 3   | 4 | 4   | 5 | 5   | 6  | 6   |
|     | D | 1 | NTC | 2 | NTC | 3 | NTC | 4 | NTC | 5 | NTC | 6  | NTC |
| 1   | E | 1 | 1   | 2 | 2   | 3 | 3   | 4 | 4   | 5 | 5   | 6  | 6   |
|     | F | 1 | NTC | 2 | NTC | 3 | NTC | 4 | NTC | 5 | NTC | 6  | NTC |
| 2   | G | 1 | 1   | 2 | 2   | 3 | 3   | 4 | 4   | 5 | 5   | 6  | 6   |
|     | H | 1 | NTC | 2 | NTC | 3 | NTC | 4 | NTC | 5 | NTC | 6  | NTC |
| 4   | I | 1 | 1   | 2 | 2   | 3 | 4   | 4 | 4   | 5 | 17  | 6  | 6   |
|     | J | 1 | NTC | 2 | NTC | 3 | NTC | 4 | NTC | 5 | NTC | 6  | NTC |
| 8   | K | 1 | 13  | 2 | 2   | 3 | 4   | 4 | 4   | 5 | 17  | 6  | 6   |
|     | L | 1 | NTC | 2 | NTC | 3 | NTC | 4 | NTC | 5 | NTC | 6  | NTC |
| 16  | M | 1 | 1   | 2 | 2   | 3 | 4   | 4 | 4   | 5 | 17  | 6  | 6   |
|     | N | 1 | NTC | 2 | NTC | 3 | NTC | 4 | NTC | 5 | NTC | 6  | NTC |
|     | O | — | —   | — | —   | — | —   | — | —   | — | —   | —  | —   |
|     | P | — | —   | — | —   | — | —   | — | —   | — | —   | —  | —   |

|     |   | 13 | 14  | 15 | 16  | 17 | 18  | 19 | 20  | 21 | 22  | 23 | 24  |
|-----|---|----|-----|----|-----|----|-----|----|-----|----|-----|----|-----|
| 0   | A | 7  | 7   | 8  | 8   | 9  | 9   | 10 | 10  | 11 | 11  | 12 | 12  |
|     | B | 7  | NTC | 8  | NTC | 9  | NTC | 10 | NTC | 11 | NTC | 12 | NTC |
| 0.5 | C | 7  | 7   | 8  | 8   | 9  | 9   | 10 | 10  | 11 | 11  | 12 | 12  |
|     | D | 7  | NTC | 8  | NTC | 9  | NTC | 10 | NTC | 11 | NTC | 12 | NTC |
| 1   | E | 7  | 7   | 8  | 8   | 9  | 9   | 10 | 10  | 11 | 11  | 12 | 12  |
|     | F | 7  | NTC | 8  | NTC | 9  | NTC | 10 | NTC | 11 | NTC | 12 | NTC |
| 2   | G | 7  | 7   | 8  | 8   | 9  | 9   | 10 | 10  | 11 | 11  | 12 | 12  |
|     | H | 7  | NTC | 8  | NTC | 9  | NTC | 10 | NTC | 11 | NTC | 12 | NTC |
| 4   | I | 7  | 7   | 8  | 8   | 9  | 9   | 10 | 10  | 11 | 11  | 12 | 12  |
|     | J | 7  | NTC | 8  | NTC | 9  | NTC | 10 | NTC | 11 | NTC | 12 | NTC |
| 8   | K | 7  | 7   | 8  | 8   | 9  | 9   | 10 | 10  | 11 | 11  | 12 | 12  |
|     | L | 7  | NTC | 8  | NTC | 9  | NTC | 10 | NTC | 11 | NTC | 12 | NTC |
| 16  | M | 7  | 7   | 8  | 8   | 9  | 9   | 10 | 10  | 11 | 11  | 12 | 12  |
|     | N | 7  | NTC | 8  | NTC | 9  | NTC | 10 | NTC | 11 | NTC | 12 | NTC |
|     | O | —  | —   | —  | —   | —  | —   | —  | —   | —  | —   | —  | —   |
|     | P | —  | —   | —  | —   | —  | —   | —  | —   | —  | —   | —  | —   |

Results

Degraded RNA Assay Performance Analysis

For each of the degradation assays, RQ Manager version 1.2 software (Applied Biosystems) plotted the magnitude of fluorescence (ΔRn) against the PCR amplification cycle number. A comprehensive logarithmic amplification plot was generated for each assay and a threshold line was manually set at the midpoint of the linear phase of the plot, intersecting to define an individual $C_T$ value for each reaction well of a given assay. Individual $C_T$ values and amplification plots were exported for qualitative and descriptive statistical analyses.

overall average $C_T$ value and overall standard deviation of all seven samples per given assay were plotted on a single histogram. Comparisons with the initial assay validation phase $C_T$ values were also visualized in a single histogram to track general trends in expression level change, confirming that degradation increased overall average $C_T$ values for each assay. To visualize the change in $C_T$ over the course of increasing degradation for each assay, the percent change in $C_T$ was plotted using native RNA $C_T$ values ($T_0$ minutes) as the baseline. The relationship between $C_T$ value and extent of degradation served as a foundation for deciding algorithm development approaches.

TABLE 5

Degraded RNA: Expression Data and Descriptive Statistics
Average $C_T$ is the average of three technical replicates
Overall Average $C_T$ is the average of three technical replicates of all four samples
'Undet.' indicates that the $C_T$ value was undetermined for that sample

| Detector | Threshold | Avg $C_T$ 0 min | Avg $C_T$ 0.5 min | Avg $C_T$ 1 min | Avg $C_T$ 2 min | Avg $C_T$ 4 min | Avg $C_T$ 8 min | Avg $C_T$ 16 min | Overall Avg $C_T$ | Overall StDev |
|---|---|---|---|---|---|---|---|---|---|---|
| ACTB_L | 0.051 | 24.98 | 25.5 | 25.82 | 25.95 | 25.74 | 25.98 | 26.31 | 25.75 | 0.5 |
| ACTB_R | 0.065 | 21.72 | 22.31 | 23.01 | 22.91 | 22.78 | 23.18 | 23.5 | 22.77 | 0.593 |
| ARPC5_L | 0.076 | 21.79 | 22.41 | 23.34 | 23.27 | 22.89 | 23.94 | 23.88 | 23.07 | 0.747 |
| ARPC5_M | 0.146 | 20.98 | 21.62 | 22.47 | 22.86 | 22.52 | 23.18 | 23.62 | 22.46 | 0.879 |
| ARPC5_R | 0.061 | 21.28 | 22.15 | 22.59 | 22.97 | 22.83 | 23.72 | 24.3 | 22.84 | 0.949 |
| F13A1_L | 0.116 | 28.51 | 29.18 | 29.73 | 28.06 | 30.26 | 30 | 29.32 | 29.27 | 0.788 |
| F13A1_M | 0.158 | 27.49 | 29.45 | 29.54 | 30.55 | 31.14 | 31.16 | 36.83 | 30.58 | 2.478 |
| F13A1_R | 0.161 | 28.14 | 29.52 | 29.23 | 31.04 | 29.7 | 31.42 | 31.35 | 30.06 | 1.19 |
| IL10RB_L | 0.086 | 29.73 | 31.22 | 30.53 | 33.3 | 32.47 | 36.23 | 35.79 | 32.75 | 2.416 |
| IL10RB_M | 0.104 | 30.64 | 31.59 | 31.79 | 32.53 | 31.48 | 33.71 | 33.83 | 32.22 | 1.174 |
| IL10RB_R | 0.096 | 29.92 | 30.49 | 31.91 | 32.15 | 30.13 | 33.59 | 34.03 | 31.75 | 1.599 |
| ITGB2_L | 0.125 | 27.48 | 27.81 | 28.64 | 28.77 | 28.7 | 29.82 | 32.1 | 29.04 | 1.469 |
| ITGB2_M | 0.078 | 27.59 | 28.43 | 28.56 | 27.71 | 28.26 | 29.09 | 28.03 | 28.22 | 0.563 |
| ITGB2_R | 0.035 | 28.92 | 29.34 | 30.7 | 30.23 | 30.15 | 29.84 | 31.24 | 30.06 | 0.999 |
| IVNS1ABP_L | 0.112 | 27.48 | 28.81 | 28.86 | 29.41 | 28.62 | 31.63 | 26.31 | 28.73 | 1.573 |
| IVNS1ABP_M | 0.035 | 27.82 | 28.31 | 29.57 | 28.87 | 29.95 | 30.35 | 31.73 | 29.51 | 1.309 |
| IVNS1ABP_R | 0.075 | 27.07 | 28.55 | 28.03 | 29.25 | 28.21 | 30.69 | 32.27 | 29.15 | 1.699 |
| KLRF1_L | 0.04 | 31.48 | 32.5 | 32.36 | 34.74 | 31.53 | 35.81 | 37.69 | 33.53 | 2.165 |
| KLRF1_M | 0.026 | 32.6 | 33.81 | 34.61 | 34.95 | 33.91 | 36.54 | 38.48 | 34.59 | 1.596 |
| KLRF1_R | 0.099 | 33.5 | 34.89 | 35.17 | 33.94 | 33.18 | 35.68 | 33.05 | 34.2 | 1.004 |
| NCF1_L | 0.119 | 25.11 | 25.59 | 25.67 | 26.11 | 26.21 | 27.22 | 26.84 | 26.11 | 0.709 |
| NCF1_M | 0.116 | 26.02 | 26.4 | 26.55 | 27.24 | 27.1 | 27.7 | 27.63 | 26.95 | 0.65 |
| NCF1_R | 0.115 | 24.8 | 24.64 | 25.17 | 24.32 | 24.3 | 23.99 | 24.67 | 24.56 | 0.385 |
| NCF2_L | 0.09 | 24.81 | 25.16 | 25.35 | 25.57 | 25.37 | 25.43 | 25.47 | 25.31 | 0.264 |
| NCF2_M | 0.193 | 23.97 | 24.4 | 24.82 | 25.17 | 24.72 | 24.9 | 26.01 | 24.85 | 0.623 |
| NCF2_R | 0.086 | 24.75 | 25.88 | 25.99 | 26.49 | 26.36 | 26.7 | 29.11 | 26.47 | 1.262 |
| NLRP1_L | 0.091 | 27.99 | 28.42 | 29.56 | 30.71 | 27.9 | 28.71 | 29.79 | 29.01 | 1.002 |
| NLRP1_M | 0.183 | 27.91 | 29.23 | 28.84 | 30.04 | 27.77 | 31.47 | 31.26 | 29.5 | 1.416 |
| NLRP1_R | 0.061 | 29.77 | 30.46 | 29.47 | 33.78 | 32.27 | 32.45 | 33.47 | 31.67 | 1.689 |
| TRPM2_L | 0.067 | 34.34 | 35.72 | 37.76 | 37.72 | 34.73 | Undet. | 37.07 | 35.96 | 1.528 |
| TRPM2_M | 0.102 | 34.86 | 34.59 | 37.49 | Undet. | 35.29 | 33.08 | Undet. | 34.58 | 1.292 |
| TRPM2_R | 0.071 | 36.99 | 35.44 | Undet. | Undet. | Undet. | Undet. | Undet. | 35.83 | 1.228 |
| ZAP70_L | 0.097 | 37.45 | Undet. | 32.5 | 38.27 | Undet. | Undet. | Undet. | 35.11 | 2.927 |
| ZAP70_M | 0.13 | 31.34 | 32.36 | 31.76 | 33.25 | 32.34 | 34.57 | Undet. | 32.6 | 1.102 |
| ZAP70_R | 0.143 | 31.37 | 30.6 | 34.49 | 33.31 | 34.54 | 32.02 | 33.74 | 32.87 | 1.493 |

Discussion

Overview

The development of a functional quality control method assessing RNA extracted from human whole blood samples is described herein. Designed to work in concert, the custom gene expression assay panel and set of class distinction algorithms provide an overall RNA quality score capable of predicting future performance on gene expression platforms. Setting it apart from current analytical quality control methodologies, this method relies on dynamic gene expression data rather than static measurements of RNA size, providing a more appropriate assessment of anticipated performance quality.

In summary, a list of candidate genes of variable expressivity in human whole blood cells was compiled, placing emphasis on intransient function and limited variability between subjects. Ultimately 62 genes were selected for Roche Universal Probe Library assay design. For each gene, assays were designed for the 3', middle, and 5' regions of each transcript; assays consisted of forward and reverse primers paired with a specific UPL probe. An assay validation phase consisting of 184 assays was conducted to assess assay performance when reactions were run with high-quality, intact RNA samples. For the top 71 best-performing assays, as determined by validation phase data, qPCR reactions were run with RNA that had been incrementally degraded by RNase A. Data generated by the experimentally degraded RNA reactions will be used to establish an expected baseline $C_T$ value (non-degraded RNA, $T_0$) for algorithm development. Additionally, $C_T$ values for incrementally degraded RNA ($T_{0.5}$, $T_1$, $T_2$, $T_4$, $T_8$, and $T_{16}$ minutes) will serve to extrapolate the relationship between extent of sample degradation and increase in $C_T$ value.

Assay Development

Assays were designed using Roche ProbeFinder software, which provided forward and reverse primer sequences and a corresponding Universal Probe Library (UPL) probe per gene queried. All efforts were made to choose designs located precisely at the 3', middle, and 5' regions of a transcript; however, designs were limited to the regions of the transcript with sequences compatible with one of the 165 possible UPL probes. Additionally, all efforts were made to choose the highest quality assay as determined by the software's in silico PCR rating. As was the case with a number of genes, for instance, the 5'-most assay design may be located closer to the middle of the transcript than the 5' end; in these cases, the most optimal assay design available was chosen. While UPL assays were cost-efficient and easy to design for the considerable number of validation reactions that were run, when finalizing the assay panel Taqman® assays might provide better results. Though more costly, these probe sequences can be custom designed, allowing for the design of assays in more optimal positions along the transcript unlike the pre-fabricated UPL probes.

Assay Validation

During assay validation analysis, assay performance was based on three criteria: (1) consistency across all regional assays of a gene, (2) amplification plot homogeneity, also reflected in standard deviations, and (3) conformity to expected gene expressivity, as established by GeneNote values. For regional assay consistency, a score of 0, 2, or 3 was given to assays designed for the same gene, reflecting the number of assays that expressed at approximately the same level. As the UPL assays were as optimally designed as possible, ideally all regions should express at the same level in intact RNA. However, variations in assay performance are possible and might account for why two assays out of three were consistent, yet the third may have simply been a poorly designed assay.

Amplification plots for individual assays were assessed subjectively, emphasis being placed on tight plots with little variation between samples from different subjects. To be used as a universal quality control method, it was important to limit expression variability between samples taken from different subjects. Assays were scored individually, either presenting tight or dispersed plots. FIG. 6 shows the difference between an ideal plot versus a plot that showed great variability between samples from different subjects.

The last criterion used to score assay performance was correspondence with the expression values provided by GeneNote microarray data. GeneNote data was presented as normalized intensity ranging from 0-10,000 and the data from the validation phase was presented as $C_T$ values, so direct correlation between expected and actual data was not possible. Approximated low, middle, and high expressivity ranges were assigned to the expected GeneNote expression score for each gene as well as the $C_T$ values generated by the qPCR reactions. Assays were assigned scores of matching expectations, borderline, or not matching expectations.

Once assays were scored by these performance features, they were sorted in two ways. The first list weighted amplification plot scores more heavily while the second list weighted regional assay consistency more heavily. As stated previously, both performance features were rightly influential but due to the possibility of poorly designed assays underperforming, it was unclear which feature should weight most heavily in determining assay performance. Once both lists were generated, many of the same assays appeared at the tops of both lists so choosing what assays moved on to the experimental RNA degradation phase became less of a challenge.

Experimental RNA Degradation and Assay Performance

Once all assays were assessed using intact, high-quality input RNA, data from reactions using degraded RNA needed to be generated for algorithm development. Based on a literature search, three methods were chosen for testing: (1) freeze/thaw cycles, (2) heating, and (3) RNase treatments. Methods were chosen to mimic conditions that extracted RNA would likely be exposed to following blood samples collection. Small scale experimental conditions were run for each method followed by assessment on a Bioanalyzer. Based on the degradation banding patterns produced by each, RNase A was chosen as the method to move forward with. RNase A was also chosen because it is an extracellular, distributive enzyme produced in abundance on human skin and in blood [4, 50]. RNase A present on gloves, benchtops, and instrument surfaces would be a likely source of degradation in a laboratory setting. As established protocols for purposefully degrading RNA were limited, trial and error testing was run for a number of RNaseA and SUPERase-In dilutions until a final protocol was adopted, as described previously.

Class Prediction Algorithm Development:

We are using a supervised, machine learning approach to discriminate between classes of degradation and ultimately provide a quality grade for each assay in the panel. Data generated by the experimentally degraded RNA reactions can be used to establish an expected baseline $C_T$ value (non-degraded RNA, $T_0$) for algorithm development. Additionally, $C_T$ values for incrementally degraded RNA ($T_{0.5}$, $T_1$, $T_2$, $T_4$, $T_8$, and $T_{16}$ minutes) will serve to extrapolate the relationship between extent of sample degradation and increase in $C_T$ value. Based on deviation from the expected $C_T$ value for a given assay, the sample will be classified as good, moderate, or poor quality. By exploiting the regional degradation patterns of RNA, algorithms have been developed to compare gene expression measurements, $C_T$ values, of a test sample to those of an intact RNA control sample and synthetic/empirically degraded RNA samples. Based on the differentially weighted $C_T$ profiles for all assays in the panel, an overall quality constant is assigned to a given RNA sample, allowing researchers to properly normalize or exclude any given sample during gene expression data analysis and interpretation. A supervised learning approach is used to create a class assignment for degraded RNA samples as a function of cDNA transcripts. Assays carry specific weights according to their expression levels (low, medium, high) and their relative position on the transcript (5', middle, 3') with the lowest weighted assay being on the 3' end of the highest expressing genes and the highest weighted assay being on the 5' end of the lowest expressing genes. Weights are assigned to $C_T$ values using a principal designed after the following formula:

$$W_2(g) = \frac{\frac{1}{n}\sum_{j=1,n} |g_{1j} - \mu_{2,m}(g)|}{\sigma_{2,m}(g)}$$

$$W_2(g) = \frac{\frac{1}{n}\sum_{j=1,n} |g_{1j} - \mu_{2,m}(g)|}{\sigma_{2,m}(g)}$$

All values are subject to voting once weighted and prior to creation of the class prediction values using the principals in the following formula:

$$V_1(g) = W_2(g) \cdot |g_x - \mu_{2TR,m}(g)|$$

$$V_2(g) = W_1(g) \cdot |g_x - \mu_{1TR,n}(g)|$$

Once weighting and vote assignments are completed votes are counted to create a class prediction set that will be used to measure the continuum of unknown samples on the quality spectrum using an approach related to the following formula:

$$P(x) = \frac{q \cdot \sum_{i=1,p} V_1(g_i) - p \cdot \sum_{i=1,q} V_2(g_i)}{q \cdot \sum_{i=1,p} V_1(g_i) + p \cdot \sum_{i=1,q} V_2(g_i)}$$

The resultant of class prediction analysis is a static quantitative class prediction matrix that is biologically specific for whole blood RNA samples yielding a value that can be used in conjunction with normalization approaches to directly improve the functional analysis of gene expression measurements as a direct correlative to transcript structure and representation.

The algorithms may be further refined as desired, for example, to reduce bias and decreases sampling variability. For example, in some embodiments, one can count the number of dropouts (defined as either no expression value or a value exceeding a specific selected threshold (e.g., a threshold empirically determined to provide desired results)) overall and/or by region. For example, one can create a 3-level categorized version of the number of dropouts, using categories of zero, one to three, and more than three dropouts. From this, one can estimate standard deviation across replicates, across regions, and across genes and estimate as well standard deviations for replicates, regions, and genes when restricted to high, medium, and low expressing genes. In some embodiments, standard deviations are estimated under a linear model with the Buckley-James estimator. This estimator allows for censored data (e.g., dropouts). Including dropouts in the estimates of standard deviations reduces bias and decreases sampling variability by including the partial information contained in dropouts.

Model fitting may also be used. In some embodiments, on can fit separate logistic/multinomial regressions to the RNA, cDNA, and microarray quality scores. In some embodiments, to reduce overfitting, one can use the lasso or elastic net methods (or other approaches), which enforce sparse regression models by shrinking all regression coefficients towards zero with a penalty that discourages non-zero coefficients. The result is a small set of predictive variables in a model that is not over-fit. Any desirable variables can be mandated into the models, if desired.

An example of a classification scheme is provided below.

| Sample Quality | Gene Panel | | |
|---|---|---|---|
| | High 3' M 5' | Moderate 3' M 5' | Low 3' M 5' |
| Very Good | No assay dropouts Tight Ct range across regions (5) Tight technical replicates | No assay dropouts Tight Ct range across regions (5) Tight technical replicates | No assay dropouts Tight Ct range across regions (4) Tight technical replicates |
| Good | No assay dropouts Tight Ct range across regions (5) Tight technical replicates | No assay dropouts Tight Ct range across regions (4) Tight technical replicate | No assay dropouts Tight Ct range across regions (4) Tight technical replicates |
| Moderate | No assay dropouts Tight Ct range across regions (4) Tight technical replicates | No assay dropouts Tight Ct range across regions (3) Moderate technical replicates | Few assay dropouts Moderate Ct range across regions (3) Moderate technical replicates |
| Poor | Few assay dropouts Moderate Ct range across regions (3) Moderate technical replicates | Few assay dropouts Moderate Ct range across regions (3) Inconsistent technical replicates | Many assay dropouts, especially in 5' region Wide Ct range across regions (2) Very inconsistent technical replicates |
| Very Poor | Few assay dropouts Wide Ct range across regions (2) Inconsistent technical replicates | Many assay dropouts, especially in 5' region Very wide Ct range across regions (2) Very inconsistent technical replicates | Many assay dropouts, especially in 5' region Very wide Ct range across regions (1) Very inconsistent technical replicates |

One approach that will utilize this methodology is in the development of clinical diagnostics using gene expression from whole blood for biomarker analysis. The use of gene expression biomarkers for measuring disease progression and treatment efficacy will be the staple of the molecular medical management of large patient populations for a variety of diseases. Given the precision needed in making clinical assessments the ability to measure the sample quality in a functional manner is of paramount importance. The class prediction algorithm will be used in this instance to qualify a sample for diagnostic analysis. If a sample does not meet the established criteria for reproducible and sensitive analysis it will not be used for making a diagnostic measurement. This application is fundamentally different from a research application where samples with varying quality can be used for discovery and normalized to meet performance expectations. In a clinical setting every sample must be qualified at a high level of performance in order to ensure that the conclusions made on gene expression levels are reproducible and accurate.

APPENDIX I

Genes for Validation Phase: Expression Scores

| Gene | Accession # | Expression Score | GenBank Definition |
|---|---|---|---|
| ACTB | NM_001101.3 | Control | *Homo sapiens* actin, beta (ACTB), mRNA |
| ACTR2 | NM_001005386.2 | 2000 | *Homo sapiens* ARP2 actin-related protein 2 homolog (yeast) (ACTR2), transcript variant 1, mRNA |
| ADAR | NM_001111.3 | 4500 | *Homo sapiens* adenosine deaminase, RNA-specific (ADAR), transcript variant 1, mRNA |
| ADD1 | NM_001119.3 | 750 | *Homo sapiens* adducin 1 (alpha) (ADD1), transcript variant 1, mRNA |
| ADD3 | NM_016824.3 | 1500 | *Homo sapiens* adducin 3 (gamma) (ADD3), transcript variant 1, mRNA |
| AIM1 | NM_001624.2 | 1000 | *Homo sapiens* absent in melanoma 1 (AIM1), mRNA |
| ARPC5 | NM_005717.2 | 5500 | *Homo sapiens* actin related protein 2/3 complex, subunit 5, 16 kDa (ARPC5), mRNA |
| BACH2 | NM_021813.2 | 150 | *Homo sapiens* BTB and CNC homology 1, basic leucine zipper transcription factor 2 (BACH2), mRNA |
| C1orf38 | NM_004848.2 | 3000 | *Homo sapiens* chromosome 1 open reading frame 38 (C1orf38), transcript variant 1, mRNA |
| CAPN2 | NM_001146068.1 | 750 | *Homo sapiens* calpain 2, (m/II) large subunit (CAPN2), transcript variant 2, mRNA |
| CD163 | NM_004244.4 | 200 | *Homo sapiens* CD163 molecule (CD163), transcript variant 1, mRNA |
| CD27 | NM_001242.4 | 650 | *Homo sapiens* CD27 molecule (CD27), mRNA |
| CD300C | NM_006678.3 | 500 | *Homo sapiens* CD300c molecule (CD300C), mRNA |
| CD53 | NM_001040033.1 | 8000 | *Homo sapiens* CD53 molecule (CD53), transcript variant 1, mRNA |
| CD68 | NM_001251.2 | 250 | *Homo sapiens* CD68 molecule (CD68), transcript variant 1, mRNA |
| CD83 | NM_004233.3 | 150 | *Homo sapiens* CD83 molecule (CD83), transcript variant 1, mRNA |
| CDC42SE1 | NM_001038707.1 | 5000 | *Homo sapiens* CDC42 small effector 1 (CDC42SE1), transcript variant 1, mRNA |
| CSF3R | NM_000760.2 | 6500 | *Homo sapiens* colony stimulating factor 3 receptor (granulocyte) (CSF3R), transcript variant 1, mRNA |
| DDX58 | NM_014314.3 | 350 | *Homo sapiens* DEAD (Asp-Glu-Ala-Asp) box polypeptide 58 (DDX58), mRNA |
| EEF2 | NM_001961.3 | 7000 | *Homo sapiens* eukaryotic translation elongation factor 2 (EEF2), mRNA |
| F13A1 | NM_000129.3 | 2300 | *Homo sapiens* coagulation factor XIII, A1 polypeptide (F13A1), mRNA |
| FCN1 | NM_002003.2 | 9000 | *Homo sapiens* ficolin (collagen/fibrinogen domain containing) 1 (FCN1), mRNA |
| GAPDH | NM_002046.3 | Control | *Homo sapiens* glyceraldehyde-3-phosphate dehydrogenase (GAPDH), mRNA |
| GZMB | NM_004131.4 | 1500 | *Homo sapiens* granzyme B (granzyme 2, cytotoxic T-lymphocyte-associated serine esterase 1) (GZMB), mRNA |
| IL10RB | NM_000628.3 | 850 | *Homo sapiens* interleukin 10 receptor, beta (IL10RB), mRNA |
| IL15RA | NM_172200.1 | 300 | *Homo sapiens* interleukin 15 receptor, alpha (IL15RA), transcript variant 2, mRNA |
| IL6R | NM_181359.1 | 500 | *Homo sapiens* interleukin 6 receptor (IL6R), transcript variant 2, mRNA |
| IL7R | NM_002185.2 | 3500 | *Homo sapiens* interleukin 7 receptor (IL7R), mRNA |
| ITGB2 | NM_001127491.1 | 10000 | *Homo sapiens* integrin, beta 2 (complement component 3 receptor 3 and 4 subunit) (ITGB2), transcript variant 2, mRNA |
| IVNS1ABP | NM_006469.4 | 750 | *Homo sapiens* influenza virus NS1A binding protein (IVNS1ABP), mRNA |
| KLRF1 | NM_016523.1 | 650 | *Homo sapiens* killer cell lectin-like receptor subfamily F, member 1 (KLRF1), mRNA |
| LASP1 | NM_006148.2 | 4500 | *Homo sapiens* LIM and SH3 protein 1 (LASP1), mRNA |
| LCP1 | NM_002298.4 | 6500 | *Homo sapiens* lymphocyte cytosolic protein 1 (L-plastin) (LCP1), mRNA |
| LILRA5 | NM_021250.2 | 900 | *Homo sapiens* leukocyte immunoglobulin-like receptor, subfamily A (with TM domain), member 5 (LILRA5), transcript variant 1, mRNA |
| LPXN | NM_004811.2 | 1100 | *Homo sapiens* leupaxin (LPXN), transcript variant 2, mRNA |
| LTF | NM_002343.2 | 200 | *Homo sapiens* lactotransferrin (LTF), mRNA |
| LY75 | NM_002349.2 | 800 | *Homo sapiens* lymphocyte antigen 75 (LY75), mRNA |
| NCF1 | NM_000265.4 | 5500 | *Homo sapiens* neutrophil cytosolic factor 1 (NCF1), mRNA |

APPENDIX I-continued

Genes for Validation Phase: Expression Scores

| Gene | Accession # | Expression Score | GenBank Definition |
|---|---|---|---|
| NCF2 | NM_000433.3 | 8500 | *Homo sapiens* neutrophil cytosolic factor 2 (NCF2), transcript variant 1, mRNA |
| NCF4 | NM_013416.3 | 4500 | *Homo sapiens* neutrophil cytosolic factor 4, 40 kDa (NCF4), transcript variant 2, mRNA |
| NCL | NM_005381.2 | 2000 | *Homo sapiens* nucleolin (NCL), mRNA |
| NCOA1 | NM_003743.4 | 850 | *Homo sapiens* nuclear receptor coactivator 1 (NCOA1), transcript variant 1, mRNA |
| NLRP1 | NM_033004.3 | 600 | *Homo sapiens* NLR family, pyrin domain containing 1 (NLRP1), transcript variant 1, mRNA |
| OAS2 | NM_002535.2 | 500 | *Homo sapiens* 2'-5'-oligoadenylate synthetase 2, 69/71 kDa (OAS2), transcript variant 2, mRNA |
| OAS3 | NM_006187.2 | 650 | *Homo sapiens* 2'-5'-oligoadenylate synthetase 3, 100 kDa (OAS3), mRNA |
| PDLIM1 | NM_020992.2 | 900 | *Homo sapiens* PDZ and LIM domain 1 (PDLIM1), mRNA |
| PDLIM2 | NM_176871.2 | 950 | *Homo sapiens* PDZ and LIM domain 2 (mystique) (PDLIM2), transcript variant 1, mRNA |
| RAF1 | NM_002880.3 | 3000 | *Homo sapiens* v-raf-1 murine leukemia viral oncogene homolog 1 (RAF1), mRNA |
| ROCK2 | NM_004850.3 | 200 | *Homo sapiens* Rho-associated, coiled-coil containing protein kinase 2 (ROCK2), mRNA |
| SELL | NM_000655.3 | 8500 | *Homo sapiens* selectin L (SELL), mRNA |
| SELP | NM_003005.3 | 700 | *Homo sapiens* selectin P (granule membrane protein 140 kDa, antigen CD62) (SELP), mRNA |
| SERPINA1 | NM_000295.4 | 7500 | *Homo sapiens* serpin peptidase inhibitor, clade A (alpha-1 antiproteinase, antitrypsin), member 1 (SERPINA1), transcript variant 1, mRNA |
| SORL1 | NM_003105.4 | 7500 | *Homo sapiens* sortilin-related receptor, L(DLR class) A repeats-containing (SORL1), mRNA |
| STAT6 | NM_003153.3 | 1000 | *Homo sapiens* signal transducer and activator of transcription 6, interleukin-4 induced (STAT6), mRNA |
| STX4 | NM_004604.3 | 600 | *Homo sapiens* syntaxin 4 (STX4), mRNA |
| SYNE2 | NM_182910.2 | 400 | *Homo sapiens* spectrin repeat containing, nuclear envelope 2 (SYNE2), transcript variant 2, mRNA |
| TES | NM_015641.2 | 750 | *Homo sapiens* testis derived transcript (3 LIM domains) (TES), transcript variant 1, mRNA |
| TREM1 | NM_018643.2 | 4500 | *Homo sapiens* triggering receptor expressed on myeloid cells 1 (TREM1), mRNA |
| TRPM2 | NM_003307.3 | 400 | *Homo sapiens* transient receptor potential cation channel, subfamily M, member 2 (TRPM2), mRNA |
| TXNIP | NM_006472.3 | 8000 | *Homo sapiens* thioredoxin interacting protein (TXNIP), mRNA |
| VIM | NM_003380.3 | 9500 | *Homo sapiens* vimentin (VIM), mRNA |
| ZAP70 | NM_001079.3 | 650 | *Homo sapiens* zeta-chain (TCR) associated protein kinase 70 kDa (ZAP70), transcript variant 1, mRNA |

APPENDIX II

Assay Designs for Validation Phase

| | | | | | 5' Design | | | | | |
|---|---|---|---|---|---|---|---|---|---|---|
| Gene | Accession # | Length | Probe ProbeSequence* | Position | Primer | Primer Sequence (SEQ ID NO:) | Start | End | Tm | GC |
| ACTB | NM_001101.3 | 1852 | 64 Cagcctgg (1) | 492 | Fwd | Ccaaccgcgagaagatga (2) | 425 | 442 | 60 | 56 |
| | | | | | Rvs | ccagaggcgtacagggat ag (3) | 502 | 521 | 59 | 60 |
| ACTR 2 | NM_001005386.2 | 3944 | 37 Ccagggca (4) | 224 | Fwd | Gcggtggctgtaggttgt (5) | 167 | 184 | 59 | 61 |
| | | | | | Rvs | Gcctgcatatccacacttc ac (6) | 267 | 287 | 60 | 52 |
| ADAR | NM_001111.3 | 6640 | 41 Cttcagcc (7) | 2011 | Fwd | Tcatcccactattccacag aga (8) | 1950 | 1971 | 59 | 45 |
| | | | | | Rvs | Gctcttcccagaaaagaa gga (9) | 2022 | 2042 | 59 | 48 |

APPENDIX II-continued

Assay Designs for Validation Phase

| ADD1 | NM_001119.3 | 3970 | 15 | Tcctgctc (10) | 714 | Fwd | Tggtctcagcttatctaca atcatatc (11) | 669 | 695 | 59 | 37 |
|---|---|---|---|---|---|---|---|---|---|---|---|
| | | | | | | Rvs | Ccaaaagggacaatgag gaa (12) | 726 | 745 | 59 | 45 |
| ADD3 | NM_016824.3 | 4454 | 75 | Cagcctcc (13) | 930 | Fwd | Tcccagaggcctatctttt c (14) | 901 | 921 | 59 | 48 |
| | | | | | | Rvs | Ttcaaattggtacttccct ggt (15) | 975 | 996 | 59 | 41 |
| AIM1 | NM_001624.2 | 7553 | 85 | Tccaggtc (16) | 3546 | Fwd | Ctggaatgtcattatcaga cacaa (17) | 3483 | 3506 | 59 | 38 |
| | | | | | | Rvs | Tcagagacgtcgggttca ct (18) | 3569 | 3588 | 60 | 55 |
| ARPC5 | NM_005717.2 | 2000 | 51 | Ctcctgcc (19) | 320 | Fwd | Caagttcgtggacgaaga aga (20) | 257 | 277 | 60 | 48 |
| | | | | | | Rvs | Gcagctgtcatgtttccttg (21) | 333 | 352 | 59 | 50 |
| BACH2 | NM_021813.2 | 9215 | 1 | Cctggagc (22) | 563 | Fwd | Aatgataaagccagaag aaagca (23) | 498 | 520 | 59 | 35 |
| | | | | | | Rvs | Cagtgcgaggaagttcttg a (24) | 585 | 604 | 59 | 50 |
| C1orf38 | NM_004848.2 | 1650 | 34 | Ctgcctct (25) | 154 | Fwd | Ctcggggtctacttcgag (26) | 103 | 121 | 59 | 63 |
| | | | | | | Rvs | Ggacctgggtgaccttgat (27) | 176 | 194 | 59 | 58 |
| CAPN2 | NM_001146068.1 | 3270 | 50 | Tctggagc (28) | 529 | Fwd | Ctgctctttgtgcattcagc (29) | 495 | 514 | 59 | 50 |
| | | | | | | Rvs | Gcttcatagcatccgttga tct (30) | 562 | 583 | 60 | 45 |
| CD163 | NM_004244.4 | 4231 | 17 | Aggagctg (31) | 274 | Fwd | Tcagtgcctgttttgtcacc (32) | 232 | 251 | 59 | 50 |
| | | | | | | Rvs | Tccactctcccgctacact t (33) | 303 | 322 | 59 | 55 |
| CD27 | NM_001242.4 | 1320 | 72 | ttcctggc (34) | 343 | Fwd | cactactgggctcaggga aa (35) | 302 | 321 | 60 | 55 |
| | | | | | | Rvs | tcacagtccttcacgagga a (36) | 353 | 372 | 59 | 50 |
| CD300C | NM_006678.3 | 1548 | 6 | ttcctctg (37) | 429 | Fwd | ctctgctcctcctgcttgtc (38) | 399 | 418 | 60 | 60 |
| | | | | | | Rvs | tcatagcgacactgcacac tc (39) | 478 | 498 | 60 | 52 |
| CD53 | NM_001040033.1 | 1572 | 5 | tgtggctg (40) | 238 | Fwd | tcctgttttcttcaacttgc tc (41) | 206 | 228 | 59 | 39 |
| | | | | | | Rvs | gtagatcccaaagcccaa aa (42) | 251 | 270 | 59 | 45 |
| CD68 | NM_001251.2 | 1872 | 3 | cccagcag (43) | 222 | Fwd | ggctggctgtgcttttct (44) | 196 | 213 | 59 | 56 |
| | | | | | | Rvs | ttttgtgaggacagtcatt cc (45) | 253 | 274 | 59 | 41 |
| CD83 | NM_004233.3 | 2478 | 36 | ctggctcc (46) | 224 | Fwd | ctccagcttctgctcctga (47) | 191 | 209 | 59 | 58 |
| | | | | | | Rvs | ggagcaagccaccttcac (48) | 245 | 262 | 59 | 61 |
| CDC42SE1 | NM_001038707.1 | 3193 | 22 | ctccacca (49) | 156 | Fwd | accagctgtagctgaacgt ct (50) | 132 | 152 | 59 | 52 |
| | | | | | | Rvs | catatctccacgtgtgtcc ag (51) | 182 | 202 | 59 | 52 |
| CSF3R | NM_000760.2 | 3003 | 18 | tcctgctg (52) | 225 | Fwd | gtccaagatcacaaagct ggt (53) | 140 | 160 | 59 | 48 |
| | | | | | | Rvs | ccgcactcctccagactc (54) | 240 | 258 | 60 | 63 |
| DDX58 | NM_014314.3 | 4759 | 69 | cttcctcc (55) | 260 | Fwd | tggaccctacctacatcct ga (56) | 217 | 237 | 59 | 52 |
| | | | | | | Rvs | ggcccttgttgttttctca (57) | 287 | 306 | 60 | 45 |

APPENDIX II-continued

Assay Designs for Validation Phase

| Gene | Accession | Len | Pos | Probe | Amp | Dir | Primer | Start | End | Tm | GC |
|---|---|---|---|---|---|---|---|---|---|---|---|
| EEF2 | NM_001961.3 | 3163 | 9 | tggtgatg (58) | 284 | Fwd | tcactgatacccggaagg ac (59) | 250 | 269 | 59 | 55 |
| | | | | | | Rvs | ttcaagtcattctccgaga gc (60) | 323 | 343 | 59 | 48 |
| F13A1 | NM_000129.3 | 3863 | 78 | agctggag (61) | 796 | Fwd | cctgaatgacatcggggta a (62) | 741 | 760 | 60 | 50 |
| | | | | | | Rvs | gtccaggatgccatcttca (63) | 816 | 834 | 59 | 53 |
| FCN1 | NM_002003.2 | 1292 | 1 | cctggagc (64) | 324 | Fwd | agaggcaggtgtcattgg ag (65) | 284 | 303 | 60 | 55 |
| | | | | | | Rvs | ctggtcctgccttttccag (66) | 334 | 351 | 59 | 61 |
| GAPDH | NM_002046.3 | 1310 | 60 | cttcccca (67) | 104 | Fwd | agccacatcgctcagaca c (68) | 83 | 101 | 60 | 58 |
| | | | | | | Rvs | gcccaatacgaccaaatc c (69) | 130 | 148 | 60 | 53 |
| GZMB | NM_004131.4 | 941 | 18 | tcctgctg (70) | 98 | Fwd | agatgcaaccaatcctgct t (71) | 65 | 84 | 59 | 45 |
| | | | | | | Rvs | catgtccccgatgatct (72) | 125 | 142 | 59 | 56 |
| IL10RB | NM_000628.3 | 1935 | 20 | ccagccag (73) | 120 | Fwd | ggtcgtgtgcttggagga (74) | 56 | 73 | 60 | 61 |
| | | | | | | Rvs | ggtaccattcccaatgctg a (75) | 145 | 164 | 60 | 50 |
| IL15RA | NM_172200.1 | 1843 | 47 | tccagtgt (76) | 343 | Fwd | ctcttcgcagtggggaca (77) | 312 | 329 | 60 | 61 |
| | | | | | | Rvs | cccagatgtctgcgtgttc (78) | 433 | 451 | 60 | 58 |
| IL6R | NM_181359.1 | 4082 | 10 | ccacctcc (79) | 521 | Fwd | gtagccgaggaggaagca t(80) | 421 | 439 | 59 | 58 |
| | | | | | | Rvs | actggtcagcacgcctct (81) | 531 | 548 | 59 | 61 |
| IL7R | NM_002185.2 | 1809 | 9 | tggtgatg (82) | 284 | Fwd | gcttttgaggacccagatg t(83) | 261 | 280 | 59 | 50 |
| | | | | | | Rvs | aggcactttacctccacga g(84) | 318 | 337 | 59 | 55 |
| ITGB2 | NM_001127491.1 | 2932 | 27 | caggcagc (85) | 519 | Fwd | gctgtccccacaaaaagt g(86) | 479 | 497 | 59 | 53 |
| | | | | | | Rvs | ccggaaggtcacgttgaa (87) | 531 | 548 | 60 | 56 |
| IVNS1ABP | NM_006469.4 | 4205 | 14 | ctgggaga (88) | 1241 | Fwd | atcaactgggtgcagcgta (89) | 1218 | 1236 | 60 | 53 |
| | | | | | | Rvs | tcagctgagtagtacaag gtttgaa (90) | 1282 | 1306 | 59 | 40 |
| KLRF1 | NM_016523.1 | 1242 | 48 | ttcccagt (91) | 184 | Fwd | tgcccaaacatctcaactt aca (92) | 121 | 142 | 60 | 41 |
| | | | | | | Rvs | aataccattcacggttcca ga (93) | 194 | 214 | 59 | 43 |
| LASP1 | NM_006148.2 | 4109 | 50 | tctggagc (94) | 568 | Fwd | gaaaaccttcgcctcaagc (95) | 539 | 557 | 59 | 53 |
| | | | | | | Rvs | tgaaacctttgcccttgttc (96) | 607 | 626 | 60 | 45 |
| LCP1 | NM_002298.4 | 3808 | 6 | ttcctctg (97) | 594 | Fwd | ttggcacccaacactccta (98) | 573 | 591 | 60 | 53 |
| | | | | | | Rvs | ccagggctttgtttatccag (99) | 622 | 641 | 59 | 50 |
| LILRA5 | NM_021250.2 | 1365 | 80 | cctggaga (100) | 813 | Fwd | agtctgcctgtggcatgg (101) | 56 | 73 | 60 | 61 |
| | | | | | | Rvs | gctgtgcagatggatgag ac (102) | 132 | 151 | 59 | 55 |

APPENDIX II-continued

Assay Designs for Validation Phase

| Gene | Accession | Length | Exon | Probe | Pos | Dir | Primer | Start | End | Tm | GC |
|------|-----------|--------|------|-------|-----|-----|--------|-------|-----|----|----|
| LPXN | NM_004811.2 | 1926 | 17 | aggagctg (103) | 219 | Fwd | ttggatgtaggacaatgga aga (104) | 132 | 153 | 59 | 41 |
| | | | | | | Rvs | cctttctggaatgctgatcc (105) | 235 | 254 | 59 | 50 |
| LTF | NM_002343.2 | 2390 | 18 | tcctgctg (106) | 58 | Fwd | gaccgcagacatgaaact tg (107) | 29 | 48 | 59 | 50 |
| | | | | | | Rvs | gccagccagacacagtcc (108) | 81 | 98 | 60 | 67 |
| LY75 | NM_002349.2 | 6927 | 6 | ttcctctg (109) | 503 | Fwd | aatgcatctgatgtctgga aga (110) | 545 | 566 | 59 | 50 |
| | | | | | | Rvs | ccataagagttcccatctc tgg (111) | 545 | 566 | 59 | 50 |
| NCF1 | NM_000265.4 | 1409 | 20 | ccagccag (112) | 129 | Fwd | cctgctgggctttgagaa (113) | 100 | 117 | 60 | 56 |
| | | | | | | Rvs | gacaggtcctgccatttca c (114) | 158 | 177 | 60 | 55 |
| NCF2 | NM_000433.3 | 2429 | 38 | ctgcttcc (115) | 775 | Fwd | aaaatcgacaaggcgatg g (116) | 747 | 765 | 60 | 47 |
| | | | | | | Rvs | gggatcaccactggctcat a (117) | 789 | 808 | 60 | 55 |
| NCF4 | NM_013416.3 | 1646 | 3 | cccagcag (118) | 195 | Fwd | gcgagactctccacctgct (119) | 146 | 164 | 60 | 63 |
| | | | | | | Rvs | catccggaagctgttcaaa g (120) | 220 | 239 | 60 | 50 |
| NCL | NM_005381.2 | 2732 | 70 | ccgccgcc (121) | 131 | Fwd | ccacttgtccgcttcaca (122) | 111 | 128 | 59 | 56 |
| | | | | | | Rvs | tcttggggtcaccttgattt (123) | 168 | 187 | 59 | 45 |
| NCOA1 | NM_003743.4 | 6895 | 58 | ctccatcc (124) | 960 | Fwd | tcacagccaaaatcaattc aa (125) | 937 | 957 | 59 | 33 |
| | | | | | | Rvs | gccgtgcaatacaaatca ga (126) | 984 | 1003 | 59 | 45 |
| NLRP1 | NM_033004.3 | 5623 | 13 | ctctgcct (127) | 1008 | Fwd | agctgcctgacacatctgg (128) | 971 | 989 | 59 | 58 |
| | | | | | | Rvs | ggagcttggaagagcttg gt (129) | 1025 | 1044 | 60 | 55 |
| OAS2 | NM_002535.2 | 3647 | 23 | cccagccc (130) | 603 | Fwd | gagaatctctttcgaggtg ctg (131) | 548 | 569 | 60 | 50 |
| | | | | | | Rvs | caaggatcttttgagctctc g (132) | 621 | 641 | 59 | 48 |
| OAS3 | NM_006187.2 | 6646 | 8 | ctgccttc (133) | 1727 | Fwd | tggatggatgttagcctgg t (134) | 508 | 527 | 60 | 50 |
| | | | | | | Rvs | cttgtggcttgggtttgac (135) | 565 | 583 | 59 | 53 |
| PDLIM1 | NM_020992.2 | 1462 | 81 | ccagggcc (136)) | 133 | Fwd | catgaccacccagcagat ag (137) | 109 | 128 | 59 | 55 |
| | | | | | | Rvs | gccttgcttccaggagtg (138) | 208 | 225 | 59 | 61 |
| PDLIM1 | NM_176871.2 | 4611 | 80 | cctggaga (139) | 267 | Fwd | gcccatcatggtgactaag g (140) | 209 | 228 | 60 | 55 |
| | | | | | | Rvs | cgttgatggccacgatta (141) | 277 | 294 | 59 | 50 |
| RAF1 | NM_002880.3 | 3291 | 13 | ctctgcct (142) | 1175 | Fwd | tgtttccaggatgcctgtt (143) | 1075 | 1093 | 59 | 47 |
| | | | | | | Rvs | ggacattaggtgtggatgt cg (144) | 1185 | 1205 | 60 | 52 |
| ROCK2 | NM_004850.3 | 6401 | 17 | aggagctg (145) | 1552 | Fwd | tcagtggcattgggataac at (146) | 1520 | 1540 | 60 | 43 |
| | | | | | | Rvs | tgctgtctatgtcactgctg ag (147) | 1572 | 1593 | 59 | 50 |

APPENDIX II-continued

Assay Designs for Validation Phase

| Gene | Accession # | Length | Probe | ProbeSequence* | Position | Primer | Primer Sequence | Start | End | Tm | GC |
|---|---|---|---|---|---|---|---|---|---|---|---|
| SELL | NM_000655.3 | 2448 | 72 | ttcctggc (148) | 286 | Fwd | ggggtggacaatgctctg (149) | 261 | 278 | 60 | 61 |
| | | | | | | Rvs | taagtccagcagtcggttc c (150) | 301 | 320 | 60 | 55 |
| SELP | NM_003005.3 | 3185 | 8 | ctgccttc (151) | 34 | Fwd | actgtaagcagtctgggtt gg (152) | 10 | 30 | 59 | 52 |
| | | | | | | Rvs | gatggctatttggcagttg g (153) | 70 | 89 | 60 | 50 |
| SERPINA1 | NM_000295.4 | 3220 | 73 | tcctcagc (154) | 216 | Fwd | gcttaaatacggacgagg aca (155) | 185 | 205 | 59 | 48 |
| | | | | | | Rvs | acgagacagaagacggc att (156) | 261 | 280 | 59 | 50 |
| SORL1 | NM_003105.4 | 10924 | 19 | ctccagcc (157) | 1444 | Fwd | gggaacctgggagtttctt c (158) | 1421 | 1440 | 59 | 55 |
| | | | | | | Rvs | acagccctgggaaagctc (159) | 1482 | 1499 | 60 | 61 |
| STAT6 | NM_003153.3 | 3993 | 54 | ctggtctc (160) | 287 | Fwd | agaagacagcagagggg ttg (161) | 226 | 245 | 59 | 55 |
| | | | | | | Rvs | cacttttctgggggcatc (162) | 298 | 316 | 60 | 53 |
| STX4 | NM_004604.3 | 1403 | 62 | cagcaggt (163) | 417 | Fwd | caaactggggaataaagt ccag (164) | 383 | 404 | 59 | 45 |
| | | | | | | Rvs | cagctcctgcttcatgctc (165) | 455 | 473 | 59 | 58 |
| SYNE2 | NM_182910.2 | 2586 | 4 | cttcctgc (166) | 506 | Fwd | ggatggtggcaaagaagg (167) | 461 | 478 | 59 | 56 |
| | | | | | | Rvs | catctcccatctgtcgaag g (168) | 553 | 572 | 60 | 55 |
| TES | NM_015641.2 | 2766 | 85 | tccaggtc (169) | 185 | Fwd | ggacccataggacgcgtt a (170) | 161 | 179 | 60 | 58 |
| | | | | | | Rvs | cgtgacctaagcccatctt c (171) | 205 | 224 | 59 | 55 |
| TREM1 | NM_018643.2 | 948 | 66 | cagcagcc (172) | 87 | Fwd | acaggaaggatgaggaa gacc (173) | 56 | 76 | 59 | 52 |
| | | | | | | Rvs | ctgcccctctttcagttcat a (174) | 149 | 169 | 59 | 48 |
| TRPM2 | NM_003307.3 | 5876 | 14 | ctgggaga (175) | 534 | Fwd | cctgagccagaaggtgaa aa (176) | 502 | 521 | 60 | 50 |
| | | | | | | Rvs | gggtcatgaggtggtagat ca (177) | 558 | 578 | 59 | 52 |
| TXNIP | NM_006472.3 | 2953 | 85 | tccaggtc (178) | 616 | Fwd | cttctggaagaccagcca ac (179) | 570 | 589 | 59 | 55 |
| | | | | | | Rvs | gaagctcaaagccgaact tg (180) | 638 | 657 | 60 | 50 |
| VIM | NM_003380.3 | 2151 | 56 | tgctgtcc (181) | 252 | Fwd | gtttcccctaaaccgctag g (182) | 217 | 236 | 59 | 55 |
| | | | | | | Rvs | agcgagagtggcagagg a (183) | 267 | 284 | 59 | 61 |
| ZAP70 | NM_001079.3 | 2450 | 3 | cccagcag (184) | 92 | Fwd | ggagctcagcagacacca g (185) | 32 | 50 | 59 | 63 |
| | | | | | | Rvs | ccaatgccaatggagagc (186) | 113 | 130 | 60 | 56 |

Middle Design

| Gene | Accession # | Length | Probe | ProbeSequence* | Position | Primer | Primer Sequence | Start | End | Tm | GC |
|---|---|---|---|---|---|---|---|---|---|---|---|
| ACTB | NM_001101.3 | 1852 | — | — | — | Fwd | — | — | — | — | — |
| | | | | | | Rvs | — | — | — | — | — |
| ACTR2 | NM_001005386.2 | 3944 | 61 | ctgggcaa (187) | 728 | Fwd | atgtagccatccaggcagt t (188) | 640 | 659 | 59 | 50 |
| | | | | | | Rvs | gatgagggagagaaaagc cttc (189) | 741 | 762 | 60 | 50 |

APPENDIX II-continued

Assay Designs for Validation Phase

| Gene | Accession | | | Probe | | | Primer | | | | |
|---|---|---|---|---|---|---|---|---|---|---|---|
| ADAR | NM_001111.3 | 6640 | 39 | ctccacct (190) | 3208 | Fwd | ttcgagaatcccaaacaag g (191) | 3174 | 3193 | 60 | 45 |
| | | | | | | Rvs | ctggattccacagggattg t (192) | 3228 | 3247 | 59 | 50 |
| ADD1 | NM_001119.3 | 3970 | 38 | ctgcttcc (193) | 1575 | Fwd | gacaagatggctgaactct gg (194) | 1520 | 1540 | 59 | 52 |
| | | | | | | Rvs | tgtccatcctctttagtcca ctt (195) | 1599 | 1621 | 59 | 43 |
| ADD3 | NM_016824.3 | 4454 | 39 | ctccacct (196) | 1357 | Fwd | gcaactagcctgtgagatt cag (197) | 1315 | 1336 | 59 | 50 |
| | | | | | | Rvs | cgctgctacagtgtaagtg aaag (198) | 1404 | 1426 | 59 | 48 |
| AIM1 | NM_001624.2 | 7553 | 1 | cctggagc (199) | 4940 | Fwd | tgtctgtctgcaatgggatg (200) | 4916 | 4935 | 60 | 50 |
| | | | | | | Rvs | gaataattgttggttcaga aaattca (201) | 4978 | 5003 | 59 | 27 |
| ARPC5 | NM_005717.2 | 2000 | 27 | caggcagc (202) | 415 | Fwd | caccaagagtcaggcagt ga (203) | 386 | 405 | 60 | 55 |
| | | | | | | Rvs | agagatgagcaccttcaag aca (204) | 425 | 446 | 59 | 45 |
| BACH2 | NM_021813.2 | 9215 | 76 | tggctgtg (205) | 1055 | Fwd | aatgatttggtggtcagctt g (206) | 1023 | 1043 | 59 | 43 |
| | | | | | | Rvs | gcttggcagtgtaggcaaa c (207) | 1085 | 1104 | 60 | 55 |
| C1orf3 | NM_004848.2 | 1650 | 20 | ccagccag (208) | 228 | Fwd | ccagaaggtggtctgtgag aa (209) | 199 | 219 | 60 | 52 |
| | | | | | | Rvs | catagctctgtggggtgttg (210) | 280 | 299 | 59 | 55 |
| CAPN2 | NM_001146.0681 | 3270 | 82 | cagagga g (211) | 1312 | Fwd | ggctttggcatctatgaggt (212) | 1290 | 1309 | 59 | 50 |
| | | | | | | Rvs | gctgaggtggatgttggtct (213) | 1330 | 1349 | 60 | 55 |
| CD163 | NM_004244.4 | 4231 | 50 | tctggagc (214) | 1238 | Fwd | gaagatgctggcgtga (215) | 1203 | 1221 | 59 | 53 |
| | | | | | | Rvs | gctgcctccacctctaagtc (216) | 1249 | 1268 | 59 | 60 |
| CD27 | NM_001242.4 | 1320 | 30 | cctcagcc (217) | 629 | Fwd | tccaaacccttcgctgac (218) | 580 | 597 | 59 | 56 |
| | | | | | | Rvs | tggcctccagcatctcac (219) | 657 | 674 | 60 | 61 |
| CD300C | NM_006678.3 | 1548 | 19 | ctccagcc (220) | 778 | Fwd | gaggttgaggtgtccgtgtt (221) | 737 | 756 | 60 | 55 |
| | | | | | | Rvs | cttcgtgggaggacctga (222) | 806 | 823 | 59 | 61 |
| CD53 | NM_001040033.1 | 1572 | 58 | ctccatcc (223) | 579 | Fwd | cactcagacaatagcacca agg (224) | 547 | 568 | 59 | 50 |
| | | | | | | Rvs | cgtgccatttataccacaa ca (225) | 601 | 621 | 59 | 43 |
| CD68 | NM_001251.2 | 1872 | 67 | tgctggag (226) | 882 | Fwd | tcagctttggattcatgcag (227) | 859 | 878 | 59 | 45 |
| | | | | | | Rvs | gagccgagaatgtccactg t (228) | 950 | 969 | 60 | 55 |
| CD83 | NM_004233.3 | 2478 | 58 | ctccatcc (229) | 354 | Fwd | acggtctcctgggtcaagt (230) | 314 | 332 | 59 | 58 |
| | | | | | | Rvs | ccctgaggtggtcttcctg (231) | 368 | 386 | 60 | 63 |
| CDC42SE1 | NM_001038707.1 | 3193 | 26 | cagcccag (232) | 592 | Fwd | gggaacatgagtgaatttt gg (233) | 565 | 585 | 59 | 43 |
| | | | | | | Rvs | cggtcaatccgtcttctctt (234) | 631 | 650 | 59 | 50 |

APPENDIX II-continued

Assay Designs for Validation Phase

| | | | | | | | | | | |
|---|---|---|---|---|---|---|---|---|---|---|
| CSF3R | NM_000760.2 | 3003 | 13 | ctctgcct (235) | 789 | Fwd | tgtaccagaatatgggcatctg (236) | 762 | 783 | 59 45 |
| | | | | | | Rvs | ggggctccagtttcacaa (237) | 849 | 866 | 59 56 |
| DDX58 | NM_014314.3 | 4759 | 13 | ctctgcct (238) | 2342 | Fwd | atgtgggcaatgtcatcaaa (239) | 2308 | 2327 | 59 40 |
| | | | | | | Rvs | aagcacttgctacctcttgctc (240) | 2353 | 2374 | 60 50 |
| EEF2 | NM_001961.3 | 3163 | 25 | ctcctcca (241) | 1765 | Fwd | ctggagatctgcctgaagga (242) | 1743 | 1762 | 60 55 |
| | | | | | | Rvs | gagacgaccgggtcagatt (243) | 1798 | 1816 | 60 58 |
| F13A1 | NM_000129.3 | 3863 | 56 | tgctgtcc (244) | 1311 | Fwd | ccttcctgttggatttggag (245) | 1278 | 1297 | 59 50 |
| | | | | | | Rvs | ggccacaccgatacatgc (246) | 1340 | 1357 | 60 61 |
| FCN1 | NM_002003.2 | 1292 | 38 | ctgcttcc (247) | 690 | Fwd | gctggggaacgacaacat (248) | 653 | 670 | 59 56 |
| | | | | | | Rvs | cctcaaagtccaccaggtct (249) | 710 | 729 | 59 55 |
| GAPDH | NM_002046.3 | 1310 | — | — | — | Fwd | — | — | — | — — |
| | | | | | | Rvs | — | — | — | — — |
| GZMB | NM_004131.4 | 941 | 78 | agctggag (250) | 404 | Fwd | cttctccaacgacatcatgc (251) | 378 | 397 | 59 50 |
| | | | | | | Rvs | acagctctggtccgcttg (252) | 420 | 437 | 60 61 |
| IL10RB | NM_000628.3 | 1935 | 1 | cctggagc (253) | 639 | Fwd | tggaaaaacggtactgatgaaa (254) | 574 | 595 | 59 36 |
| | | | | | | Rvs | aaccctcgaacttgaacacaa (255) | 660 | 680 | 59 43 |
| IL15RA | NM_172200.1 | 1843 | 37 | ccagggca (256) | 606 | Fwd | acaaccccagtctcaaatg (257) | 574 | 593 | 59 50 |
| | | | | | | Rvs | tgccgtcgttactgtggag (258) | 636 | 654 | 60 58 |
| IL6R | NM_181359.1 | 4082 | 38 | ctgcttcc (259) | 797 | Fwd | ggactgtgcacttgctggt (260) | 748 | 766 | 59 58 |
| | | | | | | Rvs | attgctgagggggctctt (261) | 807 | 824 | 59 56 |
| IL7R | NM_002185.2 | 1809 | 12 | ctccttcc (262) | 509 | Fwd | ggagaaaagagtctaacctgcaa (263) | 423 | 445 | 59 43 |
| | | | | | | Rvs | gatgtattaaatgtcaccacaaagtca (264) | 521 | 547 | 60 33 |
| ITGB2 | NM_001127491.1 | 2932 | 25 | ctcctcca (265) | 1277 | Fwd | cagcaatgtggtccaactca (266) | 1235 | 1254 | 60 50 |
| | | | | | | Rvs | gagggcgttgtgatccag (267) | 1293 | 1310 | 60 61 |
| IVNS1ABP | NM_006469.4 | 4205 | 76 | tggctgtg (268) | 1537 | Fwd | cgttgcttcagaaaagacttca (269) | 1496 | 1517 | 59 41 |
| | | | | | | Rvs | gaaaaatgacacagaatataccatcc (270) | 1547 | 1572 | 59 35 |
| KLRF1 | NM_016523.1 | 1242 | 47 | tccagtgt (271) | 312 | Fwd | tgatctccttgatcctgttgg (272) | 228 | 248 | 60 48 |
| | | | | | | Rvs | ttcttcttgtgccattattcactt (273) | 327 | 350 | 59 33 |
| LASP1 | NM_006148.2 | 4109 | 3 | cccagcag (274) | 852 | Fwd | accacatcccgaccagtg (275) | 816 | 833 | 60 61 |
| | | | | | | Rvs | ccttgtagccaccataggactg (276) | 872 | 893 | 60 55 |
| LCP1 | NM_002298.4 | 3808 | 37 | ccagggca (277) | 1504 | Fwd | aaccctcgagtcaatcatttg (278) | 1466 | 1486 | 59 43 |
| | | | | | | Rvs | ttgatcttttctatagagctggaag (279) | 1516 | 1539 | 59 38 |

APPENDIX II-continued

Assay Designs for Validation Phase

| | | | | | | | | | | |
|---|---|---|---|---|---|---|---|---|---|---|
| LILRA5 | NM_021250.2 | 1365 | 1 | cctggagc (280) | 510 | Fwd | gcagggagataccgctgtt a (281) | 451 | 470 | 60 55 |
| | | | | | | Rvs | tgagagggtgggtttgttgt (282) | 536 | 555 | 60 50 |
| LPXN | NM_004811.2 | 1926 | 77 | ccaccacc (283) | 389 | | caatatccaggagctcaat gtctac (284) | 337 | 361 | 60 44 |
| | | | | | | | tgagctcatccaactgagc a (285) | 415 | 434 | 60 50 |
| LTF | NM_002343.2 | 2390 | 53 | ctctgcca (286) | 1327 | Fwd | tgtgtacactgcaggcaaa tg (287) | 1289 | 1309 | 60 48 |
| | | | | | | Rvs | ggatcagggtcactgcttt g(288) | 1350 | 1369 | 60 55 |
| LY75 | NM_002349.2 | 6927 | 53 | ctctgcca (289) | 2008 | Fwd | taagcctgatgacccctgt c (290) | 1980 | 1999 | 60 55 |
| | | | | | | Rvs | caattctttctgcatggaa acct (291) | 2042 | 2065 | 60 38 |
| NCF1 | NM_000265.4 | 1409 | 33 | agctggga (292) | 294 | Fwd | ccgagatctacgagttcca taaa (293) | 204 | 226 | 59 43 |
| | | | | | | Rvs | ctgcccgtcaaaccactt (294) | 305 | 322 | 59 56 |
| NCF2 | NM_000433.3 | 2429 | 45 | ctggggct (295 | 1192 | Fwd | caactaccttgaaccagtt gagc (296) | 1148 | 1170 | 60 48 |
| | | | | | | Rvs | atgtcggactgcggagag (297) | 1208 | 1225 | 59 61 |
| NCF4 | NM_013416.3 | 1646 | 78 | agctggag (298) | 760 | Fwd | gcagctccgagagcagag (299) | 695 | 712 | 60 67 |
| | | | | | | Rvs | ccgactgaggaggaagat ca (300) | 771 | 790 | 60 55 |
| NCL | NM_005381.2 | 2732 | 80 | cctggaga (301) | 1218 | Fwd | gtggatgtcagaattggta tgact (302) | 1156 | 1179 | 59 42 |
| | | | | | | Rvs | caaaccagtgagttccaac g(303) | 1229 | 1248 | 59 50 |
| NCOA1 | NM_003743.4 | 6895 | 83 | cagccacc (304) | 3559 | Fwd | tgagatcaggcatgcaaca g (305) | 3527 | 3546 | 60 50 |
| | | | | | | Rvs | gtacagttcccgctgacgtt (306) | 3590 | 3609 | 60 55 |
| NLRP1 | NM_033004.3 | 5623 | 45 | ctggggct (307) | 3421 | Fwd | catcctgcctgcaaactca (308) | 3397 | 3415 | 60 53 |
| | | | | | | Rvs | cctcagttcctgcctcatct (309) | 3452 | 3471 | 59 55 |
| OAS2 | NM_002535.2 | 3647 | 38 | ctgcttcc (310) | 1280 | Fwd | tgttaacatcatccgtacat tcct (311) | 1247 | 1270 | 59 38 |
| | | | | | | Rvs | ctttggcggttgatcctc (312) | 1321 | 1338 | 59 56 |
| OAS3 | NM_006187.2 | 6646 | 43 | ctgcccca (313) | 1742 | Fwd | gacgatgttagcctgctg (314) | 1707 | 1725 | 59 58 |
| | | | | | | Rvs | tgggatttggtttggtg (315) | 1761 | 1778 | 60 50 |
| PDLIM | NM_020992.2 | 1462 | 54 | ctggtctc (316) | 373 | Fwd | aggctgcacagacaactg a (317) | 322 | 341 | 59 50 |
| | | | | | | Rvs | atggatgacgcttcccttc (318) | 395 | 413 | 60 53 |
| PDLIM2 | NM_176871.2 | 461 | 30 | cctcagcc (319) | 884 | Fwd | ccagctcctttcggctct (320) | 850 | 867 | 60 61 |
| | | | | | | Rvs | gtgagctgggcaagaagg (321) | 910 | 927 | 59 61 |
| RAF1 | NM_002880.3 | 3291 | 56 | tgctgtcc (322) | 1464 | Fwd | tgggaaatagaagccagt gga (323) | 1439 | 1459 | 59 43 |
| | | | | | | Rvs | cctttaggatctttactgca acatc (324) | 1526 | 1550 | 59 40 |

APPENDIX II-continued

Assay Designs for Validation Phase

| Gene | Accession | | | Probe | | Primer | Sequence | Start | End | Tm | GC |
|---|---|---|---|---|---|---|---|---|---|---|---|
| ROCK2 | NM_004850.3 | 6401 | 84 | tctgctgc (325) | 3140 | Fwd | tgaagaaaagaccaaact tggtaaa (326) | 3110 | 3134 | 60 | 32 |
| | | | | | | Rvs | agttgggcagccaaagag t (327) | 3175 | 3193 | 59 | 53 |
| SELL | NM_000655.3 | 2448 | 57 | ctggggcc (328) | 801 | Fwd | gccccagtgtcagtttgtg (329) | 762 | 780 | 60 | 58 |
| | | | | | | Rvs | ccaaagggtgagtacagtc ca (330) | 821 | 841 | 60 | 52 |
| SELP | NM_003005.3 | 3185 | 23 | cccagccc (331) | 1007 | Fwd | ttagttggaccggaagtgg t (332) | 957 | 976 | 59 | 50 |
| | | | | | | Rvs | caggtgctgacactgcaca (333) | 1028 | 1046 | 60 | 58 |
| SERPINA1 | NM_000295.4 | 3220 | 9 | tggtgatg (334) | 1146 | Fwd | gcacctggaaaatgaactc ac (335) | 1116 | 1136 | 59 | 48 |
| | | | | | | Rvs | gggtaaatgtaagctggca ga (336) | 1180 | 120 | 59 | 48 |
| SORL1 | NM_003105.4 | 10934 | 85 | tccaggtc (337) | 3432 | Fwd | tggagacatgagcgatga ga (338) | 3389 | 3408 | 60 | 50 |
| | | | | | | Rvs | gactcctggcaacgaaact g (339) | 3444 | 3463 | 60 | 55 |
| STAT6 | NM_003153.3 | 3993 | 3 | cccagcag (340) | 1790 | | ggtcgcagttcaacaagga (341) | 1767 | 1785 | 59 | 53 |
| | | | | | | | gtccaggacaccatcaaac c (342) | 1821 | 1840 | 60 | 55 |
| STX4 | NM_004604.3 | 1403 | 69 | cttcctcc (343) | 548 | Fwd | tgcagctgaaggccataga (344) | 520 | 538 | 60 | 53 |
| | | | | | | Rvs | cgaattgctgggacagga (345) | 610 | 627 | 60 | 56 |
| SYNE2 | NM_182910.2 | 2586 | 17 | aggagctg (346) | 1135 | Fwd | gtgtcggagggaactaatg c (347) | 1106 | 1125 | 59 | 55 |
| | | | | | | Rvs | tccacttgaggttgacgttc t (348) | 1145 | 1165 | 59 | 48 |
| TES | NM_015641.2 | 2766 | 63 | ctcctcct (349) | 522 | Fwd | tgtctccatcaatacagtta cctatga (350) | 490 | 516 | 60 | 37 |
| | | | | | | Rvs | tccttgggtagcatctgcat (351) | 560 | 579 | 60 | 60 |
| TREM1 | NM_018643.2 | 948 | 75 | cagcctcc (352) | 413 | Fwd | tctggactgtatcagtgtgt gatct (353) | 386 | 410 | 60 | 44 |
| | | | | | | Rvs | ccaggggtccctgaaaaa (354) | 472 | 489 | 60 | 56 |
| TRPM2 | NM_003307.3 | 5876 | 24 | cagctccc (355) | 2004 | Fwd | accttctcatttgggccatt (356) | 1971 | 1990 | 60 | 45 |
| | | | | | | Rvs | cgatgcagtcctggctct (357) | 2031 | 2048 | 60 | 61 |
| TXNIP | NM_006472.3 | 2953 | 26 | cagcccag (358) | 1134 | Fwd | ttcgggttcagaagatcag g (359) | 1105 | 1124 | 60 | 50 |
| | | | | | | Rvs | ggatccaggaacgctaac at (360) | 1177 | 1196 | 59 | 50 |
| VIM | NM_003380.3 | 2151 | 39 | ctccacct (361) | 928 | Fwd | gaccagctaaccaacgac aaa (362) | 897 | 917 | 60 | 48 |
| | | | | | | Rvs | gaagcatctcctcctgcaa t (363) | 977 | 996 | 59 | 50 |
| ZAP70 | NM_001079.3 | 2450 | 1 | cctggagc (364) | 618 | Fwd | gtgactacgtgcgccagac (365) | 578 | 596 | 60 | 63 |
| | | | | | | Rvs | cgtagcaatgagcttctcc ac (366) | 652 | 672 | 60 | 52 |

APPENDIX II-continued

Assay Designs for Validation Phase

| | | | | | 3' Design | | | | | |
|---|---|---|---|---|---|---|---|---|---|---|
| Gene | Accession # | Length | Probe ProbeSequence* | Position | Primer | Primer Sequence | Start | End | Tm | GC |
| ACTB | NM_001101.3 | 1852 | 11 | cttccagc (367) | 867 | Fwd | attggcaatgagcggttc (368) | 832 | 849 | 59 | 50 |
| | | | | | | Rvs | tgaaggtagtttcgtggat gc (369) | 902 | 922 | 60 | 48 |
| ACTR2 | NM_001005386.2 | 3944 | 27 | caggcagc (370) | 1089 | Fwd | ttggtgttgctgaattgctt (371) | 1057 | 1076 | 59 | 40 |
| | | | | | | Rvs | accctccagaaagcacaa tg (372) | 1130 | 1149 | 60 | 50 |
| ADAR | NM_001111.3 | 6640 | 53 | ctctgcca (373) | 3518 | Fwd | tttattgtcaaccacccca ag (374) | 3495 | 3515 | 59 | 43 |
| | | | | | | Rvs | ccttagtcttcccggattgc (375) | 3548 | 3567 | 60 | 55 |
| ADD1 | NM_001119.3 | 3970 | 69 | cttcctcc (376) | 2042 | Fwd | cccagcactcccatcaag (377) | 2022 | 2039 | 60 | 61 |
| | | | | | | Rvs | gtggcagcatcactgtcat c (378) | 2076 | 2095 | 60 | 55 |
| ADD3 | NM_016824.3 | 4454 | 15 | tcctgctc (379) | 2114 | Fwd | ggacaatcgaacgtaaac aaca (380) | 2076 | 2097 | 59 | 41 |
| | | | | | | Rvs | tgaatttgtgaaacagatg aagc (381) | 2138 | 2160 | 59 | 35 |
| AIM1 | NM_001624.2 | 7553 | 27 | caggcagc (382) | 5415 | Fwd | gaaggatgtatcaaatgc agga (383) | 5381 | 5402 | 59 | 41 |
| | | | | | | Rvs | cttggagccagatgttacc ag (384) | 5438 | 5458 | 59 | 52 |
| ARPC5 | NM_005717.2 | 2000 | 25 | ctcctcca (385) | 596 | Fwd | ctgcaatggcatgaaaag g (386) | 567 | 585 | 60 | 47 |
| | | | | | | Rvs | tgcagtcaagacacgaac aa (387) | 613 | 632 | 59 | 45 |
| BACH2 | NM_021813.2 | 9215 | 79 | ccaggagg (388) | 2639 | Fwd | cagtgagtcgtgtcctgtg c (389) | 2609 | 2628 | 60 | 60 |
| | | | | | | Rvs | tgtgatttgatctacagga aaagg (390) | 2655 | 2678 | 59 | 38 |
| C1orf38 | NM_004848.2 | 1650 | 44 | tgggcagc (391) | 710 | Fwd | gatccaagccatcatgcac (392) | 655 | 673 | 60 | 53 |
| | | | | | | Rvs | tgatgaactctggcaaggt ct (393) | 730 | 750 | 59 | 48 |
| CAPN2 | NM_001146068.1 | 3270 | 45 | ctggggct (394) | 1776 | Fwd | caaaattatggttgacatg ctagatt (395) | 1733 | 1758 | 59 | 31 |
| | | | | | | Rvs | tcgtccagagaatgtaga actcc (396) | 1787 | 1809 | 59 | 48 |
| CD163 | NM_004244.4 | 4231 | 85 | tccaggtc (397) | 3635 | Fwd | aatgggaatttataaccca gtgag (398) | 1787 | 1809 | 59 | 48 |
| | | | | | | Rvs | ggtgaatttctgctccattc a (399) | 3647 | 3667 | 60 | 43 |
| CD27 | NM_001242.4 | 1320 | 43 | ctgcccca (400) | 916 | Fwd | catcaacgaaggaaatat agatcaaac (401) | 845 | 871 | 60 | 33 |
| | | | | | | Rvs | ctcctggatgggatggt (402) | 941 | 958 | 60 | 61 |
| CD300C | NM_006678.3 | 1548 | 23 | cccagccc (403) | 872 | Fwd | agcgtgaccagaaaggac a (404) | 845 | 863 | 59 | 53 |
| | | | | | | Rvs | gaagcggacattgctgaa c (405) | 895 | 913 | 59 | 33 |
| CD53 | NM_001040033.1 | 1572 | 9 | tggtgatg (406) | 732 | Fwd | tggtttcattccaatttcct g (407) | 700 | 720 | 59 | 38 |
| | | | | | | Rvs | aggacatcccccaacacctc (408) | 757 | 775 | 59 | 58 |

APPENDIX II-continued

Assay Designs for Validation Phase

| CD68 | NM_001251.2 | 1872 | 1 | cctggagc (409) | 1079 | Fwd | gtccacctcgacctgctct (410) | 1053 | 1071 | 60 | 63 |
|---|---|---|---|---|---|---|---|---|---|---|---|
| | | | | | | Rvs | cactggggcaggagaaac t(411) | 1122 | 1140 | 60 | 58 |
| CD83 | NM_004233.3 | 2478 | 21 | tggctctg (412) | 624 | Fwd | acagagcggagattgtcct g (413) | 600 | 619 | 60 | 55 |
| | | | | | | Rvs | ctctgtagccgtgcaaact tac (414) | 666 | 687 | 59 | 50 |
| CDC42SE1 | NM_001038707.1 | 3193 | 26 | cagcccag (415) | 859 | Fwd | tctaggggcttatagctcc aataat (416) | 796 | 820 | 59 | 40 |
| | | | | | | Rvs | ctggtaggggcagcatttc (417) | 869 | 887 | 60 | 58 |
| CSF3R | NM_000760.2 | 3003 | 88 | catcctcc (418) | 2215 | Fwd | ctgggtgcccacaatcat (419) | 2194 | 2211 | 60 | 59 |
| | | | | | | Rvs | gcactgtgagcttggtgat g (420) | 2254 | 2273 | 60 | 55 |
| DDX58 | NM_014314.3 | 4759 | 29 | cttctgcc (421) | 4673 | Fwd | ccatgtaagacttgcctgc tt (422) | 4649 | 4669 | 59 | 48 |
| | | | | | | Rvs | gaggcttaatagattcaca gttcca (423) | 4716 | 4740 | 60 | 40 |
| EEF2 | NM_001961.3 | 3163 | 47 | tccagtgt (424) | 2329 | Fwd | gagcccatctaccttgtgg a (425) | 2307 | 2326 | 60 | 55 |
| | | | | | | Rvs | cctgttcaaaaccccgtag a (426) | 2359 | 2378 | 59 | 50 |
| F13A1 | NM_000129.3 | 3863 | 81 | ccagggcc (427) | 2213 | Fwd | tggagtaacaagaccaat gaagaa (428) | 2136 | 2159 | 60 | 38 |
| | | | | | | Rvs | tggctatcagcttccgatg (429) | 2230 | 2248 | 59 | 53 |
| FCN1 | NM_002003.2 | 1292 | 13 | ctctgcct (430) | 775 | Fwd | tgctaagtacaaatcattc aaggtg (431) | 743 | 767 | 59 | 36 |
| | | | | | | Rvs | ggcccgttagagaattacc c(432) | 824 | 843 | 59 | 55 |
| GAPDH | NM_002046.3 | 1310 | 45 | ctggggct (433) | 425 | Fwd | gagtccactggcgtcttca c (434) | 391 | 410 | 60 | 60 |
| | | | | | | Rvs | ttcacacccatgacgaaca t(435) | 490 | 509 | 59 | 45 |
| GZMB | NM_004131.4 | 941 | 37 | ccagggca (436) | 705 | Fwd | gggggacccagagattaa aa (437) | 633 | 652 | 60 | 50 |
| | | | | | | Rvs | ccattgtttcgtccatagga g (438) | 717 | 737 | 59 | 48 |
| IL10R | NM_000628.3 | 1935 | 7 | cttctccc (439) | 864 | Fwd | gctgtggtgcgtttacaag a (440) | 831 | 850 | 59 | 50 |
| | | | | | | Rvs | gaggatggcccaaaaact ct (441) | 900 | 919 | 60 | 50 |
| IL15RA | NM_172200.1 | 1843 | 18 | tcctgctg (442) | 953 | Fwd | gtggctatctccacgtcca c(443) | 931 | 950 | 60 | 60 |
| | | | | | | Rvs | catggcttccatttcaacg (444) | 1029 | 1047 | 60 | 47 |
| IL6R | NM_181359.1 | 4082 | 67 | tgctggag (445) | 1254 | Fwd | cggtcaaagacattcaca aca (446) | 1218 | 1238 | 59 | 43 |
| | | | | | | Rvs | gcgtcgtggatgacacagt (447) | 1264 | 1282 | 60 | 58 |
| IL7R | NM_002185.2 | 1809 | 72 | ttcctggc (448) | 598 | Fwd | aaagttttaatgcacgatg tagctt (449) | 570 | 594 | 59 | 32 |
| | | | | | | Rvs | tgtgctggataaattcaca tgc (450) | 626 | 647 | 60 | 41 |
| ITGB2 | NM_001127491.1 | 2932 | 18 | tcctgctg (451) | 2220 | Fwd | gggactcagagggctgct (452) | 2182 | 2199 | 60 | 67 |
| | | | | | | Rvs | ggcctgccacacactctc (453) | 2266 | 2283 | 60 | 67 |

APPENDIX II-continued

Assay Designs for Validation Phase

| Gene | Accession | Len | # | Probe | Pos | Dir | Primer | Start | End | Tm | GC |
|---|---|---|---|---|---|---|---|---|---|---|---|
| IVNS1ABP | NM_006469.4 | 4205 | 17 | aggagctg (454) | 2273 | Fwd | ggactttaattgcacccatga (455) | 2239 | 2259 | 59 | 43 |
| | | | | | | Rvs | aaccatcaaagccaccacat (456) | 2312 | 2331 | 60 | 45 |
| KLRF1 | NM_016523.1 | 1242 | 78 | agctggag (457) | 464 | Fwd | cgagatctgcagaccagaca (458) | 378 | 397 | 60 | 55 |
| | | | | | | Rvs | gagattttctttccaaacaatacaca (459) | 481 | 506 | 59 | 31 |
| LASP1 | NM_006148.2 | 4109 | 77 | ccaccacc (460) | 932 | Fwd | cagccccagtctccatacag (461) | 900 | 919 | 60 | 60 |
| | | | | | | Rvs | ggcggcgctgtagtcata (462) | 962 | 979 | 60 | 61 |
| LCP1 | NM_002298.4 | 3808 | 49 | tggtggcc (463) | 1771 | Fwd | gccttgatttggcagctaat (464) | 1715 | 1734 | 59 | 45 |
| | | | | | | Rvs | tttcattcacccagttgacaat (465) | 1799 | 1820 | 59 | 36 |
| LILRA5 | NM_021250.2 | 1365 | 68 | aggagcag (466) | 831 | Fwd | tggtcagaacccagtgacct (467) | 793 | 812 | 60 | 55 |
| | | | | | | Rvs | tgttttgtgacggactgagg (468) | 846 | 865 | 59 | 50 |
| LPXN | NM_004811.2 | 1926 | 83 | cagccacc (469) | 956 | Fwd | ggagaggtgtttggtgcag (470) | 866 | 884 | 59 | 58 |
| | | | | | | Rvs | gaaaggtagttttccaacactgg (471) | 971 | 993 | 59 | 43 |
| LTF | NM_002343.2 | 2390 | 79 | ccaggagg (472) | 2138 | Fwd | ctaatctgaaaaagtgctcaacctc (473) | 2110 | 2134 | 59 | 40 |
| | | | | | | Rvs | gccatcttcttcggttttacttc (474) | 2165 | 2187 | 60 | 43 |
| LY75 | NM_002349.2 | 6927 | 26 | cagcccag (475) | 3627 | Fwd | tggatcggactcttcagtca (476) | 3553 | 3572 | 59 | 50 |
| | | | | | | Rvs | cagtcttcgagttgcccatta (477) | 3639 | 3659 | 60 | 48 |
| NCF1 | NM_000265.4 | 1409 | 10 | ccacctcc (478) | 406 | Fwd | ctgccccaccaagatctcc (479) | 380 | 397 | 59 | 61 |
| | | | | | | Rvs | ttgggcatcaagtatgtctctg (480) | 477 | 498 | 60 | 45 |
| NCF2 | NM_000433.3 | 2429 | 11 | cttccagc (481) | 1757 | Fwd | ggaagggatataatcctggtg (482) | 1712 | 1733 | 60 | 50 |
| | | | | | | Rvs | ccaccttcccttcgcactc (483) | 1767 | 1785 | 60 | 58 |
| NCF4 | NM_013416.3 | 1646 | 69 | cttcctcc (484) | 1200 | Fwd | gtcaccccttagggacatc (485) | 1175 | 1194 | 60 | 60 |
| | | | | | | Rvs | gagctatgtcctctctctggaact (486) | 1259 | 1282 | 59 | 50 |
| NCL | NM_005381.2 | 2732 | 19 | ctccagcc (487) | 1802 | Fwd | gaaattgagggcagagcaat (488) | 1780 | 1799 | 59 | 45 |
| | | | | | | Rvs | tgacaaacagagttttggatgg (489) | 1849 | 1870 | 60 | 41 |
| NCOA1 | NM_003743.4 | 6895 | 3 | cccagcag (490) | 4409 | Fwd | gcaaccagctctcatccact (491) | 4361 | 4380 | 60 | 55 |
| | | | | | | Rvs | gacgtcagcaaacacctgaa (492) | 4427 | 4446 | 59 | 50 |
| NLRP1 | NM_033004.3 | 5623 | 89 | cagcatcc (493) | 4448 | Fwd | cactgtgtctgggtctgttc (494) | 4425 | 4445 | 60 | 57 |
| | | | | | | Rvs | tcttctccagggcttcgata (495) | 4486 | 4505 | 59 | 50 |
| OAS2 | NM_002535.2 | 3647 | 36 | ctggctcc (496) | 1621 | Fwd | cctgcctttaatgcactgg (497) | 1590 | 1608 | 59 | 53 |
| | | | | | | Rvs | atgagccctgcataaacctc (498) | 1641 | 1660 | 59 | 50 |

APPENDIX II-continued

Assay Designs for Validation Phase

| Gene | Accession | Len | | Probe | Pos | Dir | Primer | Start | End | Tm | GC |
|---|---|---|---|---|---|---|---|---|---|---|---|
| OA53 | NM_006187.2 | 6646 | 1 | cctggagc (499) | 2792 | Fwd | gtgctgccagcctttgac (500) | 2752 | 2769 | 60 | 61 |
| | | | | | | Rvs | ggtcgacgtagacttgagagc (501) | 2804 | 2824 | 59 | 57 |
| PDLIM1 | NM_020992.2 | 1462 | 74 | ctgctgcc (502) | 609 | Fwd | aacaatgccctggagtcaaa (503) | 587 | 606 | 60 | 45 |
| | | | | | | Rvs | aggctgagcatggtctaagg (504) | 642 | 661 | 59 | 55 |
| PDLIM2 | NM_176871.2 | 4611 | 22 | ctccacca (505) | 1171 | Fwd | gggctgaacctgaagatgc (506) | 1083 | 1101 | 60 | 58 |
| | | | | | | Rvs | cctggtcttcctcctgtcc (507) | 1193 | 1211 | 59 | 63 |
| RAF1 | NM_002880.3 | 3291 | 57 | ctggggcc (508) | 1951 | Fwd | ggttgaacaacctactggctct (509) | 1918 | 1939 | 59 | 50 |
| | | | | | | Rvs | gggttgttatcctgcattcg (510) | 1967 | 1986 | 60 | 50 |
| ROCK2 | NM_004850.3 | 6401 | 8 | ctgccttc (511) | 4617 | Fwd | acagcttgccccaaacaa (512) | 4589 | 4606 | 60 | 50 |
| | | | | | | Rvs | tggaagaatacgatcaccttga (513) | 4643 | 4664 | 59 | 41 |
| SELL | NM_000655.3 | 2448 | 59 | cagtggca (514) | 1208 | Fwd | tcaaatcctagtccaatatgtcaaaa (515) | 1126 | 1151 | 60 | 31 |
| | | | | | | Rvs | cccagagaatgcagtaaccat (516) | 1219 | 1239 | 59 | 48 |
| SELP | NM_003005.3 | 3185 | 76 | tggctgtg (517) | 2499 | Fwd | caaaaagatgatgggaaatgc (518) | 2466 | 2486 | 59 | 41 |
| | | | | | | Rvs | catgggtgtttatggaaacctt (519) | 2557 | 2578 | 59 | 41 |
| SERPINA1 | NM_000295.4 | 3220 | 82 | cagaggag (520) | 1298 | Fwd | aatggggctgacctctcc (521) | 1273 | 1290 | 60 | 61 |
| | | | | | | Rvs | gtcagcacagccttatgcac (522) | 1330 | 1349 | 59 | 55 |
| SORL1 | NM_003105.4 | 10924 | 77 | ccaccacc (523) | 5325 | Fwd | cgattctaaatccattaccacca (524) | 5285 | 5307 | 60 | 39 |
| | | | | | | Rvs | caccatagctgtcaatgtgga (525) | 5338 | 5358 | 59 | 48 |
| STAT6 | NM_003153.3 | 3993 | 64 | cagcctgg (526) | 2452 | Fwd | tcaacgtgttgtcagccttc (527) | 2406 | 2425 | 59 | 50 |
| | | | | | | Rvs | gggtgaggctggtcaaag (528) | 2476 | 2493 | 59 | 61 |
| STX4 | NM_004604.3 | 1403 | 51 | ctcctgcc (529) | 988 | Fwd | ttttctggctaccgaagtgg (530) | 899 | 918 | 60 | 50 |
| | | | | | | Rvs | gttctccagggccgtctt (531) | 1002 | 1019 | 60 | 61 |
| SYNE2 | NM_182910.2 | 2586 | 75 | cagcctcc (532) | 1365 | Fwd | taatggccttgcagggaac (533) | 1294 | 1312 | 60 | 53 |
| | | | | | | Rvs | tctcactgctctgaactttgct (534) | 1397 | 1418 | 59 | 45 |
| TES | NM_015641.2 | 2766 | 3 | cccagcag (535) | 826 | Fwd | ttcctggaggggatagaagc (536) | 804 | 823 | 60 | 55 |
| | | | | | | Rvs | atactcagtttgcagcaatagca (537) | 887 | 909 | 59 | 39 |
| TREM1 | NM_018643.2 | 948 | 20 | ccagccag (538) | 692 | Fwd | ttacaaatgtgacagatatcatcagg (539) | 639 | 664 | 59 | 35 |
| | | | | | | Rvs | aagaccaggctcttactcagga (540) | 705 | 726 | 59 | 50 |
| TRPM2 | NM_003307.3 | 5876 | 85 | tccaggtc (541) | 3587 | Fwd | cgaggacatcagcaataaggt (542) | 3544 | 3564 | 59 | 48 |
| | | | | | | Rvs | atggagcccgacctcttc (543) | 3601 | 3618 | 60 | 61 |

APPENDIX II-continued

Assay Designs for Validation Phase

| Gene | Accession | Pos1 | Len1 | Probe | Pos2 | Dir | Primer | Start | End | Tm | GC |
|---|---|---|---|---|---|---|---|---|---|---|---|
| TXNIP | NM_006472.3 | 2953 | 77 | ccaccacc (544) | 1461 | Fwd | atgcccctgagttcaagtt c (545) | 1438 | 1457 | 59 | 50 |
| | | | | | | Rvs | actgcacattgttgttgag ga (546) | 1495 | 1515 | 59 | 43 |
| VIM | NM_003380.3 | 2151 | 13 | ctctgcct (547) | 1648 | Fwd | tacaggaagctgctggaa gg (548) | 1611 | 1630 | 60 | 55 |
| | | | | | | Rvs | accagaggagtgaatcc ag (549) | 1695 | 1714 | 59 | 55 |
| ZAP70 | NM_001079.3 | 2450 | 52 | ctcctccc (550) | 1496 | Fwd | gctgcacaagttcctggtc (551) | 1470 | 1488 | 59 | 58 |
| | | | | | | Rvs | tcatccccatggacacct (552) | 1538 | 1555 | 59 | 56 |

*UPL probe sequence orientation may be as listed OR as its reverse complement.

REFERENCES

1. Vermeulen, J., K. De Preter, S. Lefever, J. Nuytens, F. De Vloed, S. Derveaux, J. Hellemans, F. Speleman, and J. Vandesompele, *Measurable impact of RNA quality on gene expression results from quantitative PCR.* Nucleic Acids Res, 2011. 39(9): p. e63.
2. Strand, C., J. Enell, I. Hedenfalk, and M. Ferno, *RNA quality in frozen breast cancer samples and the influence on gene expression analysis—a comparison of three evaluation methods using microcapillary electrophoresis traces.* BMC Mol Biol, 2007. 8: p. 38.
3. Schroeder, A., O. Mueller, S. Stocker, R. Salowsky, M. Leiber, M. Gassmann, S. Lightfoot, W. Menzel, M. Granzow, and T. Ragg, *The RIN: an RNA integrity number for assigning integrity values to RNA measurements.* BMC Mol Biol, 2006. 7: p. 3.
4. Houseley, J. and D. Tollervey, *The many pathways of RNA degradation.* Cell, 2009. 136(4): p. 763-76.
5. Samuel, M. A., K. Whitby, B. C. Keller, A. Marri, W. Barchet, B. R. Williams, R. H. Silverman, M. Gale, Jr., and M. S. Diamond, *PKR and RNase L contribute to protection against lethal West Nile Virus infection by controlling early viral spread in the periphery and replication in neurons.* J Virol, 2006. 80(14): p. 7009-19.
6. Li, X. L., J. A. Blackford, and B. A. Hassel, *RNase L mediates the antiviral effect of interferon through a selective reduction in viral RNA during encephalomyocarditis virus infection.* J Virol, 1998. 72(4): p. 2752-9.
7. Beelman, C. A. and R. Parker, *Degradation of mRNA in eukaryotes.* Cell, 1995. 81(2): p. 179-83.
8. Watson, J. D., *Molecular biology of the gene, 6th edition.* 2008, Cold Spring Harbor, N.Y.: Cold Spring Harbor Laboratory Press.
9. Newbury, S. F., O. Muhlemann, and G. Stoecklin, *Turnover in the Alps: an mRNA perspective. Workshops on mechanisms and regulation of mRNA turnover.* EMBO Rep, 2006. 7(2): p. 143-8.
10. Takano, E. A., T. Mikeska, A. Dobrovic, D. J. Byrne, and S. B. Fox, *A multiplex endpoint RT-PCR assay for quality assessment of RNA extracted from formalin-fixed paraffin-embedded tissues.* BMC Biotechnol, 2010. 10: p. 89.
11. Baechler, E. C., F. M. Batliwalla, G. Karypis, P. M. Gaffney, K. Moser, W. A. Ortmann, K. J. Espe, S. Balasubramanian, K. M. Hughes, J. P. Chan, A. Begovich, S. Y. Chang, P. K. Gregersen, and T. W. Behrens, *Expression levels for many genes in human peripheral blood cells are highly sensitive to ex vivo incubation.* Genes Immun, 2004. 5(5): p. 347-53.
12. Probst, J., S. Brechtel, B. Scheel, I. Hoerr, G. Jung, H. G. Rammensee, and S. Pascolo, *Characterization of the ribonuclease activity on the skin surface.* Genet Vaccines Ther, 2006. 4: p. 4.
13. Thompson, K. L., P. S. Pine, B. A. Rosenzweig, Y. Turpaz, and J. Retief, *Characterization of the effect of sample quality on high density oligonucleotide microarray data using progressively degraded rat liver RNA.* BMC Biotechnol, 2007. 7: p. 57.
14. Opitz, L., G. Salinas-Riester, M. Grade, K. Jung, P. Jo, G. Emons, B. M. Ghadimi, T. Beissbarth, and J. Gaedcke, *Impact of RNA degradation on gene expression profiling.* BMC Med Genomics, 2010. 3: p. 36.
15. Gingrich, J., T. Rubio, and C. Karlak, *Effect of RNA Degradation on Data Quality in Quantitative PCR and Microarray Experiments.* Bio-Rad Bulletin #5452, 2006.
16. Quellhorst, G., Y. Han, and R. Blanchard, *Validating Microarray Data Using $RT^2$ Real-Time PCR.* SABiosciences, 2005.
17. Morey, J. S., J. C. Ryan, and F. M. Van Dolah, *Microarray validation: factors influencing correlation between oligonucleotide microarrays and real-time PCR.* Biol Proced Online, 2006. 8: p. 175-93.
18. Nolan, T., R. E. Hands, and S. A. Bustin, *Quantification of mRNA using real-time RT-PCR.* Nat Protoc, 2006. 1(3): p. 1559-82.
19. Biosystems, A., *Essentials of Real Time PCR.* 2006.
20. Bustin, S. A. and T. Nolan, *Pitfalls of quantitative real-time reverse-transcription polymerase chain reaction.* J Biomol Tech, 2004. 15(3): p. 155-66.
21. Becker, C., A. Hammerle-Fickinger, I. Riedmaier, and M. W. Pfaffl, *mRNA and microRNA quality control for RT-qPCR analysis.* Methods, 2010. 50(4): p. 237-43.
22. Fleige, S. and M. W. Pfaffl, *RNA integrity and the effect on the real-time qRT-PCR performance.* Mol Aspects Med, 2006. 27(2-3): p. 126-39.
23. Schoor, O., T. Weinschenk, J. Hennenlotter, S. Corvin, A. Stenzl, H. G. Rammensee, and S. Stevanovic, *Moderate degradation does not preclude microarray analysis of small amounts of RNA.* Biotechniques, 2003. 35(6): p. 1192-6, 1198-201.
24. Mueller, O., K. Hahnenberger, M. Dittmann, H. Yee, R. Dubrow, R. Nagle, and D. Ilsley, *A microfluidic system for high-speed reproducible DNA sizing and quantitation.* Electrophoresis, 2000. 21(1): p. 128-34.
25. Kuschel, M. and W. Ausserer, *Characterization of RNA quality using the Agilent 2100 Bioanalyzer.* Agilent Application Note, 2000.

26. Palmer, M. and E. Prediger, *Assessing RNA Quality*. Ambion TechNotes, 2004. 11(1).
27. Auer, H., S. Lyianarachchi, D. Newsom, M. I. Klisovic, G. Marcucci, and K. Kornacker, *Chipping away at the chip bias: RNA degradation in microarray analysis*. Nat Genet, 2003. 35(4): p. 292-3.
28. Mueller, O., S. Lightfoot, and A. Schroeder, *RNA Integrity Number (RIN)-Standardization of RNA Quality Control*. Agilent Technologies Application Note, 2004.
29. Pfaffl, M. W., S. Fleige, and I. Riedmaier, *Validation of lab-on-chip capillary electrophoresis systems for total RNA quality and quantity control*. Biotechnology & Biotechnological Equipment, 2008. 22(3): p. 829-834.
30. Riedmaier, I., M. Bergmaier, and M. W. Pfaffl, *Comparison of two available platforms for determination of RNA quality*. Biotechnology & Biotechnological Equipment, 2010. 24(4): p. 2154-2159.
31. Port, M., H. U. Schmelz, T. Stassen, K. Mueller, M. Stockinger, R. Obermair, and M. Abend, *Correcting false gene expression measurements from degraded RNA using RTQ-PCR*. Diagn Mol Pathol, 2007. 16(1): p. 38-49.
32. Copois, V., F. Bibeau, C. Bascoul-Mollevi, N. Salvetat, P. Chalbos, C. Bareil, L. Candeil, C. Fraslon, E. Conseiller, V. Granci, P. Maziere, A. Kramar, M. Ychou, B. Pau, P. Martineau, F. Molina, and M. Del Rio, *Impact of RNA degradation on gene expression profiles: assessment of different methods to reliably determine RNA quality*. J Biotechnol, 2007. 127(4): p. 549-59.
33. Su, A. I., T. Wiltshire, S. Batalov, H. Lapp, K. A. Ching, D. Block, J. Zhang, R. Soden, M. Hayakawa, G. Kreiman, M. P. Cooke, J. R. Walker, and J. B. Hogenesch, *A gene atlas of the mouse and human protein-encoding transcriptomes*. Proc Natl Acad Sci USA, 2004. 101(16): p. 6062-7.
34. Pant, P. V., H. Tao, E. J. Beilharz, D. G. Ballinger, D. R. Cox, and K. A. Frazer, *Analysis of allelic differential expression in human white blood cells*. Genome Res, 2006. 16(3): p. 331-9.
35. Safran, M., V. Chalifa-Caspi, O. Shmueli, T. Olender, M. Lapidot, N. Rosen, M. Shmoish, Y. Peter, G. Glusman, E. Feldmesser, A. Adato, I. Peter, M. Khen, T. Atarot, Y. Groner, and D. Lancet, *Human Gene-Centric Databases at the Weizmann Institute of Science: GeneCards, UDB, CroW 21 and HORDE*. Nucleic Acids Res, 2003. 31(1): p. 142-6.
36. Min, J. L., A. Barrett, T. Watts, F. H. Pettersson, H. E. Lockstone, C. M. Lindgren, J. M. Taylor, M. Allen, K. T. Zondervan, and M. I. McCarthy, *Variability of gene expression profiles in human blood and lymphoblastoid cell lines*. BMC Genomics, 2010. 11: p. 96.
37. Yanai, I., H. Benjamin, M. Shmoish, V. Chalifa-Caspi, M. Shklar, R. Ophir, A. Bar-Even, S. Horn-Saban, M. Safran, E. Domany, D. Lancet, and O. Shmueli, *Genome-wide midrange transcription profiles reveal expression level relationships in human tissue specification*. Bioinformatics, 2005. 21(5): p. 650-9.
38. Shmueli, O., S. Horn-Saban, V. Chalifa-Caspi, M. Shmoish, R. Ophir, H. Benjamin-Rodrig, M. Safran, E. Domany, and D. Lancet, *GeneNote: whole genome expression profiles in normal human tissues*. C R Biol, 2003. 326(10-11): p. 1067-72.
39. Wu, C., C. Orozco, J. Boyer, M. Leglise, J. Goodale, S. Batalov, C. L. Hodge, J. Haase, J. Janes, J. W. Huss, 3rd, and A. I. Su, *BioGPS: an extensible and customizable portal for querying and organizing gene annotation resources*. Genome Biol, 2009. 10(11): p. R130.
40. Bijlani, R., Y. Cheng, D. A. Pearce, A. I. Brooks, and M. Ogihara, *Prediction of biologically significant components from microarray data: Independently Consistent Expression Discriminator (ICED)*. Bioinformatics, 2003. 19(1): p. 62-70.
41. Troyanskaya, O. G., M. E. Garber, P. O. Brown, D. Botstein, and R. B. Altman, *Nonparametric methods for identifying differentially expressed genes in microarray data*. Bioinformatics, 2002. 18(11): p. 1454-61.
42. Roche, *RealTime Ready Universal ProbeLibrary: Redefining and revolutionizing real-time qPCR assays*. 2009.
43. Qiagen/PreAnalytiX, *PAXgene Blood RNA Kit Handbook*. 2009.
44. Wilkes, T. M., A. S. Devonshire, S. L. Ellison, and C. A. Foy, *Evaluation of a novel approach for the measurement of RNA quality*. BMC Res Notes, 2010. 3: p. 89.
45. Ibberson, D., V. Benes, M. U. Muckenthaler, and M. Castoldi, *RNA degradation compromises the reliability of microRNA expression profiling*. BMC Biotechnol, 2009. 9: p. 102.
46. Breaker, R. R., G. M. Emilsson, D. Lazarev, S. Nakamura, I. J. Puskarz, A. Roth, and N. Sudarsan, *A common speed limit for RNA-cleaving ribozymes and deoxyribozymes*. RNA, 2003. 9(8): p. 949-57.
47. Emilsson, G. M., S. Nakamura, A. Roth, and R. R. Breaker, *Ribozyme speed limits*. RNA, 2003. 9(8): p. 907-18.
48. Ambion, *TRIzol® Reagent Manual*. 2010.
49. Qiagen, *RNeasy Mini Kit Handbook*. 2010.
50. Raines, R. T., *Ribonuclease A*. Chem Rev, 1998. 98(3): p. 1045-1066.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A method for quantifying ribonucleic acid (RNA) degradation in a blood sample, comprising;
    quantitatively amplifying a set of RNAs in the blood sample, thereby generating fluorescently labeled amplicons, wherein the set of RNAs consist of beta actin (ACTB), actin related protein 2/3 complex, subunit 5 (ARPC5), neutrophil cytosolic factor 2 (NCF2), coagulation factor XIII A1 polypeptide (F13A1), influenza virus non-structural protein 1A binding protein (IVNS1ABP), absent in melanoma 1 (AIM1), interleukin 10 receptor beta (IL10RB), and integrin, beta 2 (ITGB2), wherein the set of RNAs provide an improved ability to quantify RNA degradation in a blood sample as compared to any other set of RNAs, and wherein quantitatively amplifying the set of RNAs in the blood sample comprises amplifying a 3'-end, a middle, and a 5'-end of each RNA in the set of RNAs in the blood sample;
    generating an amplification plot of magnitude of fluorescence (ΔRn) from the fluorescently labeled amplicons against polymerase chain reaction (PCR) amplification cycle number for each RNA in the set of RNAs;
    obtaining a cycle threshold (Cτ) value from the amplification plot for each RNA in the set of RNAs, wherein the Cτ is a threshold set at a midpoint of a linear phase of the amplification plot;
    exposing a set of control RNAs to differential RNA degradation conditions selected from the group consisting of repeated freeze/thaw cycles, heat treatments, or exposure to RNase A, wherein the set of control RNAs comprise ACTB, ARPC5, NCF2, F13A1, IVNS1ABP, AIM1, IL10RB, and ITGB2, thereby generating a set of degraded control RNAs;
    quantitatively amplifying the set of degraded control RNAs, thereby generating fluorescently labeled amplicons for the degraded control RNAs, wherein quantitatively amplifying the set of degraded control RNAs comprises amplifying a 3'-end, a middle, and a 5'-end of each RNA in the set of degraded control RNAs;
    generating an amplification plot from the fluorescently labeled amplicons for each RNA in the set of degraded control RNAs;
    obtaining a Cτ value from the amplification plot for each RNA in the set of degraded control RNAs, and thereby generating a series of differentially weighted Cτ profiles corresponding to intact and incrementally degraded RNA for each of the RNAs in the set of RNAs;
    comparing the degradation of each RNA in the set of RNAs in the blood sample to the set of degraded control RNAs for each RNA in the set of RNAs; and
    quantifying an amount of RNA degradation in the blood sample.

2. The method of claim 1, wherein said blood sample is obtained from a human.

3. The method of claim 1, wherein said blood sample comprises whole blood.

4. The method of claim 1, further comprising discarding said blood sample without conducting a gene expression profile analysis if of the RNA degradation is unsuitable.

5. The method of claim 1, wherein said ribonucleic acid (RNA) is converted to complementary deoxyribonucleic acid (cDNA) during or prior to quantitative amplification.

6. The method of claim 1, wherein said quantitatively amplifying comprises polymerase chain reaction (PCR).

7. The method of claim 1, wherein said quantitatively amplifying comprises real-time quantitative polymerase chain reaction (qPCR).

8. The method of claim 1, wherein quantitatively amplifying the set of RNAs in the blood sample and the set of degraded control RNAs comprises amplifying the set of RNAs in the blood sample and the set of degraded control RNAs with primers
    ccaaccgcgagaagatga (SEQ ID NO: 1) and ccagaggcgtacagggatag (SEQ ID NO: 2) for ACTB,
    caagttcgtggacgaagaaga (SEQ ID NO: 20) and gcagctgtcatgtttccttg (SEQ ID NO: 21) for ARPC5,
    aaaatcgacaaggcgatgg (SEQ ID NO: 116) and gggatcaccactggctcata (SEQ ID NO: 117) for NCF2,
    cctgaatgacatcggggtaa (SEQ ID NO: 62) and gtccaggatgccatcttca (SEQ ID NO: 63) for F13A1,
    atcaactgggtgcagcgta (SEQ ID NO: 89) and tcagctgagtagtacaaggtttgaa (SEQ ID NO: 90) for IVNS1ABP,
    ctggaatgtcattatcagacacaa (SEQ ID NO: 17) and tcagagacgtcgggttcact (SEQ ID NO: 18) for AIM1, ggtcgtgtgcttggagga (SEQ ID NO: 74) and ggtaccattccaatgctga (SEQ ID NO: 75) for IL10RB; and
gctgtccccacaaaaagtg (SEQ ID NO: 86) and ccggaaggtcacgttgaa (SEQ ID NO: 87) for ITGB2.

9. The method of claim 1, wherein quantitatively amplifying the set of RNAs in the blood sample and the set of degraded control RNAs comprises amplifying the set of RNAs in the blood sample and the set of degraded control RNAs with primers
caccaagagtcaggcagtga (SEQ ID NO: 203) and agagatgagcaccttcaagaca (SEQ ID NO: 204) for ARPC5,
caactaccttgaaccagttgagc (SEQ ID NO: 296) and atgtcgactgcggagag (SEQ ID NO: 297) for NCF2,
ccttcctgttggatttggag (SEQ ID NO: 245) and ggccacaccgatacatgc (SEQ ID NO: 246) for F13A1,
cgttgcttcagaaaagacttca (SEQ ID NO: 269) and gaaaaatgacacagaatataccatcc (SEQ ID NO: 270) for IVNS1ABP,
tgtctgtctgcaatgggatg (SEQ ID NO: 200) and gaataattgttggttcagaaaattca (SEQ ID NO: 201) for AIM1,
tggaaaaacggtactgatgaaa (SEQ ID NO: 254) and aaccctcgaacttgaacacaa (SEQ ID NO: 255) for IL10RB; and
cagcaatgtggtccaactca (SEQ ID NO: 266) and gagggcgttgtgatccag (SEQ ID NO: 267) for ITGB2.

10. The method of claim 1, wherein quantitatively amplifying the set of RNAs in the blood sample and the set of degraded control RNAs comprises amplifying the set of RNAs in the blood sample and the set of degraded control RNAs with primers
attggcaatgagcggttc (SEQ ID NO: 368) and tgaaggtagtttcgtggatgc (SEQ ID NO:369) for ACTB,
ctgcaatggcatgaaaagg (SEQ ID NO: 386) and tgcagtcaagacacgaacaa (SEQ ID NO: 387) for ARPC5,
ggaagggggatataatcctggtg (SEQ ID NO: 482) and ccaccttccctttgcactc (SEQ ID NO: 483) for NCF2,
tggagtaacaagaccaatgaagaa (SEQ ID NO: 428) and tggctatcagcttccgatg (SEQ ID NO: 429) for F13A1,
ggactttaattgcacccatga (SEQ ID NO: 455) and aaccatcaaagccaccacat (SEQ ID NO: 456) for IVNS1ABP,
gaaggatgtatcaaatgcagga (SEQ ID NO: 383) and cttggagccagatgttaccag (SEQ ID NO: 384) for AIM1,
gctgtggtgcgtttacaaga (SEQ ID NO: 440) and gaggatggcccaaaaactct (SEQ ID NO: 441) for IL10RB; and
ggggactcagagggctgct (SEQ ID NO:452) and ggcctgccacacactctc (SEQ ID NO: 453) for ITGB2.

11. The method of claim 1, wherein the differential RNA degradation conditions comprise exposure of the control RNAs to repeated freeze/thaw cycles.

12. The method of claim 1, wherein the differential RNA degradation conditions comprise exposure of the set of control RNAs to RNase A.

13. The method of claim 12, wherein exposure of the control RNAs to RNase A comprises exposing the set of control RNAs to a 1:5,000,000 dilution of RNase A for 8 minutes at 37° C.

* * * * *

UNITED STATES PATENT AND TRADEMARK OFFICE
CERTIFICATE OF CORRECTION

PATENT NO. : 9,994,893 B2
APPLICATION NO. : 14/365060
DATED : June 12, 2018
INVENTOR(S) : Tischfield et al.

Page 1 of 1

It is certified that error appears in the above-identified patent and that said Letters Patent is hereby corrected as shown below:

In the Specification

Column 1, Lines 10-15:
"Pursuant to 35 U.S.C. §202(c), it is acknowledged that the U.S. Government has rights in the invention described, which was made in part with funds from the National Institutes of Health, Grant Numbers, 5U24MH068457 (NIMH); 5U10 AA008401 (NIAAA); SN271200900012C (NIDA) and HHSN276201100016C (NIDDK)."

Should read:
--This invention was made with government support under grants AA008401, HHSN271200900012C, HHSN276201100016C, and MH068457 awarded by the National Institutes of Health. The government has certain rights in the invention.--

Signed and Sealed this
Second Day of June, 2020

Andrei Iancu
*Director of the United States Patent and Trademark Office*